(12) United States Patent
Buggy et al.

(10) Patent No.: US 9,717,731 B2
(45) Date of Patent: Aug. 1, 2017

(54) TEC FAMILY KINASE INHIBITOR ADJUVANT THERAPY

(71) Applicant: Pharmacyclics LLC, Sunnyvale, CA (US)

(72) Inventors: Joseph J. Buggy, Mountain View, CA (US); Tarak D. Mody, Sunnyvale, CA (US); John C. Byrd, Columbus, OH (US); Betty Y. Chang, Cupertino, CA (US); Jason A. Dubovsky, Columbus, OH (US); Natarajan Muthusamy, Columbus, OH (US); Amy Jo Johnson, Columbus, OH (US)

(73) Assignee: Pharmacyclics LLC, Sunnyvale, CA (US)

( * ) Notice: Subject to any disclaimer, the term of this patent is extended or adjusted under 35 U.S.C. 154(b) by 0 days.

(21) Appl. No.: 14/070,420

(22) Filed: Nov. 1, 2013

(65) Prior Publication Data

US 2014/0134265 A1    May 15, 2014

Related U.S. Application Data

(60) Provisional application No. 61/785,868, filed on Mar. 14, 2013, provisional application No. 61/722,107, filed on Nov. 2, 2012.

(51) Int. Cl.
*A61K 31/519* (2006.01)
*A61N 5/10* (2006.01)
*A61K 45/06* (2006.01)

(52) U.S. Cl.
CPC ............ *A61K 31/519* (2013.01); *A61K 45/06* (2013.01)

(58) Field of Classification Search
USPC ....................................... 424/577; 514/265.1
See application file for complete search history.

(56) References Cited

U.S. PATENT DOCUMENTS

| | | | |
|---|---|---|---|
| 6,824,768 B2 | 11/2004 | Stalgis et al. | |
| 7,547,689 B2 | 6/2009 | Sessler et al. | |
| 7,960,396 B2 | 6/2011 | Honigberg et al. | |
| 8,058,249 B2 | 11/2011 | Krieg et al. | |
| 2002/0004584 A1 | 1/2002 | Laughlin | |
| 2002/0039734 A1 | 4/2002 | Hanrahan et al. | |
| 2002/0127203 A1 | 9/2002 | Albrecht | |
| 2003/0013118 A1 | 1/2003 | Edge et al. | |
| 2003/0103938 A1 | 6/2003 | Jinquan et al. | |
| 2004/0136954 A1 | 7/2004 | Grusby et al. | |
| 2005/0064464 A1 | 3/2005 | Punnonen et al. | |
| 2006/0292181 A1 | 12/2006 | Brayden | |
| 2007/0032457 A1 | 2/2007 | Blatt | |
| 2007/0122417 A1 | 5/2007 | Holt et al. | |
| 2009/0047353 A1 | 2/2009 | Ohagan | |
| 2009/0197853 A1 | 8/2009 | Magda | |
| 2009/0297551 A1 | 12/2009 | Sattentau et al. | |
| 2010/0158866 A1 | 6/2010 | Zhu | |
| 2010/0266589 A1 | 10/2010 | Hedrick et al. | |
| 2011/0306599 A1 | 12/2011 | Inoue et al. | |
| 2012/0039734 A1 | 2/2012 | McNair et al. | |
| 2012/0065201 A1 | 3/2012 | Honigberg et al. | |
| 2013/0184342 A1 | 7/2013 | Mills et al. | |
| 2014/0371241 A1 | 12/2014 | Buggy et al. | |

FOREIGN PATENT DOCUMENTS

| | | |
|---|---|---|
| EP | 1046399 | 10/2000 |
| EP | 1240899 | 9/2002 |
| EP | 1132393 | 4/2003 |
| EP | 2220116 A1 | 8/2010 |
| WO | WO-03-004053 | 1/2003 |
| WO | WO-2004-060319 | 7/2004 |
| WO | WO-2008-063727 A2 | 5/2008 |
| WO | WO-2009-118523 | 10/2009 |
| WO | WO-2009-140853 | 11/2009 |
| WO | WO-2009-149179 A2 | 12/2009 |
| WO | WO-2010-034670 A2 | 4/2010 |
| WO | WO-2010-069809 | 6/2010 |
| WO | WO-2010-093843 | 8/2010 |
| WO | WO-2012-001090 | 1/2012 |
| WO | WO-2013-036994 | 3/2013 |
| WO | WO-2013-085893 A1 | 6/2013 |
| WO | WO-2013184572 A1 | 12/2013 |

OTHER PUBLICATIONS

Lemery (US Food and Drug Administration Approval: Ofatumumab for the Treatment of Patients with Chronic Lymphocytic Leukemia Refractory to Fludarabine and Alemtuzumab, Clinical Cancer Research, 2010, pp. 4331-4338).*
Watters, Cancer pharmacogenomics: current and future application, Biochimica, 2003, pp. 99-111.*
Ko (Everyone's Guide to Cancer Therapy: How Cancer is Diagnosed, Treated and Managed Day to Day, 2009, 3 pages).*
Guo (Molecular Characteristic of CTA056, a Novel interleukin-2-Inducible T-cell Kinase Inhibitor that Selectively Target Malignat T Cell and Modulate Oncomirs, Molecular Pharmacology, Aug. 2012, 82: pp. 938-947).*
Ansell, Two targets for the price of one, Blood, 122(15):2529-2531 (Oct. 10, 2013).
Atsukawa et al. Ribavirin downmodulates inducible costimulator on Cd4+ T cells and their interleukin-10 secretion to assist in hepatitis C virus clearance. J Gastoenterology and Hepatology. 27:823-831. 2012.
Biocompare, Th1 and Th2 balance, Regulation, and Involvement in Disease, http://www.biocompare.com/Application-Notes/43518-Th1-And-Th2-Balance-Regulation-And-Involvement-In-Disease. Apr. 24, 2006.

(Continued)

*Primary Examiner* — Kathrien Cruz

(74) *Attorney, Agent, or Firm* — Foley Hoag LLP

(57) ABSTRACT

Described herein are methods and compositions comprising a covalent TEC family kinase inhibitor for use in adjuvant therapy, including adjuvant cancer therapy, vaccination and treatment of immune disorders and pathogenic infections.

6 Claims, 43 Drawing Sheets

(56) References Cited

OTHER PUBLICATIONS

Bowen et al. Adaptive immune responses in acute and chronic hepatitis C virus infection. Nature. 436(7053):946-952. 2005.

Clark et al. The role of ribavirin in direct acting antiviral drug regimens for chronic hepatitis C. Liver Int. 32(01):103-107. 2012.

Dolganiuc et al. T cells with regulatory activity in hepatitis C virus infection: what we know and what we don't. J Leukoc Biol. 84(3):614-622. 2008.

Dubovsky et al. Ibrutinib is an irreversible molecular inhibitor of ITK driving a Th1 selective pressure in T-lymphocytes, Blood. 122(15):2539-2549 (2013).

Dubovsky et al., Epigenetic repolarization of T lymphocytes from chronic lymphocytic leukemia patients using 5-aza-2'-deoxycytidine, Leukemia research 35, 1193-1199 (2011).

Dubovsky, et al., Restoring the functional immunogenicity of chronic lymphocytic leukemia using epigenetic modifiers, Leukemia Research 35(3):394-404 (2011).

Fallahi et al. Cytokines and HCV-Related Disorders. Clinical and Developmental Immunology. 2012. Article IDs 468102. 10 pgs.

Flynn et al. Maintenance of Th1 HCV-specific responses in individuals with acute HCV who achieve sustained virological clearance after treatment. Centre for Biomedical Research. Doi:10.111/jgh.12265 (no date available).

Fowell et al., Impaired NFATc translocation and failure of Th2 development in Itk-deficient CD4+ T cells, Immunity 11, 399-409 (1999).

Fritsche, et al. National academy of clinical biochemistry guidelines for the use of tumor markers in bladder cancer, NACB: Practice guidelines and recommendations for use of tumor markers in the clinic bladder cancer (3H)1; (Oct. 30, 2013), http://www.aacc.org/SiteCollectionDocuments/NACB/LMPG/tumor/chp3h_bladder.pdf.

Gad, et al. Distinct immunoregulatory cytokine pattern in Egyptian patients with occult Hepatitis C infection and unexplained persistently elevated liver transaminases, Asian J. Transfus Sci. 6(1):24-28 (2012).

Goggins, M. Markers of pancreatic cancer: working toward early detection, Clin. Cancer Res. 17(4):635-7 (2011).

Gomez-Rodriguez et al., Tec family kinases Itk and Rlk/Txk in T lymphocytes cross-regulation of cytokine production and T-cell fates, FEBS Journal, 278(12):1980-1989 (2011).

Hahtola et al. Th1 response and cytotoxicity genes are down-regulated in cutaneous T-cell lymphoma. Clin Cancer Res. 12(16):4812-4821. 2006.

Honigberg et al., The Bruton tyrosine kinase inhibitor PCI-32765 blocks B-cell activation and is efficacious in models of autoimmune disease and B-cell malignancy, PNAS USA 107:13075-13080 (2010).

Kang et al. Dynamic analysis of Th1/Th2 cytokine concentration during antiretroviral therapy of HIV-1/HCV co-infected Patients, MCS Infectious Diseases. 12:102. 10 pgs. 2012.

Karanjawala, et al. New markers of pancreatic cancer identified through differential gene expression analyses: claudin 18 and annexin A8, Am J. Surg. Pathol. 32(2):188-196 (2008).

Kaur et al. Inhibitors of interleukin-2 inducible T-cell kinase as potential therapeutic candidates for the treatment of various inflammatory disease conditions. Eur J Pharm Sci 47(3):574-578. 2012.

Khan et al. Circulating Biomarkers and their Possible Role in Pathogenesis of Chronic Hepatitis B and C Viral Infections. Ind J Clin biochem 46(2):161-168 (2011).

Langhans et al. Ribavirin Exerts Differential Effects on Function of Cd4+Th1, Th2, and Regulator T Cell clones in Hepatitis C, PLOS One. 7(7):e42094. 9 pgs. 2012.

Lau et al. Mechanism of action of ribavirin in the combination treatment of chronic HCV infection. Hepatology. 2002. 35(5):1002-1009.

Lester et al. Interleukin 2-inducible T cell kinase (ITK) facilitates efficient egress of HIV-1 by coordinating Gag distribution and actin organization. Virology. 436(1): 235-243. 2013.

Liao et al. Interleukin-2 at the Crossroads of Effector Responses, Tolerance, and Immunotherapy. Immunity. 38(1)13-25. 2013.

Lo et al. Itk inhibitors: a patent review. Expert Opin. The. Patents. 20(4):459-469, 2010.

Luban, J. TRIM5 and the regulation of HIV-1 infectivity, Mol. Biol. Int. 2012:426840 (2012).

Mishan-Eisenberg et al., Differential regulation of Th1/Th2 cytokine responses by placental protein 14, The Journal of Immunology, 173(9):5524-5530 (2004).

Moingeon. Strategies for designing vaccines eliciting Th1 responses in humans. Journal of Biotechnology. 98:189-198. 2002.

Myrmel et al. The hepatitis C virus enigma, APMIS. 117:427-439. 2009.

Nicolaou, et al. Calicheamicin θ1: a rationally designed molecule with extremely potent and selective DNA cleaving properties and apoptosis inducing activity, Angewandte Chemie International Edition in English, 33:183-186 (1994).

PCT/US2013/068132 International Search Report and Written Opinion dated Jan. 29, 2014.

Readinger et al. Selective targeting of ITK blocks multiple steps of HIV replication. PNAS USA 105(18):6684-6689. 2008.

Sahu et al. ITK inhibitors in inflammation and immune-mediated disorders. Curr Top Med Chem 9(8):690-703. 2009.

Schiffner, et al. Development of prophylactic vaccines against HIV-1, Retrovirology 10:72 (2013).

Scott et al. Monoclonal antibodies in cancer therapy, Cancer Immunity. 12:14 (2012).

Sofian et al. Serum profile of T helper 1 and T helper 2 cytokines in hepatitis C virus infected patients. Hepat Mon. 12(12):e6156. 2012.

Specialty Pharmacy Times, MedCart Specialty pharmacy: preparing for the next advancements in hepatitis C therapy, Dec. 18, 2012 http://www.specialtypharmacytimes.com/publications/specialty-pharmacy-times/2012/December-2012/MedCart-Specialty-Pharmacy-Preparing-for-the-Next-Advancements-in-Hepatitis-C-Therapy.

Suzuki et al., Skewed Th1 responses caused by excessive expression of Txk, a member of the Tec family of tyrosine kinases, in patients with Behcet's disease, Clinical Medicine & Research, 4(2):147-151 (2006).

Teta et al. Exercise is medicine: using exercise to manipulate TH1 and TH2 immune function. Http://www.freelibrary.com/_/print/PrintArticle.aspx?id=202661767. Jul. 1, 2009.

Thimme et al. Determinants of viral clearance and persistence during acute hepatitis C virus infection. J Exp Med 194(10):1395-1406. 2001.

Tsai et al. Detection of type 2-like T-helper cells in hepatitis C virus infection: implications for hepatitis C virus chronicity. Hepatology 25(2):449-458. 1997.

Tufman, et al. Biological markers in lung cancer: a clinician's perspective, Cancer Biomark 6(3-4):123-135 (2010).

Vargas et al. Inhibitors of BTK and ITK: State of the New Drugs for Cancer, Autoimmunity and Inflammatory Diseases, Scandinavian J of Immun 78:130-139. 2013.

Ward et al., Isoform-specific phosphoinositide 3-kinase inhibitors as therapeutic agents, Current Opinion in Pharmacology, 3(4):426-434 (2003).

Yu et al. Proteasome inhibitors block HIV-1 replication by affecting both cellular and viral targets. Biochem Biophys Res Commun 385(1):100-105. 2009.

Yue et al. Th1 and Th2 cytokine profiles induced by hepatitis C virus F protein in peripheral blood mononuclear cells from chronic hepatitis C patients Immunol Lett 152(2):89-95. 2013.

Dohner et al. Genomic Aberrations and Survival in Chronic Lymphocytic Leukemia. The New England Journal of Medicine. 2000.pp. 1910-1916.

Stanford School of Medicine. Precursor B lymphoblastic lymphoma, p. 1-7 (2005).

Tse et al. ABT-263: A Potent and Orally Bioavailable Bcl-2 Family Inhibitor. Cancer Res 68:3421-3428 (2008).

U.S. Appl. No. 14/198,559 Office Action mailed Oct. 24, 2014.

U.S. Appl. No. 14/198,559 Final Office Action dated Jul. 9, 2015.

(56) References Cited

OTHER PUBLICATIONS

Anonymous: "NCT01217749 on Apr. 16, 2012: Clinical Trials.gov Archive," Apr. 16, 2012 (Apr. 16, 2012), XP055260251, Retrieved from the Internet: URL:https://clinicaltrials.gov/archive/NCT01217749/2012_04_16.

Supplementary European Search Report for EP13850097 dated Mar. 31, 2016.

* cited by examiner

A

| | Tyrosine Kinase | Ibrutinib IC50(nM) |
|---|---|---|
| Irreversible Inhibition (Contain Cys-481) | ITK | 2.2 |
| | BTK | 0.1 |
| | Bmx | 0.7 |
| | Tec | 0.4 |
| | EGFR | 4.5 |
| | JAK3 | 3.8 |
| | HER2 | 1.4 |
| | HER4 | <0.5 |
| | Blk | <0.5 |
| Reversible Inhibition | Lck | 0.9 |
| | C-src | 148.5 |
| | Lyn | 0.9 |
| | Yes | <0.5 |
| | Csk | 4.2 |
| | VEGFR2 | 241 |

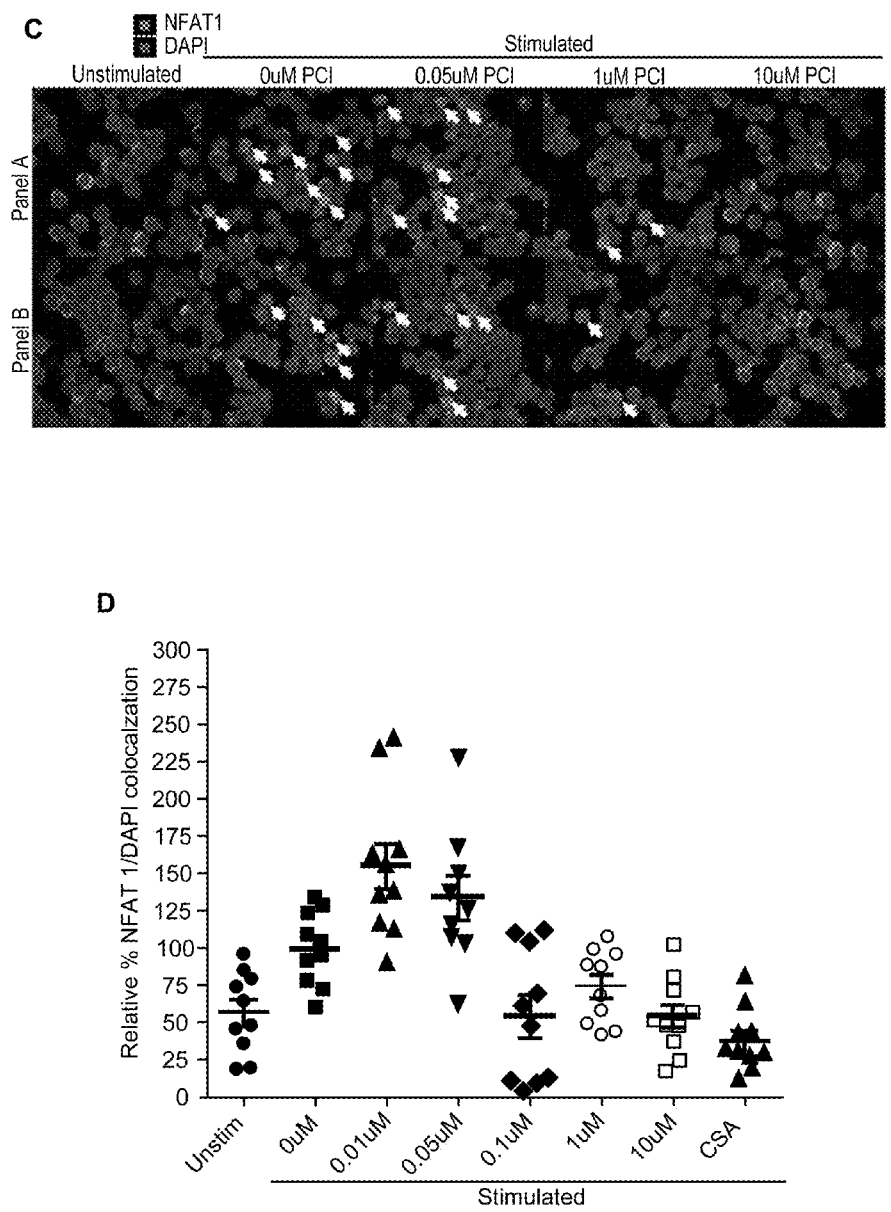

D

E

A

B

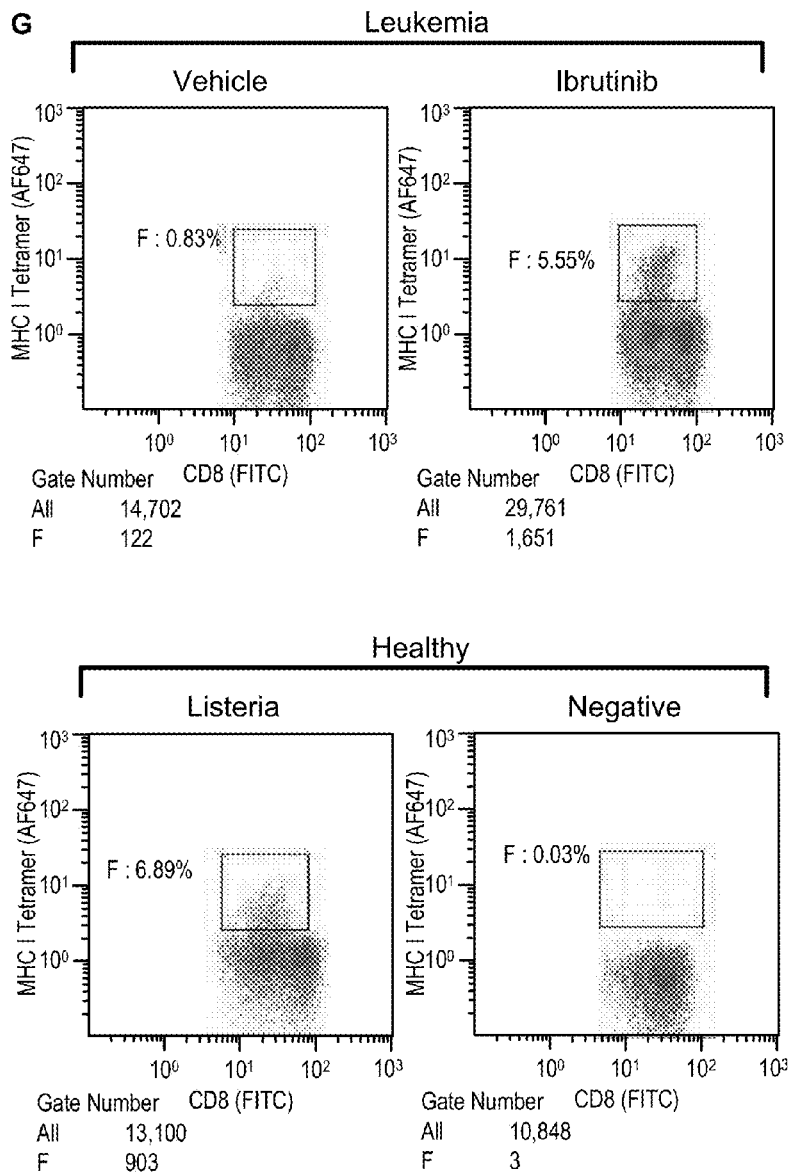

FIG. 14

| | Tyrosine Kinase | Ibrutinib IC 50 (nM) | Alt BTK Inhib IC50 (nM) | PCI-45292 IC50(nM) |
|---|---|---|---|---|
| Irreversible Inhibition (Contain Cys 481) | ITK | 2.2 | 22.5 | 139 |
| | BTK | 0.1 | 1.8 | 0.78 |
| | Bmx | 0.7 | 1.2 | 0.77 |
| | Tec | 0.4 | 2.2 | 32 |
| | EGFR | 4.5 | 108.9 | 4,156 |
| | JAK3 | 3.8 | 0.9 | >10,000 |
| | HER2 | 1.4 | 141 | 3,256 |
| | HER4 | <0.5 | 7.5 | 3.9 |
| | Blk | <0.5 | 20.5 | 2.6 |
| Reversible Inhibition | Lck | 0.9 | 352.9 | 4.3 |
| | C-src | 148.5 | 378.2 | 147 |
| | Lyn | 0.9 | 904 | 40 |
| | Yes | <0.5 | 88.3 | 0.94 |
| | Csk | 4.2 | 3931 | 3.2 |
| | VEGFR2 | 241 | nd | 4,437 |

Alt BTK inhib.

Chemical Formula: $C_{22}H_{22}FN_5O_3$
Exact Mass: 423.17
Molecular Weight: 423.44
Formula Weight: 581.62

TEC FAMILY KINASE INHIBITOR ADJUVANT THERAPY

RELATED APPLICATION

The present application claims the benefit of priority from U.S. Provisional Patent Application Nos. 61/722,107, filed Nov. 2, 2012, and 61/785,868, filed Mar. 14, 2013, each of which is herein incorporated by reference in its entirety.

SEQUENCE LISTING

The instant application contains a Sequence Listing which has been submitted in ASCII format via EFS-Web and is hereby incorporated by reference in its entirety. Said ASCII copy, created on Jan. 21, 2014, is named 25922-869-201SE-Q.txt and is 2,319 bytes in size.

BACKGROUND

T-lymphocytes comprise an indispensable component of the adaptive immune response, yet certain autoimmune, infectious, parasitic, and neoplastic diseases subvert adaptive immunity by specifically misdirecting T-helper cell polarity. A common mechanism of immune subversion is the aberrant recruitment of a Th2 dominant response that directly promotes B-cell antibody production and interferes with direct effector cell cytotoxicity. In contrast, a Th1 dominant response evokes cytotoxic effects with the production of IFNγ and IL2, which contribute to effector cell-based immune surveillance. Clearance of certain intracellular bacterial pathogens such as *Listeria* and parasites such as *Leishmania*, as well as tumor immune surveillance, hinge upon the capacity to elicit robust Th1 and CD8 T-cell responses.

Interleukin-2 Inducible Kinase (ITK) is a T-cell dominant member of the TEC-kinase family that drives proximal T-cell receptor (TCR) signaling. Upon TCR ligation in Th1 and CD8 T-cells, ITK and redundant resting lymphocyte kinase (RLK or TXK) activate PLCγ, launching a signaling cascade that includes the NFAT, NFκB, and MAPK pathways resulting in cellular activation, cytokine release, and rapid proliferation. ITK plays a supportive yet dispensable role to RLK in Th1 polarized and CD8 effector cells, but is indispensable for signaling in Th2 polarized T-cells.

SUMMARY OF THE INVENTION

Described herein, in certain embodiments, are methods of adjuvant therapy for cancer and for the treatment of immune disorders and pathogenic infections comprising administration of a TEC family kinase inhibitor. In some embodiments, the TEC family kinase inhibitor is a covalent TEC family kinase inhibitor. In some embodiments, the covalent TEC family kinase inhibitor is ibrutinib.

Described herein, in certain embodiments, are methods of treating a subject having a cancer characterized by a cytokine profile in which Th1 response is suppressed and Th2 response is enhanced, comprising administering a covalent TEC family kinase inhibitor to promote the Th1 response and suppress the Th2 response. In some embodiments, the methods further comprise measuring the level one or more Th1 or Th2 cytokines in the subject prior to administering a covalent TEC family kinase. In some embodiments, the covalent TEC family kinase inhibitor is administered following treatment of the cancer with a first anticancer therapy, wherein the first anticancer therapy does not comprise administration of a covalent TEC family kinase inhibitor. In some embodiments, administration of the covalent TEC family kinase inhibitor decreases the number of Th2 polarized T cells in the subject compared to no administration with the covalent TEC family kinase inhibitor. In some embodiments, administration of the covalent TEC family kinase inhibitor increases the number of Th1 polarized T cells in the subject compared to no administration with the covalent TEC family kinase inhibitor. In some embodiments, administration of the covalent TEC family kinase inhibitor increases the number of activated CD8+ cytotoxic T cells in the subject compared to no administration with the covalent TEC family kinase inhibitor. In some embodiments, administration of the covalent TEC family kinase inhibitor increases the ratio of Th1 polarized T cells to Th2 polarized T cells in the subject compared to no administration with the covalent TEC family kinase inhibitor. In some embodiments, administration of the covalent TEC family kinase inhibitor decreases IL-10, IL-4 or IL-13 expression in the subject compared to no administration with the covalent TEC family kinase inhibitor. In some embodiments, administration of the covalent TEC family kinase inhibitor increases IFN-γ expression in the subject compared to no administration with the covalent TEC family kinase inhibitor. In some embodiments, administration of the covalent TEC family kinase inhibitor increases IL-2 expression in the subject compared to no administration with the covalent TEC family kinase inhibitor. In some embodiments, administration of the covalent TEC family kinase inhibitor increases IL-12 expression in the subject compared to no administration with the covalent TEC family kinase inhibitor. In some embodiments, the first anticancer therapy comprises administration of a chemotherapeutic agent, a biologic agent, radiation therapy, bone marrow transplant, surgery, photosensitizing agents, toxins, or a combination thereof. In some embodiments, treatment with the chemotherapeutic agent or a biologic agent is discontinued prior to initiation of treatment with the covalent TEC family kinase inhibitor. In some embodiments, treatment with a chemotherapeutic agent or a biologic agent is continued prior to initiation of treatment with the covalent TEC family kinase inhibitor. In some embodiments, the chemotherapeutic agent or biologic agent is selected from among an antibody, a B cell receptor pathway inhibitor, a T cell receptor inhibitor, a PI3K inhibitor, an IAP inhibitor, an mTOR inhibitor, a radioimmunotherapeutic, a DNA damaging agent, a histone deacetylase inhibitor, a protein kinase inhibitor, a hedgehog inhibitor, an Hsp90 inhibitor, a telomerase inhibitor, a Jak1/2 inhibitor, a protease inhibitor, an IRAK inhibitor, a PKC inhibitor, a PARP inhibitor, a CYP3A4 inhibitor, an AKT inhibitor, an Erk inhibitor, a proteosome inhibitor, an alkylating agent, an anti metabolite, a plant alkaloid, a terpenoid, a cytotoxin, a topoisomerase inhibitor, or a combination thereof. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, a CD22 inhibitor, a Bcl-2 inhibitor, an IRAK 1/4 inhibitor, a JAK inhibitor (e.g., ruxolitinib, baricitinib, CYT387, lestauritinib, pacritinib, TG101348, SAR302503, tofacitinib (Xeljanz), etanercept (Enbrel), GLPG0634, R256), a microtubule inhibitor, a Topo II inhibitor, anti TWEAK antibody, anti-IL17 bispecific antibody, a CK2 inhibitor, anaplastic lymphoma kinase (ALK) and c-Met inhibitors, demethylase enzyme inhibitors such as demethylase, HDM, LSDI and KDM, fatty acid synthase inhibitors such as spirocyclic piperidine derivatives, glucocorticosteriod receptor agonist, fusion anti-CD 19-cytotoxic agent conjugate, antimetabolite, p70S6K inhibitor, immune modulators, AKT/PKB inhibitor, procaspase-3 activator PAC-1, BRAF inhibitor, lactate dehydrogenase A (LDH-A) inhibitor, CCR2 inhibitor, CXCR4 inhibitor, chemokine receptor antagonists, DNA double stranded break repair inhibitors, NOR202, GA-101, TLR2 inhibitor, or a combination thereof. In some embodiments, the T cell receptor inhibitor is Muromonab-CD3. In some embodiments, the chemotherapeutic agent is selected from among rituximab (rituxan), carfilzomib, fludarabine, cyclophosphamide, vincristine, prednisalone. chlorambucil, ifosfamide, doxorubicin, mesalazine, thalidomide, revlimid, lenalidomide, temsirolimus, everolimus, fostamatinib, paclitaxel, docetaxel, ofatumumab, dexamethasone, bendamustine, prednisone, CAL-101, ibritumomab, tositumomab, bortezomib, pentostatin, endostatin, ritonavir, ketoconazole, an anti-VEGF antibody, herceptin, cetuximab, cisplatin, carboplatin, docetaxel, erlotinib, etopiside, 5-fluorouracil, gemcitabine, ifosphamide, imatinib mesylate (Gleevec), gefitinib, erlotinib, procarbazine, prednisone, irinotecan, leucovorin, mechlorethamine, methotrexate, oxaliplatin, paclitaxel, sorafenib, sunitinib, topotecan, vinblastine, GA-1101, dasatinib, Sipuleucel-T, disulfiram, epigallocatechin-3-gallate, salinosporamide A, ONX0912, CEP-18770, MLN9708, R-406, lenalinomide, spirocyclic piperidine derivatives, quinazoline carboxamide azetidine compounds, thiotepa, DWA2114R, NK121, IS 3 295, 254-S, alkyl sulfonates such as busulfan, improsulfan and piposulfan; aziridines such as benzodepa, carboquone, meturedepa and uredepa; ethylenimine, methylmelamines such as altretamine, triethylenemelamine, triethylenephosphoramide, triethylenethiophosphoramide and trimethylmelamine; chlornaphazine; estramustine; ifosfamide; mechlorethamine; oxide hydrochloride; novobiocin; phenesterine; prednimustine; trofosfamide; uracil mustard; nitrosoureas such as carmustine, chlorozotocin, fotemustine, lomustine, nimustine, ranimustine; antibiotics such as aclacinomycins, actinomycin, anthramycin, azaserine, bleomycins, cactinomycin, calicheamicin, carubicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatrexate; defosfamide; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide-K; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; cytosine arabinoside; taxoids, e.g., paclitaxel and docetaxel; 6-thioguanine; mercaptopurine; methotrexate; platinum analogs; platinum; etoposide (VP-16); ifosfamide; mitomycin C; mitoxantrone; vincristine; vinorelbine; Navelbine; Novantrone; teniposide; daunomycin; aminopterin; Xeloda; ibandronate; CPT1 1; topoisomerase inhibitor RFS 2000; difluoromethylornithine (DMFO); retinoic acid; esperamycins; capecitabine; and pharmaceutically acceptable salts, acids or derivatives of; anti-hormonal agents such as anti-estrogens including for example tamoxifen, raloxifene, aromatase inhibiting 4(5)-imidazoles, 4-hydroxytamoxifen, trioxifene, keoxifene, LY117018, onapristone and toremifene (Fareston); antiandrogens such as flutamide, nilutamide, bicalutamide, leuprolide and goserelin; ACK inhibitors such as AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) or a combination thereof. In some embodiments, the patient has a tumor. In some embodiments, administering the covalent TEC family kinase inhibitor thereby decreases the size of a tumor, prevents or delays progression of the tumor, promotes further regression of the tumor, or eliminates the tumor. In some embodiments, the tumor is a sarcoma, carcinoma, lymphoma, or a melanoma. In some embodiments, the subject has a brain, breast, bladder, bone, colon, kidney, liver, lung, ovarian, pancreatic, prostate, skin or proximal or distal bile duct carcinoma. In some embodiments, the lymphoma is an enlarged lymph node or an extranodal lymphoma. In some embodiments, the cancer is a leukemia, a lymphoma, or a myeloma. In some embodiments, the cancer is non-Hodgkin's lymphoma. In some embodiments, wherein the non-Hodgkin's lymphoma is chronic lymphocytic leukemia/small lymphocytic lymphoma (CLL/SLL), follicular lymphoma (FL), diffuse large B-cell lymphoma (DLBCL), mantle cell lymphoma (MCL), Waldenström's macroglobulinemia, multiple myeloma, marginal zone lymphoma, Burkitt's lymphoma, non-Burkitt high grade B cell lymphoma, or extranodal marginal zone B cell lymphoma. In some embodiments, the non-Hodgkin's lymphoma is a relapsed or refractory non-Hodgkin's lymphoma. In some embodiments, the cancer is a T-cell malignancy. In some embodiments, the T-cell malignancy is peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas. In some embodiments, the T-cell malignancy is a relapsed or refractory T-cell malignancy. In some embodiments, treatment with the covalent TEC family kinase inhibitor extends disease free survival (DFS) or overall survival (OS) in the subject. In some embodiments, the covalent TEC family kinase inhibitor inhibits one or more TEC family kinases selected from among ITK, BTK, TEC, RLK/TXK and BMX. In some embodiments, the covalent TEC family kinase inhibitor is an IL2-inducible T-cell kinase (ITK) inhibitor. In some embodiments, the covalent TEC family kinase inhibitor is a Bruton's tyrosine kinase (BTK) inhibitor. In some embodiments, the subject is a mammal. In some embodiments, the mammal is a human. In some embodiments, the covalent TEC family kinase inhibitor is administered daily. In some embodiments, the covalent TEC family kinase inhibitor is administered 1, 2, 3, 4, 5 times or more per day. In some embodiments, the covalent TEC family kinase inhibitor is administered once per day. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib. In some embodiments, the covalent TEC family kinase inhibitor is administered at a dosage of about 40 mg/day to about 1000 mg/day. In some embodiments, covalent TEC family kinase inhibitor is administered for about 1 week to 5 years. In some embodiments, covalent TEC family kinase inhibitor is administered orally. In some embodiments, the risk of relapsed or refractory disease is reduced by about 10%, 20%, 30%, 40%, 50%, 60%, 70%, 80%, 90% or greater compared to no treatment with the covalent TEC family kinase inhibitor. In some embodiments, the subject is disease free for about 6 months, 1 year, 2 years, 3 years, 4 years, 5 years, 6 years, 7 years, 8 years, 9 years, 10 years or longer following last administration of the covalent TEC family kinase inhibitor. In some embodiments, the subject has a high risk of cancer recurrence prior to administration of the covalent TEC family kinase inhibitor. In some embodiments, the methods further comprise administration of an additional chemotherapeutic agent or biologic agent.

Described herein, in certain embodiments are methods of adjuvant therapy comprising administering to a subject having cancer, following treatment of a tumor with a first anticancer therapy to decrease the size of a tumor or eliminate the tumor, an effective amount of a covalent TEC family kinase inhibitor to prevent or delay progression of the tumor, promote further regression of the tumor, or eliminate the tumor, wherein the first anticancer therapy does not comprise administration of a covalent TEC family kinase inhibitor. In some embodiments, the first anticancer therapy comprises administration of a chemotherapeutic agent, a biologic agent, radiation therapy, bone marrow transplant, surgery, photosensitizing agents, toxins, or a combination thereof. In some embodiments, the covalent TEC family kinase inhibitor extends disease free survival (DFS) or overall survival (OS) in the subject. In some embodiments, disease free survival (DFS) or overall survival (OS) is assessed one or more years following initiation of covalent TEC family kinase inhibitor administration. In some embodiments, the covalent TEC family kinase inhibitor therapy is initiated following a decrease in size of the tumor following administration of the anticancer therapy. In some embodiments, treatment with a chemotherapeutic agent or a biologic agent is discontinued prior to initiation of treatment with the covalent TEC family kinase inhibitor. In some embodiments, treatment with a chemotherapeutic agent or a biologic agent is continued prior to initiation of treatment with the covalent TEC family kinase inhibitor. In some embodiments, the covalent TEC family kinase inhibitor inhibits one or more TEC family kinases selected from among ITK, BTK, TEC, RLK/TXK and BMX. In some embodiments, the covalent TEC family kinase inhibitor is an IL2-inducible T-cell kinase (ITK) inhibitor. In some embodiments, the covalent TEC family kinase inhibitor is a Bruton's tyrosine kinase (BTK) inhibitor. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib. In some embodiments, the chemotherapeutic agent is selected from among an antibody, a B cell receptor pathway inhibitor, a T cell receptor inhibitor, a PI3K inhibitor, an IAP inhibitor, an mTOR inhibitor, a radioimmunotherapeutic, a DNA damaging agent, a histone deacetylase inhibitor, a protein kinase inhibitor, a hedgehog inhibitor, an Hsp90 inhibitor, a telomerase inhibitor, a Jak1/2 inhibitor, a protease inhibitor, an IRAK inhibitor, a proteosome inhibitor, a PKC inhibitor, a PARP inhibitor, a CYP3A4 inhibitor, an AKT inhibitor, an Erk inhibitor, an alkylating agent, an anti metabolite, a plant alkaloid, a terpenoid, a cytotoxin, a topoisomerase inhibitor, or a combination thereof. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, a CD22 inhibitor, a Bcl-2 inhibitor, an IRAK 1/4 inhibitor, a JAK inhibitor (e.g., ruxolitinib, baricitinib, CYT387, lestaurtinib, pacritinib, TG101348, SAR302503, tofacitinib (Xeljanz), etanercept (Enbrel), GLPG0634, R256), a microtubule inhibitor, a Topo II inhibitor, anti TWEAK, anti-IL17 bispecific antibody, a CK2 inhibitor, anaplastic lymphoma kinase (ALK) and c-Met inhibitors, demethylase enzyme inhibitors such as demethylase, HDM, LSDI and KDM, fatty acid synthase inhibitors such as spirocyclic piperidine derivatives, glucocorticosteriod receptor agonist, fusion anti-CD 19-cytotoxic agent conjugate, antimetabolite, p70S6K inhibitor, immune modulators, AKT/PKB inhibitor, procaspase-3 activator PAC-1, BRAF inhibitor, lactate dehydrogenase A (LDH-A) inhibitor, CCR2 inhibitor, CXCR4 inhibitor, chemokine receptor antagonists, DNA double stranded break repair inhibitors, NOR202, GA-101, TLR2 inhibitor, or a combination thereof. In some embodiments, the T cell receptor inhibitor is Muromonab-CD3. In some embodiments, the chemotherapeutic agent is selected from among rituximab (rituxan), carfilzomib, fludarabine, cyclophosphamide, vincristine, prednisalone. chlorambucil, ifosphamide, doxorubicin, mesalazine, thalidomide, revlimid, lenalidomide, temsirolimus, everolimus, fostamatinib, paclitaxel, docetaxel, ofatumumab, dexamethasone, bendamustine, prednisone, CAL-101, ibritumomab, tositumomab, bortezomib, pentostatin, endostatin, ritonavir, ketoconazole, an anti-VEGF antibody, herceptin, cetuximab, cisplatin, carboplatin, docetaxel, erlotinib, etopiside, 5-fluorouracil, gemcitabine, ifosphamide, imatinib mesylate (Gleevec), gefitinib, erlotinib, procarbazine, prednisone, irinotecan, leucovorin, mechlorethamine, methotrexate, oxaliplatin, paclitaxel, sorafenib, sunitinib, topotecan, vinblastine, GA-1101, dasatinib, Sipuleucel-T, disulfiram, epigallocatechin-3-gallate, salinosporamide A, ONX0912, CEP-18770, MLN9708, R-406, lenalinomide, spirocyclic piperidine derivatives, quinazoline carboxamide azetidine compounds, thiotepa, DWA2114R, NK121, IS 3 295, 254-S, alkyl sulfonates such as busulfan, improsulfan and piposulfan; aziridines such as benzodepa, carboquone, meturedepa and uredepa; ethylenimine, methylmelamines such as altretamine, triethylenemelamine, triethylenephosphoramide, triethylenethiophosphoramide and trimethylmelamine; chlornaphazine; estramustine; ifosfamide; mechlorethamine; oxide hydrochloride; novobiocin; phenesterine; prednimustine; trofosfamide; uracil mustard; nitrosoureas such as carmustine, chlorozotocin, fotemustine, lomustine, nimustine, ranimustine; antibiotics such as aclacinomycins, actinomycin, anthramycin, azaserine, bleomycins, cactinomycin, calicheamicin, carubicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatrexate; defosfamide; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide-K; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; cytosine arabinoside; taxoids, e.g., paclitaxel and docetaxel; 6-thioguanine; mercaptopurine; methotrexate; platinum analogs; platinum; etoposide (VP-16); ifosfamide; mitomycin C; mitoxantrone; vincristine; vinorelbine; Navelbine; Novantrone; teniposide; daunomycin; aminopterin; Xeloda; ibandronate; CPT1 1; topoisomerase inhibitor RFS 2000; difluoromethylornithine (DMFO); retinoic acid; esperamycins; capecitabine; and pharmaceutically acceptable salts, acids or derivatives of; anti-hormonal agents such as anti-estrogens including for example tamoxifen, raloxifene, aromatase inhibiting 4(5)-imidazoles, 4-hydroxytamoxifen, trioxifene, keoxifene, LY117018, onapristone and toremifene (Fareston); antiandrogens such as flutamide, nilutamide, bicalutamide, leuprolide and goserelin; ACK inhibitors such as AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) or a combination thereof. In some embodiments, the subject has no detectable tumors following treatment with the first anticancer therapy, prior to initiation of covalent TEC family kinase inhibitor administration. In some embodiments, the subject has no detectable circulating tumor cells following treatment with the first anticancer therapy, prior to initiation of covalent TEC family kinase inhibitor administration. In some embodiments, the subject is a mammal. In some embodiments, the mammal is a human. In some embodiments, the covalent TEC family kinase inhibitor is administered daily. In some embodiments, the covalent TEC family kinase inhibitor is administered 1, 2, 3, 4, 5 times or more per day. In some embodiments, the covalent TEC family kinase inhibitor is administered once per day. In some embodiments, the covalent TEC family kinase inhibitor is administered at a dosage of about 40 mg/day to about 1000 mg/day. In some embodiments, covalent TEC family kinase inhibitor is administered for about 1 week to 5 years. In some embodiments, covalent TEC family kinase inhibitor is administered orally. In some embodiments, the risk of relapsed or refractory disease is reduced by about 10%, 20%, 30%, 40%, 50%, 60%, 70%, 80%, 90% or greater compared to no treatment with the covalent TEC family kinase inhibitor. In some embodiments, the subject is disease free for about 6 months, 1 year, 2 years, 3 years, 4 years, 5 years, 6 years, 7 years, 8 years, 9 years, 10 years or longer following last administration of the covalent TEC family kinase inhibitor. In some embodiments, the subject has a high risk of cancer recurrence prior to administration of the covalent TEC family kinase inhibitor. In some embodiments, the tumor is a sarcoma, carcinoma, lymphoma, or a melanoma. In some embodiments, the lymphoma is an enlarged lymph node or an extranodal lymphoma. In some embodiments, the subject has a brain, breast, bladder, bone, colon, kidney, liver, lung, ovarian, pancreatic, prostate, skin or proximal or distal bile duct carcinoma. In some embodiments, the subject has a hematologic cancer. In some embodiments, the cancer is a leukemia, a lymphoma, or a myeloma. In some embodiments, the subject has a non-Hodgkin's lymphoma. In some embodiments, the non-Hodgkin's lymphoma is chronic lymphocytic leukemia/small lymphocytic lymphoma (CLL/SLL), follicular lymphoma (FL), diffuse large B-cell lymphoma (DLBCL), mantle cell lymphoma (MCL), Waldenström's macroglobulinemia, multiple myeloma, marginal zone lymphoma, Burkitt's lymphoma, non-Burkitt high grade B cell lymphoma, or extranodal marginal zone B cell lymphoma. In some embodiments, the non-Hodgkin's lymphoma is a relapsed or refractory non-Hodgkin's lymphoma. In some embodiments, the subject has a T-cell malignancy. In some embodiments, the T-cell malignancy is peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas. In some embodiments, the T-cell malignancy is a relapsed or refractory T-cell malignancy. In some embodiments, the risk of a secondary tumor is decreased compared to no treatment with the covalent TEC family kinase inhibitor. In some embodiments, DFS or OS is evaluated about 1, 2, 3, 4, 5, 6, 7, 8, 9, 10 years or longer after initiation of the covalent TEC family kinase inhibitor treatment. In some embodiments, the covalent TEC family kinase inhibitor is administered in combination with an additional chemotherapeutic agent or biologic agent. In some embodiments, the additional chemotherapeutic agent or biologic agent is selected from among an antibody, a B cell receptor pathway inhibitor, a T cell receptor inhibitor, a PI3K inhibitor, an IAP inhibitor, an mTOR inhibitor, a radioimmunotherapeutic, a DNA damaging agent, a histone deacetylase inhibitor, a protein kinase inhibitor, a hedgehog inhibitor, an Hsp90 inhibitor, a telomerase inhibitor, a Jak1/2 inhibitor, a protease inhibitor, an IRAK inhibitor, a PKC inhibitor, a PARP inhibitor, a CYP3A4 inhibitor, a proteosome inhibitor, an alkylating agent, an anti metabolite, a plant alkaloid, a terpenoid, a cytotoxin, a topoisomerase inhibitor, or a combination thereof. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, a JAK inhibitor (e.g., ruxolitinib, baricitinib, CYT387, lestauritinib, pacritinib, TG101348, SAR302503, tofacitinib (Xeljanz), etanercept (Enbrel), GLPG0634, R256), or a combination thereof. In some embodiments, the additional chemotherapeutic agent or biologic agent is selected from among rituximab (rituxan), carfilzomib, fludarabine, cyclophosphamide, vincristine, prednisalone. chlorambucil, ifosphamide, doxorubicin, mesalazine, thalidomide, lenalidomide, temsirolimus, everolimus, fostamatinib, paclitaxel, docetaxel, ofatumumab, dexamethasone, prednisone, CAL-101, ibritumomab, tositumomab, bortezomib, pentostatin, endostatin, ritonavir, ketoconazole, an anti-VEGF antibody, herceptin, cetuximab, cisplatin, carboplatin, docetaxel, erlotinib, etopiside, 5-fluorouracil, gemcitabine, ifosphamide, imatinib mesylate (Gleevec), gefitinib, procarbazine, prednisone, irinotecan, leucovorin, mechlorethamine, methotrexate, oxaliplatin, paclitaxel, sorafenib, sunitinib, topotecan, vinblastine, GA-1101, dasatinib, Sipuleucel-T, disulfiram, epigallocatechin-3-gallate, salinosporamide A, ONX0912, CEP-18770, MLN9708, R-406, lenalinomide, spirocyclic piperidine derivatives, quinazoline carboxamide azetidine compounds, thiotepa, DWA2114R, NK121, IS 3 295, 254-S, alkyl sulfonates such as busulfan, improsulfan and piposulfan; aziridines such as benzodepa, carboquone, meturedepa and uredepa; ethylenimine, methylmelamines such as altretamine, triethylenemelamine, triethylenephosphoramide, triethylenethiophosphoramide and trimethylmelamine; chlornaphazine; estramustine; ifosfamide; mechlorethamine; oxide hydrochloride; novobiocin; phenesterine; prednimustine; trofosfamide; uracil mustard; nitrosoureas such as carmustine, chlorozotocin, fotemustine, lomustine, nimustine, ranimustine; antibiotics such as aclacinomycins, actinomycin, anthramycin, azaserine, bleomycins, cactinomycin, calicheamicin, carubicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatrexate; defosfamide; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide-K; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; cytosine arabinoside; taxoids, e.g., paclitaxel and docetaxel; 6-thioguanine; mercaptopurine; methotrexate; platinum analogs; platinum; etoposide (VP-16); ifosfamide; mitomycin C; mitoxantrone; vincristine; vinorelbine; Navelbine; Novantrone; teniposide; daunomycin; aminopterin; Xeloda; ibandronate; CPT1 1; topoisomerase inhibitor RFS 2000; difluoromethylornithine (DMFO); retinoic acid; esperamycins; capecitabine; and pharmaceutically acceptable salts, acids or derivatives of; anti-hormonal agents such as anti-estrogens including for example tamoxifen, raloxifene, aromatase inhibiting 4(5)-imidazoles, 4-hydroxytamoxifen, trioxifene, keoxifene, LY117018, onapristone and toremifene (Fareston); antiandrogens such as flutamide, nilutamide, bicalutamide, leuprolide and goserelin; ACK inhibitors such as AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) or a combination thereof.

Described herein, in certain embodiments, are methods of adjuvant therapy comprising administering to a subject, characterized as disease free or having minimal residual disease (MRD) following treatment of a cancer with a first anticancer therapy, an effective amount of the covalent TEC family kinase inhibitor to prevent, reduce the risk of, or delay relapsed or refractory disease, wherein the first anticancer therapy does not comprise administration a covalent TEC family kinase inhibitor. In some embodiments, the anticancer therapy comprises administration of a chemotherapeutic agent, a biologic agent, radiation therapy, bone marrow transplant, surgery, photosensitizing agents, toxins, or a combination thereof. In some embodiments, treatment covalent TEC family kinase inhibitor extends disease free survival (DFS) or overall survival (OS) in the subject. In some embodiments, disease free survival (DFS) or overall survival (OS) is assessed 1, 2, 3, 4, 5, 6, 7, 8, 9, 10 years or longer following initiation of TEC family kinase inhibitor administration. In some embodiments, treatment with a chemotherapeutic agent or a biologic agent is discontinued prior to initiation of treatment with the covalent TEC family kinase inhibitor. In some embodiments, treatment with a chemotherapeutic agent or a biologic agent is continued prior to initiation of treatment with the covalent TEC family kinase inhibitor. In some embodiments, the covalent TEC family kinase inhibitor inhibits one or more TEC family kinases selected from among ITK, BTK, TEC, RLK/TXK and BMX. In some embodiments, the covalent TEC family kinase inhibitor is an IL2-inducible T-cell kinase (ITK) inhibitor. In some embodiments, the covalent TEC family kinase inhibitor is a Bruton's tyrosine kinase (BTK) inhibitor. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib. In some embodiments, the chemotherapeutic agent or biologic agent is selected from among an antibody, a B cell receptor pathway inhibitor, a T cell receptor inhibitor, a PI3K inhibitor, an IAP inhibitor, an mTOR inhibitor, a radioimmunotherapeutic, a DNA damaging agent, a histone deacetylase inhibitor, a protein kinase inhibitor, a hedgehog inhibitor, an Hsp90 inhibitor, a telomerase inhibitor, a Jak1/2 inhibitor, a protease inhibitor, an IRAK inhibitor, a PKC inhibitor, a PARP inhibitor, a CYP3A4 inhibitor, an AKT inhibitor, an Erk inhibitor, a proteosome inhibitor, an alkylating agent, an anti metabolite, a plant alkaloid, a terpenoid, a cytotoxin, a topoisomerase inhibitor, or a combination thereof. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, a CD22 inhibitor, a Bcl-2 inhibitor, an IRAK 1/4 inhibitor, a microtubule inhibitor, a Topo II inhibitor, anti TWEAK, anti-IL17 bispecific antibody, a CK2 inhibitor, anaplastic lymphoma kinase (ALK) and c-Met inhibitors, demethylase enzyme inhibitors such as demethylase, HDM, LSDI and KDM, fatty acid synthase inhibitors such as spirocyclic piperidine derivatives, glucocorticosteriod receptor agonist, fusion anti-CD 19-cytotoxic agent conjugate, antimetabolite, p70S6K inhibitor, immune modulators, AKT/PKB inhibitor, procaspase-3 activator PAC-1, BRAF inhibitor, lactate dehydrogenase A (LDH-A) inhibitor, CCR2 inhibitor, CXCR4 inhibitor, chemokine receptor antagonists, DNA double stranded break repair inhibitors, NOR202, GA-101, TLR2 inhibitor, a JAK inhibitor (e.g., ruxolitinib, baricitinib, CYT387, lestauritinib, pacritinib, TG101348, SAR302503, tofacitinib (Xeljanz), etanercept (Enbrel), GLPG0634, R256), or a combination thereof. In some embodiments, the T cell receptor inhibitor is Muromonab-CD3. In some embodiments, the chemotherapeutic agent or biologic agent is selected from among rituximab (rituxan), carfilzomib, fludarabine, cyclophosphamide, vincristine, prednisalone. chlorambucil, ifosphamide, doxorubicin, mesalazine, thalidomide, lenalidomide, temsirolimus, everolimus, fostamatinib, paclitaxel, docetaxel, ofatumumab, dexamethasone, prednisone, CAL-101, ibritumomab, tositumomab, bortezomib, pentostatin, endostatin, ritonavir, ketoconazole, an anti-VEGF antibody, herceptin, cetuximab, cisplatin, carboplatin, docetaxel, erlotinib, etopiside, 5-fluorouracil, gemcitabine, ifosphamide, imatinib mesylate (Gleevec), gefitinib, procarbazine, prednisone, irinotecan, leucovorin, mechlorethamine, methotrexate, oxaliplatin, paclitaxel, sorafenib, sunitinib, topotecan, vinblastine, GA-1101, dasatinib, Sipuleucel-T, disulfiram, epigallocatechin-3-gallate, salinosporamide A, ONX0912, CEP-18770, MLN9708, R-406, lenalinomide, spirocyclic piperidine derivatives, quinazoline carboxamide azetidine compounds, thiotepa, DWA2114R, NK121, IS 3 295, 254-S, alkyl sulfonates such as busulfan, improsulfan and piposulfan; aziridines such as benzodepa, carboquone, meturedepa and uredepa; ethylenimine, methylmelamines such as altretamine, triethylenemelamine, triethylenephosphoramide, triethylenethiophosphoramide and trimethylmelamine; chlornaphazine; estramustine; ifosfamide; mechlorethamine; oxide hydrochloride; novobiocin; phenesterine; prednimustine; trofosfamide; uracil mustard; nitrosoureas such as carmustine, chlorozotocin, fotemustine, lomustine, nimustine, ranimustine; antibiotics such as aclacinomycins, actinomycin, anthramycin, azaserine, bleomycins, cactinomycin, calicheamicin, carubicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatrexate; defosfamide; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide-K; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; cytosine arabinoside; taxoids, e.g., paclitaxel and docetaxel; 6-thioguanine; mercaptopurine; methotrexate; platinum analogs; platinum; etoposide (VP-16); ifosfamide; mitomycin C; mitoxantrone; vincristine; vinorelbine; Navelbine; Novantrone; teniposide; daunomycin; aminopterin; Xeloda; ibandronate; CPT1 1; topoisomerase inhibitor RFS 2000; difluoromethylornithine (DMFO); retinoic acid; esperamycins; capecitabine; and pharmaceutically acceptable salts, acids or derivatives of; anti-hormonal agents such as anti-estrogens including for example tamoxifen, raloxifene, aromatase inhibiting 4(5)-imidazoles, 4-hydroxytamoxifen, trioxifene, keoxifene, LY117018, onapristone and toremifene (Fareston); antiandrogens such as flutamide, nilutamide, bicalutamide, leuprolide and goserelin; ACK inhibitors such as AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) or a combination thereof. In some embodiments, the subject has no detectable cancer following treatment of the cancer with the first anticancer therapy and prior to administration of the covalent TEC family kinase inhibitor. In some embodiments, the subject has no detectable primary or metastatic tumors following treatment of the cancer with the first anticancer therapy and prior to administration of the covalent TEC family kinase inhibitor. In some embodiments, the first anticancer therapy decreases the size of a primary or metastatic tumor. In some embodiments, the subject has no detectable circulating tumor cells following treatment of the cancer with the first anticancer therapy and prior to administration of the covalent TEC family kinase inhibitor. In some embodiments, the subject is a mammal. In some embodiments, the mammal is a human. In some embodiments, the covalent TEC family kinase inhibitor is administered daily. In some embodiments, the covalent TEC family kinase inhibitor is administered 1, 2, 3, 4, 5 times or more per day. In some embodiments, the covalent TEC family kinase inhibitor is administered once per day. In some embodiments, the covalent TEC family kinase inhibitor is administered at a dosage of about 40 mg/day to about 1000 mg/day. In some embodiments, the covalent TEC family kinase inhibitor is administered for about 1 week to 5 years. In some embodiments, the covalent TEC family kinase inhibitor is administered orally. In some embodiments, the risk of relapsed or refractory disease is reduced by about 10%, 20%, 30%, 40%, 50%, 60%, 70%, 80%, 90% or greater compared to no treatment with TEC family kinase inhibitor. In some embodiments, the subject is disease free for about 6 months, 1 year, 2 years, 3 years, 4 years, 5 years, 6 years, 7 years, 8 years, 9 years, or 10 years following last administration of TEC family kinase inhibitor. In some embodiments, the risk of a secondary tumor is decreased compared to no treatment with the covalent TEC family kinase inhibitor. In some embodiments, the subject has a high risk of cancer recurrence prior to administration of the covalent TEC family kinase inhibitor. In some embodiments, the covalent TEC family kinase inhibitor is administered with an additional chemotherapeutic agent or biologic agent. In some embodiments, the additional chemotherapeutic agent or biologic agent is selected from among an antibody, a B cell receptor pathway inhibitor, a T cell receptor inhibitor, a PI3K inhibitor, an IAP inhibitor, an mTOR inhibitor, a radioimmunotherapeutic, a DNA damaging agent, a histone deacetylase inhibitor, a protein kinase inhibitor, a hedgehog inhibitor, an Hsp90 inhibitor, a telomerase inhibitor, a Jak1/2 inhibitor, a protease inhibitor, an IRAK inhibitor, a PKC inhibitor, a PARP inhibitor, a CYP3A4 inhibitor, an AKT inhibitor, an Erk inhibitor, an alkylating agent, an anti metabolite, a plant alkaloid, a terpenoid, a cytotoxin, a topoisomerase inhibitor, a CD22 inhibitor, a Bcl-2 inhibitor, an IRAK 1/4 inhibitor, a microtubule inhibitor, a Topo II inhibitor, anti TWEAK, anti-IL17 bispecific antibody, a CK2 inhibitor, anaplastic lymphoma kinase (ALK) and c-Met inhibitors, demethylase enzyme inhibitors such as demethylase, HDM, LSDI and KDM, fatty acid synthase inhibitors such as spirocyclic piperidine derivatives, glucocorticosteriod receptor agonist, fusion anti-CD 19-cytotoxic agent conjugate, antimetabolite, p70S6K inhibitor, immune modulators, AKT/PKB inhibitor, procaspase-3 activator PAC-1, BRAF inhibitor, lactate dehydrogenase A (LDH-A) inhibitor, CCR2 inhibitor, CXCR4 inhibitor, chemokine receptor antagonists, DNA double stranded break repair inhibitors, NOR202, GA-101, TLR2 inhibitor, or a combination thereof. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, a JAK inhibitor (e.g., ruxolitinib, baricitinib, CYT387, lestauritinib, pacritinib, TG101348, SAR302503, tofacitinib (Xeljanz), etanercept (Enbrel), GLPG0634, R256), or a combination thereof. In some embodiments, the additional chemotherapeutic agent or biologic agent is selected from among rituximab (rituxan), carfilzomib, fludarabine, cyclophosphamide, vincristine, prednisalone. chlorambucil, ifosfamide, doxorubicin, mesalazine, thalidomide, lenalidomide, temsirolimus, everolimus, fostamatinib, paclitaxel, docetaxel, ofatumumab, dexamethasone, prednisone, CAL-101, ibritumomab, tositumomab, bortezomib, pentostatin, endostatin, ritonavir, ketoconazole, an anti-VEGF antibody, herceptin, cetuximab, cisplatin, carboplatin, docetaxel, erlotinib, etopiside, 5-fluorouracil, gemcitabine, ifosfamide, imatinib mesylate (Gleevec), gefitinib, procarbazine, prednisone, irinotecan, leucovorin, mechlorethamine, methotrexate, oxaliplatin, paclitaxel, sorafenib, sunitinib, topotecan, vinblastine, GA-1101, dasatinib, Sipuleucel-T, disulfiram, epigallocatechin-3-gallate, salinosporamide A, ONX0912, CEP-18770, MLN9708, R-406, lenalinomide, spirocyclic piperidine derivatives, quinazoline carboxamide azetidine compounds, thiotepa, DWA2114R, NK121, IS 3 295, 254-S, alkyl sulfonates such as busulfan, improsulfan and piposulfan; aziridines such as benzodepa, carboquone, meturedepa and uredepa; ethylenimine, methylmelamines such as altretamine, triethylenemelamine, triethylenephosphoramide, triethylenethiophosphoramide and trimethylmelamine; chlornaphazine; estramustine; ifosfamide; mechlorethamine; oxide hydrochloride; novobiocin; phenesterine; prednimustine; trofosfamide; uracil mustard; nitrosoureas such as carmustine, chlorozotocin, fotemustine, lomustine, nimustine, ranimustine; antibiotics such as aclacinomycins, actinomycin, anthramycin, azaserine, bleomycins, cactinomycin, calicheamicin, carubicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatrexate; defosfamide; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide-K; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; cytosine arabinoside; taxoids, e.g., paclitaxel and docetaxel; 6-thioguanine; mercaptopurine; methotrexate; platinum analogs; platinum; etoposide (VP-16); ifosfamide; mitomycin C; mitoxantrone; vincristine; vinorelbine; Navelbine; Novantrone; teniposide; daunomycin; aminopterin; Xeloda; ibandronate; CPT1 1; topoisomerase inhibitor RFS 2000; difluoromethylornithine (DMFO); retinoic acid; esperamycins; capecitabine; and pharmaceutically acceptable salts, acids or derivatives of; anti-hormonal agents such as anti-estrogens including for example tamoxifen, raloxifene, aromatase inhibiting 4(5)-imidazoles, 4-hydroxytamoxifen, trioxifene, keoxifene, LY117018, onapristone and toremifene (Fareston); antiandrogens such as flutamide, nilutamide, bicalutamide, leuprolide and goserelin; ACK inhibitors such as AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) or a combination thereof.

Described herein, in certain embodiments, are methods of adjuvant therapy comprising administering to a subject with cancer, following surgery for removal of a tumor, an effective amount of a covalent TEC family kinase inhibitor to prevent, reduce the risk of, or delay relapsed or refractory disease. In some embodiments, the covalent TEC family kinase inhibitor inhibits one or more TEC family kinases selected from among ITK, BTK, TEC, RLK/TXK and BMX. In some embodiments, the covalent TEC family kinase inhibitor is an IL2-inducible T-cell kinase (ITK) inhibitor. In some embodiments, the covalent TEC family kinase inhibitor is a Bruton's tyrosine kinase (BTK) inhibitor. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib. In some embodiments, disease free survival (DFS) or overall survival (OS) is assessed 1, 2, 3, 4, 5, 6, 7, 8, 9, 10 years or longer following initiation of covalent TEC family kinase inhibitor administration. In some embodiments, the surgery for removal of a tumor is a definitive surgery. In some embodiments, the subject has no detectable tumors following surgery. In some embodiments, the subject has no detectable circulating tumor cells following surgery. In some embodiments, the surgery for removal of a tumor is a partial removal of the tumor. In some embodiments, the subject has not been administered chemotherapy for treatment of the cancer. In some embodiments, the subject has been administered a chemotherapeutic agent or biologic agent for treatment of the cancer. In some embodiments, the subject is a mammal. In some embodiments, the mammal is a human. In some embodiments, the covalent TEC family kinase inhibitor is administered daily. In some embodiments, the covalent TEC family kinase inhibitor is administered 1, 2, 3, 4, 5 times or more per day. In some embodiments, the covalent TEC family kinase inhibitor is administered once per day. In some embodiments, the covalent TEC family kinase inhibitor is administered at a dosage of about 40 mg/day to about 1000 mg/day. In some embodiments, the covalent TEC family kinase inhibitor is administered for about 1 week to 5 years. In some embodiments, the covalent TEC family kinase inhibitor is administered orally. In some embodiments, the risk of relapsed or refractory disease is reduced by about 10%, 20%, 30%, 40%, 50%, 60%, 70%, 80%, 90% or greater compared to no treatment with the covalent TEC family kinase inhibitor. In some embodiments, the subject is disease free for about 6 months, 1 year, 2 years, 3 years, 4 years, 5 years, 6 years, 7 years, 8 years, 9 years, 10 years or longer following last administration of the covalent TEC family kinase inhibitor. In some embodiments, the risk of a secondary tumor is decreased compared to no treatment with the covalent TEC family kinase inhibitor. In some embodiments, the subject has a high risk of cancer recurrence prior to treatment with the covalent TEC family kinase inhibitor. In some embodiments, the tumor is a sarcoma, carcinoma, neurofibromatoma or a lymphoma. In some embodiments, the lymphoma is an enlarged lymph node or an extranodal lymphoma. In some embodiments, the subject has a brain, breast, bladder, bone, colon, kidney, liver, lung, ovarian, pancreatic, prostate, skin or proximal or distal bile duct carcinoma. In some embodiments, the subject has a hematologic cancer. In some embodiments, the cancer is a lymphoma. In some embodiments, the subject has a non-Hodgkin's lymphoma. In some embodiments, the non-Hodgkin's lymphoma is chronic lymphocytic leukemia/small lymphocytic lymphoma (CLL/SLL), follicular lymphoma (FL), diffuse large B-cell lymphoma (DLBCL), mantle cell lymphoma (MCL), Waldenström's macroglobulinemia, multiple myeloma, marginal zone lymphoma, Burkitt's lymphoma, non-Burkitt high grade B cell lymphoma, or extranodal marginal zone B cell lymphoma. In some embodiments, the non-Hodgkin's lymphoma is a relapsed or refractory non-Hodgkin's lymphoma. In some embodiments, the subject has a T-cell malignancy. In some embodiments, the T-cell malignancy is peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas. In some embodiments, the T-cell malignancy is a relapsed or refractory T-cell malignancy. In some embodiments, DFS or OS is evaluated about 1, 2, 3, 4, 5, 6, 7, 8, 9, 10 years after initiation of the covalent TEC family kinase inhibitor treatment. In some embodiments, the covalent TEC family kinase inhibitor is administered in combination with an additional chemotherapeutic agent or biologic agent. In some embodiments, the additional chemotherapeutic agent or biologic agent is selected from among an antibody, a B cell receptor pathway inhibitor, a T cell receptor inhibitor, a PI3K inhibitor, an IAP inhibitor, a proteosome inhibitor, an mTOR inhibitor, a radioimmunotherapeutic, a DNA damaging agent, a histone deacetylase inhibitor, a protein kinase inhibitor, a hedgehog inhibitor, an Hsp90 inhibitor, a telomerase inhibitor, a Jak1/2 inhibitor, a protease inhibitor, an IRAK inhibitor, a PKC inhibitor, a PARP inhibitor, a CYP3A4 inhibitor, an AKT inhibitor, an Erk inhibitor, an alkylating agent, an anti metabolite, a plant alkaloid, a terpenoid, a cytotoxin, a topoisomerase inhibitor, a CD22 inhibitor, a Bcl-2 inhibitor, an IRAK 1/4 inhibitor, a microtubule inhibitor, a Topo II inhibitor, anti TWEAK, anti-IL17 bispecific antibody, a CK2 inhibitor, anaplastic lymphoma kinase (ALK) and c-Met inhibitors, demethylase enzyme inhibitors such as demethylase, HDM, LSDI and KDM, fatty acid synthase inhibitors such as spirocyclic piperidine derivatives, glucocorticosteriod receptor agonist, fusion anti-CD 19-cytotoxic agent conjugate, antimetabolite, p70S6K inhibitor, immune modulators, AKT/PKB inhibitor, procaspase-3 activator PAC-1, BRAF inhibitor, lactate dehydrogenase A (LDH-A) inhibitor, CCR2 inhibitor, CXCR4 inhibitor, chemokine receptor antagonists, DNA double stranded break repair inhibitors, NOR202, GA-101, TLR2 inhibitor, or a combination thereof. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, a JAK inhibitor (e.g., ruxolitinib, baricitinib, CYT387, lestauritinib, pacritinib, TG101348, SAR302503, tofacitinib (Xeljanz), etanercept (Enbrel), GLPG0634, R256), or a combination thereof. In some embodiments, the T cell receptor inhibitor is Muromonab-CD3. In some embodiments, the additional chemotherapeutic agent or biologic agent is selected from among rituximab (rituxan), carfilzomib, fludarabine, cyclophosphamide, vincristine, prednisalone. chlorambucil, ifosphamide, doxorubicin, mesalazine, thalidomide, lenalidomide, temsirolimus, everolimus, fostamatinib, paclitaxel, docetaxel, ofatumumab, dexamethasone, prednisone, CAL-101, ibritumomab, tositumomab, bortezomib, pentostatin, endostatin, ritonavir, ketoconazole, an anti-VEGF antibody, herceptin, cetuximab, cisplatin, carboplatin, docetaxel, erlotinib, etopiside, 5-fluorouracil, gemcitabine, ifosphamide, imatinib mesylate (Gleevec), gefitinib, procarbazine, prednisone, irinotecan, leucovorin, mechlorethamine, methotrexate, oxaliplatin, paclitaxel, sorafenib, sunitinib, topotecan, vinblastine, GA-1101, dasatinib, Sipuleucel-T, disulfiram, epigallocatechin-3-gallate, salinosporamide A, ONX0912, CEP-18770, MLN9708, R-406, lenalinomide, spirocyclic piperidine derivatives, quinazoline carboxamide azetidine compounds, thiotepa, DWA2114R, NK121, IS 3 295, 254-S, alkyl sulfonates such as busulfan, improsulfan and piposulfan; aziridines such as benzodepa, carboquone, meturedepa and uredepa; ethylenimine, methylmelamines such as altretamine, triethylenemelamine, triethylenephosphoramide, triethylenethiophosphoramide and trimethylmelamine; chlornaphazine; estramustine; ifosfamide; mechlorethamine; oxide hydrochloride; novobiocin; phenesterine; prednimustine; trofosfamide; uracil mustard; nitrosoureas such as carmustine, chlorozotocin, fotemustine, lomustine, nimustine, ranimustine; antibiotics such as aclacinomycins, actinomycin, anthramycin, azaserine, bleomycins, cactinomycin, calicheamicin, carubicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatrexate; defosfamide; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide-K; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; cytosine arabinoside; taxoids, e.g., paclitaxel and docetaxel; 6-thioguanine; mercaptopurine; methotrexate; platinum analogs; platinum; etoposide (VP-16); ifosfamide; mitomycin C; mitoxantrone; vincristine; vinorelbine; Navelbine; Novantrone; teniposide; daunomycin; aminopterin; Xeloda; ibandronate; CPT1 1; topoisomerase inhibitor RFS 2000; difluoromethylornithine (DMFO); retinoic acid; esperamycins; capecitabine; and pharmaceutically acceptable salts, acids or derivatives of; anti-hormonal agents such as anti-estrogens including for example tamoxifen, raloxifene, aromatase inhibiting 4(5)-imidazoles, 4-hydroxytamoxifen, trioxifene, keoxifene, LY117018, onapristone and toremifene (Fareston); antiandrogens such as flutamide, nilutamide, bicalutamide, leuprolide and goserelin; ACK inhibitors such as AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) or a combination thereof.

Described herein, in certain embodiments, are methods adjuvant therapy comprising administering to a subject with cancer, following surgery for removal of a tumor, an effective amount of a covalent TEC family kinase inhibitor so as to extend disease free survival (DFS) or overall survival (OS) in the subject. In some embodiments, the covalent TEC family kinase inhibitor inhibits one or more TEC family kinases selected from among ITK, BTK, TEC, RLK/TXK and BMX. In some embodiments, the covalent TEC family kinase inhibitor is an IL2-inducible T-cell kinase (ITK) inhibitor. In some embodiments, the covalent TEC family kinase inhibitor is a Bruton's tyrosine kinase (BTK) inhibitor. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib. In some embodiments, disease free survival (DFS) or overall survival (OS) is assessed 1, 2, 3, 4, 5, 6, 7, 8, 9, 10 years or longer following initiation of covalent TEC family kinase inhibitor administration. In some embodiments, the surgery for removal of a tumor is a definitive surgery. In some embodiments, the subject has no detectable tumors following surgery. In some embodiments, the subject has no detectable circulating tumor cells following surgery. In some embodiments, the surgery for removal of a tumor is a partial removal of the tumor. In some embodiments, the subject has not been administered chemotherapy for treatment of the cancer. In some embodiments, the subject has been administered a chemotherapeutic agent or biologic agent for treatment of the cancer. In some embodiments, the subject is a mammal. In some embodiments, the mammal is a human. In some embodiments, the covalent TEC family kinase inhibitor is administered daily. In some embodiments, the covalent TEC family kinase inhibitor is administered 1, 2, 3, 4, 5 times or more per day. In some embodiments, the covalent TEC family kinase inhibitor is administered once per day. In some embodiments, the covalent TEC family kinase inhibitor is administered at a dosage of about 40 mg/day to about 1000 mg/day. In some embodiments, the covalent TEC family kinase inhibitor is administered for about 1 week to 5 years. In some embodiments, the covalent TEC family kinase inhibitor is administered orally. In some embodiments, the risk of relapsed or refractory disease is reduced by about 10%, 20%, 30%, 40%, 50%, 60%, 70%, 80%, 90% or greater compared to no treatment with the covalent TEC family kinase inhibitor. In some embodiments, the subject is disease free for about 6 months, 1 year, 2 years, 3 years, 4 years, 5 years, 6 years, 7 years, 8 years, 9 years, 10 years or longer following last administration of the covalent TEC family kinase inhibitor. In some embodiments, the risk of a secondary tumor is decreased compared to no treatment with the covalent TEC family kinase inhibitor. In some embodiments, the subject has a high risk of cancer recurrence prior to treatment with the covalent TEC family kinase inhibitor. In some embodiments, the tumor is a sarcoma, carcinoma, neurofibromatoma or a lymphoma. In some embodiments, the lymphoma is an enlarged lymph node or an extranodal lymphoma. In some embodiments, the subject has a brain, breast, bladder, bone, colon, kidney, liver, lung, ovarian, pancreatic, prostate, skin or proximal or distal bile duct carcinoma. In some embodiments, the subject has a hematologic cancer. In some embodiments, the cancer is a lymphoma. In some embodiments, the subject has a non-Hodgkin's lymphoma. In some embodiments, the non-Hodgkin's lymphoma is chronic lymphocytic leukemia/small lymphocytic lymphoma (CLL/SLL), follicular lymphoma (FL), diffuse large B-cell lymphoma (DLBCL), mantle cell lymphoma (MCL), Waldenström's macroglobulinemia, multiple myeloma, marginal zone lymphoma, Burkitt's lymphoma, non-Burkitt high grade B cell lymphoma, or extranodal marginal zone B cell lymphoma. In some embodiments, the non-Hodgkin's lymphoma is a relapsed or refractory non-Hodgkin's lymphoma. In some embodiments, the subject has a T-cell malignancy. In some embodiments, the T-cell malignancy is peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas. In some embodiments, the T-cell malignancy is a relapsed or refractory T-cell malignancy. In some embodiments, DFS or OS is evaluated about 1, 2, 3, 4, 5, 6, 7, 8, 9, 10 years after initiation of the covalent TEC family kinase inhibitor treatment. In some embodiments, the covalent TEC family kinase inhibitor is administered in combination with an additional chemotherapeutic agent or biologic agent. In some embodiments, the additional chemotherapeutic agent or biologic agent is selected from among an antibody, a B cell receptor pathway inhibitor, a T cell receptor inhibitor, a PI3K inhibitor, an IAP inhibitor, an mTOR inhibitor, a radioimmunotherapeutic, a DNA damaging agent, a histone deacetylase inhibitor, a protein kinase inhibitor, a hedgehog inhibitor, an Hsp90 inhibitor, a telomerase inhibitor, a Jak1/2 inhibitor, a protease inhibitor, an IRAK inhibitor, a PKC inhibitor, a PARP inhibitor, a proteomsome inhibitor, a CYP3A4 inhibitor, an AKT inhibitor, an Erk inhibitor, an alkylating agent, an anti metabolite, a plant alkaloid, a terpenoid, a cytotoxin, a topoisomerase inhibitor, or a combination thereof. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, a CD22 inhibitor, a Bcl-2 inhibitor, an IRAK 1/4 inhibitor, a microtubule inhibitor, a Topo II inhibitor, anti TWEAK, anti-IL17 bispecific antibody, a CK2 inhibitor, anaplastic lymphoma kinase (ALK) and c-Met inhibitors, demethylase enzyme inhibitors such as demethylase, HDM, LSDI and KDM, fatty acid synthase inhibitors such as spirocyclic piperidine derivatives, glucocorticosteriod receptor agonist, fusion anti-CD 19-cytotoxic agent conjugate, antimetabolite, p70S6K inhibitor, immune modulators, AKT/PKB inhibitor, procaspase-3 activator PAC-1, BRAF inhibitor, lactate dehydrogenase A (LDH-A) inhibitor, CCR2 inhibitor, CXCR4 inhibitor, chemokine receptor antagonists, DNA double stranded break repair inhibitors, NOR202, GA-101, TLR2 inhibitor, a JAK inhibitor (e.g., ruxolitinib, baricitinib, CYT387, lestauritinib, pacritinib, TG101348, SAR302503, tofacitinib (Xeljanz), etanercept (Enbrel), GLPG0634, R256), or a combination thereof. In some embodiments, the T cell receptor inhibitor is Muromonab-CD3. In some embodiments, the additional chemotherapeutic agent or biologic agent is selected from among rituximab, carfilzomib, fludarabine, cyclophosphamide, vincristine, prednisalone, chlorambucil, ifosphamide, doxorubicin, mesalazine, thalidomide, lenalidomide, temsirolimus, everolimus, fostamatinib, paclitaxel, docetaxel, ofatumumab, dexamethasone, prednisone, CAL-101, ibritumomab, tositumomab, bortezomib, pentostatin, endostatin, ritonavir, ketoconazole, an anti-VEGF antibody, herceptin, cetuximab, cisplatin, carboplatin, docetaxel, erlotinib, etopiside, 5-fluorouracil, gemcitabine, ifosphamide, imatinib mesylate (Gleevec), gefitinib, procarbazine, prednisone, irinotecan, leucovorin, mechlorethamine, methotrexate, oxaliplatin, paclitaxel, sorafenib, sunitinib, topotecan, vinblastine, GA-1101, dasatinib, Sipuleucel-T, disulfiram, epigallocatechin-3-gallate, salinosporamide A, ONX0912, CEP-18770, MLN9708, R-406, lenalinomide, spirocyclic piperidine derivatives, quinazoline carboxamide azetidine compounds, thiotepa, DWA2114R, NK121, IS 3 295, 254-S, alkyl sulfonates such as busulfan, improsulfan and piposulfan; aziridines such as benzodepa, carboquone, meturedepa and uredepa; ethylenimine, methylmelamines such as altretamine, triethylenemelamine, triethylenephosphoramide, triethylenethiophosphoramide and trimethylmelamine; chlornaphazine; estramustine; ifosfamide; mechlorethamine; oxide hydrochloride; novobiocin; phenesterine; prednimustine; trofosfamide; uracil mustard; nitrosoureas such as carmustine, chlorozotocin, fotemustine, lomustine, nimustine, ranimustine; antibiotics such as aclacinomycins, actinomycin, anthramycin, azaserine, bleomycins, cactinomycin, calicheamicin, carubicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatrexate; defosfamide; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide-K; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; cytosine arabinoside; taxoids, e.g., paclitaxel and docetaxel; 6-thioguanine; mercaptopurine; methotrexate; platinum analogs; platinum; etoposide (VP-16); ifosfamide; mitomycin C; mitoxantrone; vincristine; vinorelbine; Navelbine; Novantrone; teniposide; daunomycin; aminopterin; Xeloda; ibandronate; CPT1 1; topoisomerase inhibitor RFS 2000; difluoromethylornithine (DMFO); retinoic acid; esperamycins; capecitabine; and pharmaceutically acceptable salts, acids or derivatives of; anti-hormonal agents such as anti-estrogens including for example tamoxifen, raloxifene, aromatase inhibiting 4(5)-imidazoles, 4-hydroxytamoxifen, trioxifene, keoxifene, LY117018, onapristone and toremifene (Fareston); antiandrogens such as flutamide, nilutamide, bicalutamide, leuprolide and goserelin; ACK inhibitors such as AVL-263

(Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) or a combination thereof.

Described herein, in certain embodiments, are methods of treating T-cell malignancy in the subject comprising administering to the subject an effective amount of a covalent TEC family kinase inhibitor thereby treating the T-cell malignancy. In some embodiments, the covalent TEC family kinase inhibitor inhibits one or more TEC family kinases selected from among ITK, BTK, TEC, RLK/TXK and BMX. In some embodiments, the covalent TEC family kinase inhibitor inhibits ITK. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib. In some embodiments, the T-cell malignancy is selected from among peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas. In some embodiments, the T-cell malignancy is a relapsed or refractory T-cell malignancy.

Described herein, in certain embodiments, are methods of treating a subject having an immune disorder characterized by an impaired Th1 immune response or an overactive Th2 response comprising administering to the subject an effective amount of a covalent TEC family kinase inhibitor to increase the Th1 immune response or decrease the Th2 response in the subject, whereby the immune disorder is treated. In some embodiments, the subject has a pathogenic infection. In some embodiments, the pathogenic infection is a viral, a bacterial, a fungal, a parasitic or a protozoal infection. In some embodiments, the pathogenic infection is a viral or a bacterial infection. In some embodiments, the immune disorder is associated with a hematologic cancer. In some embodiments, the immune disorder is associated with a leukemia, a lymphoma, or a myeloma. In some embodiments, the immune disorder is associated with non-Hodgkin's lymphoma. In some embodiments, the immune disorder is associated with chronic lymphocytic leukemia (CLL), small lymphocytic lymphoma (SLL), high risk CLL, follicular lymphoma (FL), diffuse large B-cell lymphoma (DLBCL), mantle cell lymphoma (MCL), Waldenström's macroglobulinemia, multiple myeloma, marginal zone lymphoma, Burkitt's lymphoma, non-Burkitt high grade B cell lymphoma, extranodal marginal zone B cell lymphoma or Sezary syndrome. In some embodiments, the subject has an autoimmune disease characterized by an impaired Th1 immune response or an overactive Th2 response. In some embodiments, the autoimmune disease is associated with a viral infection. In some embodiments, wherein the subject has a human immunodeficiency virus (HIV) infection. In some embodiments, the subject has a hepatitis infection. In some embodiments, the hepatitis infection is an A, B or C type hepatitis infection. In some embodiments, the subject has an influenza infection. In some embodiments, the subject has measles virus infection. In some embodiments, the subject has a Human papilloma virus infection. In some embodiments, the subject has a Human herpesvirus 6A, Human herpesvirus 6B, or Human herpesvirus 7. In some embodiments, the subject has a Herpes Simplex virus. In some embodiments, the subject has an Epstein-Bar virus. In some embodiments, the subject has a Human cytomegalovirus. In some embodiments, the subject has a Rous sarcoma virus. In some embodiments, the subject has a chronic granulomatous disease. In some embodiments, the autoimmune disease is autoimmune arthritis. In some embodiments, the immune disorder is atopic dermatitis, inflammatory bowel disease, an unspecified T-cell lymphoma (U-PTCLs), rheumatoid arthritis, bronchial asthma, allergic airway inflammatory disease or aplastic anemia. In some embodiments, the pathogenic infection is a *Listeria monocytogenes* infection. In some embodiments, the pathogenic infection is a *Leishmania major* infection. In some embodiments, the covalent TEC family kinase inhibitor inhibits one or more TEC family kinases selected from among ITK, BTK, TEC, RLK/TXK and BMX. In some embodiments, the covalent TEC family kinase inhibitor inhibits ITK. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib. In some embodiments, the covalent TEC family kinase inhibitor is administered in combination with a T-cell immunotherapy. In some embodiments, the T-cell immunotherapy is selected from among adoptive T cell transfer, a vaccine, a cytokine, an interleukin, a chemokine, a cytokine inducer, an interleukin inducer, a chemokine inducer, or an immunomodulatory antibody.

Described herein, in certain embodiments, is a method for treating a Th2 cell-mediated disease or condition by increasing the Th1:Th2 ratio in the subject comprising administering to the subject an effective amount of a covalent TEC family kinase inhibitor thereby treating the Th2 cell-mediated disease or condition. In some embodiments, the covalent TEC family kinase inhibitor inhibits one or more TEC family kinases selected from among ITK, BTK, TEC, RLK/TXK and BMX. In some embodiments, the covalent TEC family kinase inhibitor inhibits ITK. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib. In some embodiments, the Th2 cell-mediated disease or condition is selected from among cancer (e.g., hematologic malignancies and solid tumors), exacerbation of infection with infectious diseases (e.g., *Leishmania major, Listeria monocytogenes, Mycobacterium leprae, Candida albicans, Toxoplasma gondi*, Hepatitis C virus (HCV), Respiratory Syncytial virus (RSV), human immunodeficiency virus (HIV), influenzavirus A) and allergic disorders, such as anaphylactic hypersensitivity, asthma, allergic rhinitis, atopic dermatitis, vernal conjunctivitis, eczema, urticaria and food allergies, autoimmune diseases, inflammatory diseases, inflammatory bowel disease, ulcerative colitis, systemic lupus erythematodes, myasthenia gravis, systemic progressive scleroderma, rheumatoid arthritis, interstitial cystitis, Hashimoto's diseases, Basedow's diseases, autoimmune hemolytic anemia, idiopathic thrombocytopenic purpura, Goodpasture's syndrome, atrophic gastritis, pernicious anemia, Addison diseases, pemphigus, pemphigoid, lenticular uveitis, sympathetic ophthalmia, primary biliary cirrhosis, active chronic hepatitis, Sjogren's syndrome, multiple myositis, dermatomyositis, polyarteritis nodosa, rheumatic fever, glomerular nephritis (lupus nephritis, IgA nephropathy, and the like), allergic encephalitis, atopic allergic diseases (for example, bronchial asthma, allergic rhinitis, allergic dermatitis, allergic conjunctivitis, pollinosis, urticaria, food allergy and the like), Omenn's syndrome, vernal conjunctivitis and hypereosinophilic syndrome.

Described herein, in certain embodiments, are methods of treating a pathogenic infection in a subject having an immune disorder characterized by an impaired Th1 immune response or an overactive Th2 response comprising administering to the subject an effective amount of a covalent TEC family kinase inhibitor, whereby the pathogenic infection is treated. In some embodiments, the pathogenic infection is a viral, a bacterial, a fungal, a parasitic or a protozoal infection. In some embodiments, the pathogenic infection is a viral or a bacterial infection. In some embodiments, the immune disorder is associated with a hematologic cancer. In some embodiments, the immune disorder is associated with a leukemia, a lymphoma, or a myeloma. In some embodiments, the immune disorder is associated with non-Hodgkin's lymphoma. In some embodiments, the immune disorder is associated with chronic lymphocytic leukemia (CLL), small lymphocytic lymphoma (SLL), high risk CLL, follicular lymphoma (FL), diffuse large B-cell lymphoma (DLBCL), mantle cell lymphoma (MCL), Waldenström's macroglobulinemia, multiple myeloma, marginal zone lymphoma, Burkitt's lymphoma, non-Burkitt high grade B cell lymphoma, or extranodal marginal zone B cell lymphoma. In some embodiments, the subject has an autoimmune disease characterized by an impaired Th1 immune response or an overactive Th2 response. In some embodiments, the autoimmune disease is associated with a viral infection. In some embodiments, wherein the subject has a human immunodeficiency virus (HIV) infection. In some embodiments, the subject has a hepatitis infection. In some embodiments, the hepatitis infection is an A, B or C type hepatitis infection. In some embodiments, the subject has an influenza infection. In some embodiments, the subject has measles virus infection. In some embodiments, the subject has a Human papilloma virus infection. In some embodiments, the subject has a Human herpesvirus 6A, Human herpesvirus 6B, or Human herpesvirus 7. In some embodiments, the subject has a Herpes Simplex virus. In some embodiments, the subject has an Epstein-Bar virus. In some embodiments, the subject has a Human cytomegalovirus. In some embodiments, the subject has a Rous sarcoma virus. In some embodiments, the subject has a chronic granulomatous disease. In some embodiments, the autoimmune disease is autoimmune arthritis. In some embodiments, the immune disorder is atopic dermatitis, inflammatory bowel disease, an unspecified T-cell lymphoma (U-PTCLs), rheumatoid arthritis, bronchial asthma, allergic airway inflammatory disease or aplastic anemia. In some embodiments, the pathogenic infection is a *Listeria monocytogenes* infection. In some embodiments, the pathogenic infection is a *Leishmania major* infection. In some embodiments, the covalent TEC family kinase inhibitor inhibits one or more TEC family kinases selected from among ITK, BTK, TEC, RLK/TXK and BMX. In some embodiments, the covalent TEC family kinase inhibitor inhibits ITK. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib.

In some embodiments, the covalent TEC family kinase inhibitor is administered in combination with a T-cell immunotherapy. In some embodiments, the T-cell immunotherapy is selected from among adoptive T cell transfer, a vaccine, a cytokine, an interleukin, a chemokine, a cytokine inducer, an interleukin inducer, a chemokine inducer, or an immunomodulatory antibody.

Described herein, in certain embodiments, are methods of treating a pathogenic infection in a subject comprising administering to the subject an effective amount of a covalent TEC family kinase inhibitor whereby the pathogenic infection is treated. In some embodiments, the pathogenic infection is associated with an impaired Th1 immune response or an overactive Th2 response in the individual. In some embodiments, the pathogenic infection is a chronic viral infection. In some embodiments, the chronic viral infection is a chronic HCV infection. In some embodiments, the pathogenic infection is an HIV infection. In some embodiments, the pathogenic infection is an influenza infection. In some embodiments, the methods further comprise administering an antiviral agent. In some embodiments, the antiviral agent is acyclovir, famciclovir, ganciclovir, penciclovir, valacyclovir, valganciclovir, idoxuridine, trifluridine, brivudine, cidofovir, docosanol, fomivirsen, foscarnet, tromantadine, imiquimod, podophyllotoxin, entecavir, lamivudine, telbivudine, clevudine, adefovir, tenofovir, boceprevir, telaprevir, pleconaril, arbidol, amantadine, rimantadine, oseltamivir, zanamivir, peramivir, inosine, interferon (e.g., Interferon alfa-2b, Peginterferon alfa-2a), ribavirin/taribavirin, abacavir, emtricitabine, lamivudine, didanosine, zidovudine, apricitabine, stampidine, elvucitabine, racivir, amdoxovir, stavudine, zalcitabine, tenofovir, efavirenz, nevirapine, etravirine, rilpivirine, loviride, delavirdine, atazanavir, fosamprenavir, lopinavir, darunavir, nelfinavir, ritonavir, saquinavir, tipranavir, amprenavir, indinavir, enfuvirtide, maraviroc, vicriviroc, PRO 140, ibalizumab, raltegravir, elvitegravir, bevirimat, or vivecon. In some embodiments, the antiviral agent is ribavirin. In some embodiments, the antiviral agent is IFN-α. In some embodiments, the methods further comprise administering ribavirin and IFN-α in combination with the covalent TEC family kinase inhibitor. In some embodiments, the covalent TEC family kinase inhibitor inhibits one or more TEC family kinases selected from among ITK, BTK, TEC, RLK/TXK and BMX. In some embodiments, the covalent TEC family kinase inhibitor is an IL2-inducible T-cell kinase (ITK) inhibitor. In some embodiments, the covalent TEC family kinase inhibitor is a Bruton's tyrosine kinase (BTK) inhibitor. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib. In some embodiments, the subject is a mammal. In some embodiments, the mammal is a human. In some embodiments, the covalent TEC family kinase inhibitor is administered daily. In some embodiments, the covalent TEC family kinase inhibitor is administered 1, 2, 3, 4, 5 times or more per day. In some embodiments, the covalent TEC family kinase inhibitor is administered once per day. In some embodiments, the covalent TEC family kinase inhibitor is administered at a dosage of about 40 mg/day to about 1000 mg/day. In some embodiments, the covalent TEC family kinase inhibitor is administered for about 1 week to 5 years. In some embodiments, the covalent TEC family kinase inhibitor is administered orally. In some embodiments, administration of a covalent TEC family kinase inhibitor decreases the number of Th2 polarized T cells in the subject. In some embodiments, administration of a covalent TEC family kinase inhibitor increases the number of Th1 polarized T cells in the subject. In some embodiments, administration of a covalent TEC family kinase inhibitor increases the number of activated CD8+ cytotoxic T cells in the subject. In some embodiments, administration of a covalent TEC family kinase inhibitor increases the ratio of Th1 polarized T cells to Th2 polarized T cells in the subject. In some embodiments, administration of a covalent TEC family kinase inhibitor decreases the expression of one or more Th2 cytokines in the subject. In some embodiments, administration of a covalent TEC family kinase inhibitor decreases IL-10, IL-4 or IL-13 expression in the subject. In some embodiments, administration of a covalent TEC family kinase inhibitor increases the expression of one or more Th1 cytokines in the subject. In some embodiments, administration of a covalent TEC family kinase inhibitor increases IL-2, GM-CSF, IFN-γ, IL-12(p70) and TNF-α expression in the subject. In some embodiments, administration of a covalent TEC family kinase inhibitor increase the number of cytotoxic CD8+ T cells in the subject. In some embodiments, a covalent TEC family kinase inhibitor inhibits the kinase activity of IL2-inducible T-cell kinase (ITK). In some embodiments, a covalent TEC family kinase inhibitor covalently binds to Cysteine 442 of ITK. In some embodiments, the covalent TEC family kinase inhibitor covalently binds to Cysteine 481 of BTK. In some embodiments, the covalent TEC family kinase inhibitor covalently inhibits the kinase activity of BTK and ITK. In some embodiments, the covalent TEC family kinase inhibitor is administered in combination with an immune cell modulator. In some embodiments, the immune modulator is a T cell immune modulator. In some embodiments, the immune modulator is a recombinant T cell, a vaccine, a cytokine, an interleukin, a chemokine, a cytokine inducer, an interleukin inducer, a chemokine inducer, or an immunomodulatory antibody. In some embodiments, the immune modulator is Sipuleucel-T.

Described herein, in certain embodiments, are methods of vaccination of a subject comprising administering to the subject an effective amount of a covalent TEC family kinase inhibitor in combination with a vaccine. In some embodiments, the covalent TEC family kinase inhibitor and the vaccine are administered simultaneously, sequentially, or intermittently. In some embodiments, the vaccine comprises a tumor antigen. In some embodiments, the vaccine comprises an antigen from a virus, bacterium, or a parasite. In some embodiments, the vaccine comprises an attenuated virus or inactivated virus. In some embodiments, the vaccine comprises attenuated bacteria or killed bacteria. In some embodiments, the covalent TEC family kinase inhibitor inhibits one or more TEC family kinases selected from among ITK, BTK, TEC, RLK/TXK and BMX. In some embodiments, the covalent TEC family kinase inhibitor is an IL2-inducible T-cell kinase (ITK) inhibitor. In some embodiments, the covalent TEC family kinase inhibitor is a Bruton's tyrosine kinase (BTK) inhibitor. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib.

Described herein, in certain embodiments, are compositions comprising: a covalent TEC family kinase inhibitor; and an antiviral agent. In some embodiments, the antiviral agent comprises a cytokine, a protease inhibitor or a nucleoside analog. In some embodiments, the antiviral agent comprises ribavirin. In some embodiments, the antiviral agent comprises IFN-α. In some embodiments, the antiviral agent comprises ribavirin and IFN-α. In some embodiments, the covalent TEC family kinase inhibitor inhibits one or more TEC family kinases selected from among ITK, BTK, TEC, RLK/TXK and BMX. In some embodiments, the covalent TEC family kinase inhibitor is an IL2-inducible T-cell kinase (ITK) inhibitor. In some embodiments, the covalent TEC family kinase inhibitor is a Bruton's tyrosine kinase (BTK) inhibitor. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib.

Described herein, in certain embodiments, are uses of covalent TEC family kinase inhibitors for treating a subject having a cancer characterized by a cytokine profile in which Th1 response is suppressed and Th2 response is enhanced. In some embodiments, the covalent TEC family kinase inhibitor suppresses the Th2 response in the subject. In some embodiments, the covalent TEC family kinase inhibitor inhibits one or more TEC family kinases selected from among ITK, BTK, TEC, RLK/TXK and BMX. In some embodiments, the covalent TEC family kinase inhibitor inhibits ITK. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib.

Described herein, in certain embodiments, are uses of covalent TEC family kinase inhibitors for the manufacture of a medicament for treating a subject having a cancer characterized by a cytokine profile in which Th1 response is suppressed and Th2 response is enhanced. In some embodiments, the covalent TEC family kinase inhibitor suppresses the Th2 response in the subject. In some embodiments, the covalent TEC family kinase inhibitor inhibits one or more TEC family kinases selected from among ITK, BTK, TEC, RLK/TXK and BMX. In some embodiments, the covalent TEC family kinase inhibitor inhibits ITK. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib.

Described herein, in certain embodiments, are uses of covalent TEC family kinase inhibitors for increasing the Th1:Th2 biomarker ratio in a subject having cancer. In some embodiments, the covalent TEC family kinase inhibitor suppresses the Th2 response in the subject. In some embodiments, the covalent TEC family kinase inhibitor inhibits one or more TEC family kinases selected from among ITK, BTK, TEC, RLK/TXK and BMX. In some embodiments, the covalent TEC family kinase inhibitor inhibits ITK. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib.

Described herein, in certain embodiments, are uses of covalent TEC family kinase inhibitors for the manufacture of a medicament for increasing the Th1:Th2 biomarker ratio in a subject having cancer. In some embodiments, the covalent TEC family kinase inhibitor suppresses the Th2 response in the subject. In some embodiments, the covalent TEC family kinase inhibitor inhibits one or more TEC family kinases selected from among ITK, BTK, TEC, RLK/

TXK and BMX. In some embodiments, the covalent TEC family kinase inhibitor inhibits ITK. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib.

Described herein, in certain embodiments, are uses of covalent TEC family kinase inhibitors (e.g. ibrutinib) for treating a subject having a T-cell malignancy following treatment with a first anticancer therapy, to prevent, reduce the risk of, or delay relapsed or refractory disease, wherein the first anticancer therapy does not comprise the covalent TEC family kinase inhibitor. In some embodiments, the covalent TEC family kinase inhibitor suppresses the Th2 response in the subject. In some embodiments, the covalent TEC family kinase inhibitor inhibits one or more TEC family kinases selected from among ITK, BTK, TEC, RLK/TXK and BMX. In some embodiments, the covalent TEC family kinase inhibitor inhibits ITK. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib.

Described herein, in certain embodiments, are uses of covalent TEC family kinase inhibitors (e.g. ibrutinib) for the manufacture of a medicament for treating a subject having a T-cell malignancy following treatment with a first anticancer therapy, to prevent, reduce the risk of, or delay relapsed or refractory disease, wherein the first anticancer therapy does not comprise the covalent TEC family kinase inhibitor. In some embodiments, the covalent TEC family kinase inhibitor suppresses the Th2 response in the subject. In some embodiments, the covalent TEC family kinase inhibitor inhibits ITK. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib.

Described herein, in certain embodiments, are uses of covalent TEC family kinase inhibitors for treating a Th2-mediated disease or disorder. In some embodiments, Th2-mediated disease or disorder is cancer, an inflammatory disease, an autoimmune disease or an pathogenic infection. In some embodiments, the covalent TEC family kinase inhibitor suppresses the Th2 response in the subject. In some embodiments, the covalent TEC family kinase inhibitor inhibits one or more TEC family kinases selected from among ITK, BTK, TEC, RLK/TXK and BMX. In some embodiments, the covalent TEC family kinase inhibitor inhibits ITK. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib.

Described herein, in certain embodiments, are uses of covalent TEC family kinase inhibitors (e.g. ibrutinib) for the manufacture of a medicament for treating a Th2-mediated disease or disorder. In some embodiments, Th2-mediated disease or disorder is cancer, an inflammatory disease, an autoimmune disease or an pathogenic infection. In some embodiments, the covalent TEC family kinase inhibitor suppresses the Th2 response in the subject. In some embodiments, the covalent TEC family kinase inhibitor inhibits one or more TEC family kinases selected from among ITK, BTK, TEC, RLK/TXK and BMX. In some embodiments, the covalent TEC family kinase inhibitor inhibits ITK. In some embodiments, the covalent TEC family kinase inhibi-tor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib.

BRIEF DESCRIPTION OF THE DRAWINGS

FIG. 1 illustrates ibrutinib as an irreversible molecular inhibitor of ITK, displaying BTK-independent antileukemic potential and inhibiting ITK as well as distal markers of T-cell activation and components of Th2 signaling. FIG. 1C illustrates in silico representation of docked ibrutinib within the active site of crystallized ITK (PDB databank code: 3QGW) showing close approximation of Cys442 to reactive moiety of ibrutinib (bottom panel). Shape and chemical complementarity of ibrutinib shown in surface representation (top panel). FIG. 1D illustrates fluorescent probe assay was used to calculate the percent irreversible occupancy of total ITK in Jurkat whole cell lysates irreversibly bound by ibrutinib. Error bars=s.e.m. FIG. 1E illustrates qRT-PCR analysis of relative ITK and BTK mRNA levels in CD8 T-cell leukemia derived from EμTCL1 mice. Fold change is calculated by Pfaffl method using splenocytes from a healthy C57BL/6 mouse as a control. Error bars=s.e.m. FIG. 1F illustrates annexin V/PI viability assay conducted on 72 hr in vitro CD8 T-cell leukemia splenocyte cultures. Data were averaged across 5 replicates and normalized to untreated samples; cells from 3 independent donor mice were examined. Error bars, s.e.m. FIG. 1G illustrates fluorescent probe assay was used to calculate the percent irreversible occupancy of ITK by ibrutinib in cryopreserved PBMCs obtained immediately prior to (predose) and 8 days into (ibrutinib) daily oral ibrutinib therapy for CLL (n=8). Error bars=s.e.m. FIG. 1H illustrates immunoblot analysis of ibrutinib pretreated, 2 hr anti-CD3/anti-CD28 stimulated (or unstimulated), Jurkat whole cell lysates. Blot probed for pITK-Y180, Total ITK, pIkBα-$S_{32/36}$, Total IkBα, and Actin. FIG. 1I illustrates immunoblot analysis of ibrutinib pretreated, 2 hr anti-CD3/anti-CD28 stimulated (or unstimulated), Jurkat whole cell lysates. Blot probed for pSTAT6-Y641, Total STAT6, pIkBα-532/36, Total IkBα, JunB, and Actin. FIG. 1J illustrates immunoblot analysis of ibrutinib pretreated, 45 minute anti-CD3/anti-CD28 stimulated (or unstimulated), Jurkat cytoplasmic and nuclear lysates. Blots probed for NFAT (and activated hyper-dephosphorlyated NFAT), Brg1 (nuclear loading control), and Actin (cytoplasmic loading control). In FIGS. 1H-1J, each blot was repeated in a minimum of 3 independent experiments.

FIG. 2A illustrates immunoblot analysis of freshly isolated ibrutinib pretreated primary CD4+ cells from a healthy donor, 2 hr anti-CD3/anti-CD28 stimulated (or unstimulated), whole cell lysates. Blot probed for pITK-Y180, Total ITK, pSTAT1-Y701, Total STAT1, pSTAT6-Y641, Total STAT6, pIkBα-S32/36, Total IkBα, JunB, and Actin. FIG. 2B illustrates immunoblot analysis of freshly isolated ibrutinib pretreated primary CD4+ cells from a healthy donor, 45 minute anti-CD3/anti-CD28 stimulated (or unstimulated), cytoplasmic and nuclear lysates. Blots probed for NFAT (and activated hyper-dephosphorlyated NFAT), Brg1, and Actin. In FIGS. 2A-2B, each blot was repeated in a minimum of 3 independent experiments. FIG. 2C illustrates immunofluorescence microscopy of ibrutinib pretreated, freshly isolated, primary CD4+ cells from healthy donors (Panels A and B) were stimulated for 45 minutes with anti-CD3/anti-CD28 (or unstimulated), fixed, and stained for NFAT and nuclei (DAPI). Activated cells are characterized by influx of NFAT into nuclear region and are denoted by white arrows. FIG. 2D illustrates percent relative NFAT1/DAPI colocalization derived from Pearson correlation analysis of 10 independent immunofluorescence microscopy fields (different donors than pictured in FIG. 2C) and normalized to the average unstimulated value. CSA, cyclosporin A treatment was used as an additional negative control. Error bars, s.e.m. FIG. 2E illustrates phosflow analysis of pPLCγ1-Tyr783 in 1 hr anti-CD3/anti-CD28 stimulated cryopreserved PBMCs obtained immediately predose or after 8 days of receiving ibrutinib therapy for CLL (n=11). A minimum of 400,000 events were collected, graph displays the overall percent of live CD3+CD4+pPLCγ1-Tyr783+ events in each sample. Error bars, s.e.m. In FIG. 2F, Top panel: CFSE stained, freshly isolated, ibrutinib pretreated, and anti-CD3/anti-CD28 stimulated (or unstimulated) CD4+ cells from a healthy donor were assayed by flow cytometry after 7 days of in vitro culture. Bottom panel: cells from first week were re-stained with PKH26 and restimulated for an additional 7 days of in vitro culture. Flow cytometric analysis was conducted at the end of each week. Gated cells represent at least 1 cellular division.

FIG. 3A illustrates immunoblot analysis of 45 minute nuclear and 2 hr whole cell extracts from ibrutinib or alternate BTK inhibitor pretreated, freshly purified healthy donor primary CD4+ cells stimulated with anti-CD3/anti-CD28. Nuclear extracts were probed for NFAT1 and Brg1; whole cell extracts were probed for pSTAT1-Y701, Total STAT1, pSTAT6-Y641, Total STATE, pIkBα-532/36, Total IkBα, JunB, and Actin. FIG. 3B illustrates fluorescent probe assay was used to calculate the percent occupancy of total ITK in Jurkat whole cell lysates irreversibly bound by ibrutinib (dark bars) or Alt. BTK inhibitor (open bars). Error bars, s.e.m. FIG. 3C illustrates Sanger sequencing reaction chromatograms conducted on amplified mRNA from Jurkat-ITKC442A, Jurkat-ITKwt, and Jurkat parental cell lines. Highlighted base pairs are the first two nucleotides in ITK codon 442 which code for a wt-Cys (TGC) or a mutant-Ala (GCC). FIG. 3D illustrates immunoblot analysis of Jurkat parental, Jurkat-ITKwt, and Jurkat-ITKC442A nuclear lysates after ibrutinib pretreatment and 45 minute anti-CD3/anti-CD28 stimulation. Blots were probed for NFAT1 and Brg1. FIG. 3E illustrates cytokine analysis of IL4 (black bars and right Y-axis) and IFNγ (open bars and left Y-axis) media levels in anti-CD3/anti-CD28 stimulated Th1 and Th2 polarized cell cultures. These are the same cell cultures utilized in panel FIG. 3F. FIG. 3F illustrates Th1, Th2, and CD8 purified primary cells were stimulated for 45 minutes (nuclear) and 2 hr (whole cell) with anti-CD3/anti-CD28 after pretreatment with ibrutinib. Immunoblot analysis was conducted probing for NFAT and Brg1 as well as pIkBα-532/36, Total IkBα, and Actin. FIG. 3G illustrates average qRT-PCR cycle of transmittance (Ct) values are depicted for GAPDH (control gene) and RLK in the stable clones of Jurkat parental, Jurkat-EV (Empty Vector), and Jurkat-RLK. FIG. 3H illustrates immunoblot analysis of Jurkat parental, Jurkat-RLK, and Jurkat-EV (empty vector) nuclear lysates after ibrutinib pretreatment and 45 minute anti-CD3/anti-CD28 stimulation. Blots were probed for NFAT1 and Brg1.

FIG. 4A illustrates intracellular staining analysis of IFNγ (left) and IL4 (right) in bulk 5 day anti-CD3/anti-CD28 stimulated CD4+ T-cell cultures pretreated with Ibrutinib or vehicle. Experiment was repeated 5 times, isotype staining control is provided. FIG. 4B illustrates immunoblot analysis of JunB (top) and Tbet (bottom) levels in bulk CD4+ cultures pretreated with ibrutinib and anti-CD3/anti-CD28 stimulated (or unstimulated) for 3 days in-vitro, Actin is used as loading control. FIG. 4C illustrates intracellular staining of IFNγ and IL4 in CD4+ cells freshly isolated from a CLL donor, pretreated with ibrutinib, and stimulated with anti-CD3/anti-CD28. FIG. 4D illustrates normalized intracellular staining analysis of IL4 (open bars) and IFNγ (closed bars) in healthy donor CD4+ cells pretreated with ibrutinib and stimulated with anti-CD3/anti-CD28 (n=3). Error bars, s.e.m. FIG. 4E illustrates normalized intracellular staining analysis of IL4 (open bars n=6) and IFNγ (closed bars n=9) CD4+ cells derived from CLL patients pretreated with ibrutinib and stimulated with anti-CD3/anti-CD28. Error bars, s.e.m.

FIG. 5A illustrates a schematic representation of *L. major* mouse experiment timecourse. Mice were initiated on ibrutinib or vehicle 2 days prior to being infected with 2E6 stationary phase *L. major* promastigotes. Lesion size was tracked for 9 weeks and immune correlates were collected upon sacrifice at week 9. FIG. 5B illustrates Lymphocytes isolated from draining lymph nodes were stimulated with *L. major* antigens for 72 hr and culture supernatant was analyzed by ELISA for IL4 and IL10. Error bars, s.e.m. FIG. 5C illustrates Lymphocytes isolated from draining lymph nodes were stimulated with *L. major* antigens for 72 hr and culture supernatant was analyzed by ELISA for IFNγ. IFNγ responses are displayed as a ratio with IL4 (left panel) or IL10 (right panel) to compare relative Th1 and Th2 immunity in ibrutinib or vehicle treated groups. FIG. 5D illustrates whole mount gross histological preparations of vehicle and ibrutinib treated *L. major* infected footpads are depicted along with a centimeter ruler for size comparison. Cutaneous lesions are visible on the underside of the footpad. FIG. 5E illustrates log dilution of parasites obtained from footpad lesions are displayed. Error bars, s.e.m. FIG. 5F illustrates timecourse analysis of cutaneous lesion size over the 9 week period of *L. major* infection. Measurements were taken at weekly intervals. Error bars, s.e.m.

FIG. 6 illustrates ibrutinib skewed Th1/Th2 plasma cytokines and IgG subisotypes in human CLL patients as well as TCL1 leukemic mice and functionally restores immunity in a leukemia/listeriosis mouse model. FIG. 6C illustrates a schematic representation of the leukemia/listeriosis mouse experiment timecourse. Mice were engrafted via I.V. injection with leukemic cells purified from the spleen of a EµTCL1 transgenic animal. I.V. L. monocytogenes inoculation (5000 CFU) was conducted 14 days after engraftment. FIG. 6D illustrates plasma cytokine analysis of IFNγ 2 days after *Listeria* inoculation. FIG. 6E illustrates plasma cytokine analysis of TNFα 2 days after *Listeria* inoculation. FIG. 6F illustrates plasma cytokine analysis of IL6 2 days after *Listeria* inoculation. FIG. 6G illustrates OVA-MHC I tetramer analysis of peripheral CD8+ T-cells 8 days after *Listeria* m. infection. Percent tetramer positive is displayed along with total number. FIG. 6H illustrates a time course analysis of OVA-MHC I tetramer positive peripheral CD8 T-cells from leukemia/listeriosis mouse study. 5000 CFU of OVA expressing-*Listeria* m. was injected at day 0. Error bars, s.e.m. FIG. 6I illustrates *Listeria* m. cultures derived from mouse livers diluted 1:3 (grams:milliliters) at interim analysis points on day 2 (top row) and day 8 (bottom row) post infection. Colony forming units (CFU) are displayed as calculated from each plate. A 1:1000 dilution of *Listeria* m. innoculum confirms the viability of pre-injected *Listeria* m.

FIG. 9F illustrates large numbers of intermediate-sized, round, neoplastic lymphocytes with moderate amounts of pale basophilic cytoplasm fill the cortex and medullary cords of the lymph nodes, expand the pulp of the spleen, and are scattered in the thymic cortex, in contrast to B220 (B-Cells) (FIG. 9G). These cells in FIG. 9F are widely dispersed in the white fat associated with the lymph nodes and thymus. The cells seem fairly well differentiated as indicated by their regular features and low mitotic rate. The immunohistochemical analysis confirms that the tumor cells arose from the T-cell lineage.

FIG. 14 illustrates in vitro kinase screening data from ibrutinib, alternate BTK inhibitor, and PCI-45292. In-vitro kinase assay IC50 data for ibrutinib, Alternate BTK inhibitor, and PCI-45292. Targets considered irreversible all contain a cysteine residue homologous to Cys488 in BTK which is covalently bound by ibrutinib.

FIG. 21 illustrates ibrutinib PCYC-04753 phase I clinical trial which demonstrates Th1/Th2 skewing due to an elevated level of IFNγ.

DETAILED DESCRIPTION OF THE INVENTION

Certain Terminology

Figure 1A:
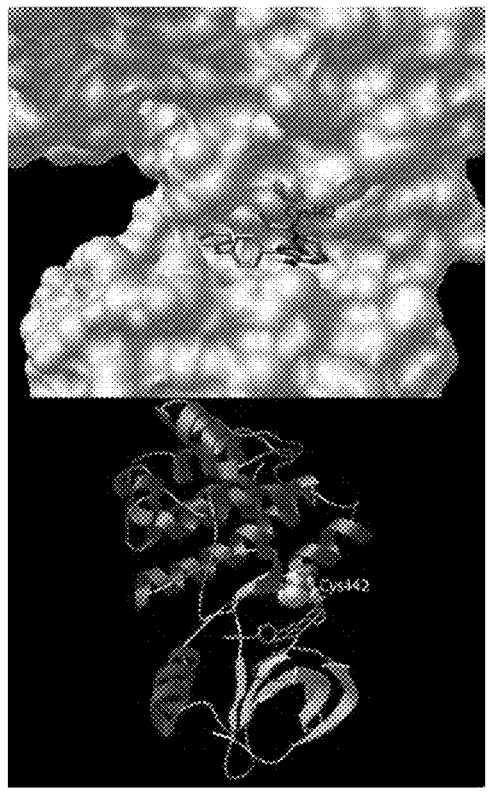
FIG. 1A illustrates in vitro kinase assay $IC_{50}$ data for ibrutinib. Targets considered irreversible all contain a Cys residue homologous to Cys481 in BTK which is covalently bound by ibrutinib.
Figure 1A:
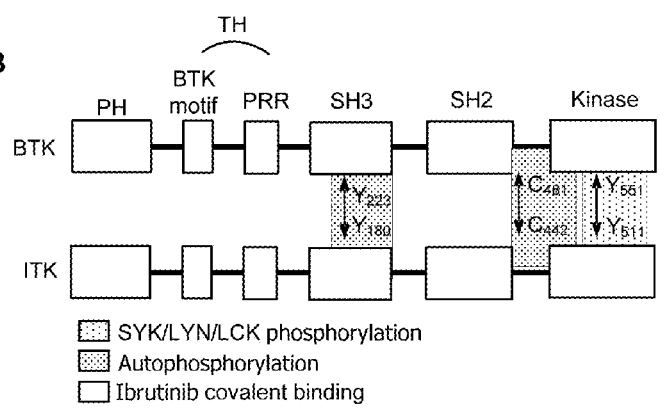
Figure 1A:
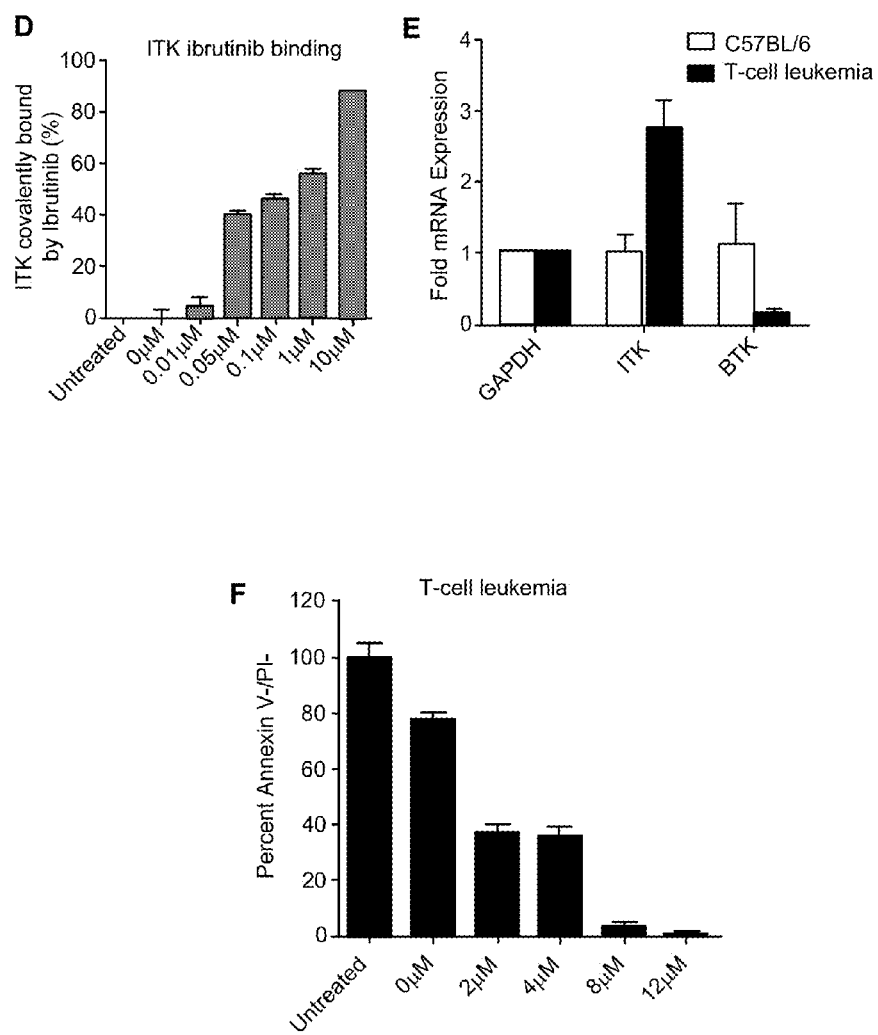

Unless defined otherwise, all technical and scientific terms used herein have the same meaning as is commonly understood by one of skill in the art to which the claimed subject matter belongs. All patents, patent applications, published applications and publications, GENBANK sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information. Generally, the procedures for cell culture, cell infection, antibody production and molecular biology methods are methods commonly used in the art. Such standard techniques can be found, for example, in reference manual, such as, for example, Sambrook et al. (2000) and Ausubel et al. (1994).

As used herein, the singular forms "a," "an" and "the" include plural referents unless the context clearly dictates otherwise. In this application, the use of the singular includes the plural unless specifically stated otherwise. As used herein, the use of "or" means "and/or" unless stated otherwise. Furthermore, use of the term "including" as well as other forms (e.g., "include", "includes", and "included") is not limiting.

As used herein, ranges and amounts can be expressed as "about" a particular value or range. About also includes the exact amount. Hence "about 40 mg" means "about 40 mg" and also "40 mg." Generally, the term "about" includes an amount that would be expected to be within experimental error.

The term "irreversible inhibitor," as used herein, refers to a compound that, upon contact with a target protein (e.g., a kinase) causes the formation of a new covalent bond with or within the protein, whereby one or more of the target protein's biological activities (e.g., phosphotransferase activity) is diminished or abolished notwithstanding the subsequent presence or absence of the irreversible inhibitor.

As used herein, "ACK" and "Accessible Cysteine Kinase" are synonyms. They mean a kinase with an accessible cysteine residue. ACKs include, but are not limited to, BTK, ITK, Bmx/ETK, TEC, EFGR, HER4, HER4, LCK, BLK, C-src, FGR, Fyn, HCK, Lyn, YES, ABL, Brk, CSK, FER, JAK3, SYK.

As used herein, a "covalent TEC family kinase inhibitor" refers to any irreversible inhibitor that reduces or inhibits one more activities of a kinase protein of the covalent Tec kinase family. Exemplary members of the covalent Tec kinase family include ITK (IL-2-Inducible T-cell Kinase), BTK (Bruton's tyrosine kinase), TEC, RLK/TXK (Resting Lymphocyte Kinase) and BMX (Bone Marrow Kinase). In some embodiments, the covalent TEC family kinase inhibitor inhibits two or more members of the covalent Tec kinase family. In some embodiments, the covalent TEC family kinase inhibitor inhibits ITK and BTK. In some embodiments, the covalent TEC family kinase inhibitor inhibits ITK by covalent binding to Cysteine 442 of ITK. In some embodiments, the covalent TEC family kinase inhibitor inhibits BTK by covalent binding to Cysteine 481 of BTK.

As used herein, inhibition of kinase activity refers any decrease in kinase activity in the presence of an inhibitor compared to the same activity in the absence of the inhibitor.

The terms "cancer" and "cancerous" refer to or describe the physiological condition in mammals that is typically characterized by unregulated cell growth. Examples of cancer include, but are not limited to, B-cell lymphoproliferative disorders (BCLDs), such as lymphoma and leukemia, and solid tumors.

By "refractory" in the context of a cancer is intended the particular cancer is resistant to, or non-responsive to, therapy with a particular therapeutic agent. A cancer is refractory to therapy with a particular therapeutic agent either from the onset of treatment with the particular therapeutic agent (i.e., non-responsive to initial exposure to the therapeutic agent), or as a result of developing resistance to the therapeutic agent, either over the course of a first treatment period with the therapeutic agent or during a subsequent treatment period with the therapeutic agent.

As used herein, the $IC_{50}$ refers to an amount, concentration or dosage of a particular test compound that achieves a 50% inhibition of a maximal response, such as inhibition of a TEC kinase, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, the terms "treat," "treating" or "treatment," and other grammatical equivalents, include alleviating, abating or ameliorating one or more symptoms of a disease or condition, ameliorating, preventing or reducing the appearance, severity or frequency of one or more additional symptoms of a disease or condition, ameliorating or preventing the underlying metabolic causes of one or more symptoms of a disease or condition, inhibiting the disease or condition, such as, for example, arresting the development of the disease or condition, relieving the disease or condition, causing regression of the disease or condition, relieving a condition caused by the disease or condition, or inhibiting the symptoms of the disease or condition either prophylactically and/or therapeutically.

As used herein, prevention or prophylaxis refers to the reduction in the risk of developing a disease or condition.

The terms "effective amount", "therapeutically effective amount" or "pharmaceutically effective amount" as used herein, refer to an amount of a BTK inhibitor compound that is sufficient to treat a disorder. In some embodiments, the result is a reduction in and/or alleviation of the signs, symptoms, or causes of a disorder, or any other desired alteration of a biological system. For example, an "effective amount" for therapeutic uses is the amount of the composition comprising a BTK inhibitor compound disclosed herein required to provide a clinically significant decrease in a disorder. An appropriate "effective" amount in any individual case is determined using any suitable technique, (e.g., a dose escalation study).

The term "pharmaceutically acceptable" as used herein, refers to a material, (e.g., a carrier or diluent), which does not abrogate the biological activity or properties of a BTK inhibitor compound described herein, and is relatively non-toxic (i.e., the material is administered to an individual without causing undesirable biological effects or interacting in a deleterious manner with any of the components of the composition in which it is contained).

As used herein, "minimal residual disease (MRD)" refers to small numbers of cancer cells that remain in the patient during treatment, or after treatment when the patient is in remission (i.e. no symptoms or signs of disease).

As used herein, "survival" refers to the patient remaining alive, and includes disease free survival (DFS) and overall survival (OS). Survival is estimated by the Kaplan-Meier method, and any differences in survival are computed using the stratified log-rank test.

As used herein, "disease free survival (DFS)" refers to the patient remaining alive, without return of the cancer, for a defined period of time such as about 1 year, about 2 years, about 3 years, about 4 years, about 5 years, about 10 years, or more from initiation of treatment or from initial diagnosis. In one embodiment, DFS is analyzed according to the intent-to-treat principle, i.e., patients are evaluated on the basis of their assigned therapy. The events used in the analysis of DFS include local, regional and distant recurrence of cancer, occurrence of secondary cancer, and death from any cause in patients without a prior event (e.g., cancer recurrence or second primary cancer).

As used herein, "overall survival" refers to the patient remaining alive for a defined period of time, such as about 1 year, about 2 years, about 3 years, about 4 years, about 5 years, about 10 years, or more from initiation of treatment or from initial diagnosis.

As used herein, "extending survival" or "increasing the likelihood of survival" refers to increasing DFS and/or OS or increasing the probability of remaining alive and/or disease-free at a given point in time in a treated patient relative to an untreated patient (i.e. relative to a patient not treated with a covalent TEC family kinase inhibitor), or relative to a control treatment protocol, such as treatment only with the chemotherapeutic agent or biologic agent, such as those use in the standard of care for a particular cancer). Survival is monitored for at least about two months, four months, six months, nine months, or at least about 1 year, or at least about 2 years, or at least about 3 years, or at least about 4 years, or at least about 5 years, or at least about 10 years, etc., following the initiation of treatment or following the initial diagnosis.

As used herein, the term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

As used herein, "monotherapy" refers to a therapeutic regimen that includes only a single therapeutic agent for the treatment of the cancer or tumor during the course of the treatment period. Monotherapy using a covalent TEC family kinase inhibitor means that the covalent TEC family kinase inhibitor is administered in the absence of an additional anticancer therapy during treatment period.

As used herein, "adjuvant therapy" refers to a therapy administered in combination with or following a primary therapy in order to enhance or modify the effect of the first therapy. In some embodiments, an adjuvant for cancer therapy is administered following an anticancer therapy, so as to reduce the risk of disease recurrence of the cancer, either local or metastatic. In some embodiments, an adjuvant for vaccine therapy, such as an anticancer vaccine or a antiviral vaccine therapy, is administered in combination with a vaccine in order to enhance the efficacy of the vaccine. In some embodiments, an adjuvant for viral therapy is administered in combination with one or more antiviral agents in or to enhance the efficacy of the antiviral therapy. In some embodiments, an adjuvant therapy administered to an individual enhances the Th1 or cytotoxic immune response in the individual.

As used herein, "standard of care" therapy refers to a therapy routinely used to treat a particular disease or disorder. As used herein, "standard of care" chemotherapy refers to the chemotherapeutic agents routinely used to treat a particular cancer. As used herein, "standard of care" antiviral therapy refers to the antiviral agents routinely used to treat a particular virus infection. As used herein, "standard of care" antibacterial therapy refers to the antibacterial agents routinely used to treat a particular bacterial infection.

As used herein, "definitive surgery" is used as that term is used within the medical community, and typically refers to surgery where the outcome is potentially curative. Definitive surgery includes, for example, procedures, surgical or otherwise, that result in removal or resection of the tumor, including those that result in the removal or resection of all grossly visible tumor. Definitive surgery includes, for example, complete or curative resection or complete gross resection of the tumor. Definitive surgery includes procedures that occurs in one or more stages, and includes, for example, multi-stage surgical procedures where one or more surgical or other procedures are performed prior to resection of the tumor. Definitive surgery includes procedures to remove or resect the tumor including involved organs, parts of organs and tissues, as well as surrounding organs, such as lymph nodes, parts of organs, or tissues.

As used herein, the terms "cancer" and "cancerous" refer to or describe the physiological condition in mammals that is typically characterized by unregulated cell growth. Included in this definition are benign and malignant cancers as well as dormant tumors or micrometastatses. The term cancer includes solid tumors and hematologic cancers. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, ovarian cancer, thyroid cancer, proximal or distal bile duct carcinoma, hepatic carcinoma and various types of head and neck cancer, T-cell lymphoma, as well as B-cell lymphoma, including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenström's Macroglobulinemia; chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

As used herein the term "T-helper type 2 (Th2)-mediated disease" means a disease which is characterized by the overproduction of Th2 cytokines, including those that result from an overproduction or bias in the differentiation of T-cells into the Th2 subtype. Such diseases include, for example, cancer (e.g., hematologic malignancies and solid tumors), exacerbation of infection with infectious diseases (e.g., *Leishmania major, Listeria monocytogenes, Mycobacterium leprae, Candida albicans, Toxoplasma gondi*, Hepatitis C virus (HCV), Respiratory Syncytial virus (RSV), human immunodeficiency virus (HIV)) and allergic disorders, such as anaphylactic hypersensitivity, asthma, allergic rhinitis, atopic dermatitis, vernal conjunctivitis, eczema, urticaria and food allergies, autoimmune diseases, inflammatory diseases, inflammatory bowel disease, ulcerative colitis, systemic lupus erythematodes, myasthenia gravis, systemic progressive scleroderma, rheumatoid arthritis, interstitial cystitis, Hashimoto's diseases, Basedow's diseases, autoimmune hemolytic anemia, idiopathic thrombocytopenic purpura, Goodpasture's syndrome, atrophic gastritis, pernicious anemia, Addison diseases, pemphigus, pemphigoid, lenticular uveitis, sympathetic ophthalmia, primary biliary cirrhosis, active chronic hepatitis, Sjogren's syndrome, multiple myositis, dermatomyositis, polyarteritis nodosa, rheumatic fever, glomerular nephritis (lupus nephritis, IgA nephropathy, and the like), allergic encephalitis, atopic allergic diseases (for example, bronchial asthma, allergic rhinitis, allergic dermatitis, allergic conjunctivitis, pollinosis, urticaria, food allergy and the like), Omenn's syndrome, vernal conjunctivitis and hypereosinophilic syndrome.

As used herein, "metastasis" refers to the spread of cancer from its primary site to other places in the body. In certain embodiments, cancer cells break away from a primary tumor, penetrate into lymphatic and blood vessels, circulate through the bloodstream, and grow in a distant focus (metastasize) in normal tissues elsewhere in the body. In certain embodiments, metastasis is either local or distant. Metastasis is believed to be a sequential process, contingent on tumor cells breaking off from the primary tumor, traveling through the bloodstream, and stopping at a distant site. At the new site, the cells establish a blood supply and grow to form a life-threatening mass. Both stimulatory and inhibitory molecular pathways within the tumor cell regulate this behavior, and interactions between the tumor cell and host cells in the distant site are also significant.

As used herein, "cancer recurrence", "cancer relapse", "relapsed or refractory disease" are used interchangeably herein to refer to a return of cancer following treatment, and includes return of cancer in the primary organ, as well as distant recurrence, where the cancer returns outside of the primary organ.

As used herein, a subject at "high risk of cancer recurrence or relapse" is one who has a greater chance of experiencing recurrence of cancer. A subject's risk level can be determined by a skilled physician.

"Decrease in risk of cancer recurrence or relapse" is meant reducing the likelihood of experiencing recurrence of cancer relative to an untreated patient (i.e., relative to a patient not treated with a covalent TEC family kinase inhibitor), or relative to a control treatment protocol, such as treatment only with the chemotherapeutic agent, such as those used in the standard of care for the particular cancer. Cancer recurrence is monitored for at least about two months, four months, six months, nine months, or at least about 1 year, or at least about 2 years, or at least about 3 years, or at least about 4 years, or at least about 5 years, or at least about 10 years, etc., following the initiation of treatment or following the initial diagnosis.

As used herein, "anticancer therapy" refers to a therapy useful in treating cancer. Examples of anticancer therapeutic agents include, but are limited to, e.g., surgery, chemotherapeutic agents, biologic agents, growth inhibitory agents, cytotoxic agents, nanoparticle agents, agents used in radiation therapy, agents used in photodynamic therapy, agents used in hyperthermia therapy (e.g., radiofrequency ablation), anti-angiogenesis agents, apoptotic agents, anti-tubulin agents, siRNA agents, enzyme/pro-drug agents, nucleic acid agents, oliopeptide agents, and other agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (Tarceva®), platelet derived growth factor inhibitors (e.g., Gleevec® (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, or combination thereof.

As used herein, "cytotoxic agent" as used herein refers to a substance that inhibits or prevents the function of cells and/or causes destruction of cells. The term is intended to include radioactive isotopes, chemotherapeutic agents, and toxins such as small molecule toxins or enzymatically active toxins of bacterial, fungal, plant or animal origin, including fragments and/or variants thereof.

As used herein, a "chemotherapeutic agent" is a chemical compound useful in the treatment of cancer. Examples of chemotherapeutic agents include is a chemical compound useful in the treatment of cancer. Examples of chemotherapeutic agents include alkylating agents such as rituximab, carfilzomib, fludarabine, cyclophosphamide, vincristine, prednisalone. chlorambucil, ifosfamide, doxorubicin, mesalazine, thalidomide, revlimid, lenalidomide, temsirolimus, everolimus, fostamatinib, paclitaxel, docetaxel, ofatumumab, dexamethasone, prednisone, CAL-101, ibritumomab, tositumomab, bortezomib, pentostatin, endostatin, ritonavir, ketoconazole, thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as bendamustine, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); gefitinib; erlotinib; procarbazine; prednisone; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); a CD22 inhibitor, a Bcl-2 inhibitor, an IRAK 1/4 inhibitor, a microtubule inhibitor, a Topo II inhibitor, anti TWEAK, anti-IL17 bispecific antibody, a CK2 inhibitor, anaplastic lymphoma kinase (ALK) and c-Met inhibitors, demethylase enzyme inhibitors such as demethylase, HDM, LSDI and KDM, fatty acid synthase inhibitors such as spirocyclic piperidine derivatives, glucocorticosteriod receptor agonist, fusion anti-CD 19-cytotoxic agent conjugate, antimetabolite, p70S6K inhibitor, immune modulators, AKT/PKB inhibitor, procaspase-3 activator PAC-1, BRAF inhibitor, lactate dehydrogenase A (LDH-A) inhibitor, CCR2 inhibitor, CXCR4 inhibitor, chemokine receptor antagonists, DNA double stranded break repair inhibitors, NOR202, GA-101, TLR2 inhibitor; inhibitors of PKC-alpha, Raf, H-Ras, HDAC, Cyp3A4, IRAK, protease, AKT, Erk, JAK (e.g., ruxolitinib, baricitinib, CYT387, lestauritinib, pacritinib, TG101348, SAR302503, tofacitinib (Xeljanz), etanercept (Enbrel), GLPG0634, R256), EGFR (e.g., erlotinib (Tarceva®)) and VEGF-A that reduce cell proliferation and pharmaceutically acceptable salts, acids or derivatives of any of the above; GA-1101; proteosome inhibitors such as disulfiram, epigallocatechin-3-gallate, salinosporamide A, ONX0912, CEP-18770, or MLN9708; R-406; lenalinomide; spirocyclic piperidine derivatives; quinazoline carboxamide azetidine compounds; ACK inhibitors such as AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), or HM71224 (Hanmi Pharmaceutical Company Limited).

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

As used herein, the term "biologic agent" is a generic term referring to any biological molecules derived from protein, carbohydrate, lipid or nucleic acid and is useful in the treatment of a disease. A non-exhaustive list of biologic agents include: TNF blockers (e.g., etanercept, infliximab, adalimumab, certolizumab pegol, and golimumab); interleukin 1 (IL-1) blockers such as anakinra; monoclonal antibodies (e.g., Trastuzumab (Herceptin), Bevacizumab (Avastin), Cetuximab (Erbitux), Panitumumab (Vectibix), Ipilimumab (Yervoy), Rituximab (Rituxan and Mabthera), Alemtuzumab (Campath), Ofaturmumab (Arzerra), Gemtuzumab ozogamicin (Mylotarg), Brentuximab vedotin (Adcetris), $^{90}$Y-Ibritumomab Tiuxetan (Zevalin) and $^{131}$I-Tositumomab (Bexxar)); T-cell costimulation blockers such as abatacept; Interleukin 6 (IL-6) blockers such as tocilizumab and antibodies against oxidized phospholipids and/or oxidized lipoproteins and/or fragments or derivatives thereof.

As used herein, the terms "biomarkers" and "markers" are used interchangeably and are generic terms referring to any biological molecules found either in blood, other body fluids, or tissues. A non-exhaustive list of biomarkers and markers include: ZAP70, t(14,18), 13-2 microglobulin, p53 mutational status, ATM mutational status, del(17)p, del(11)q, del(6)q, CD3, CD4, CD5, CD11c, CD19, CD20, CD22, CD25, CD26, CD28, CD30, CD33, CD38, CD45, CD52, CD62, CD81, CD94, CD103, CD119, CD152, CD138, CD183, CD184, CD191 (CCR1), CD195, CD197 (CCR7), CD212, CD278, CCR3, CCR4, CCR8, TBX21, NKG7, XCL1 (lymphotactin), TXK, GZMB (granzyme B), S100P, LIR9, KIR3DL2, VAV3, DLG5, MMP-9, MS4A4A, lymphotoxin, perforin, t-bet, Tim-1, Tim-3, TRANCE, GATA-3, c-maf, CRTH2, ST2L/T1, secreted, surface or cytoplasmic immunoglobulin expression, $V_H$ mutation status; chemokines such as GCP-2 (granulocyte chemotactic protein 2), Gro-a (growth related oncogene a), Gro-β (growth related oncogene β), Gro-γ (growth related oncogene γ), NAP-2 (neutrophil activating protein), ENA-78 (epithelial-cell-derived neutrophil-activating chernokine), IP-10(Interferon-inducible protein-10), Mig (monokine induced by interferone γ), 1-TAC (Interferon-inducible T-cell alpha chemoattractant), SDF-1 (stromal cell-derived factor-1), PBSF (pre-B-cell growth stimulating factor), BCA-1 (B-lymphocyte chemoattractant 1), MIP-1 (macrophage inflammatory protein 1), RANTES (regulated upon activation, normal T-cell expressed and secreted), MIP-5 (macrophage inflammatory protein 5), MCP-1 (monocyte chemoattractant protein 1), MCP-2 (monocyte chemoattractant protein 2), MCP-3 (monocyte chemoattractant protein 3), MCP-4 (monocyte chemoattractant protein 4), Eotaxin, TARC (thymus- and acticvation-regulated chemokine), MIP-1 a (macrophage inflammatory protein 1a), MIP-1 β (macrophage inflammatory protein 1 β), Exodus-1, ELC (Ebl1 ligand chemokine); cytokines such as lymphokines, monokines, traditional polypeptide hormones, growth hormone (e.g., human growth hormone, N-methionyl human growth hormone, bovine growth hormone); parathyroid hormone; thyroxine; insulin; proinsulin; relaxin; prorelaxin; glycoprotein hormones (e.g., follicle stimulating hormone (FSH), thyroid stimulating hormone (TSH) and luteinizing hormone (LH)); epidermal growth factor; hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) (e.g., TGF-alpha and TGF-beta); insulin-like growth factor-I and -II; erythropoietin (EPO); osteoinductive factors; interferons (e.g., interferon-alpha, -beta and -gamma); colony stimulating factors (CSFs) (e.g., macrophage-CSF (M-CSF), granulocyte-macrophage-CSF (GM-CSF) and granulocyte-CSF (G-CSF)); interleukins (ILs) (e.g., IL-1, IL-1α, IL-2, IL-3, IL-4, IL-5, IL-6, IL-7, IL-8, IL-9, IL-10, IL-11, IL-12, IL-13, IL-15, IL-16, IL-17, IL-18, IL-19, IL-20, IL-21, IL-22, IL-23, IL-24, IL-25, IL-26, IL-27, IL-28, IL-29, IL-32, IL-33, IL-35 and IL-36); a tumor necrosis factor (e.g., TNF-αlpha and TNF-beta) and other polypeptide factors including LIF and kit ligand (KL). As used herein, the terms biomarker and marker include proteins from natural sources or from recombinant cell culture and biologically active equivalents of the native sequence biomarkers/markers.

As used herein, the term "radiation therapy" includes, but is not limited to, x-rays or gamma rays that are delivered form either an externally applied source such as a beam, or by implantation of small radioactive sources. Radionuclides, which depending up the radionuclide, amount and application can be used for diagnosis and/or for treatment. They include, but are not limited to, for example, a compound or molecule containing 32Phosphorus, 60Cobalt, 90Yttrium, 99Technitium, 103Palladium, 106Ruthenium, 111indium, 117Lutetium, 125Iodine, 131Iodine, 137Cesium, 153Samarium, 186Rhenium, 188Rhenium, 192Iridium, 198Gold, 211Astatine, 212Bismuth or 213Bismuth.

As used herein, the term "photosensitizing agents" includes, but is not limited to, indocyanine green, toluidine blue, aminolevulinic acid, texaphyrins, benzoporphyrins, phenothiazines, phthalocyanines, porphyrins such as sodium porfimer, chlorins such as tetra(m-hydroxyphenyl)chlorin or tin(IV) chlorin e6, purpurins such as tin ethyl etiopurpurin, purpurinimides, bacteriochlorins, pheophorbides, pyropheophorbides or cationic dyes.

As used herein, the term "pathogenic infection" is a generic term for infection due to a virus or a bacterium. Examples of infectious virus include: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bunyaviridae (e.g., Hantaan viruses, bunya viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses'); Poxyiridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Helicobacter pyloris, Borelia burgdorferi, Legionella pneumophilia, Mycobacteria* spp. (e.g., *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus Bovis, Streptococcus* (anaerobic spp.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidum, Treponema pertenue, Leptospira*, and *Actinomyces israelli*.

Examples of infectious fungi include: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium falciparum* and *Toxoplasma gondii*.

As used herein, the term "antibody" is used in the broadest sense and covers fully assembled antibodies, antibody fragments that bind antigen (e.g., Fab, F(ab')$_2$, Fv, single chain antibodies, diabodies, antibody chimeras, hybrid antibodies, bispecific antibodies, humanized antibodies, and the like), and recombinant peptides comprising the forgoing.

As used herein, the terms "monoclonal antibody" and "mAb" as used herein refer to an antibody obtained from a substantially homogeneous population of antibodies, i.e., the individual antibodies comprising the population are identical except for possible naturally occurring mutations that are present in minor amounts.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

As used herein, the term "variable" refers to the fact that certain portions of the variable domains differ extensively in sequence among antibodies. Variable regions confer antigen-binding specificity. However, the variability is not evenly distributed throughout the variable domains of antibodies. It is concentrated in three segments called complementarity determining regions (CDRs) or hypervariable regions, both in the light chain and the heavy-chain variable domains. The more highly conserved portions of variable domains are celled in the framework (FR) regions. The variable domains of native heavy and light chains each comprise four FR regions, largely adopting a 13-pleated-sheet configuration, connected by three CDRs, which form loops connecting, and in some cases forming part of, the f3-pleated-sheet structure. The CDRs in each chain are held together in close proximity by the FR regions and, with the CDRs from the other chain, contribute to the formation of the antigen-binding site of antibodies (see, Kabat et al. (1991) NIH PubL. No. 91-3242, Vol. I, pages 647-669). The constant domains are not involved directly in binding an antibody to an antigen, but exhibit various effector functions, such as Fc receptor (FcR) binding, participation of the antibody in antibody-dependent cellular toxicity, initiation of complement dependent cytotoxicity, and mast cell degranulation.

As used herein, the term "hypervariable region," when used herein, refers to the amino acid residues of an antibody that are responsible for antigen-binding. The hypervariable region comprises amino acid residues from a "complementarily determining region" or "CDR" (i.e., residues 24-34 (L1), 5056 (L2), and 89-97 (L3) in the light-chain variable domain and 31-35 (H1), 50-65 (H2), and 95-102 (H3) in the heavy-chain variable domain; Kabat et al. (1991) Sequences of Proteins of Immunological Interest, 5th Ed. Public Health Service, National Institute of Health, Bethesda, Md.) and/or those residues from a "hypervariable loop" (i.e., residues 26-32 (L1), 50-52 (L2), and 91-96 (L3) in the light-chain variable domain and (H1), 53-55 (H2), and 96-101 (13) in the heavy chain variable domain; Clothia and Lesk, (1987) J. Mol. Biol., 196:901-917). "Framework" or "FR" residues are those variable domain residues other than the hypervariable region residues, as herein deemed.

"Antibody fragments" comprise a portion of an intact antibody. In some embodiments, the portion of an intact antibody is an antigen-binding or variable region of the intact antibody. Examples of antibody fragments include Fab, Fab, F(ab')2, and Fv fragments; diabodies; linear antibodies (Zapata et al. (1995) Protein Eng. 10:1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_{H1}$) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

The "light chains" of antibodies (immunoglobulins) from any vertebrate species assigned to one of two clearly distinct types, called kappa (κ) and lambda (λ), based on the amino acid sequences of their constant domains.

Depending on the amino acid sequence of the constant domain of their heavy chains, immunoglobulins are assigned to different classes. There are five major classes of human immunoglobulins: IgA, IgD, IgE, IgG, and IgM, and several of these are further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Different isotypes have different effector functions. For example, human IgG1 and IgG3 isotypes have ADCC (antibody dependent cell-mediated cytotoxicity) activity.

As used herein, the term "viral load" refers to the amount of viral particles or toxic fragments thereof in a biological fluid, such as blood or plasma. "Viral load" encompasses all viral particles, infectious, replicative and non-infective, and fragments thereof. Therefore, viral load represents the total number of viral particles and/or fragments thereof circulating in the biological fluid. Viral load can therefore be a measure of any of a variety of indicators of the presence of a virus, such as viral copy number per unit of blood or plasma or units of viral proteins or fragments thereof per unit of blood or plasma. Viral load can be determined by techniques known by one of skill in the art, e.g., polymerase-chain reaction (PCR) test and plaque-forming unit test. For example, viral load values can be determined by measuring the quantity of viral nucleic acid at the beginning of a treatment as well as at each of the virus measurement time points before, during, or after the treatment. A reduction in viral load during the course of treatment can be determined by comparing the viral load values obtained at different virus measurement time points. The rate at which the viral load of a patient is reduced can be determined by plotting the reduction in viral load value against time.

As used herein, the terms "subject", "individual" and "patient" are used interchangeably. None of the terms are to be interpreted as requiring the supervision of a medical professional (e.g., a doctor, nurse, physician's assistant, orderly, hospice worker). As used herein, the subject can be any animal, including mammals (e.g., a human or non-human animal) and non-mammals. In one embodiment of the methods and compositions provided herein, the mammal is a human.

Ibrutinib and Modulation of the Immune Response

In chronic lymphocytic leukemia (CLL), mounting evidence points to an aberrant tumor associated Th2 bias that drives leukemic cell immune evasion, promotes formation of a supportive niche microenvironment, and functionally cripples innate and adaptive immunity. The end result is a high incidence of infections which is the primary cause of mortality in CLL. This same Th2 bias is induced by many other types of cancer. Th2 CD4 T-cells are singularly dependent upon IL-2-inducible T-cell kinase (ITK) for activation whereas Th1 CD4 and CD8 T-cells have compensatory resting lymphocyte kinase (RLK) which conducts T-cell receptor activation even in the absence of ITK. In some embodiments, a clinically viable ITK inhibitor would be suitable for targeting immune suppression associated with CLL and other types of cancer.

Ibrutinib, a confirmed inhibitor of the Bruton's tyrosine kinase (BTK) that irreversibly blocks downstream B-cell receptor activation, has demonstrated clinical activity in phase I/II clinical trials resulting in durable remissions in CLL. Similarly, combination therapy with ibrutinib has advanced into phase III clinical trials. Recently, studies have unveiled a previously uncharacterized Th1 cytokine switch in ibrutinib-treated CLL patients, which was not attributed to B-lymphocytes. As described herein, this ibrutinib-induced Th1 T-cell skewing was confirmed using the EμTCL1 mouse model of leukemia. Such alterations in cytokine patterns were similar to mouse studies in which genetic ablation of ITK subverted Th2 immunity, thereby potentiating Th1-based adaptive immunity. The striking homology between BTK and ITK combined with in silico docking studies and in vitro kinase inhibition profiles with ibrutinib suggest that ibrutinib is a clinically viable irreversible ITK inhibitor.

Cellular probe assays described herein confirmed that the active site of ITK was covalently blocked by ibrutinib at pharmacologically relevant doses. Comprehensive molecular analyses of T-cell signaling confirmed this in the Jurkat cell line. It was further confirmed both molecular and functional outcomes in primary and in vitro polarized Th1 and Th2 CD4 T-cells. In addition, it was found that mutation of the ITK-Cys442 covalent binding residue for ibrutinib alleviated molecular inhibition. It was also demonstrated that Th1 and CD8 T-cell restricted expression of RLK provides a compensatory platform for T-cell activation offering a molecular explanation for the selective outgrowth of cytotoxic Th1 biased immunity. This effect was further confirmed using T-cells directly derived from CLL patients.

To demonstrate that ibrutinib-induced ITK inhibition had direct clinical relevance in the setting of CLL a novel listeriosis/leukemia mouse model was utilized. In this model, complete recovery of functional immunity was demonstrated, and all ibrutinib treated mice survived a potentially lethal *Listeria monocytogenes* infection. In certain embodiments, ibrutinib's irreversible ITK inhibitory effects are applicable for use as an adjuvant for cancer therapy and for the treatment of a number of other autoimmune, inflammatory, and viral diseases, including Hepatitis C virus, influenza A and human immunodeficiency virus (HIV) infection.

Anticancer Therapy Adjuvant

Described herein, in certain embodiments, are methods of adjuvant therapy for cancer comprising administering to a subject with cancer an effective amount of a covalent TEC family kinase inhibitor. In some embodiments, the covalent TEC family kinase inhibitor inhibits the kinase activity of one or more members of the TEC family of kinases (e.g. ITK, BTK, TEC, RLK and BMX). In some embodiments, the covalent TEC family kinase inhibitor inhibits the kinase activity of ITK. In some embodiments, the covalent TEC family kinase inhibitor covalently binds to Cysteine 442 of ITK. In some embodiments, the covalent TEC family kinase inhibitor covalently binds to Cysteine 481 of BTK. In some embodiments, the covalent TEC family kinase inhibitor is selected from among ibrutinib (PCI-32765), PCI-45292, PCI-45466, AVL-101, AVL-263, AVL-291, AVL-292, ONO-WG-37, BMS-488516, BMS-509744, CGI-1746, CTA-056, GDC-0834, HY-11066 (also, CTK4I7891, HMS3265G21, HMS3265G22, HMS3265H21, HMS3265H22, 439574-61-5, AG-F-54930), ONO-4059, ONO-WG37, PLS-123, RN486, HM71224, or a combination thereof. In some embodiments, the covalent TEC family kinase inhibitor is ibrutinib. Additional covalent TEC family kinase inhibitors for use in any of the methods provided herein are found, for example, in U.S. Pat. Nos. 7,547,689, 7,960,396 and U.S. Patent Publication Nos. US 2009-0197853 A1 and US 2012-0065201 A1, all of which are incorporated by reference in their entirety.

In some embodiments, the methods of adjuvant therapy for cancer comprise administering to a subject with cancer an effective amount of a covalent TEC family kinase inhibitor to treat the cancer by modulation of an immune response. In some embodiments, the covalent TEC family kinase inhibitor increases a Th1 immune response against the cancer compared to no treatment with the covalent TEC family kinase inhibitor. In some embodiments, the covalent TEC family kinase inhibitor decreases a Th2 immune response against the cancer compared to no treatment with the covalent TEC family kinase inhibitor. In some embodiments, the covalent TEC family kinase inhibitor alters the ratio of Th1-Th2 immune response against the cancer compared to no treatment with the covalent TEC family kinase inhibitor. In some embodiments, the covalent TEC family kinase inhibitor increases the ratio of Th1-Th2 immune response against the cancer compared to no treatment with the covalent TEC family kinase inhibitor. In some embodiments, the covalent TEC family kinase inhibitor increases the population of Th1 cells by about 1%, 2%, 3%, 4%, 5%, 10%, 20%, 30%, 40%, 50%, 60%, 70%, 80%, 90% or greater compared to no treatment with the covalent TEC family kinase inhibitor. In some embodiments, the covalent TEC family kinase inhibitor decreases the population of Th2 cells by about 1%, 2%, 3%, 4%, 5%, 10%, 20%, 30%, 40%, 50%, 60%, 70%, 80%, 90% or greater compared to no treatment with the covalent TEC family kinase inhibitor. In some embodiments, the covalent TEC family kinase inhibitor increases the expression of one or more Th1 related markers. In some embodiments, the covalent TEC family kinase inhibitor increases the expression of one or more Th1 related markers by about 1%, 2%, 3%, 4%, 5%, 10%, 20%, 30%, 40%, 50%, 60%, 70%, 80%, 90% or greater compared to no treatment with the covalent TEC family kinase inhibitor. In some embodiments, the one or more Th1 related marker includes CCR1, CD4, CD26, CD94, CD119, CD183, CD195, CD212, GM-CSF, Granzyme B, IFN-α, IFN-γ, IL-2, IL-12, IL-15, IL-18R, IL-23, IL-27, IL-27R, Lymphotoxin, perforin, t-bet, Tim-3, TNF-α, TRANCE, sCD40L, or any combination thereof. In some embodiments, the one or more Th1 related markers includes IFN-γ, IL-2, IL-12 or any combination thereof. In some embodiments, the covalent TEC family kinase inhibitor decreases the expression of Th2 related markers. In some embodiments, the covalent TEC family kinase inhibitor decreases the expression of Th2 related markers by about 1%, 2%, 3%, 4%, 5%, 10%, 20%, 30%, 40%, 50%, 60%, 70%, 80%, 90% or greater compared to no treatment with the covalent TEC family kinase inhibitor. In some embodiments, the one or more Th2 related markers includes CCR3, CCR4, CCR7, CCR8, CD4, CD30, CD81, CD184, CD278, c-maf, CRTH2, Gata-3, GM-CSF, IFN γR, IgD, IL-1R, IL-4, IL-5, IL-6, IL-9, IL-10, IL-13, IL-15, ST2L/T1, Tim-1, or any combination thereof. In some embodiments, the one or more Th1 related markers includes IL-4, IL-10, IL-13, or any combination thereof.

In certain embodiments, Th1 and Th2 related markers are analyzed from a solid or a fluid sample from a subject. In some embodiments, a solid sample comprises peripheral blood mononuclear cells (PBMC). In some embodiments, a fluid sample comprises blood, urine or spinal fluid.

Described herein, in certain embodiments, are methods of adjuvant therapy for cancer comprising administering to a subject with cancer an effective amount of a covalent TEC family kinase inhibitor to prevent, reduce the risk of, or delay relapsed or refractory disease. In some embodiments, the risk of relapsed or refractory disease is reduced by about 10%, 20%, 30%, 40%, 50%, 60%, 70%, 80%, 90% or greater compared to no treatment with the covalent TEC family kinase inhibitor.

In some embodiments, the covalent TEC family kinase inhibitor is administered so as to extend disease free survival (DFS) in the subject. In some embodiments, DFS is assessed 1, 2, 3, 4, 5, 6, 7, 8, 9, 10, 15, 20, 25 years or later following initiation of covalent TEC family kinase inhibitor administration. In some embodiments, DFS is improved by about 5 years, 10 years, 15 years, 20 years, 25 years or longer compared to no treatment with the covalent TEC family kinase inhibitor. In some embodiments, the subject is disease free for about 6 months, 1 year, 2 years, 3 years, 4 years, 5 years, 6 years, 7 years, 8 years, 9 years, 10 years, 15 years, 20 years, 25 years or longer following last administration of the covalent TEC family kinase inhibitor.

In some embodiments, the covalent TEC family kinase inhibitor is administered so as to extend overall survival (OS) in the subject. In some embodiments, OS is assessed 1, 2, 3, 4, 5, 6, 7, 8, 9, 10, 15, 20, 25 years or later following initiation of covalent TEC family kinase inhibitor administration. In some embodiments, OS is improved by about 5 years, 10 years, 15 years, 20 years, 25 years or longer compared to no treatment with the covalent TEC family kinase inhibitor. In some embodiments, the subject is disease free for about 6 months, 1 year, 2 years, 3 years, 4 years, 5 years, 6 years, 7 years, 8 years, 9 years, 10 years, 15 years, 20 years, 25 years or longer following last administration of the covalent TEC family kinase inhibitor.

In some embodiments, the methods of adjuvant therapy comprise administering to a subject, characterized as disease free or having minimal residual disease (MRD) following treatment of a cancer with a first anticancer therapy, an effective amount of the covalent TEC family kinase inhibitor to prevent, reduce the risk of, or delay relapsed or refractory disease, wherein the first anticancer therapy is not a covalent TEC family kinase inhibitor. In some embodiments, the risk of relapsed or refractory disease is reduced by about 10%, 20%, 30%, 40%, 50%, 60%, 70%, 80%, 90% or greater compared to no treatment with the covalent TEC family kinase inhibitor. In some embodiments, the anticancer therapy is selected from among administration of a chemotherapeutic agent, a biologic agent, radiation therapy, bone marrow transplant or surgery. In some embodiments, the subject has no detectable cancer following treatment of the cancer with the first anticancer therapy and prior to administration of the covalent TEC family kinase inhibitor. In some embodiments, the subject has no detectable primary or metastatic tumors following treatment of the cancer with the first anticancer therapy and prior to administration of the covalent TEC family kinase inhibitor. In some embodiments, the subject has no detectable circulating tumor cells in a fluid sample following treatment of the cancer with the first anticancer therapy and prior to administration of the covalent TEC family kinase inhibitor. In some embodiments, the fluid sample is a blood, spinal fluid or urine sample.

In some embodiments, the methods of adjuvant therapy comprise administering to a subject having a tumor an effective amount of a covalent TEC family kinase inhibitor to prevent or delay progression of the tumor, wherein the subject is administered a first anticancer therapy prior to administration of the covalent TEC family kinase inhibitor, wherein the first anticancer therapy does not comprise a covalent TEC family kinase inhibitor. In some embodiments, the methods of adjuvant therapy comprise administering to a subject having a tumor an effective amount of a covalent TEC family kinase inhibitor to promote further regression of the tumor, wherein the subject is administered a first anticancer therapy prior to administration of the covalent TEC family kinase inhibitor, wherein the first anticancer therapy does not comprise a covalent TEC family kinase inhibitor. In some embodiments, the methods of adjuvant therapy comprise administering to a subject having a tumor an effective amount of a covalent TEC family kinase inhibitor to eliminate the tumor, wherein the subject is administered a first anticancer therapy prior to administration of the covalent TEC family kinase inhibitor, wherein the first anticancer therapy does not comprise a covalent TEC family kinase inhibitor. In some embodiments, the first anticancer therapy is selected from among administration of a chemotherapeutic agent, a biologic agent, radiation therapy, bone marrow transplant or surgery. In some embodiments, the subject has no detectable circulating tumor cells following treatment with the anticancer therapy, prior to initiation of covalent TEC family kinase inhibitor administration. In some embodiments, the subject, prior to initiation of covalent TEC family kinase inhibitor administration, has a decreased amount of detectable circulating tumor cells following treatment with the anticancer therapy compared to before treatment with the anticancer therapy. In some embodiments, the subject has no detectable cancer following treatment of the cancer with the first anticancer therapy and prior to administration of the covalent TEC family kinase inhibitor. In some embodiments, the subject has no detectable primary or metastatic tumors following treatment of the cancer with the first anticancer therapy and prior to administration of the covalent TEC family kinase inhibitor.

In some embodiments, the covalent TEC family kinase inhibitor is administered following surgery for removal of a tumor. In some embodiments, the surgery for removal of a tumor is a definitive surgery. In some embodiments, the subject has no detectable tumors following surgery. In some embodiments, the surgery for removal of a tumor is a partial removal of the tumor. In some embodiments, the subject has not been administered chemotherapy for treatment of the cancer. In some embodiments, the subject has been administered a chemotherapeutic agent or a biologic agent for treatment of the cancer. In some embodiments, the tumor is a sarcoma, carcinoma, lymphoma, or a melanoma. In some embodiments, the lymphoma is an enlarged lymph node or an extranodal lymphoma. In some embodiments, the subject has no detectable cancer following surgery and prior to administration of the covalent TEC family kinase inhibitor. In some embodiments, the subject has no detectable primary or metastatic tumors following surgery and prior to administration of the covalent TEC family kinase inhibitor. In some embodiments, the subject has no detectable circulating tumor cells following surgery. In some embodiments, the subject has detectable circulating tumor cells in a fluid sample following surgery. In some embodiments, the fluid sample is a blood, spinal fluid or urine sample.

In some embodiments, administration of a covalent TEC family kinase inhibitor to an individual decreases the risk of metastasis of a primary tumor compared to the absence of the covalent TEC family kinase inhibitor. In some embodiments, administration of a covalent TEC family kinase inhibitor to an individual decreases the risk of a secondary tumor compared to the absence of the covalent TEC family kinase inhibitor.

In some embodiments, the subject has a bladder, brain, breast, bladder, bone, cervical, colon, esophageal, kidney, liver, lung, ovarian, pancreatic, proximal or distal bile duct, prostate, skin, stomach, thyroid, or uterine cancer. In some embodiments, the subject has a metastatic cancer. In some embodiments, the subject has a cancer that is acute lymphoblastic leukemia, acute lymphoblastic leukemia, acute myeloid leukemia, acute promyelocytic leukemia, adenocarcinoma, adenoma, adrenal cancer, adrenocortical carcinoma, AIDS-related cancer, AIDS-related lymphoma, anal cancer, appendix cancer, astrocytoma, basal cell carcinoma, bile duct cancer, bladder cancer, bone cancer, osteosarcoma/malignant fibrous histiocytoma, brainstem glioma, brain cancer, carcinoma, cerebellar astrocytoma, cerebral astrocytoma/malignant glioma, ependymoma, medulloblastoma, supratentorial primitive neuroectodermal tumor, visual pathway or hypothalamic glioma, breast cancer, bronchial adenoma/carcinoid, Burkitt lymphoma, carcinoid tumor, carcinoma, central nervous system lymphoma, cervical cancer, chronic lymphocytic leukemia, chronic myelogenous leukemia, chronic myeloproliferative disorder, colon cancer, cutaneous T-cell lymphoma, desmoplastic small round cell tumor, endometrial cancer, ependymoma. epidermoid carcinoma, esophageal cancer, Ewing's sarcoma, extracranial germ cell tumor, extragonadal germ cell tumor, extrahepatic bile duct cancer, eye cancer/intraocular melanoma, eye cancer/retinoblastoma, gallbladder cancer, gallstone tumor, gastric/stomach cancer, gastrointestinal carcinoid tumor, gastrointestinal stromal tumor, giant cell tumor, glioblastoma multiforme, glioma, hairy-cell tumor, head and neck cancer, heart cancer, hepatocellular/liver cancer, Hodgkin lymphoma, hyperplasia, hyperplastic corneal nerve tumor, in situ carcinoma, hypopharyngeal cancer, intestinal ganglioneuroma, islet cell tumor, Kaposi's sarcoma, kidney/renal cell cancer, laryngeal cancer, leiomyoma tumor, lip and oral cavity cancer, liposarcoma, liver cancer, non-small cell lung cancer, small cell lung cancer, lymphomas, macroglobulinemia, malignant carcinoid, malignant fibrous histiocytoma of bone, malignant hypercalcemia, malignant melanomas, marfanoid habitus tumor, medullary carcinoma, melanoma, merkel cell carcinoma, mesothelioma, metastatic skin carcinoma, metastatic squamous neck cancer, mouth cancer, mucosal neuromas, multiple myeloma, mycosis fungoides, myelodysplastic syndrome, myeloma, myeloproliferative disorder, nasal cavity and paranasal sinus cancer, nasopharyngeal carcinoma, neck cancer, neural tissue cancer, neuroblastoma, oral cancer, oropharyngeal cancer, osteosarcoma, ovarian cancer, ovarian epithelial tumor, ovarian germ cell tumor, pancreatic cancer, parathyroid cancer, penile cancer, pharyngeal cancer, pheochromocytoma, pineal astrocytoma, pineal germinoma, pineoblastoma, pituitary adenoma, pleuropulmonary blastoma, polycythemia vera, primary brain tumor, prostate cancer, rectal cancer, renal cell tumor, reticulum cell sarcoma, retinoblastoma, rhabdomyosarcoma, salivary gland cancer, seminoma, Sezary syndrome, skin cancer, small intestine cancer, soft tissue sarcoma, squamous cell carcinoma, squamous neck carcinoma, stomach cancer, supratentorial primitive neuroectodermal tumor, testicular cancer, throat cancer, thymoma, thyroid cancer, topical skin lesion, trophoblastic tumor, urethral cancer, uterine/endometrial cancer, uterine sarcoma, vaginal cancer, vulvar cancer, Waldenström's macroglobulinemia or Wilm's tumor.

In some embodiments, the subject has a solid tumor. In some embodiments, the subject has a sarcoma, carcinoma, a neurofibromatoma or a lymphoma. In some embodiments, the subject has a colon cancer. In some embodiments, the subject has a lung cancer. In some embodiments, the subject has an ovarian cancer. In some embodiments, the subject has a pancreatic cancer. In some embodiments, the subject has a prostate cancer. In some embodiments, the subject has a proximal or distal bile duct carcinoma. In some embodiments, the subject has a breast cancer. In some embodiments, the subject has a HER2-positive breast cancer. In some embodiments, the subject has a HER2-negative breast cancer.

In some embodiments, the cancer is a hematologic cancer. In some embodiments, cancer is a leukemia, a lymphoma, or a myeloma. In some embodiments, cancer is a non-Hodgkin lymphoma. In some embodiments, cancer is a Hodgkin lymphoma. In some embodiments, cancer is a B-cell malignancy. In some embodiments, the B-cell malignancy is chronic lymphocytic leukemia (CLL), small lymphocytic lymphoma (SLL), diffuse large B-cell lymphoma (DLBCL), follicular lymphoma (FL), activated B-cell diffuse large B-cell lymphoma (ABC-DLBCL), germinal center diffuse large B-cell lymphoma (GCB DLBCL), primary mediastinal B-cell lymphoma (PMBL), Burkitt's lymphoma, immunoblastic large cell lymphoma, precursor B-lymphoblastic lymphoma, mantle cell lymphoma (MCL), B cell prolymphocytic leukemia, lymphoplasmacytic lymphoma, Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, cancer is a T-cell malignancy. In some embodiments, the T-cell malignancy is peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas. In some embodiments, the subject has multiple myeloma. In some embodiments, the regression of a cancer ceases.

In some embodiments, the subject has a relapsed or refractory cancer. In some embodiments, the relapsed or refractory cancer is a bladder cancer. In some embodiments, the relapsed or refractory cancer is a colon cancer. In some embodiments, the relapsed or refractory cancer is a lung cancer. In some embodiments, the relapsed or refractory cancer is an ovarian cancer. In some embodiments, the relapsed or refractory cancer is a pancreatic cancer. In some embodiments, the relapsed or refractory cancer is a prostate cancer. In some embodiments, the relapsed or refractory cancer is a proximal or distal bile duct carcinoma. In some embodiments, the relapsed or refractory cancer is a breast cancer.

In some embodiments, the subject has a relapsed or refractory hematologic cancer. In some embodiments, the relapsed or refractory hematologic cancer is a leukemia, a lymphoma, or a myeloma. In some embodiments, the relapsed or refractory hematologic cancer is a non-Hodgkin lymphoma. In some embodiments, the relapsed or refractory hematologic cancer is a Hodgkin lymphoma. In some embodiments, the relapsed or refractory hematologic cancer is a B-cell malignancy. In some embodiments, the B-cell malignancy is chronic lymphocytic leukemia (CLL), small lymphocytic lymphoma (SLL), diffuse large B-cell lymphoma (DLBCL), follicular lymphoma (FL), activated B-cell diffuse large B-cell lymphoma (ABC-DLBCL), germinal center diffuse large B-cell lymphoma (GCB DLBCL), primary mediastinal B-cell lymphoma (PMBL), Burkitt's lymphoma, immunoblastic large cell lymphoma, precursor B-lymphoblastic lymphoma, mantle cell lymphoma (MCL), B cell prolymphocytic leukemia, lymphoplasmacytic lymphoma, Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the relapsed or refractory hematologic cancer is a T-cell malignancy. In some embodiments, the T-cell malignancy is peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas. In some embodiments, the subject has a relapsed or refractory multiple myeloma. In some embodiments, the regression of a relapsed or refractory cancer ceases.

In some embodiments, the subject exhibits one or more symptoms of a hematologic cancer. In some embodiments, the subject exhibits one or more symptoms of a B-cell malignancy. In some embodiments, the subject exhibits one or more symptoms of a T-cell malignancy. In some embodiments, the subject exhibits one or more symptoms of a leukemia, a lymphoma, or a myeloma. In some embodiments, the subject exhibits one or more symptoms such as, but not limited to, abnormal B-cell function, abnormal B-cell size or shape, abnormal B-cell count, fatigue, fever, night sweats, frequent infection, enlarged lymph nodes, paleness, anemia, easy bleeding or bruising, loss of appetite, weight loss, bone or joint pain, headaches, and petechie.

In some embodiments, the subject has a high risk of cancer recurrence. In some embodiments, the subject is a mammal, such as, but not limited to a human, a non-human primate, mouse, rat, rabbit, goat, dog, cat, or cow. In some embodiments, the mammal is a human. In some embodiments, a high risk of cancer recurrence is determined based on the expression or presence of a biomarker. In some embodiments, the biomarker includes PMSB1 P11A G/C heterozygote, CD68, suppressor of cytokine signaling 1 (SOCS1), LIM domain only 2 (LMO2), CD137, or a combination thereof.

In some embodiments, a high risk cancer includes bladder, colon, lung, ovarian, pancreatic, prostate, proximal or distal bile duct and breast cancer. In some embodiments, a high risk of bladder, colon, lung, ovarian, pancreatic, prostate and proximal or distal bile duct cancer recurrence is determined based on the expression or presence of a biomarker. In some embodiments, biomarkers for bladder cancer include BTA Stat, BTA Track, NMP 22, Bladder Chek, immunocyt, UroVysion, cytokeratins 8, 18 and 19, telomerase TRAP, hTert and hTR, BLCA-4, survivn, hyaluronic acid/hyaluronidase, DD23 monoclonal antibody, fibronectin and HCG. In some embodiments, biomarkers for colon cancer include CEA, CA 19-9, CYFRA 21-1, ferritin, osteopontin, p53, seprase and EGFR. In some embodiments, biomarkers for lung cancer include ERCC-1, NSE, ProGRP, SCC, beta-tubulin, RRM1, EGFR, VEGF, CYFRA-21-1, CEA, CRP, LDH, CA125, CgA, NCAM and TPA. In some embodiments, biomarkers for ovarian cancer include CA125, Her-2/neu, Akt-2, inhibin, HLA-G, TATI, CASA, TPA, CEA, LPA, PAI-1, IL-6, kallikreins 5, 6, 7, 8, 9, 10, 11, 13, 14, 15, $hCG_{\beta cf}$, prostasin, osteopontin, HE4, mitogen-activated protein kinase, IGFBP-2, RSF-1 and NAC-1. In some embodiments, biomarkers for pancreatic cancer include CA19-9, CEA, TIMP-1, CA50, CA242, MUC1, MUC5AC, Claudin 18 and annexin A8. In some embodiments, biomarkers for prostate cancer include PSA, human kallikrein 2, IGF-1, IGFBP-3, PCA3, AMACR, GSTPi, CDKN1B, Ki-67, PTEN, and PSCA. In some embodiments, biomarkers for proximal or distal bile duct carcinoma include CA125, CA19-9, CEA, CgA, MUC1, MUC5AC, PML, p53, DPC4, Ki67, matrix metalloproteinases, alpha-fetoprotein, N-cadherin, VEGF-C, claudins, thrombospondin-1, cytokeratins and CYFRA 21-1. In some embodiments, biomarkers for breast cancer include HER-1, -2, -3, -4; EGFR and HER-2/neu.

In some embodiments, the covalent TEC family kinase inhibitor inhibits the kinase activity of one or more members of the TEC family of kinases (e.g. ITK, BTK, TEC, RLK and BMX). In some embodiments, the covalent TEC family kinase inhibitor inhibits the kinase activity of ITK. In some embodiments, the covalent TEC family kinase inhibitor covalently binds to Cysteine 442 of ITK. In some embodiments, the covalent TEC family kinase inhibitor covalently binds to Cysteine 481 of BTK. In some embodiments, the covalent TEC family kinase inhibitor is selected from among ibrutinib (PCI-32765), PCI-45292, PCI-45466, AVL-101, AVL-263, AVL-291, AVL-292, ONO-WG-37, BMS-488516, BMS-509744, CGI-1746, CTA-056, GDC-0834, HY-11066 (also, CTK4I7891, HMS3265G21, HMS3265G22, HMS3265H21, HMS3265H22, 439574-61-5, AG-F-54930), ONO-4059, ONO-WG37, PLS-123, RN486, HM71224, or a combination thereof. In some embodiments, the covalent TEC family kinase inhibitor is ibrutinib. Additional covalent TEC family kinase inhibitors for use in any of the methods provided herein are found, for example, in U.S. Pat. Nos. 7,547,689, 7,960,396 and U.S. Patent Publication Nos. US 2009-0197853 A1 and US 2012-0065201 A1, all of which are incorporated by reference in their entirety.

In some embodiments, a covalent TEC family kinase inhibitor is administered for adjuvant therapy of a bladder cancer. In some embodiments, a covalent TEC family kinase inhibitor is administered in combination with one or more therapies for the treatment of the bladder cancer. Exemplary therapies for the treatment of bladder cancer include, but are not limited to, doxorubicin hydrochloride (Adriamycin PFS/RDF), cisplatin, mitomycin, fluorouracil, gemcitabine, methotrexate, vinblastine, carboplatin, paclitaxel, docetaxel, thiotepa (Thioplex, Tepadina), immunotherapeutic agents (e.g. Bacille Calmette-Guerin, interferon alfa-2b), and radiation therapeutic agents. In some embodiments, the covalent TEC family kinase inhibitor is administered in combination with doxorubicin hydrochloride (Adriamycin PFS/RDF), cisplatin, mitomycin, fluorouracil, gemcitabine, methotrexate, vinblastine, carboplatin, paclitaxel, docetaxel, thiotepa (Thioplex, Tepadina), immunotherapeutic agents (e.g. Bacille Calmette-Guerin, interferon alfa-2b), and radiation therapeutic agents. In some embodiments, the covalent TEC family kinase inhibitor is ibrutinib. In some embodiments, ibrutinib is administered in combination with doxorubicin hydrochloride (Adriamycin PFS/RDF), cisplatin, mitomycin, fluorouracil, gemcitabine, methotrexate, vinblastine, carboplatin, paclitaxel, docetaxel, thiotepa (Thioplex, Tepadina), immunotherapeutic agents (e.g. Bacille Calmette-Guerin, interferon alfa-2b), and radiation therapeutic agents for the treatment of a bladder cancer. In some embodiments, the covalent TEC family kinase inhibitor (e.g., ibrutinib) is administered sequentially, simultaneously, or intermittently with the one or more therapies for the treatment of a bladder cancer.

In some embodiments, a covalent TEC family kinase inhibitor is administered for adjuvant therapy of a colon cancer. In some embodiments, a covalent TEC family kinase inhibitor is administered in combination with one or more therapies for the treatment of the colon cancer. Exemplary therapies for the treatment of colon cancer include, but are not limited to, fluorouracil (Adrucil), bevacizumab (Avastin), irinotecan hydrochloride (Camptosar), capecitabine, cetuximab, Efudex, oxaliplatin (Eloxatin), Erbutix, Fluoroplex, leucovorin calcium (Wellcovorin), panitumamab (Vectibix), regorafenib (Stivarga), ziv-aflibercept, CAPDX, FOLFIRI, FOLFOX, and XELOX. In some embodiments, the covalent TEC family kinase inhibitor is administered in combination with fluorouracil (Adrucil), bevacizumab (Avastin), irinotecan hydrochloride (Camptosar), capecitabine, cetuximab, Efudex, oxaliplatin (Eloxatin), Erbutix, Fluoroplex, leucovorin calcium (Wellcovorin), panitumamab (Vectibix), regorafenib (Stivarga), ziv-aflibercept, CAPDX, FOLFIRI, FOLFOX, and XELOX. In some embodiments, the covalent TEC family kinase inhibitor is ibrutinib. In some embodiments, ibrutinib is administered in combination with fluorouracil (Adrucil), bevacizumab (Avastin), irinotecan hydrochloride (Camptosar), capecitabine, cetuximab, Efudex, oxaliplatin (Eloxatin), Erbutix, Fluoroplex, leucovorin calcium (Wellcovorin), panitumamab (Vectibix), regorafenib (Stivarga), ziv-aflibercept, CAPDX, FOLFIRI, FOLFOX, and XELOX for the treatment of a colon cancer. In some embodiments, the covalent TEC family kinase inhibitor (e.g., ibrutinib) is administered sequentially, simultaneously, or intermittently with the one or more therapies for the treatment of a colon cancer.

In some embodiments, a covalent TEC family kinase inhibitor is administered for adjuvant therapy of a lung cancer. In some embodiments, a covalent TEC family kinase inhibitor is administered in combination with one or more therapies for the treatment of the lung cancer. Exemplary therapies for the treatment of lung cancer include, but are not limited to, Adriamycin IV, Rheumatrex, Mustargen, methotrexate (Abitrexate), Abraxane, afatinib dimaleate (Gilotrif), pemetrexed disodium (Alimta), bevacixumab, carboplatin, cisplatin, crizotinib, erlotinib hydrochloride, Etopophos (etoposide phosphate), Folex, Folex PFS, gefitinib (Iressa), gemcitabine hydrochloride (Gemzar), topotecan hydrochloride (Hycamtin), Methotrexate LPF, Mexate, Mexate-AQ, paclitaxel, Paraplat, Paraplatin, Platinol, Platinol-AQ, Tarceva, Taxol, Xalkori, Toposar, VePesid and MPDL3280A. In some embodiments, the covalent TEC family kinase inhibitor is administered in combination with Adriamycin IV, Rheumatrex, Mustargen, methotrexate (Abitrexate), Abraxane, afatinib dimaleate (Gilotrif), pemetrexed disodium (Alimta), bevacixumab, carboplatin, cisplatin, crizotinib, erlotinib hydrochloride, Etopophos (etoposide phosphate), Folex, Folex PFS, gefitinib (Iressa), gemcitabine hydrochloride (Gemzar), topotecan hydrochloride (Hycamtin), Methotrexate LPF, Mexate, Mexate-AQ, paclitaxel, Paraplat, Paraplatin, Platinol, Platinol-AQ, Tarceva, Taxol, Xalkori, Toposar, VePesid and MPDL3280A. In some embodiments, the covalent TEC family kinase inhibitor is ibrutinib. In some embodiments, ibrutinib is administered in combination with Adriamycin IV, Rheumatrex, Mustargen, methotrexate (Abitrexate), Abraxane, afatinib dimaleate (Gilotrif), pemetrexed disodium (Alimta), bevacixumab, carboplatin, cisplatin, crizotinib, erlotinib hydrochloride, Etopophos (etoposide phosphate), Folex, Folex PFS, gefitinib (Iressa), gemcitabine hydrochloride (Gemzar), topotecan hydrochloride (Hycamtin), Methotrexate LPF, Mexate, Mexate-AQ, paclitaxel, Paraplat, Paraplatin, Platinol, Platinol-AQ, Tarceva, Taxol, Xalkori, Toposar, VePesid and MPDL3280A for the treatment of a lung cancer. In some embodiments, the covalent TEC family kinase inhibitor (e.g., ibrutinib) is administered sequentially, simultaneously, or intermittently with the one or more therapies for the treatment of a lung cancer.

In some embodiments, a covalent TEC family kinase inhibitor is administered for adjuvant therapy of an ovarian cancer. In some embodiments, a covalent TEC family kinase inhibitor is administered in combination with one or more therapies for the treatment of the ovarian cancer. Exemplary therapies for the treatment of ovarian cancer include, but are not limited to, doxorubicin hydrochloride (Adriamycin PFS/RDF), carboplatin, cyclophosphamide (Clafen), cisplatin, Cytoxan, Dox-SL, DOXIL, doxorubicin hydrochloride liposome (Evacet), gemcitabine hydrochloride (Gemzar), topotecan hydrochloride (Hycamtin), Neosar, Paclitaxel, Paraplat, Paraplatin, Platinol, Platinol-AQ, Taxol and BEP. In some embodiments, the covalent TEC family kinase inhibitor is administered in combination with doxorubicin hydrochloride (Adriamycin PFS/RDF), carboplatin, cyclophosphamide (Clafen), cisplatin, Cytoxan, Dox-SL, DOXIL, doxorubicin hydrochloride liposome (Evacet), gemcitabine hydrochloride (Gemzar), topotecan hydrochloride (Hycamtin), Neosar, Paclitaxel, Paraplat, Paraplatin, Platinol, Platinol-AQ, Taxol and BEP. In some embodiments, the covalent TEC family kinase inhibitor is ibrutinib. In some embodiments, ibrutinib is administered in combination with doxorubicin hydrochloride (Adriamycin PFS/RDF), carboplatin, cyclophosphamide (Clafen), cisplatin, Cytoxan, Dox-SL, DOXIL, doxorubicin hydrochloride liposome (Evacet), gemcitabine hydrochloride (Gemzar), topotecan hydrochloride (Hycamtin), Neosar, Paclitaxel, Paraplat, Paraplatin, Platinol, Platinol-AQ, Taxol and BEP for the treatment of an ovarian cancer. In some embodiments, the covalent TEC family kinase inhibitor (e.g., ibrutinib) is administered sequentially, simultaneously, or intermittently with the one or more therapies for the treatment of an ovarian cancer.

In some embodiments, a covalent TEC family kinase inhibitor is administered for adjuvant therapy of a pancreatic cancer. In some embodiments, a covalent TEC family kinase inhibitor is administered in combination with one or more therapies for the treatment of the pancreatic cancer. Exemplary therapies for the treatment of pancreatic cancer include, but are not limited to, Adriamycin PFS IV, Adrucil, Efudex, erlotinib hydrochloride, Fluoroplex, fluorouracil, gemcitabine hydrochloride (Gemzar), mitomycin C, Tarceva, Oxaliplatin paclitaxel-protein bound IV, anc capecitabine. In some embodiments, the covalent TEC family kinase inhibitor is administered in combination with Adriamycin PFS IV, Adrucil, Efudex, erlotinib hydrochloride, Fluoroplex, fluorouracil, gemcitabine hydrochloride (Gemzar), mitomycin C, Tarceva, Oxaliplatin paclitaxel-protein bound IV, anc capecitabine. In some embodiments, the covalent TEC family kinase inhibitor is ibrutinib. In some embodiments, ibrutinib is administered in combination with Adriamycin PFS IV, Adrucil, Efudex, erlotinib hydrochloride, Fluoroplex, fluorouracil, gemcitabine hydrochloride (Gemzar), mitomycin C, Tarceva, Oxaliplatin paclitaxel-protein bound IV, anc capecitabine for the treatment of a pancreatic cancer. In some embodiments, the covalent TEC family kinase inhibitor (e.g., ibrutinib) is administered sequentially, simultaneously, or intermittently with the one or more therapies for the treatment of a pancreatic cancer.

In some embodiments, a covalent TEC family kinase inhibitor is administered for adjuvant therapy of a prostate cancer. In some embodiments, a covalent TEC family kinase inhibitor is administered in combination with one or more therapies for the treatment of the prostate cancer. Exemplary therapies for the treatment of prostate cancer include, but are not limited to, abiraterone acetate, cabazitaxel, degarelix, docetaxel, enzalutamide, leuprolide acetate, prednisone, denosumab, sipuleucel-T, and radium 223 dichloride. In some embodiments, the covalent TEC family kinase inhibitor is administered in combination with abiraterone acetate, cabazitaxel, degarelix, docetaxel, enzalutamide, leuprolide acetate, prednisone, denosumab, sipuleucel-T, or radium 223 dichloride. In some embodiments, the covalent TEC family kinase inhibitor is ibrutinib. In some embodiments, ibrutinib is administered in combination with abiraterone acetate, cabazitaxel, degarelix, docetaxel, enzalutamide, leuprolide acetate, prednisone, denosumab, sipuleucel-T, or radium 223 dichloride for the treatment of prostate cancer. In some embodiments, the covalent TEC family kinase inhibitor (e.g., ibrutinib) is administered sequentially, simultaneously, or intermittently with the one or more therapies for the treatment of prostate cancer.

In some embodiments, a covalent TEC family kinase inhibitor is administered for adjuvant therapy of a proximal or distal bile duct cancer. In some embodiments, a covalent TEC family kinase inhibitor is administered in combination with one or more therapies for the treatment of the proximal or distal bile duct cancer. Exemplary therapies for the treatment of proximal or distal bile duct cancer include, but are not limited to, cisplatin, gemcitabine, fluorouracil, and doxorubicin. In some embodiments, the covalent TEC family kinase inhibitor is administered in combination with cisplatin, gemcitabine, fluorouracil, or doxorubicin. In some embodiments, the covalent TEC family kinase inhibitor is ibrutinib. In some embodiments, ibrutinib is administered in combination with cisplatin, gemcitabine, fluorouracil, or doxorubicin for the treatment of a proximal or distal bile duct cancer. In some embodiments, the covalent TEC family kinase inhibitor (e.g., ibrutinib) is administered sequentially, simultaneously, or intermittently with the one or more therapies for the treatment of a proximal or distal bile duct cancer.

In some embodiments, a covalent TEC family kinase inhibitor is administered for adjuvant therapy of a breast cancer. In some embodiments, a covalent TEC family kinase inhibitor is administered in combination with one or more therapies for the treatment of the breast cancer. Exemplary therapies for the treatment of breast cancer include, but are not limited to, ado-trastuzumab emtansine, anastrozole, capecitabine, cyclophosphamide, docetaxel, doxorubicin hydrochloride, epirubicin hydrochloride, everolimus, exemestane, fluorouracil, fulvestrant, gemcitabine hydrochloride, ixabepilone, lapatinib ditosylate, letrozole, megestrol acetate, methotrexate, paclitaxel, paclitaxel albumin-stabilized nanoparticle formulation, pamidronate disodium, tamoxifen citrate, toremifene, and trastuzumab. In some embodiments, the covalent TEC family kinase inhibitor is administered in combination with ado-trastuzumab emtansine, anastrozole, capecitabine, cyclophosphamide, docetaxel, doxorubicin hydrochloride, epirubicin hydrochloride, everolimus, exemestane, fluorouracil, fulvestrant, gemcitabine hydrochloride, ixabepilone, lapatinib ditosylate, letrozole, megestrol acetate, methotrexate, paclitaxel, paclitaxel albumin-stabilized nanoparticle formulation, pamidronate disodium, tamoxifen citrate, toremifene, or trastuzumab. In some embodiments, the covalent TEC family kinase inhibitor is ibrutinib. In some embodiments, ibrutinib is administered in combination with ado-trastuzumab emtansine, anastrozole, capecitabine, cyclophosphamide, docetaxel, doxorubicin hydrochloride, epirubicin hydrochloride, everolimus, exemestane, fluorouracil, fulvestrant, gemcitabine hydrochloride, ixabepilone, lapatinib ditosylate, letrozole, megestrol acetate, methotrexate, paclitaxel, paclitaxel albumin-stabilized nanoparticle formulation, pamidronate disodium, tamoxifen citrate, toremifene, or trastuzumab for the treatment of a breast cancer. In some embodiments, the covalent TEC family kinase inhibitor (e.g., ibrutinib) is administered sequentially, simultaneously, or intermittently with the one or more therapies for the treatment of a breast cancer.

In some embodiments, a covalent TEC family kinase inhibitor is administered for adjuvant therapy of a T-cell or NK cell malignancy. In some embodiments, a covalent TEC family kinase inhibitor is administered for adjuvant therapy of an aggressive T-cell or NK cell malignancy. In some embodiments, a covalent TEC family kinase inhibitor is administered for adjuvant therapy of an indolent T-cell or NK cell malignancy. In some embodiments, the T-cell or NK cell malignancy is a cutaneous malignancy. In some embodiments, the cutaneous malignancy is Mycosis Fungoides (MF), transformed MF, Sézary syndrome, a primary cutaneous CD30+ T-cell disorder, or a primary cutaneous gamma/delta T-cell lymphoma. In some embodiments, the T-cell or NK cell malignancy is an extranodal T-cell or NK cell malignancy. In some embodiments, the extranodal malignancy is a nasal NK/T-cell lymphoma, an enteropathy-type T-cell lymphoma, hepatosplenic T-cell lymphoma. In some embodiments, the T-cell or NK cell malignancy is an nodal T-cell or NK cell malignancy. In some embodiments, the nodal malignancy is peripheral T-cell lymphoma not otherwise specified (PTCL-NOS), anaplastic large cell lymphoma, angioimmunoblastic lymphoma, blastic NK-cell lymphoma, lymphoblastic lymphoma. In some embodiments, the T-cell or NK cell malignancy is a leukemic cell or NK cell malignancy. In some embodiments, the leukemic malignancy is adult T-cell leukemia/lymphoma (ATLL), aggressive NK-cell leukemia, T-cell prolymphocytic leukemia, or T-cell large granular lymphocytic leukemia. In some embodiments, the T-cell or NK cell malignancy is a treatment-related T-cell lymphoma.

In some embodiments, a covalent TEC family kinase inhibitor is administered in combination with one or more therapies for the treatment of a T-cell or NK cell malignancy. Exemplary therapies for the treatment of a T-cell or NK cell malignancies include, but are not limited to, CHOP (cyclophosphamide, hydroxydoxorubicin, vincristine, and prednisone), EPOCH (etoposide, prednisone, vincristine, cyclophosphamide, hydroxydoxorubicin), Hyper-CVAD (cyclophosphamide, vincristine, hydroxydoxorubicin, dexamethasone), ICE (ifosfamide, carboplatin, etoposide), DHAP (high-dose cytarabine [ara-C], dexamethasone, cisplatin), ESHAP (etoposide, methylprednisolone, cytarabine [ara-C], cisplatin), anthracycline-based chemotherapy, histone deacetylase (HDAC) inhibitors, such as abexinostat, resminostat, vorinostat, belinostat and panobinostat, proteasome inhibitors such as bortezomib, immunomodulatory drugs, such as lenalidomide, monoclonal antibodies, such as alemtuzumab and brentuximab vedotin, and nucleoside analogs, such as gemcitabine, nelarabine. In some embodiments, the covalent TEC family kinase inhibitor is administered in combination with CHOP (cyclophosphamide, hydroxydoxorubicin, vincristine, and prednisone), EPOCH (etoposide, prednisone, vincristine, cyclophosphamide, hydroxydoxorubicin), Hyper-CVAD (cyclophosphamide, vincristine, hydroxydoxorubicin, dexamethasone), ICE (ifosfamide, carboplatin, etoposide), DHAP (high-dose cytarabine [ara-C], dexamethasone, cisplatin), and ESHAP (etoposide, methylprednisolone, cytarabine [ara-C], cisplatin) for the treatment of a T-cell or NK cell malignancy. In some embodiments, the covalent TEC family kinase inhibitor is ibrutinib. In some embodiments, ibrutinib is administered in combination with CHOP (cyclophosphamide, hydroxydoxorubicin, vincristine, and prednisone), EPOCH (etoposide, prednisone, vincristine, cyclophosphamide, hydroxydoxorubicin), Hyper-CVAD (cyclophosphamide, vincristine, hydroxydoxorubicin, dexamethasone), ICE (ifosfamide, carboplatin, etoposide), DHAP (high-dose cytarabine [ara-C], dexamethasone, cisplatin), or ESHAP (etoposide, methylprednisolone, cytarabine [ara-C], cisplatin) for the treatment of a T-cell or NK cell malignancy. In some embodiments, ibrutinib is administered in combination with bortezomib for the treatment of a T-cell or NK cell malignancy. In some embodiments, ibrutinib is administered in combination with an HDAC inhibitor, such as abexinostat, resminostat, vorinostat, belinostat and panobinostat for the treatment of a T-cell or NK cell malignancy. In some embodiments, the covalent TEC family kinase inhibitor (e.g., ibrutinib) is administered sequentially, simultaneously, or intermittently with the one or more therapies for the treatment of a T-cell or NK cell malignancy.

In some embodiments, a covalent TEC family kinase inhibitor is administered in combination with one or more therapies for the treatment of a relapsed or refractory T-cell or NK cell malignancy. Exemplary therapies for the treatment of a relapsed or refractory T-cell or NK cell malignancies include, but are not limited to, CHOP (cyclophosphamide, hydroxydoxorubicin, vincristine, and prednisone), EPOCH (etoposide, prednisone, vincristine, cyclophosphamide, hydroxydoxorubicin), Hyper-CVAD (cyclophosphamide, vincristine, hydroxydoxorubicin, dexamethasone), ICE (ifosfamide, carboplatin, etoposide), DHAP (high-dose cytarabine [ara-C], dexamethasone, cisplatin), ESHAP (etoposide, methylprednisolone, cytarabine [ara-C], cisplatin), anthracycline-based chemotherapy, histone deacetylase (HDAC) inhibitors, such as abexinostat, resminostat, vorinostat, belinostat and panobinostat, proteasome inhibitors such as bortezomib, immunomodulatory drugs, such as lenalidomide, monoclonal antibodies, such as alemtuzumab and brentuximab vedotin, and nucleoside analogs, such as gemcitabine, nelarabine. In some embodiments, the covalent TEC family kinase inhibitor is administered in combination with CHOP (cyclophosphamide, hydroxydoxorubicin, vincristine, and prednisone), EPOCH (etoposide, prednisone, vincristine, cyclophosphamide, hydroxydoxorubicin), Hyper-CVAD (cyclophosphamide, vincristine, hydroxydoxorubicin, dexamethasone), ICE (ifosfamide, carboplatin, etoposide), DHAP (high-dose cytarabine [ara-C], dexamethasone, cisplatin), and ESHAP (etoposide, methylprednisolone, cytarabine [ara-C], cisplatin) for the treatment of a relapsed or refractory T-cell or NK cell malignancy. In some embodiments, the covalent TEC family kinase inhibitor is ibrutinib. In some embodiments, ibrutinib is administered in combination with CHOP (cyclophosphamide, hydroxydoxorubicin, vincristine, and prednisone), EPOCH (etoposide, prednisone, vincristine, cyclophosphamide, hydroxydoxorubicin), Hyper-CVAD (cyclophosphamide, vincristine, hydroxydoxorubicin, dexamethasone), ICE (ifosfamide, carboplatin, etoposide), DHAP (high-dose cytarabine [ara-C], dexamethasone, cisplatin), or ESHAP (etoposide, methylprednisolone, cytarabine [ara-C], cisplatin) for the treatment of a relapsed or refractory T-cell or NK cell malignancy. In some embodiments, ibrutinib is administered in combination with bortezomib for the treatment of a T-cell or NK cell malignancy. In some embodiments, ibrutinib is administered in combination with an HDAC inhibitor, such as abexinostat, resminostat, vorinostat, belinostat and panobinostat for the treatment of a T-cell or NK cell malignancy. In some embodiments, the covalent TEC family kinase inhibitor (e.g., ibrutinib) is administered sequentially, simultaneously, or intermittently with the one or more therapies for the treatment of a relapsed or refractory T-cell or NK cell malignancy.

Described herein, in certain embodiments, are methods of selecting a patient having cancer for adjuvant therapy with a covalent TEC Family kinase inhibitor comprising measuring the the expressing of one more Th1 and/or Th2 cytokines and characterizing the patient as a candidate for therapy with a covalent TEC Family kinase inhibitor if the level of the one or more Th1 cytokines is decreased and/or the level of the one or more Th2 cytokines is increased compared to a normal control. In some embodiments, a patient having an defective Th1 response is selected as a candidate for therapy with a covalent TEC Family kinase inhibitor. In some embodiments, a patient having an overactive Th2 response is selected as a candidate for therapy with a covalent TEC Family kinase inhibitor. In some embodiments, a patient having a low Th1:Th2 ratio is selected as a candidate for therapy with a covalent Tec Family kinase inhibitor.

Adjuvant for Treatment of Cancer Associated Immune Disorders

Described herein, in certain embodiments, are methods of adjuvant therapy for the treatment of an immune disorder comprising administration of a covalent TEC Family kinase inhibitor. In some embodiments, the immune disorder is a cancer associated immune disorder. Described herein, in certain embodiments, are methods of adjuvant therapy for the treatment of a immune disorder characterized by an impaired Th1 immune response or an overactive Th2 response. In some embodiments, the methods of adjuvant therapy comprise administering to a subject having an immune disorder characterized by an impaired Th1 immune response or an overactive Th2 response an effective amount of a covalent TEC family kinase inhibitor to increase the Th1 immune response or decrease the Th2 response in the subject. In some embodiments, the disease or condition is associated with increased Th2 activity, such as an allergic or asthmatic disorder. In some embodiments, the autoimmune disease is autoimmune arthritis. In some embodiments, the immune disorder is atopic dermatitis, inflammatory bowel disease, an unspecified T-cell lymphoma (U-PTCLs), rheumatoid arthritis, bronchial asthma, allergic airway inflammatory disease or aplastic anemia.

In some embodiments, the immune disorder is associated with a hematologic cancer. In some embodiments, the immune disorder is associated with a leukemia, a lymphoma, or a myeloma. In some embodiments, immune disorder is associated with non-Hodgkin's lymphoma. In some embodiments, the immune disorder is associated with Hodgkin's lymphoma. In some embodiments, the immune disorder is associated with chronic lymphocytic leukemia (CLL), small lymphocytic lymphoma (SLL), high risk CLL, follicular lymphoma (FL), diffuse large B-cell lymphoma (DLBCL), mantle cell lymphoma (MCL), Waldenström's macroglobulinemia, multiple myeloma, marginal zone lymphoma, Burkitt's lymphoma, non-Burkitt high grade B cell lymphoma, or extranodal marginal zone B cell lymphoma. In some embodiments, the subject has an autoimmune disease.

In some embodiments, the subject is a mammal, such as, but not limited to a human, a non-human primate, mouse, rat, rabbit, goat, dog, cat, or cow. In some embodiments, the mammal is a human.

In some embodiments, the covalent TEC family kinase inhibitor inhibits the kinase activity of one or more members of the TEC family of kinases (e.g. ITK, BTK, TEC, RLK and BMX). In some embodiments, the covalent TEC family kinase inhibitor inhibits the kinase activity of ITK. In some embodiments, the covalent TEC family kinase inhibitor covalently binds to Cysteine 442 of ITK. In some embodiments, the covalent TEC family kinase inhibitor covalently binds to Cysteine 481 of BTK. In some embodiments, the covalent TEC family kinase inhibitor is selected from among ibrutinib (PCI-32765), PCI-45292, PCI-45466, AVL-101, AVL-263, AVL-291, AVL-292, ONO-WG-37, BMS-488516, BMS-509744, CGI-1746, CTA-056, GDC-0834, HY-11066 (also, CTK4I7891, HMS3265G21, HMS3265G22, HMS3265H21, HMS3265H22, 439574-61-5, AG-F-54930), ONO-4059, ONO-WG37, PLS-123, RN486, HM71224, or a combination thereof. In some embodiments, the covalent TEC family kinase inhibitor is ibrutinib. Additional covalent TEC family kinase inhibitors for use in any of the methods provided herein are found, for example, in U.S. Pat. Nos. 7,547,689, 7,960,396 and U.S. Patent Publication Nos. US 2009-0197853 A1 and US 2012-0065201 A1, all of which are incorporated by reference in their entirety.

Treatment Assessment Utilizing Biomarker Profiles

Disclosed herein, in certain embodiments, is a method for assessing a cancer therapy in an individual following treatment of a tumor with a first anticancer therapy to decrease the size of a tumor or eliminate the tumor in need thereof. In some embodiments, the method comprises of creating a biomarker profile. In some embodiments, the biomarker profile is a Th2 polarized T cell biomarker profile. In some embodiments, the biomarker profile is a Th1 polarized T cell biomarker profile. In some embodiments, the biomarker profile shows a decrease in Th2 polarized T cell population following treatment with the covalent Tec family kinase inhibitor. In some embodiments, the biomarker profile shows an increase in Th1 polarized T cell population following treatment with the covalent Tec family kinase inhibitor.

In some embodiments, the biomarker profile indicates the expression of a biomarker, the expression level of a biomarker, mutations in a biomarker, or the presence of a biomarker. In some embodiments, the biomarker is any cytogenetic, cell surface molecular or protein or RNA expression marker. In some embodiments, the biomarker is: CCR1, CCR3, CCR4, CCR7, CCR8, CD4, CD26, CD28, CD30, CD81, CD94, CD119, CD183, CD184, CD195, CD212, CD278, c-maf, CRTH2, Gata-3, GM-CSF, IFN yR, IgD, IL-1R, IL-4, IL-5, IL-6, IL-9, IL-10, IL-12β1, IL-13, IL-15, IL-2, IL-12, IL-15, IL-18R, IL-23, IL-27, IL-27R, ST2L/T1, Tim-1, Tim-3, GM-CSF, Granzyme B, IFN-α, IFN-γ, Lymphotoxin, perforin, t-bet, TNF-α, TRANCE, sCD40L, or a combination thereof.

In some embodiments, administration of a covalent TEC family kinase inhibitor decreases the biomarker profile of one population of cells. In some embodiments, the population of cells is Th2 polarized T cells. In some embodiments, administration of a covalent TEC family kinase inhibitor decreases the biomarker profile of Th2 polarized T cell population. In some embodiments, administration of a covalent TEC family kinase inhibitor decreases the biomarker profile of Th2 polarized T cell population in a subject.

In some embodiments, administration of a covalent TEC family kinase inhibitor increases the biomarker profile of a second population of cells. In some embodiments, the second population of cells is Th1 polarized T cells. In some embodiments, administration of a covalent TEC family kinase inhibitor increases the biomarker profile of Th1 polarized T cells populations. In some embodiments, administration of a covalent TEC family kinase inhibitor increases the biomarker profile of Th1 polarized T cells populations in a subject.

In some embodiments, administration of a covalent TEC family kinase inhibitor increases the ratio of Th1 polarized T cells to Th2 polarized T cells in the subject. In some embodiments, administration of a covalent TEC family kinase inhibitor increases the ratio of Th1 polarized T cells to Th2 polarized T cells in the subject by about 5 fold, 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold or greater. In some embodiments, administration of a covalent TEC family kinase inhibitor increase the number of cytotoxic CD8+ T cells in the subject.

In some embodiments, administration of a covalent TEC family kinase inhibitor decreases the expression of one or more biomarkers in a subject. In some embodiments, the biomarker is a Th2 related marker in the subject. In some embodiments, administration of a covalent TEC family kinase inhibitor decreases the expression of one or more Th2 related markers selected from among CCR3, CCR4, CCR7, CCR8, CD4, CD30, CD81, CD184, CD278, c-maf, CRTH2, Gata-3, GM-CSF, IFN yR, IgD, IL-1R, IL-4, IL-5, IL-6, IL-9, IL-10, IL-13, IL-15, ST2L/T1 and Tim-1. In some embodiments, administration of a covalent TEC family kinase inhibitor decreases IL-4, IL-5, IL-6, IL-10, IL-13, or IL-15 expression in the subject. In some embodiments, administration of a covalent TEC family kinase inhibitor decreases IL-4 expression in the subject. In some embodiments, administration of a covalent TEC family kinase inhibitor decreases IL-5 expression in the subject. In some embodiments, administration of a covalent TEC family kinase inhibitor decreases IL-6 expression in the subject. In some embodiments, administration of a covalent TEC family kinase inhibitor decreases IL-10 expression in the subject. In some embodiments, administration of a covalent TEC family kinase inhibitor decreases IL-13 expression in the subject. In some embodiments, administration of a covalent TEC family kinase inhibitor decreases IL-15 expression in the subject.

In some embodiments, the covalent TEC family kinase inhibitor is ibrutinib. In some embodiments, administration of ibrutinib decreases the expression of one or more biomarkers in a subject. In some embodiments, the biomarker is a Th2 related marker in the subject. In some embodiments, administration of ibrutinib decreases the expression of one or more Th2 related markers selected from among CCR3, CCR4, CCR7, CCR8, CD4, CD30, CD81, CD184, CD278, c-maf, CRTH2, Gata-3, GM-CSF, IFN yR, IgD, IL-1R, IL-4, IL-5, IL-6, IL-9, IL-10, IL-13, IL-15, ST2L/T1 and Tim-1. In some embodiments, administration of ibrutinib decreases IL-4, IL-5, IL-6, IL-10, IL-13, or IL-15 expression in the subject. In some embodiments, administration of ibrutinib decreases IL-4 expression in the subject. In some embodiments, administration of ibrutinib decreases IL-5 expression in the subject. In some embodiments, administration of ibrutinib decreases IL-6 expression in the subject. In some embodiments, administration of ibrutinib decreases IL-10 expression in the subject. In some embodiments, administration of ibrutinib decreases IL-13 expression in the subject. In some embodiments, administration of ibrutinib decreases IL-15 expression in the subject.

In some embodiments, administration of a covalent TEC family kinase inhibitor increases the expression of one or more biomarkers in a subject. In some embodiments, the biomarker is a Th1 related marker in the subject. In some embodiments, administration of a covalent TEC family kinase inhibitor increases the expression of one or more Th1 related markers selected from among CCR1, CD4, CD26, CD94, CD119, CD183, CD195, CD212, GM-CSF, Granzyme B, IFN-α, IFN-γ, IL-2, IL-12, IL-15, IL-18R, IL-23, IL-27, IL-27R, Lymphotoxin, perforin, t-bet, Tim-3, TNF-α, TRANCE, and sCD40L. In some embodiments, administration of a covalent TEC family kinase inhibitor increases IFN-γ, GM-CSF, IL-2, IL-12(p70) expression in the subject. In some embodiments, administration of a covalent TEC family kinase inhibitor increases IFN-γ expression in the subject. In some embodiments, administration of a covalent TEC family kinase inhibitor increases GM-CSF expression in the subject. In some embodiments, administration of a covalent TEC family kinase inhibitor increases IL-2 expression in the subject. In some embodiments, administration of a covalent TEC family kinase inhibitor increases IL-12(p70) expression in the subject.

In some embodiments, the covalent TEC family kinase inhibitor is ibrutinib. In some embodiments, administration of ibrutinib increases the expression of one or more biomarkers in a subject. In some embodiments, the biomarker is a Th1 related marker in the subject. In some embodiments, administration of ibrutinib increases the expression of one or more Th1 related markers selected from among CCR1, CD4, CD26, CD94, CD119, CD183, CD195, CD212, GM-CSF, Granzyme B, IFN-α, IFN-γ, IL-2, IL-12, IL-15, IL-18R, IL-23, IL-27, IL-27R, Lymphotoxin, perforin, t-bet, Tim-3, TNF-α, TRANCE and sCD40L. In some embodiments, administration of ibrutinib increases IFN-γ, GM-CSF, IL-2, IL-12(p70) expression in the subject. In some embodiments, administration of ibrutinib increases IFN-γ expression in the subject. In some embodiments, administration of ibrutinib increases GM-CSF expression in the subject. In some embodiments, administration of ibrutinib increases IL-2 expression in the subject. In some embodiments, administration of ibrutinib increases IL-12(p70) expression in the subject.

In some embodiments, the method further comprises providing a continuation of a first cancer therapy or an initiation of a second cancer treatment regimen based on the biomarker profile after the discontinuation of a first anticancer therapy. In some embodiments, the method further comprises not administering based on the biomarker profile. In some embodiments, the method further comprises assessing the efficacy of a treatment regimen based on the biomarker profile. In some embodiments, the biomarkers include: IL-4, IL-5, IL-6, IL-10, IL-13, IL-15, IFN-γ, GM-CSF, TNF-α, IL-2, or IL-12. In some embodiments, the biomarker is IFN-γ. In some embodiments, the biomarker is IL-4. In some embodiments, the biomarker is IL-10. In some embodiments, the biomarker is IL-13. In some embodiments, the biomarker is IL-2. In some embodiments, the biomarker is IL-12.

Methods for determining the expression or presence of biomarkers are well known in the art. Circulating levels of biomarkers in a blood sample obtained from a candidate subject are measured, for example, by ELISA, radioimmunoassay (RIA), electrochemiluminescence (ECL), Western blot, multiplexing technologies, or other similar methods. Cell surface expression of biomarkers are measured, for example, by flow cytometry, immunohistochemistry, Western Blot, immunoprecipitation, magnetic bead selection, and quantification of cells expressing either of these cell surface markers. Biomarker RNA expression levels could be measured by RT-PCR, Qt-PCR, microarray, Northern blot, or other similar technologies.

As previously noted, determining the expression or presence of the biomarker of interest at the protein or nucleotide level are accomplished using any detection method known to those of skill in the art. By "detecting expression" or "detecting the level" of is intended determining the expression level or presence of a biomarker protein or gene in the biological sample. Thus, "detecting expression" encompasses instances where a biomarker is determined not to be expressed, not to be detectably expressed, expressed at a low level, expressed at a normal level, or overexpressed.

In certain aspects of the method provided herein, the one or more subpopulation of lymphocytes are isolated, detected or measured. In certain embodiments, the one or more subpopulation of lymphocytes are isolated, detected or measured using immunophenotyping techniques. In other embodiments, the one or more subpopulation of lymphocytes are isolated, detected or measured using fluorescence activated cell sorting (FACS) techniques.

In certain embodiments of the methods provided herein, the one or more biomarkers comprises IL-4, IL-5, IL-6, IL-10, IL-13, IL-15, IFN-γ, GM-CSF, TNF-α, IL-2 or IL-12.

In certain aspects, the methods described herein, the determining step requires determining the expression or presence of a combination of biomarkers. In certain embodiment, the combination of biomarkers is CD3 and CD28.

In certain aspects, the expression or presence of these various biomarkers and any clinically useful prognostic markers in a biological sample are detected at the protein or nucleic acid level, using, for example, immunohistochemistry techniques or nucleic acid-based techniques such as in situ hybridization and RT-PCR. In one embodiments, the expression or presence of one or more biomarkers is carried out by a means for nucleic acid amplification, a means for nucleic acid sequencing, a means utilizing a nucleic acid microarray (DNA and RNA), or a means for in situ hybridization using specifically labeled probes.

In other embodiments, the determining the expression or presence of one or more biomarkers is carried out through gel electrophoresis. In one embodiment, the determination is carried out through transfer to a membrane and hybridization with a specific probe.

In other embodiments, the determining the expression or presence of one or more biomarkers carried out by a diagnostic imaging technique.

In still other embodiments, the determining the expression or presence of one or more biomarkers carried out by a detectable solid substrate. In one embodiment, the detectable solid substrate is paramagnetic nanoparticles functionalized with antibodies.

In another aspect, provided herein are methods for detecting or measuring residual lymphoma following a course of treatment in order to guide continuing or discontinuing treatment or changing from one therapeutic regimen to another comprising determining the expression or presence of one or more biomarkers from one or more subpopulation of lymphocytes in a subject wherein the course of treatment is treatment with a covalent TEC family kinase inhibitor.

Methods for detecting expression of the biomarkers described herein, within the test and control biological samples comprise any methods that determine the quantity or the presence of these markers either at the nucleic acid or protein level. Such methods are well known in the art and include but are not limited to western blots, northern blots, ELISA, immunoprecipitation, immunofluorescence, flow cytometry, immunohistochemistry, nucleic acid hybridization techniques, nucleic acid reverse transcription methods, and nucleic acid amplification methods. In particular embodiments, expression of a biomarker is detected on a protein level using, for example, antibodies that are directed against specific biomarker proteins. These antibodies are used in various methods such as Western blot, ELISA, multiplexing technologies, immunoprecipitation, or immunohistochemistry techniques. In some embodiments, detection of biomarkers is accomplished by ELISA. In some embodiments, detection of biomarkers is accomplished by electrochemiluminescence (ECL).

Any means for specifically identifying and quantifying a biomarker (for example, biomarker, a biomarker of cell survival or proliferation, a biomarker of apoptosis, a biomarker of a Btk-mediated signaling pathway) in the biological sample of a candidate subject is contemplated. Thus, in some embodiments, expression level of a biomarker protein of interest in a biological sample is detected by means of a binding protein capable of interacting specifically with that biomarker protein or a biologically active variant thereof. In some embodiments, labeled antibodies, binding portions thereof, or other binding partners are used. The word "label" when used herein refers to a detectable compound or composition that is conjugated directly or indirectly to the antibody so as to generate a "labeled" antibody. In some embodiments, the label is detectable by itself (e.g., radioisotope labels or fluorescent labels) or, in the case of an enzymatic label, catalyzes chemical alteration of a substrate compound or composition that is detectable.

The antibodies for detection of a biomarker protein are either monoclonal or polyclonal in origin, or are synthetically or recombinantly produced. The amount of complexed protein, for example, the amount of biomarker protein associated with the binding protein, for example, an antibody that specifically binds to the biomarker protein, is determined using standard protein detection methodologies known to those of skill in the art. A detailed review of immunological assay design, theory and protocols are found in numerous texts in the art (see, for example, Ausubel et al., eds. (1995) Current Protocols in Molecular Biology) (Greene Publishing and Wiley-Interscience, NY)); Coligan et al., eds. (1994) Current Protocols in Immunology (John Wiley & Sons, Inc., New York, N.Y.).

The choice of marker used to label the antibodies will vary depending upon the application. However, the choice of the marker is readily determinable to one skilled in the art. These labeled antibodies are used in immunoassays as well as in histological applications to detect the presence of any biomarker or protein of interest. The labeled antibodies are either polyclonal or monoclonal. Further, the antibodies for use in detecting a protein of interest are labeled with a radioactive atom, an enzyme, a chromophoric or fluorescent moiety, or a colorimetric tag as described elsewhere herein. The choice of tagging label also will depend on the detection limitations desired. Enzyme assays (ELISAs) typically allow detection of a colored product formed by interaction of the enzyme-tagged complex with an enzyme substrate. Radionuclides that serve as detectable labels include, for example, 1-131, 1-123, 1-125, Y-90, Re-188, Re-186, At-211, Cu-67, Bi-212, and Pd-109. Examples of enzymes that serve as detectable labels include, but are not limited to, horseradish peroxidase, alkaline phosphatase, beta-galactosidase, and glucose-6-phosphate dehydrogenase. Chromophoric moieties include, but are not limited to, fluorescein and rhodamine. The antibodies are conjugated to these labels by methods known in the art. For example, enzymes and chromophoric molecules are conjugated to the antibodies by means of coupling agents, such as dialdehydes, carbodiimides, dimaleimides, and the like. Alternatively, conjugation occurs through a ligand-receptor pair. Examples of suitable ligand-receptor pairs are biotin-avidin or biotin-streptavidin, and antibody-antigen.

In certain embodiments, expression or presence of one or more biomarkers or other proteins of interest within a biological sample, for example, a sample of bodily fluid, is determined by radioimmunoassays or enzyme-linked immunoassays (ELISAs), competitive binding enzyme-linked immunoassays, dot blot (see, for example, Promega Protocols and Applications Guide, Promega Corporation (1991), Western blot (see, for example, Sambrook et al. (1989) Molecular Cloning, A Laboratory Manual, Vol. 3, Chapter 18 (Cold Spring Harbor Laboratory Press, Plainview, N.Y.), chromatography such as high performance liquid chromatography (HPLC), or other assays known in the art. Thus, the detection assays involve steps such as, but not limited to, immunoblotting, immunodiffusion, immunoelectrophoresis, or immunoprecipitation.

In certain other embodiments, the methods of the invention are useful for identifying and treating cancer, including those listed above, that are refractory to (i.e., resistant to, or have become resistant to) first-line oncotherapeutic treatments.

In some embodiments, the expression or presence of one or more of the biomarkers described herein are also determined at the nucleic acid level. Nucleic acid-based techniques for assessing expression are well known in the art and include, for example, determining the level of biomarker mRNA in a biological sample. Many expression detection methods use isolated RNA. Any RNA isolation technique that does not select against the isolation of mRNA is utilized for the purification of RNA (see, e.g., Ausubel et al., ed. (1987-1999) Current Protocols in Molecular Biology (John Wiley & Sons, New York). Additionally, large numbers of tissue samples are readily processed using techniques well known to those of skill in the art, such as, for example, the single-step RNA isolation process disclosed in U.S. Pat. No. 4,843,155.

Thus, in some embodiments, the detection of a biomarker or other protein of interest is assayed at the nucleic acid level using nucleic acid probes. The term "nucleic acid probe" refers to any molecule that is capable of selectively binding to a specifically intended target nucleic acid molecule, for example, a nucleotide transcript. Probes are synthesized by one of skill in the art, or derived from appropriate biological preparations. Probes are specifically designed to be labeled, for example, with a radioactive label, a fluorescent label, an enzyme, a chemiluminescent tag, a colorimetric tag, or other labels or tags that are discussed above or that are known in the art. Examples of molecules that are utilized as probes include, but are not limited to, RNA and DNA.

For example, isolated mRNA are used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that hybridize to the mRNA encoded by the gene being detected. The nucleic acid probe comprises of, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker, biomarker described herein above. Hybridization of an mRNA with the probe indicates that the biomarker or other target protein of interest is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in a gene chip array. A skilled artisan readily adapts known mRNA detection methods for use in detecting the level of mRNA encoding the biomarkers or other proteins of interest.

An alternative method for determining the level of an mRNA of interest in a sample involves the process of nucleic acid amplification, e.g., by RT-PCR (see, for example, U.S. Pat. No. 4,683,202), ligase chain reaction (Barany (1991) Proc. Natl. Acad. Sci. USA 88:189 193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, biomarker expression is assessed by quantitative fluorogenic RT-PCR (i.e., the TaqMan0 System).

Expression levels of an RNA of interest are monitored using a membrane blot (such as used in hybridization analysis such as Northern, dot, and the like), or microwells, sample tubes, gels, beads or fibers (or any solid support comprising bound nucleic acids). See U.S. Pat. Nos. 5,770, 722, 5,874,219, 5,744,305, 5,677,195 and 5,445,934, which are incorporated herein by reference. The detection of expression also comprises using nucleic acid probes in solution.

In one embodiment of the invention, microarrays are used to determine expression or presence of one or more biomarkers. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning Hybridization intensities for each probe on the array are determined and converted to a quantitative value representing relative gene expression levels. See, U.S. Pat. Nos. 6,040,138, 5,800,992 and 6,020,135, 6,033,860, and 6,344,316, which are incorporated herein by reference. High-density oligonucleotide arrays are particularly useful for determining the gene expression profile for a large number of RNA's in a sample.

Techniques for the synthesis of these arrays using mechanical synthesis methods are described in, e.g., U.S. Pat. No. 5,384,261, incorporated herein by reference in its entirety. In some embodiments, an array is fabricated on a surface of virtually any shape or even a multiplicity of surfaces. In some embodiments, an array is a planar array surface. In some embodiments, arrays include peptides or nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. In some embodiments, arrays are packaged in such a manner as to allow for diagnostics or other manipulation of an all-inclusive device. See, for example, U.S. Pat. Nos. 5,856,174 and 5,922,591, herein incorporated by reference.

Dosages, Routes of Administration and Therapeutic Regimens

Described herein methods of administration of a covalent TEC family kinase inhibitor via any conventional means including oral, buccal, rectal, parenteral, intraperitoneal, intradermal, intravenous, subcutaneous, intramuscular, intratumoral, transdermal, intratracheal, intracerobrospinal, intra-articular, intrasynovial, systemic, mucosal, topical, inhalation, etc., administration. In some embodiments, two different routes of administration are used. For example, in some embodiments, the first anticancer therapy is administered by a route such as intramuscular, subcutaneous, or intravenous, and the covalent TEC family kinase inhibitor is administered orally.

Subcutaneous administration of the covalent TEC family kinase inhibitor is accomplished using standard methods and devices, e.g., needle and syringe, a subcutaneous injection port delivery system, and the like. See, e.g., U.S. Pat. Nos. 3,547,119; 4,755,173; 4,531,937; 4,311,137; and 6,017,328. In some embodiments, subcutaneous administration is achieved by a combination of devices, e.g., bolus delivery by needle and syringe, followed by delivery using a continuous delivery system. The term "continuous delivery system" encompasses continuous (e.g., controlled) delivery devices (e.g., pumps) in combination with catheters, injection devices, and the like, a wide variety of which are known in the art. In some embodiments, the covalent TEC family kinase inhibitor is delivered by a continuous delivery system.

Mechanical or electromechanical infusion pumps are also suitable for use with the present invention. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, the present methods of drug delivery are accomplished using any of a variety of refillable, pump systems. Pumps provide consistent, controlled release over time. Typically, the covalent TEC family kinase inhibitor is in a liquid formulation in a drug-impermeable reservoir, and is delivered in a continuous fashion to the individual.

A drug delivery system is at least partially an implantable device. The implantable device is implanted at any suitable implantation site using methods and devices well known in the art. An implantation site is a site within the body of a subject at which a drug delivery device is introduced and positioned. Implantation sites include, but are not necessarily limited to a subdermal, subcutaneous, intramuscular, or other suitable site within a subject's body.

Drug release devices suitable for use in the invention are based on any of a variety of modes of operation. For example, the drug release device is based upon a diffusive system, a convective system, or an erodible system (e.g., an erosion-based system). For example, the drug release device is an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

In some embodiments, in pharmaceutical dosage forms, a covalent TEC family kinase inhibitor is administered in the form of its pharmaceutically acceptable salts. The following methods and excipients are merely exemplary and are in no way limiting.

In some embodiments, as oral preparations, the covalent TEC family kinase inhibitor is used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The covalent TEC family kinase inhibitor is formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Furthermore, the covalent TEC family kinase inhibitor is made into suppositories by mixing with a variety of bases such as emulsifying bases or water-soluble bases. The suppository includes vehicles such as cocoa butter, carbowaxes and polyethylene glycols, which melt at body temperature, yet are solidified at room temperature.

Described herein methods of treatment with a covalent TEC family kinase inhibitor following administration of a first anticancer therapy. In some embodiments, treatment with the covalent TEC family kinase inhibitor is initiated following a decrease in size of the tumor following administration of a first anticancer therapy. In some embodiments, treatment with the covalent TEC family kinase inhibitor is initiated following an elimination of the tumor following administration of a first anticancer therapy. In some embodiments, the covalent TEC family kinase inhibitor is ibrutinib. In some embodiments, treatment with ibrutinib is initiated following a decrease in size of the tumor following administration of a first anticancer therapy. In some embodiments, treatment with ibrutinib is initiated following an elimination of the tumor following administration of a first anticancer therapy.

In some embodiments, treatment with the covalent TEC family kinase inhibitor is initiated after the discontinuation of a first anticancer therapy. In some embodiments, the covalent TEC family kinase inhibitor is initiated in less than 1 hour, 1 hour, 2 hour, 3 hour, 4 hour, 5 hour, 6 hour, 7 hour, 8 hour, 9 hour, 10 hour, 1 day, 2 days, 3 days, 4 days, 5 days, 1 week, 2 weeks, 3 weeks or longer after the discontinuation of a first anticancer therapy. In some embodiments, treatment with the covalent TEC family kinase inhibitor is initiated after a continuation of a first anticancer therapy. In some embodiments, the covalent TEC family kinase inhibitor is initiated in less than 1 hour, 1 hour, 2 hour, 3 hour, 4 hour, 5 hour, 6 hour, 7 hour, 8 hour, 9 hour, 10 hour, 1 day, 2 days, 3 days, 4 days, 5 days, 1 week, 2 weeks, 3 weeks or longer after a continuation of a first anticancer therapy. In some embodiments, treatment with the covalent TEC family kinase inhibitor is initiated after the continuation of a first anticancer therapy and after an initiation of a second anticancer therapy. In some embodiments, the covalent TEC family kinase inhibitor is initiated in less than 1 hour, 1 hour, 2 hour, 3 hour, 4 hour, 5 hour, 6 hour, 7 hour, 8 hour, 9 hour, 10 hour, 1 day, 2 days, 3 days, 4 days, 5 days, 1 week, 2 weeks, 3 weeks or longer after the continuation of a first anticancer therapy and after an initiation of a second anticancer therapy. In some embodiments, treatment with the covalent TEC family kinase inhibitor is initiated after the continuation of a first anticancer therapy but simultaneously or intermittently with an initiation of a second anticancer therapy. In some embodiments, the covalent TEC family kinase inhibitor is initiated in less than 1 hour, 1 hour, 2 hour, 3 hour, 4 hour, 5 hour, 6 hour, 7 hour, 8 hour, 9 hour, 10 hour, 1 day, 2 days, 3 days, 4 days, 5 days, 1 week, 2 weeks, 3 weeks or longer after the continuation of a first anticancer therapy but simultaneously or intermittently with an initiation of a second anticancer therapy. In some embodiments, treatment with the covalent TEC family kinase inhibitor is initiated after the discontinuation of a first anticancer therapy and after an initiation of a second anticancer therapy. In some embodiments, the covalent TEC family kinase inhibitor is initiated in less than 1 hour, 1 hour, 2 hour, 3 hour, 4 hour, 5 hour, 6 hour, 7 hour, 8 hour, 9 hour, 10 hour, 1 day, 2 days, 3 days, 4 days, 5 days, 1 week, 2 weeks, 3 weeks or longer after the discontinuation of a first anticancer therapy and after an initiation of a second anticancer therapy. In some embodiments, treatment with the covalent TEC family kinase inhibitor is initiated after the discontinuation of a first anticancer therapy but simultaneously or intermittently with an initiation of a second anticancer therapy. In some embodiments, the covalent TEC family kinase inhibitor is initiated in less than 1 hour, 1 hour, 2 hour, 3 hour, 4 hour, 5 hour, 6 hour, 7 hour, 8 hour, 9 hour, 10 hour, 1 day, 2 days, 3 days, 4 days, 5 days, 1 week, 2 weeks, 3 weeks or longer after the discontinuation of a first anticancer therapy but simultaneously or intermittently with an initiation of a second anticancer therapy.

In some embodiment, the covalent TEC family kinase inhibitor is ibrutinib. In some embodiments, treatment with ibrutinib is initiated after the discontinuation of a first anticancer therapy. In some embodiments, ibrutinib is initiated in less than 1 hour, 1 hour, 2 hour, 3 hour, 4 hour, 5 hour, 6 hour, 7 hour, 8 hour, 9 hour, 10 hour, 1 day, 2 days, 3 days, 4 days, 5 days, 1 week, 2 weeks, 3 weeks or longer after the discontinuation of a first anticancer therapy. In some embodiments, treatment with ibrutinib is initiated after a continuation of a first anticancer therapy. In some embodiments, ibrutinib is initiated in less than 1 hour, 1 hour, 2 hour, 3 hour, 4 hour, 5 hour, 6 hour, 7 hour, 8 hour, 9 hour, 10 hour, 1 day, 2 days, 3 days, 4 days, 5 days, 1 week, 2 weeks, 3 weeks or longer after a continuation of a first anticancer therapy. In some embodiments, treatment with ibrutinib is initiated after the continuation of a first anticancer therapy and after an initiation of a second anticancer therapy. In some embodiments, ibrutinib is initiated in less than 1 hour, 1 hour, 2 hour, 3 hour, 4 hour, 5 hour, 6 hour, 7 hour, 8 hour, 9 hour, 10 hour, 1 day, 2 days, 3 days, 4 days, 5 days, 1 week, 2 weeks, 3 weeks or longer after the continuation of a first anticancer therapy and after an initiation of a second anticancer therapy. In some embodiments, treatment with ibrutinib is initiated after the continuation of a first anticancer therapy but simultaneously or intermittently with an initiation of a second anticancer therapy. In some embodiments, ibrutinib is initiated in less than 1 hour, 1 hour, 2 hour, 3 hour, 4 hour, 5 hour, 6 hour, 7 hour, 8 hour, 9 hour, 10 hour, 1 day, 2 days, 3 days, 4 days, 5 days, 1 week, 2 weeks, 3 weeks or longer after the continuation of a first anticancer therapy but simultaneously or intermittently with an initiation of a second anticancer therapy. In some embodiments, treatment with ibrutinib is initiated after the discontinuation of a first anticancer therapy and after an initiation of a second anticancer therapy. In some embodiments, ibrutinib is initiated in less than 1 hour, 1 hour, 2 hour, 3 hour, 4 hour, 5 hour, 6 hour, 7 hour, 8 hour, 9 hour, 10 hour, 1 day, 2 days, 3 days, 4 days, 5 days, 1 week, 2 weeks, 3 weeks or longer after the discontinuation of a first anticancer therapy and after an initiation of a second anticancer therapy. In some embodiments, treatment with ibrutinib is initiated after the discontinuation of a first anticancer therapy but simultaneously or intermittently with an initiation of a second anticancer therapy. In some embodiments, ibrutinib is initiated in less than 1 hour, 1 hour, 2 hour, 3 hour, 4 hour, 5 hour, 6 hour, 7 hour, 8 hour, 9 hour, 10 hour, 1 day, 2 days, 3 days, 4 days, 5 days, 1 week, 2 weeks, 3 weeks or longer after the discontinuation of a first anticancer therapy but simultaneously or intermittently with an initiation of a second anticancer therapy.

In some embodiments, the covalent TEC family kinase inhibitor is administered during the entire course of the continued first anticancer therapy treatment. In some embodiments, the covalent TEC family kinase inhibitor is administered during the entire course of the continued first anticancer therapy and the second anticancer therapy treatments. In some embodiments, the covalent TEC family kinase inhibitor is administered for a period of time that is overlapping with the treatments of the continued first anticancer therapy and the second anticancer therapy, e.g. the covalent TEC family kinase inhibitor treatment ends before the treatments of the continued first anticancer therapy and the second anticancer therapy end; the covalent TEC family kinase inhibitor treatment ends after the treatments of the continued first anticancer therapy and the second anticancer therapy end.

In some embodiments, the covalent TEC family kinase inhibitor is ibrutinib. In some embodiments, ibrutinib is administered during the entire course of the continued first anticancer therapy treatment. In some embodiments, ibrutinib is administered during the entire course of the continued first anticancer therapy and the second anticancer therapy treatments. In some embodiments, ibrutinib is administered for a period of time that is overlapping with the treatments of the continued first anticancer therapy and the second anticancer therapy, e.g. ibrutinib treatment ends before the treatments of the continued first anticancer therapy and the second anticancer therapy end; ibrutinib treatment ends after the treatments of the continued first anticancer therapy and the second anticancer therapy end.

In some embodiments, a biomarker profile is measured to assess or evaluate a therapeutic regimen after the administration of the covalent TEC family kinase inhibitor. In some embodiments, the biomarker profile is measured daily, once per week, two times per week, three times per week, once every two weeks, once a month, twice a month, three times a month, once, twice, three times, four times, five times, six times, seven times, eight times, nine times, ten times or more during the entire course of the treatment. In some embodiments, the biomarker is: CCR1, CCR3, CCR4, CCR7, CCR8, CD4, CD26, CD28, CD30, CD81, CD94, CD119, CD183, CD184, CD195, CD212, CD278, c-maf, CRTH2, Gata-3, GM-CSF, IFN γR, IgD, IL-1R, IL-4, IL-5, IL-6, IL-9, IL-10, IL-13, IL-15, IL-2, IL-12, IL-15, IL-18R, IL-23, IL-27, IL-27R, ST2L/T1, Tim-1, Tim-3, GM-CSF, Granzyme B, IFN-α, IFN-γ, Lymphotoxin, perforin, t-bet, TNF-α, TRANCE, sCD40L, or a combination thereof. In some embodiments, the biomarker is a Th1 related marker. In some embodiments, Th1 related markers include CCR1, CD4, CD26, CD94, CD119, CD183, CD195, CD212, GM-CSF, Granzyme B, IFN-α, IFN-γ, IL-2, IL-12, IL-15, IL-18R, IL-23, IL-27, IL-27R, Lymphotoxin, perforin, t-bet, Tim-3, TNF-α, TRANCE and sCD40L. In some embodiments, the Th1 biomarker is IFN-γ. In some embodiments, the Th1 biomarker is IL-2. In some embodiments, the Th1 biomarker is IL-12. In some embodiments, the biomarker is a Th2 related marker. In some embodiments, Th2 related markers include CCR3, CCR4, CCR7, CCR8, CD4, CD30, CD81, CD184, CD278, c-maf, CRTH2, Gata-3, GM-CSF, IFN γR, IgD, IL-1R, IL-4, IL-5, IL-6, IL-9, IL-10, IL-13, IL-15, ST2L/T1 and Tim-1. In some embodiments, the Th2 biomarker is 11-4. In some embodiments, the Th2 biomarker is IL-10. In some embodiments, the Th2 biomarker is IL-13. In some embodiments, the treatment with ibrutinib is modified based on the biomarker profile. In some embodiments, the amount of ibrutinib administered to the patient is increased, decreased or not altered based on the biomarker profile. In some embodiments, the frequency of administration of ibrutinib to the patient is increased, decreased or not altered based on the biomarker profile. In some embodiments, the cytokine biomarker profile is used to calculate a Th1:Th2 ratio in the patient. In some embodiments, the treatment with ibrutinib is modified based on the Th1:Th2 ratio. In some embodiments, the amount of ibrutinib administered to the patient is increased, decreased or not altered based on the Th1:Th2 ratio. In some embodiments, the frequency of administration of ibrutinib to the patient is increased, decreased or not altered based on the Th1:Th2 ratio. In some embodiments, the number of cells expressing a Th1 biomarker is measured in a patient sample. In some embodiments, the number of cells expressing a Th2 biomarker is measured in a patient sample. In some embodiments, the ratio of Th1:Th2 ratio is calculated based on the the number of cells expressing a Th1 biomarker versus the number of cells expressing a Th2 biomarker measured in a patient sample. In some embodiments, the ratio of Th1:Th2 ratio is calculated based on the total expression of a Th1 biomarker versus a Th2 biomarker in a patient sample.

In some embodiments, adjuvant therapy comprises a single administration. In some embodiments, adjuvant therapy comprises multiple cycles of administration. In some embodiments, a cycle of administration is one month, 2 months, 3 months, 4 months, 5 months, 6 months, 7 months, 8 months, 9 months, 10 months, 11 months, 12 months or longer. In some embodiments, a cycle of administration comprises administration of a single therapeutic dosage of the covalent TEC family kinase inhibitor over the cycle. In some embodiments, a cycle of administration comprises two or more different dosages of the covalent TEC family kinase inhibitor over the cycle. In some embodiments, the dosage of the covalent TEC family kinase inhibitor differs over consecutive cycles. In some embodiments, the dosage of the covalent TEC family kinase inhibitor increases over consecutive cycles. In some embodiments, the dosage of the covalent TEC family kinase inhibitor is the same over consecutive cycles. In some embodiments, the covalent TEC family kinase inhibitor is administered for about 1 week to 5 years.

In some embodiments, adjuvant therapy comprises administration of a daily dosage of the covalent TEC family kinase inhibitor. In some embodiments, the daily dosage of the covalent TEC family kinase inhibitor administered is at or about 10 mg per day to about 2000 mg per day, such as for example, about 40 mg per day to about 1500 mg per day, such as for example, about 40 mg per day to about 1000 mg per day, such as for example about 100 mg per day to about 1000 mg per day, such as for example about 250 mg per day to about 850 mg per day, such as for example about 300 mg per day to about 600 mg per day. In a particular embodiment, daily dosage of the covalent TEC family kinase inhibitor is about 420 mg per day. In a particular embodiment, the covalent TEC family kinase inhibitor is ibrutinib and the daily dosage is about 420 mg per day. In a particular embodiment, daily dosage of the covalent TEC family kinase inhibitor is about 140 mg per day. In a particular embodiment, the covalent TEC family kinase inhibitor is ibrutinib and the daily dosage is about 140 mg ibrutinib per day.

In some embodiments, the covalent TEC family kinase inhibitor is administered once per month, twice per month, three times per month, every other week, once per week, twice per week, three times per week, four times per week, five times per week, six times per week, every other day, daily, twice a day, three times a day or more frequent, continuously over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In a particular embodiment, the covalent TEC family kinase inhibitor is administered once per day. In some embodiments, the covalent TEC family kinase inhibitor that is ibrutinib is administered once per month, twice per month, three times per month, every other week, once per week, twice per week, three times per week, four times per week, five times per week, six times per week, every other day, daily, twice a day, three times a day or more frequent, continuously over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In a particular embodiment, the covalent TEC family kinase inhibitor that is ibrutinib is administered once per day.

In some embodiments, the covalent TEC family kinase inhibitor is administered by any suitable route of administration. In some embodiments, the covalent TEC family kinase inhibitor is administered orally.

In some embodiments, DFS or OS is evaluated following administration of the covalent TEC family kinase inhibitor. In some embodiments, DFS or OS is evaluated about 1, 2, 3, 4, 5, 6, 7, 8, 9, 10 years or longer after initiation of the covalent TEC family kinase inhibitor.

In some embodiments, a cycle of administration comprises administration of the covalent TEC family kinase inhibitor in combination with an additional therapeutic agent. In some embodiments the additional therapeutic agent is administered simultaneously, sequentially, or intermittently with the covalent TEC family kinase inhibitor. In some embodiments, the covalent TEC family kinase inhibitor and the additional therapeutic agent are administered as a single composition. In some embodiments, the covalent TEC family kinase inhibitor and the additional therapeutic agent are administered as separate compositions.

In some embodiments the additional therapeutic agent or biologic agent is an anticancer agent. In some embodiments the additional therapeutic agent is an anticancer agent for the treatment of a solid tumor. In some embodiments the additional therapeutic agent is an anticancer agent for the treatment of a hematologic cancer. In some embodiments, the additional therapeutic agent is an anticancer agent for the treatment of a leukemia, lymphoma or a myeloma. In some embodiments, the additional therapeutic agent is an anticancer agent for the treatment of bladder, breast, colon, pancreatic, lung, prostate, ovarian and proximal or distal bile duct cancer. Exemplary anticancer agents for administration in a combination with a covalent TEC family kinase inhibitor are provided elsewhere herein and include, but are not limited to chemotherapeutic agents, biologic agents, radiation therapy, thermal therapy, or surgery. In a particular embodiment, the anticancer agent is an anti-CD 20 antibody (e.g. Rituxan). In a particular embodiment, the anticancer agent bendamustine. In some embodiments, the additional anticancer agent is a reversible TEC family kinase inhibitor. In some embodiments, the additional anticancer agent is a reversible ITK inhibitor. In some embodiments, the additional anticancer agent is a reversible BTK inhibitor that does not depend on cysteine 442 for binding to ITK. In some embodiments, the additional anticancer agent is a reversible BTK inhibitor. In some embodiments, the additional anticancer agent is a reversible BTK inhibitor that does not depend on cysteine 481 for binding to BTK.

In some embodiments, the covalent TEC family kinase inhibitor is administered alone (e.g. monotherapy). In some embodiments, the covalent TEC family kinase inhibitor is administered in combination with an additional chemotherapeutic agent or biologic agent. In some embodiments, the additional chemotherapeutic agent or biologic agent is selected from among an antibody, a B cell receptor pathway inhibitor, a T cell receptor inhibitor, a PI3K inhibitor, an IAP inhibitor, an mTOR inhibitor, a radioimmunotherapeutic, a DNA damaging agent, a proteasome inhibitor, a histone deacetylase (HDCA) inhibitor, a protein kinase inhibitor, an IRAK inhibitor, a hedgehog inhibitor, an Hsp90 inhibitor, a telomerase inhibitor, a Jak1/2 inhibitor (e.g., ruxolitinib, baricitinib, CYT387, lestauritinib, pacritinib, TG101348, SAR302503, tofacitinib (Xeljanz), etanercept (Enbrel), GLPG0634, R256), a protease inhibitor, a PKC inhibitor, a PARP inhibitor, a proteosome inhibitor, a CYP3A4 inhibitor, an AKT inhibitor, an Erk inhibitor, an alkylating agent, an anti metabolite, a plant alkaloid, a terpenoid, a cytotoxin, a topoisomerase inhibitor, or a combination thereof. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, a CD22 inhibitor, a Bcl-2 inhibitor, an IRAK 1/4 inhibitor, a microtubule inhibitor, a Topo II inhibitor, anti TWEAK, anti-IL17 bispecific antibody, a CK2 inhibitor, anaplastic lymphoma kinase (ALK) and c-Met inhibitors, a T cell receptor inhibitor is Muromonab-CD3, demethylase enzyme inhibitors such as demethylase, HDM, LSDI and KDM, fatty acid synthase inhibitors such as spirocyclic piperidine derivatives, glucocorticosteriod receptor agonist, fusion anti-CD 19-cytotoxic agent conjugate, antimetabolite, p70S6K inhibitor, immune modulators, AKT/PKB inhibitor, procaspase-3 activator PAC-1, BRAF inhibitor, lactate dehydrogenase A (LDH-A) inhibitor, CCR2 inhibitor, CXCR4 inhibitor, chemokine receptor antagonists, DNA double stranded break repair inhibitors, NOR202, GA-101, TLR2 inhibitor, or a combination thereof. In some embodiments, the chemotherapeutic agent or biologic agent is selected from among rituximab, carfilzomib, fludarabine, cyclophosphamide, vincristine, prednisalone. chlorambucil, ifosphamide, doxorubicin, mesalazine, thalidomide, lenalidomide, temsirolimus, everolimus, fostamatinib, paclitaxel, docetaxel, ofatumumab, dexamethasone, prednisone, CAL-101, ibritumomab, tositumomab, bortezomib, pentostatin, endostatin, ritonavir, ketoconazole, an anti-VEGF antibody, herceptin, cetuximab, cisplatin, carboplatin, docetaxel, erlotinib, etopiside, 5-fluorouracil, gemcitabine, ifosphamide, imatinib mesylate (Gleevec), gefitinib, procarbazine, prednisone, irinotecan, leucovorin, mechlorethamine, methotrexate, oxaliplatin, paclitaxel, sorafenib, sunitinib, topotecan, vinblastine, disulfiram, epigallocatechin-3-gallate, salinosporamide A, ONX0912, CEP-18770, MLN9708, R-406, lenalinomide, spirocyclic piperidine derivatives, quinazoline carboxamide azetidine compounds, thiotepa, DWA2114R, NK121, IS 3 295, 254-S, alkyl sulfonates such as busulfan, improsulfan and piposulfan; aziridines such as benzodepa, carboquone, meturedepa and uredepa; ethylenimine, methylmelamines such as altretamine, triethylenemelamine, triethylenephosphoramide, triethylenethiophosphoramide and trimethylmelamine; chlornaphazine; estramustine; ifosfamide; mechlorethamine; oxide hydrochloride; novobiocin; phenesterine; prednimustine; trofosfamide; uracil mustard; nitrosoureas such as carmustine, chlorozotocin, fotemustine, lomustine, nimustine, ranimustine; antibiotics such as aclacinomycins, actinomycin, anthramycin, azaserine, bleomycins, cactinomycin, calicheamicin, carubicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatrexate; defosfamide; demecolcine; diaziquone; eflornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide-K; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; cytosine arabinoside; taxoids, e.g., paclitaxel and docetaxel; 6-thioguanine; mercaptopurine; methotrexate; platinum analogs; platinum; etoposide (VP-16); ifosfamide; mitomycin C; mitoxantrone; vincristine; vinorelbine; Navelbine; Novantrone; teniposide; daunomycin; aminopterin; Xeloda; ibandronate; CPT1 1; topoisomerase inhibitor RFS 2000; difluoromethylornithine (DMFO); retinoic acid; esperamycins; capecitabine; and pharmaceutically acceptable salts, acids or derivatives of; anti-hormonal agents such as anti-estrogens including for example tamoxifen, raloxifene, aromatase inhibiting 4(5)-imidazoles, 4-hydroxytamoxifen, trioxifene, keoxifene, LY117018, onapristone and toremifene (Fareston); antiandrogens such as flutamide, nilutamide, bicalutamide, leuprolide and goserelin; or a combination thereof. In some embodiments, the chemotherapeutic agent or biologic agent is selected from among AVL-263 (Avila Therapeutics/Celgene Corporation), AVL-292 (Avila Therapeutics/Celgene Corporation), AVL-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited) or a combination thereof.

In some embodiments, the covalent TEC family kinase inhibitor is administered in combination with an additional chemotherapeutic agent or biologic agent for the treatment of a leukemia, lymphoma or a myeloma. Exemplary chemotherapeutic agents for the treatment of a leukemia, lymphoma or a myeloma include but are not limited to adriamycin (doxorubicin), bexxar, bendamustine, bleomycin, blenoxane, bortezomib, dacarbazine, deltasone, cisplatin, cyclophosphamide, cytoxan, DTIC daca rbazine, dasatinib, doxorubicin, etoposide, fludarabine, granisetron, kytril, lenalidomide, matulane, mechlorethamine, mustargen, mustine, natulan, Rituxan (rituximab, anti-CD20 antibody), VCR, neosar, nitrogen mustard, oncovin, ondansetron, orasone, prednisone, procarbazine, thalidomide, VP-16, velban, velbe, velsar, VePesid, vinblastine, vincristine, Zevalin®, zofran, stem cell transplantation, radiation therapy or combination therapies, such as, for example, ABVD (adriamycin, bleomycin, vinblastine and dacarbazine), Ch1vPP (chlorambucil, vinblastine, procarbazine and prednisolone), Stanford V (mustine, doxorubicin, vinblastine, vincristine, bleomycin, etoposide and steroids), BEACOPP (bleomycin, etoposide, doxorubicin, cyclophosphamide, vincristine, procarbazine and prednisolone), BEAM (carmustine (BiCNU) etoposide, cytarabine (Ara-C, cytosine arabinoside), and melphalan), CHOP (cyclophosphamide, doxorubicin, vincristine, and prednisone), R-CHOP (rituximab, doxorubicin, cyclophosphamide, vincristine, and prednisone), EPOCH (etoposide, vincristine, doxorubicin, cyclophosphamide, and prednisone), CVP (cyclophosphamide, vincristine, and prednisone), ICE (ifosfamide-carboplatin-etoposide), R-ACVBP (rituximab, doxorubicin, cyclophosphamide, vindesine, bleomycin, and prednisone), DHAP (dexamethasone, high-dose cytarabine, (Ara C), cisplatin), R-DHAP (rituximab, dexamethasone, high-dose cytarabine, (Ara C), cisplatin), ESHAP (etoposide (VP-16), methyl-prednisolone, and high-dose cytarabine (Ara-C), cisplatin), CDE (cyclophosphamide, doxorubicin and etoposide), Velcade® (bortezomib) plus Doxil® (liposomal doxorubicin), Revlimid® (lenalidomide) plus dexamethasone, and bortezomib plus dexamethasone.

In some embodiments, anticancer agent is fludarabine. In some embodiments, anticancer agent is bendamustine. In some embodiments, the anticancer agent is Rituxan. In some embodiments, the anticancer agent is dasatinib. In some embodiments, anticancer agent is a HDAC inhibitor. In some embodiments, anticancer agent is a Cyp3A4 inhibitor. In some embodiments, anticancer agent is carfilzomib. In some embodiments, anticancer agent is bortezomib (Veload). In some embodiments, anticancer agent is an IRAK inhibitor. In some embodiments, anticancer agent is revlimid. In some embodiments, anticancer agent is lenalidomide. In some embodiments, anticancer agent is dexamethasone. In some embodiments, anticancer agent is a protease inhibitor. In some embodiments, anticancer agent is a JAK inhibitor. In some embodiments, anticancer agent is an AKT inhibitor. In some embodiments, anticancer agent is an Erk inhibitor.

In some embodiments, the covalent TEC family kinase inhibitor is administered alone (e.g. monotherapy). In some embodiments, the covalent TEC family kinase inhibitor is administered in combination with an additional therapeutic agent. In some embodiments, the covalent TEC family kinase inhibitor is administered in combination with an immunotherapy. In some embodiments, the T-cell immunotherapy is selected from among adoptive T cell transfer, a vaccine, a cytokine, an interleukin, a chemokine, a cytokine inducer, an interleukin inducer, a chemokine inducer, or an immunomodulatory antibody. In some embodiments, the vaccine is an anti cancer vaccine, such as for example, Sipuleucel-T. In some embodiments, the covalent TEC family kinase inhibitor is administered in combination with an anticancer, antiviral or antibacterial agent.

Adjuvant for Treatment of a Pathogenic Infection

Described herein, in certain embodiments, are methods of adjuvant therapy for the treatment of an immune disorder. In some embodiments, the methods of adjuvant therapy comprise administering to a subject having an immune disorder an effective amount of a covalent TEC family kinase to treat the immune disorder. In some embodiments, the methods of adjuvant therapy comprise administering to a subject having an immune disorder an effective amount of a covalent TEC family kinase to treat a pathogenic infection associated with the immune disorder. In some embodiments, the methods of adjuvant therapy comprise administering to a subject having an a pathogenic infection an effective amount of a covalent TEC family kinase to treat the pathogenic infection.

Described herein, in certain embodiments, are methods of adjuvant therapy for the treatment of an immune disorder characterized by an impaired Th1 immune response or an overactive Th2 response. In some embodiments, the methods of adjuvant therapy comprise administering to a subject having an immune disorder characterized by an impaired Th1 immune response or an overactive Th2 response an effective amount of a covalent TEC family kinase inhibitor to increase the Th1 immune response or decrease the Th2 response in the subject. In some embodiments, the subject has a pathogenic infection. In some embodiments, the disease or condition is associated with increased Th2 activity, such an allergic or asthmatic disorder. In some embodiments, the pathogenic infection is a viral, bacterial, fungal or parasitic infection. In some embodiments, the autoimmune disease is autoimmune arthritis. In some embodiments, the immune disorder is atopic dermatitis, inflammatory bowel disease, an unspecified T-cell lymphoma (U-PTCLs), rheumatoid arthritis, bronchial asthma, allergic airway inflammatory disease or aplastic anemia.

In some embodiments, methods of adjuvant therapy are for the treatment of a pathogenic infection in an individual. In some embodiments, methods of adjuvant therapy are for the treatment of a pathogenic infection in an individual, wherein the pathogenic infection is characterized by an impaired Th1 immune response or an overactive Th2 response. In some embodiments, methods of adjuvant therapy comprise administering to a subject an effective amount of a covalent TEC family kinase inhibitor to treat the pathogenic infection. In some embodiments, methods of adjuvant therapy comprise administering to a subject an effective amount of a covalent TEC family kinase inhibitor in combination with one or more therapeutic agents to treat the pathogenic infection.

In some embodiments, methods of adjuvant therapy are for the treatment of a viral infection. In some embodiments, the subject has a chronic viral infection. In some embodiments, the subject has an acute viral infection.

In some embodiments, the virus infection is a DNA virus infection. In some embodiments, the virus is an adenovirus, a papilloma virus, a parvovirus, a herpes viruses, a pox virus, a hepatitis virus. In some embodiments, the virus infection is a RNA virus infection. In some embodiments, the virus is a reovirus, a picorna viruse, a calicivirus, a togavirus, an arenavirus, a flavivirus, a orthmyxoviurs, a paramyxovirus, a bunyavirus, a rhabdovirus, a filovirus, a coronavirus, an astrovirus, a bornavirus, an arterivirus, or a hepevirus. In some embodiments, the virus infection is a retrovirus infection. In some embodiments, the virus infection is a hepatitis B infection. In some embodiments, the virus infection is a cytoplasmic virus infection. In some embodiments, the virus infection is a nuclear virus infection. In some embodiments, the virus is a hepatitis virus (e.g., HCV), an influenza virus, a human immunodeficiency virus infection, a measles virus, a human papilloma virus (HPV), a human herpes virus (HHV-6A, -6B, 7), an herpes simplex virus (HSV), an epstein bar virus (EBV), a cytomegalovirus, a respiratory syncytial virus or chronic granulomatous disease.

In certain embodiments, the progression of a viral infection from an acute viral infection into a chronic viral infection is characterized by and increased Th2 immune profile and a decreased Th1 immune profile. In some embodiments, administration of a covalent TEC family kinase inhibitor inhibits or delays the progression of a viral infection from an acute viral infection into a chronic viral infection. In some embodiments, administration of a covalent TEC family kinase inhibitor increases the Th1 immune response in a subject having a chronic viral infection.

In some embodiments, the subject has a hepatitis infection. In some embodiments, the hepatitis infection is an A type hepatitis infection. In some embodiments, the hepatitis infection is a B type hepatitis infection. In some embodiments, the hepatitis infection is a C type hepatitis infection. In some embodiments, the hepatitis infection is a D type hepatitis infection. In some embodiments, the hepatitis infection is an E type hepatitis infection. In some embodiments, the hepatitis infection is an HCV infection. In some embodiments, the subject having an HCV infection is infected with multiple HCV genotypes. In some embodiments, multiple HCV genotypes include type 1, 2, 3, 4, 5 or 6 or any combination thereof. Genotype 1 is further defined as 1a or 1b. Genotype 2 is further defined as 2a, 2b, 2c or 2d. Genotype 3 is further defined as 3a, 3b, 3c, 3d, 3e or 3f. Genotype 4 is further defined as 4a, 4b, 4c, 4d, 4e, 4f, 4g, 4h, 4i or 4j. Genotype 5 is further defined as 5a. Genotype 6 is further defined as 6a. In some embodiments, multiple HCV genotypes include type 1 and 2 or any combination thereof. In some embodiments, multiple HCV genotypes include type 1 and 3 or any combination thereof. In some embodiments, multiple HCV genotypes include type 1, 2 and 3 or any combination thereof. In some embodiments, the subject has a chronic HCV infection. In some embodiments, a chronic HCV infection is characterized by the presence of anti-HCV and HCV RNA in the serum for more than six months. In some embodiments, the subject has an acute HCV infection. In some embodiments, an acute HCV infection is characterized by the presence of anti-HCV and HCV RNA in the serum within six months of initial HCV exposure. In some embodiments, the subject has an occult HCV infection. In some embodiments, an occult HCV infection is characterized by the presence of HCV-RNA in liver cells with undetectable anti-HCV and serum viral RNA.

In certain embodiments, the progression of HCV infection from an acute viral infection into a chronic viral infection is characterized by and increased Th2 immune profile and a decreased Th1 immune profile. In some embodiments, administration of a covalent TEC family kinase inhibitor inhibits or delays the progression of a HCV infection from an acute HCV infection into a chronic HCV infection. In some embodiments, administration of a covalent TEC family kinase inhibitor increases the Th1 immune response in a subject having a chronic HCV infection.

In some embodiments, the subject has an influenza infection. In some embodiments, the subject having an influenza infection is infected with influenza A virus. In some embodiments, influenza A virus include all subtypes-H1N1, H2N2, H3N2, H5N1, H7N7, H1N2, H9N2, H7N2, H7N3, H10N7 and H7N9.

In some embodiments, the subject has AIDS. In some embodiments, the subject having AIDS is infected with human immunodeficiency virus (HIV). In some embodiments, HIV includes HIV-1 and HIV-2.

In some embodiments, the subject has a bacterial infection. In some embodiments, the subject has a chronic bacterial infection. In some embodiments, the bacterium is an intracellular bacterium. In some embodiments, the subject has a *Listeria monocytogenes* infection.

In some embodiments, the subject has a fungal infection. In some embodiment, the subject has a chronic fungal infection. In some embodiments, the subject has a parasitic infection.

In some embodiments, the subject is a mammal, such as, but not limited to a human, a non-human primate, mouse, rat, rabbit, goat, dog, cat, or cow. In some embodiments, the mammal is a human. In some embodiments, the human is a patient having an HCV infection. In some embodiments, the patient has a chronic HCV infection. In some embodiments, the patient having chronic HCV infection means any patient having chronic HCV and includes treatment naive patients, relapsers and non-responders. In some embodiments, the patient has infections caused by multiple viruses. In some embodiments, the patient has a primary infection followed by a secondary infection. In some embodiments, the patient has infections caused by HCV and HIV. In some embodiments, the primary infection is an HIV infection and the secondary infection is a viral, bacterial, fungal or parasitic infection. In some embodiments, the primary infection is an HIV infection and the secondary infection is a HCV infection.

Adjuvant Treatment Regimens

In some embodiments, the covalent TEC family kinase inhibitor is administered in combination with a T-cell immunotherapy. In some embodiments, the T-cell immunotherapy is selected from among adoptive T cell transfer, a vaccine, a cytokine, an interleukin, a chemokine, a cytokine inducer, an interleukin inducer, a chemokine inducer, or an immunomodulatory antibody. In some embodiments, the vaccine is an anti cancer vaccine, such as for example, Sipuleucel-T.

In some embodiments, the covalent TEC family kinase inhibitor is administered alone (e.g. monotherapy) for treatment of a viral infection. In some embodiments, the covalent TEC family kinase inhibitor is administered in combination with an antiviral agent. Exemplary antiviral agents for use in combination with a covalent TEC family kinase inhibitor for adjuvant therapy include, but are not limited to, immunostimulants such as interferon (e.g., alpha interferons, beta interferons, gamma interferons, pegylated alpha interferons, pegylated beta interferons, pegylated gamma interferons and mixtures of any two or more thereof), granulocyte macrophage colony-stimulating factor, echinacin, isoprinosine, adjuvants, biodegradable microspheres (e.g., polylactic galactide) and liposomes (into which the compound is incorporated), and thymus factors; immunosuppressants such as cyclosporin, azatioprin, methotrexate, cyclophsphamide, FK 506, Cortisol, betametasone, cortisone, desametasone, flunisolide, prednisolone, methylprednisolone, prednisone, triamcinolone, alclometasone, amcinonide desonide, desoxymetasone, prednisone, cyclosporine, mycophenolate mofetil, and tacrolimus; nucleoside and nucleotide antiviral agents such as abacavir, acyclovir (ACV), adefovir, zidovudine (ZDV), ribavirin, lamivudine, adefovir and entecavir, tenofovir, emtricitabine, telbuvidine, clevudine, valtorcitabine, cidofovir, and derivatives thereof; protease inhibitors such as saquinavir, ritonavir, indinavir, nelfinavir, amprenavir, atazanavir, boceprevir, and HCV NS3 protease inhibitors; inosine 5'-monophosphate dehydrogenase (IMPDH) inhibitors such as merimepodib (VX-497); viral entry inhibitors; viral maturation inhibitors; viral uncoating inhibitors such as amantadine, rimantadine, pleconaril, and derivatives thereof; integrase inhibitors; viral enzyme inhibitors; antisense antiviral molecules; ribozyme antiviral agents such as RNase P ribozyme; nanoviricides, antisense antiviral molecules include, but are not limited to, oligonucleotides designed to recognize and inactivate viral genes and antibodies.

Antibodies for use in combination with the covalent TEC family kinase inhibitor provided herein include, but are not limited to, monoclonal antibodies, multispecific antibodies, synthetic antibodies, human antibodies, humanized antibodies, chimeric antibodies, intrabodies, single-chain Fvs (scFv), single chain antibodies, Fab fragments, F(ab') fragments, disulfide-linked Fvs (sdFv), and anti-idiotypic (anti- Id) antibodies (including, e.g., anti-Id antibodies to antibodies provided herein), and epitope-binding fragments of any of the above. The antibodies for use in combination with the covalent TEC family kinase inhibitor provided herein can be of any type (e.g., IgG, IgE, IgM, IgD, IgA and IgY), class (e.g., IgGi, IgG2, IgG3, IgG4, IgAi and IgA2) or subclass of immunoglobulin molecule.

Antibodies for use in combination with the covalent TEC family kinase inhibitor provided herein can be from any animal origin, including birds and mammals (e.g., human, murine, donkey, sheep, rabbit, goat, guinea pig, camel, horse, shark, llama, or chicken). Typically, the antibodies for use in combination with covalent TEC family kinase inhibitor provided herein are human or humanized antibodies. The antibodies for use in combination with covalent TEC family kinase inhibitor provided herein can be monospecific, bispecific, trispecific or of greater multispecificity.

The antibodies for use in combination with covalent TEC family kinase inhibitor provided herein can include derivative antibodies that are modified, for example, by the attachment of any type of molecule to the antibody or antigen-binding fragment thereof such as by covalent attachment. Exemplary antibody or antigen-binding fragment thereof derivatives include antibodies that have been modified, for example, by glycosylation, acetylation, pegylation, phosphorylation, amidation, derivatization by known protecting/blocking groups, proteolytic cleavage, linkage to a cellular ligand or other protein, or contain heterologous Fc domain with higher affinities for the FcRN receptor (see, e.g. U.S. Pat. No. 7,083,784). Any of numerous chemical modifications can be carried out by known techniques, including, but not limited to, specific chemical cleavage, acetylation, formylation, or synthesis in the presence of tunicamycin. Additionally, the derivative can contain one or more non-classical amino acids.

In some embodiments, antibodies include actoxumab, bezlotoxumab, afelimomab, bavituximab, CR6261, edobacomab, efungumab, felvizumab, ibalizumab, libivirumab, motavizumab, nebacumab, pagibaximab, palivizumab, panobacumab, pidilizumab, PRO 140, rafivirumab, regavirumab, sevirumab, suvizumab and tefibazumab.

In some embodiments, the covalent TEC family kinase inhibitor is administered in combination with one or more agents capable of stimulating cellular immunity, such as cellular mucosal immunity. Any agent capable of stimulatory cellular immunity can be used. Exemplary immunostimulatory agents include, cytokines, such as, but not limited to, interferons (e.g., IFN-a, β, γ, ω), lymphokines and hematopoietic growth factors, such as, for example, GM-CSF, (granulocyte macrophage colony stimulating factor), Interleukin-2 (IL-2), Interleukin-3 (IL-3), Interleukin-4 (IL-4), Interleukin-7 (IL-7), Interleukin-10 (IL-10), Interleukin-12 (IL-12), Interleukin-14 (IL-14), and Tumor Necrosis Factor (TNF).

In some embodiments, the covalent TEC family kinase inhibitor improves the efficacy of an antiviral agent. In some embodiments, the covalent TEC family kinase inhibitor improves the efficacy of an antiviral agent by promoting a Th1 response against the virus (e.g. a Th1 response against a virus infected cell) in the infected patient. In some embodiments, the covalent TEC family kinase inhibitor improves clearance of virus from the subject when administered in combination with the antiviral agent. In some embodiments, the subject having a viral infection has an overactive Th2 response. In some embodiments, the subject having a viral infection has a defective Th1 response against the virus.

In some embodiments, the covalent TEC family kinase inhibitor is administered alone (e.g. monotherapy) for treatment of a bacterial infection. In some embodiments, the covalent TEC family kinase inhibitor is administered in combination with an antibacterial agent. Exemplary antibacterial agents for use in combination with a covalent TEC family kinase inhibitor for adjuvant therapy include, but are not limited to aminoglycosides such as amikacin, arbekacin, bekanamycin, dibekacin, framycetin, gentamicin, kanamycin, neomycin, netilmicin, paromomycin, ribostamycin, rhodostreptomycin, spectinomycin, hygromycin B, paromomycin sulfate, sisomicin, isepamicin, verdamicin, astromicin, streptomycin, tobramycin, and apramycin; ansamycins such as geldanamycin, herbimycin, rifaximin or streptomycin; carbapenem (beta-lactam) such as Imipenem, meropenem, ertapenem, doripenem, panipenem/betamipron, biapenem, razupenem, tebipenem, lenapenem or tomopenem; cephalosporin such as Cefacetrile (cephacetrile), Cefadroxil (cefadroxyl; Duricef), Cephalexin (cefalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym, Xorimax), Cefoperazone (Cefobid), Ceftazidime (Meezat, Fortum, Fortaz), Ceftobiprole, Ceftaroline; glycopeptide antibiotics such as vancomycin, teicoplanin, telavancin, bleomycin, ramoplanin, and decaplanin; lincosamides such as clindamycin or lincomycin; lipopeptide such as daptomycin; macrolides such as azithromycin, clarithromycin, dirithromycin, erythromycin, roxithromycin, telithromycin, josamycin, kitasamycin, midecamycin, oleandomycin, solithromycin, spiramycin, troleandomycin, or tylosin; ketolides such as telithromycin, cethromycin, solithromycin, spiramycin, ansamycin, oleandomycin, or carbomycin; monobactam such as aztreonam; nitrofurans such as furazolidone, furylfuramide, nitrofurantoin, nitrofurazone, nifuratel, nifurquinazol, nifurtoinol, nifuroxazide or ranbezolid; oxazolidinones such as linezolid, posizolid, torezolid, radezolid, cycloserine, rivaroxaban or oxazolidinone and derivatives of; penicillins such as all natural penicillins (e.g. penicillins that are naturally produced by *P. chrysogenum*—e.g., penicillin G), biosynthetic penicillin (e.g. penicillins that are produced by *P. chrysogenum* through directed biosynthesis when a side chain acid is added to the medium—e.g., penicillin V), semi-synthetic penicillin (penicillin that are made by chemical means from natural or biosynthetic penicillin—e.g., ampicillin), synthetic penicillin (e.g. penicillin that are made wholly synthetically), adipyl-6-APA, amoxicillin, ampicillin, butyryl-6-APA, decanoyl-6-APA, heptanoyl-6-APA, hexanoyl-6-APA, nonanoyl-6-APA, octanoyl-6-APA, penicillin F, penicillin G, penicillin V, penicillin mX, penicillin X, 2-thiopheynlacetyl-6-APA, or valeryl-6-APA, azlocillin, flucloxacillin, amoxicillin/clavulanate, ampicillin/sulbactam, piperacillin/tazobactam, ticarcillin/clavulanate; polypeptides such as bacitracin, colistin or polymyxin B; quinolones such as cinoxacin, nalidixic acid, oxolinic acid, piromidic acid, pipemidic acid, rosoxacin, ciprofloxacin, enoxacin, fleroxacin, iomefloxacin, nadifloxacin, norfloxacin, ofloxacin, pefloxacin, rufloxacin, balofloxacin, grepafloxacin, levofloxacin, pazufloxacin, sparfloxacin, temafloxacin, tosufloxacin, clinafloxacin, gatifloxacin, gemifloxacin, moxifloxacin, sitafloxacin, trovafloxacin, prulifloxacin, delafloxacin, JNJ-Q2 or nemonoxacin; sulfonamides such as mafenide, sulfacetamide, sulfadiazine, silver sulfadiazine, sulfadimethoxine, sulfamethizole, sulfamethoxazole, sulfasalazine, sulfisoxazole, TMP-SMX, or sulfonamidochrysoidine; tetracycline such as naturally occurring tetracycline, chlortetracycline, oxytetracycline, demeclocycline, doxycycline, lymecycline, meclocycline, methacycline, minocycline or rolitetracycline; antimycobacteria agents such as clofazimine, dapsone, capreomycin, cycloserine, ethambutol, ethionamide, isoniazid, pyrazinamide, rifampin (rifampicin), rifabutin, rifapentine or streptomycin.

In some embodiments, the covalent TEC family kinase inhibitor improves the efficacy of an antibacterial agent. In some embodiments, the covalent TEC family kinase inhibitor improves the efficacy of an antibacterial agent by promoting a Th1 response against the bacteria in the infected subject (e.g. a Th1 response against a cell infected with an intracellular bacterium). In some embodiments, the covalent TEC family kinase inhibitor improves the efficacy of an antibacterial agent by promoting a Th17 response against the bacteria in the infected subject. In some embodiments, the bacteria is an intracellular bacteria (e.g., *Mycobacterium tuberculosis, Listeria monocytogenes, Shigella flexneri, Yersinia pestis*). In some embodiments, the bacteria is an extracellular bacteria (e.g. *Staphylococcus aureus, Neisseria gonorrhoea, Chlamydia trachomatis, Streptococcus pyogenes, Streptococcus pneimoniae, Haemophilus influenza, Escherichia coli, Salmonella, Clostridium*). In some embodiments, the covalent TEC family kinase inhibitor improves clearance of bacteria from the subject when administered in combination with the antibacterial agent. In some embodiments, the subject having a bacterial infection has an overactive Th2 response. In some embodiments, the subject having a bacterial infection has a defective Th1 or Th17 response against the bacteria.

In some embodiments, the patient has listeriosis (i.e. a *Listeria monocytogenes* infection). In some embodiments, the patient having listeriosis is administered a covalent TEC family kinase inhibitor for adjuvant therapy of listeriosis. In some embodiments, the patient having listeriosis is administered a covalent family kinase inhibitor in combination with one or more therapies for the treatment of listeriosis. Exemplary therapies for the treatment of listeriosis include, but are not limited to, antibiotics, such as ampicillin and gentamicin, trimethoprim/sulfamethoxazole, erythromycin, vancomycin, and fluoroquinolones. In some embodiments, the covalent TEC family kinase inhibitor is administered in combination with ampicillin and gentamicin for the treatment of listeriosis. In some embodiments, the covalent TEC family kinase inhibitor is ibrutinib. In some embodiments, ibrutinib is administered in combination with ampicillin and gentamicin for the treatment of listeriosis. In some embodiments, the covalent TEC family kinase inhibitor (e.g., ibrutinib) is administered sequentially, simultaneously, or intermittently with the one or more therapies for the treatment of listeriosis.

In some embodiments, the covalent TEC family kinase inhibitor is administered alone (e.g. monotherapy) for treatment of a fungal infection. In some embodiments, the covalent TEC family kinase inhibitor is administered in combination with an antifungal agent. Exemplary antifungal agents for use in combination with a covalent TEC family kinase inhibitor for adjuvant therapy include, but are not limited to polyene antifungals such as amphotericin B, candicidin, filipin, hamycin, natamycin, nystatin or rimocidin; imidazoles such as bifonazole, butoconazole, clotrimazole, econazole, fenticonazole, isoconazole, ketoconazole, miconazole, omoconazole, oxiconazole, sertaconazole, sulconazole or tioconazole; triazoles such as albaconazole, fluconazole, isavuconazole, itraconazole, posaconazole, ravuconazole, terconazole or voriconazole; thiazoles such as abafungin; allylamines such as amorolfin, butenafine, naftifine or terbinafine; echinocandins include anidulafungin, caspofungin or micafungin; antifungal macrolides such as polyene antimycotics (e.g., amphotericin B, nystatin benzoic acid); ciclopirox; flucytosine; griseofulvin; haloprogin; polygodial; tolnaftate; undecylenic acid; or crystal violet; and natural alternatives such as oregano, allicin, citronella oil, cocnut oil, iodine, lemon myrtle, neem seed oil, olife leaf, orange oil, palmarosa oil, patchouli, selenium, tea tree oil, zinc, horopito, turnip, chives, radish and garlic.

In some embodiments, the covalent TEC family kinase inhibitor improves the efficacy of an antifungal agent. In some embodiments, the covalent TEC family kinase inhibitor improves the efficacy of an antifungal agent by promoting a Th17 response against the fungi in the infected subject. In some embodiments, the covalent TEC family kinase inhibitor improves the efficacy of an antibacterial agent by promoting a Th1 response against the bacteria in the infected subject (e.g. a Th1 response against a cell infected with an intracellular fungus). In some embodiments, the fungi is an intracellular fungi (e.g., *Cryptococcus neoformans*). In some embodiments, the bacteria is an extracellular fungi (e.g. *Candida albicans, Coccidiodes, Aspergillus*). In some embodiments, the subject having a fungal infection has an overactive Th2 response. In some embodiments, the subject having a fungal infection has a defective Th17 response against the fungi. In some embodiments, the subject having a fungal infection has a defective Th1 response against the fungi.

In some embodiments, the covalent TEC family kinase inhibitor is administered alone (e.g. monotherapy) for treatment of a parasitic infection. In some embodiments, the covalent TEC family kinase inhibitor is administered in combination with an antiparasitic agent. In some embodiments, the covalent TEC family kinase inhibitor is ibrutinib. Exemplary antiparasitic agents for use in combination with a covalent TEC family kinase inhibitor for adjuvant therapy include, but are not limited to antinematodes such as mebendazole, pyrantel pamoate, thiabendazole, diethylcarbamazine or ivermectin; anticestodes such as niclosamide, praziquantel or albendazole; antitrematodes such as praziquantel, antiamoebics such as rafampin or amphotericin B; antiprotozoals such as melarsoprol, eflornithine, metronidazole, tinidazole or miltefosine.

In some embodiments, the covalent TEC family kinase inhibitor improves the efficacy of an antiparasitic agent. In some embodiments, the covalent TEC family kinase inhibitor improves the efficacy of an antiparasitic agent by promoting a Th1 response against the parasite in the infected subject. In some embodiments, the covalent TEC family kinase inhibitor improves the efficacy of an antiparasitic agent by promoting a Th17 response against the parasite in the infected subject. In some embodiments, the covalent TEC family kinase inhibitor improves the efficacy of an antiparasitic agent by promoting a Th1 response against the parasite in the infected subject (e.g. a Th1 response against a cell infected with an intracellular parasite). In some embodiments, the parasite is an intracellular parasite (e.g. *Leishmania*). In some embodiments, the parasite is an extracellular parasite. In some embodiments, the subject having a parasitic infection has an overactive Th2 response. In some embodiments, the subject having a parasitic infection has a defective Th17 response against the parasite. In some embodiments, the subject having a parasitic infection has a defective Th1 response against the parasite.

In some embodiments, the patient has leishmaniasis In some embodiments, the patient having leishmaniasis is administered a covalent TEC family kinase inhibitor for adjuvant therapy of leishmaniasis (e.g. infection by a *Leishmania* parasite). In some embodiments, the patient having leishmaniasis is administered a covalent TEC family kinase inhibitor in combination with one or more therapies for the treatment of leishmaniasis. Exemplary therapies for the treatment of leishmaniasis include, but are not limited to, antimony-containing compounds, such as meglumine antimoniate and sodium stibogluconate, amphotericin B, ketoconazole, itraconazole, fluconazole, miltefosine, paromomycin, and pentamidine. In some embodiments, the covalent TEC family kinase inhibitor is administered in combination with an antimony-containing compound, such as meglumine antimoniate and sodium stibogluconate, amphotericin B, ketoconazole, itraconazole, fluconazole, miltefosine, paromomycin, pentamidine, or any combination thereof for the treatment of leishmaniasis. In some embodiments, the covalent family kinase inhibitor is ibrutinib. In some embodiments, ibrutinib is administered in combination with an antimony-containing compound, such as meglumine antimoniate and sodium stibogluconate, amphotericin B, ketoconazole, itraconazole, fluconazole, miltefosine, paromomycin, pentamidine, or any combination thereof for the treatment of leishmaniasis. In some embodiments, the covalent TEC family kinase inhibitor (e.g., ibrutinib) is administered sequentially, simultaneously, or intermittently with the one or more therapies for the treatment of leishmaniasis.

In some embodiments, the covalent TEC family kinase inhibitor is administered alone (e.g. monotherapy) for treatment of a protozoal infection. In some embodiments, the covalent TEC family kinase inhibitor is administered in combination with an antiprotozoal agent. In some embodiments, the covalent TEC family kinase inhibitor is ibrutinib. Exemplary antiprotozoal agents for use in combination with a covalent TEC family kinase inhibitor for adjuvant therapy include, but are not limited to, Acetarsol, Azanidazole, Chloroquine, Metronidazole, Nifuratel, Nimorazole, Omidazole, Propenidazole, Secnidazole, Sineflngin, Tenonitrozole, Temidazole, Tinidazole, and pharmaceutically acceptable salts or esters thereof.

In certain instances, the covalent TEC family kinase inhibitor permits the antiviral or antibacterial agent to be administered at a lower dosage to achieve the same therapeutic effect compared to standard dosage for administration of the antiviral or antibacterial agent in the absence of the covalent TEC family kinase inhibitor. In some embodiments, administration of a covalent TEC family kinase inhibitor for the treatment of HCV in combination with ribavirin or peginterferon alfa-2a and allows ribavirin or peginterferon alfa-2a to be administered at a lower dosage compared to standard therapy. In certain instances, the standard therapy for the treatment of chronic HCV in an individual is 100-200 μg peginterferon alfa-2a and 500-2000 mg ribavirin per day. In some embodiments, the dosage of peginterferon alfa-2a is about or at 135 μg peginterferon alfa-2a per day. In some embodiments, the dosage of peginterferon alfa-2a is about or at 180 μg peginterferon alfa-2a per day. In some embodiments, the dosage of ribavirin is about or at 500 mg ribavirin per day. In some embodiments, the dosage of ribavirin is about or at 600 mg ribavirin per day. In some embodiments, the dosage of ribavirin is about or at 700 mg ribavirin per day. In some embodiments, the dosage of ribavirin is about or at 800 mg ribavirin per day. In some embodiments, the dosage of ribavirin is about or at 900 mg ribavirin per day. In some embodiments, the dosage of ribavirin is about or at 1000 mg ribavirin per day. In some embodiments, the dosage of ribavirin is about or at 1100 mg ribavirin per day. In some embodiments, the dosage of ribavirin is about or at 1200 mg ribavirin per day. In some embodiments, the dosage of ribavirin is about or at 1300 mg ribavirin per day. In some embodiments, the dosage of ribavirin is about or at 1400 mg ribavirin per day. In some embodiments, the dosage of ribavirin is about or at 1500 mg ribavirin per day. In some embodiments, the dosage of ribavirin is about or at 1600 mg ribavirin per day. In some embodiments, the dosage of ribavirin is about or at 1700 mg ribavirin per day. In some embodiments, the dosage of ribavirin is about or at 1800 mg ribavirin per day. In some embodiments, the dosage of ribavirin is about or at 1900 mg ribavirin per day. In some embodiments, the dosage of ribavirin is about or at 2000 mg ribavirin per day.

In some embodiments, the antiviral agent inhibits one or more steps of the viral life cycle. For example, in some embodiments, the antiviral agent inhibits attachment to a host cell, release of viral nucleic acid or enzymes into the host cell, replication of viral component using the host-cell machinery, assembly of viral component into complete viral particles, or release of viral particles from the host cell. In some embodiments, the antiviral agent includes, but is not limited to a receptor, a ligand, an antibody, a protease inhibitor, a cytokine, a ribozyme, a reverse transcriptase inhibitor, a polymerase inhibitor, an integrase inhibitor, a HDAC inhibitor, a Cyp3A4 inhibitor, an IRAK inhibitor, a JAK inhibitor, an antisense nucleic acid, or a purine nucleoside analog. In some embodiments, the antiviral agent includes, but is not limited to acyclovir, famciclovir, ganciclovir, penciclovir, valacyclovir, valganciclovir, idoxuridine, trifluridine, brivudine, cidofovir, docosanol, fomivirsen, foscarnet, tromantadine, imiquimod, podophyllotoxin, entecavir, lamivudine, telbivudine, clevudine, adefovir, tenofovir, an antiviral nucleoside inhibitor of NS5B polymerase (e.g., 4-amino-7-(2-C-methyl-D-ribofuranosyl)-pyrrolo[2,1-f][1,2,4]triazine; PSI-7977; PSI-938; mericitabine; IDX-184; INX-189), a non-nucleoside inhibitor of NS5B polymerase (e.g., tegobuvir; filibuvir; VX-222; IDX-375; ABT-072; ABT-333; VX-135; setrobuvir; BI207127; JTK-853; GS-9669), a NS3/4A protease inhibitor (e.g., boceprevir; telaprevir; B1-201335; TMC-435; danoprevir; vaniprevir; GS-9451; GS-9256; BMS-650032; ACH-1625; ACH-2684; MK-5172; ABT-450; IDX-320; SCH-900518), an NS5A inhibitor (e.g., daclatasvir; GS-5885; ABT-267; PPI-461; ACH-2928; GSK2336805), carfilzomib, bortezomib, revlimid, lenalidomide, dexamethasone, Bendamustine, pleconaril, arbidol, amantadine, rimantadine, oseltamivir, zanamivir, peramivir, inosine, interferon or interferon derivative (e.g., Interferon alfa-2a, Interferon alfa-2b, Peginterferon alfa-2a, Peginterferon alfa-2b), consensus interferon (e.g., interferon alphacon-1), recombinant interferon alpha 2A, lymphoblastoid interferon tau, pegylated interferon lambda, an inhibitor of inosine-5'-monophosphate dehydrogenase (IMPDH), ribavirin/taribavirin, D-ribavirin, L-ribavirin, abacavir, emtricitabine, lamivudine, didanosine, asunaprevir, daclatasvir, sofosbuvir, zidovudine, apricitabine, stampidine, elvucitabine, racivir, amdoxovir, stavudine, zalcitabine, tenofovir, efavirenz, nevirapine, etravirine, rilpivirine, loviride, delavirdine, atazanavir, fosamprenavir, lopinavir, darunavir, nelfinavir, ritonavir, saquinavir, tipranavir, amprenavir, indinavir, enfuvirtide, maraviroc, vicriviroc, PRO 140, ibalizumab, raltegravir, elvitegravir, bevirimat, vivecon, including tautomeric forms, analogs, isomers, polymorphs, solvates, derivatives, or salts thereof. In a particular embodiment, the antiviral agent is ribavirin (1-β-D-ribofuranosyl-1,2,4-triazole-3-carboximide).

In some embodiments, the antibacterial agent includes, but is not limited to, antibacterial agents that target the bacterial cell wall (e.g. penicillins and cephalosporins) or the cell membrane (e.g., polymixins), antibacterial agents that interfere with essential bacterial enzymes (e.g., rifamycins, lipiarmycins, quinolones, and sulfonamides), and antibacterial agents that target bacterial protein synthesis (e.g., aminoglycosides, macrolides, and tetracyclines). In some embodiments, the antibacterial agent includes, but is not limited to penicillins, cephalosporins, polymixins, carbapenems, sulfonamides, rifamycins, quinolones, oxaolidinones (e.g., linezolid), cyclic lipopeptides (e.g., daptomycin), glycylcyclines (e.g., tigecycline) and lipiarmycins (e.g., fidaxomicin).

In some embodiments, a covalent TEC family kinase inhibitor is administered for adjuvant therapy of an HCV infection. In some embodiments, a covalent TEC family kinase inhibitor is administered in combination with one or more therapies for the treatment of the HCV infection. Exemplary therapies for the treatment of HCV infection include, but are not limited to, interferon or interferon derivatives such as Interferon alfa-2a, Interferon alfa-2b, Peginterferon alfa-2a, Peginterferon alfa-2b, recombinant interferon alfa-2a, Sumiferon (a purified blend of natural alpha interferons), ALFERON® (a mixture of natural alpha interferons), consensus alpha interferon, pegylated interferon lambda; nucleoside analogs such as ribavirin or its derivatives, D-ribavirin, L-ribavirin, or taribavirin; nucleoside and nucleotide NS5B polymerase inhibitors such as sofosbuvir; NS5A inhibitors such as daclatasvir, ledipasvir, ABT-267, ACH-3102, GS-5816, GS-5885, IDX719, MK-8742 or PPI-668; non-nucleoside NS5B polymerase inhibitors such as deleobuvir, ABT-072, ABT-333, BMS-791325, VX-222, or tegobuvir; protease inhibitors such as boceprevir, danoprevir, faldaprevir, incivek, telaprevir, simeprevir, victrelis, ACH-1625, ACH-2684, ABT-450/r or VX-950; polymerase inhibitors such as deleobuvir, sofosbuvir or VX-135; NS3/4A protease inhibitors such as asunaprevir, danoprevir, MK-5172 or VX-950; ALN-VSP; PV-10; HDAC inhibitor such as abexinostat, resminostat, vorinostat, belinostat and panobinostat; thiazolides such as alinia (nitazoxanide); A3AR agonist such as CF102; GI-5005 (Tarmogen); MBL-HCV1; microRNA such as miravirsen; oral interferon; cyclophilin inhibitor such as SCY-635; TG4040; doxorubicin, livatag; immunomodulatory agents, such as Cc-, β-, and γ-interferons or thymosin, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase, polymerase, and metalloprotease inhibitors; inhibitors of internal ribosome entry; broad-spectrum viral inhibitors, such as IMPDH inhibitors (e.g., compounds described in U.S. Pat. Nos. 5,807,876, 6,498,178, 6,344,465, and 6,054,472; and PCT publications WO 97/40028, WO 98/40381, and WO 00/56331; and mycophenolic acid and derivatives thereof, and including, but not limited to, VX-497, VX-148, and VX-944); cytochrome P-450 inhibitor such as ritonavir (WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497; kinase inhibitors such as methyl 2-cyano-3,12-dioxoolean-1,9-dien-28-oate (for the inhibition of CHUK); cetuximab (for the inhibition of EGFR), AEE 788, panitumumab, BMS-599626, ARRY-334543, XL647, canertinib, gefitinib, HKI-272, PD 153035, lapatinib, vandetanib, and erlotinib (for the inhibition of EGFR); BMS-387032 and fiavopiridol (for the inhibition of CDK2, CDK3, CDK4, and CDK8); XL647 (for the inhibition of EPHB4); dasatinib and AZM-475271 (for the inhibition of SRC); imatinib (for the inhibition of BCR); dasatinib (for the inhibition of EPHA2); and AZD-1152 (for the inhibition of AURKB). Other examples of known kinase inhibitors include, but are not limited to, sorafenib (for the inhibition of BRAF); BMS-599626 (for the inhibition of ERBB4); PD-0332991 and flavopiridol (for the inhibition of CDK4).

In some embodiments, the covalent TEC family kinase inhibitor is administered in combination with interferon or interferon derivatives such as Interferon alfa-2a, Interferon alfa-2b, Peginterferon alfa-2a, Peginterferon alfa-2b, recombinant interferon alfa-2a, Sumiferon (a purified blend of natural alpha interferons), ALFERON® (a mixture of natural alpha interferons), consensus alpha interferon, pegylated interferon lambda; nucleoside analogs such as ribavirin or its derivatives, D-ribavirin, L-ribavirin, or taribavirin; nucleoside and nucleotide NS5B polymerase inhibitors such as sofosbuvir; NS5A inhibitors such as daclatasvir, ledipasvir, ABT-267, ACH-3102, GS-5816, GS-5885, IDX719, MK-8742 or PPI-668; non-nucleoside NS5B polymerase inhibitors such as deleobuvir, ABT-072, ABT-333, BMS-791325, VX-222, or tegobuvir; protease inhibitors such as boceprevir, danoprevir, faldaprevir, incivek, telaprevir, simeprevir, victrelis, ACH-1625, ACH-2684, ABT-450/r or VX-950; polymerase inhibitors such as deleobuvir, sofosbuvir or VX-135; NS3/4A protease inhibitors such as asunaprevir, danoprevir, MK-5172 or VX-950; ALN-VSP; PV-10; HDAC inhibitor such as abexinostat, resminostat, vorinostat, belinostat and panobinostat; thiazolides such as alinia (nitazoxanide); A3AR agonist such as CF102; GI-5005 (Tarmogen); MBL-HCV1; microRNA such as miravirsen; oral interferon; cyclophilin inhibitor such as SCY-635; TG4040; doxorubicin, livatag; immunomodulatory agents, such as Cc-, β-, and γ-interferons or thymosin, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase, polymerase, and metalloprotease inhibitors; inhibitors of internal ribosome entry; broad-spectrum viral inhibitors, such as IMPDH inhibitors (e.g., compounds described in U.S. Pat. Nos. 5,807,876, 6,498,178, 6,344,465, and 6,054,472; and PCT publications WO 97/40028, WO 98/40381, and WO 00/56331; and mycophenolic acid and derivatives thereof, and including, but not limited to, VX-497, VX-148, and VX-944); cytochrome P-450 inhibitor such as ritonavir (WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497; kinase inhibitors such as methyl 2-cyano-3,12-dioxoolean-1,9-dien-28-oate (for the inhibition of CHUK); cetuximab (for the inhibition of EGFR), AEE 788, panitumumab, BMS-599626, ARRY-334543, XL647, canertinib, gefitinib, HKI-272, PD 153035, lapatinib, vandetanib, and erlotinib (for the inhibition of EGFR); BMS-387032 and fiavopiridol (for the inhibition of CDK2, CDK3, CDK4, and CDK8); XL647 (for the inhibition of EPHB4); dasatinib and AZM-475271 (for the inhibition of SRC); imatinib (for the inhibition of BCR); dasatinib (for the inhibition of EPHA2); and AZD-1152 (for the inhibition of AURKB). Other examples of known kinase inhibitors include, but are not limited to, sorafenib (for the inhibition of BRAF); BMS-599626 (for the inhibition of ERBB4); PD-0332991 and flavopiridol (for the inhibition of CDK4).

In some embodiments, a covalent TEC family kinase inhibitor is administered in combination with ribavirin for the treatment of an HCV infection. In some embodiments, a covalent TEC family kinase inhibitor is administered in combination with IFN-α for the treatment of an HCV infection. In some embodiments, a covalent TEC family kinase inhibitor is administered in combination with ribavirin and IFN-α for the treatment of an HCV infection.

In some embodiments, the covalent TEC family kinase inhibitor is ibrutinib. In some embodiments, ibrutinib is administered in combination with interferon or interferon derivatives such as Interferon alfa-2a, Interferon alfa-2b, Peginterferon alfa-2a, Peginterferon alfa-2b, recombinant interferon alfa-2a, Sumiferon (a purified blend of natural alpha interferons), ALFERON® (a mixture of natural alpha interferons), consensus alpha interferon, pegylated interferon lambda; nucleoside analogs such as ribavirin or its derivatives, D-ribavirin, L-ribavirin, or taribavirin; nucleoside and nucleotide NS5B polymerase inhibitors such as sofosbuvir; NS5A inhibitors such as daclatasvir, ledipasvir, ABT-267, ACH-3102, GS-5816, GS-5885, IDX719, MK-8742 or PPI-668; non-nucleoside NS5B polymerase inhibitors such as deleobuvir, ABT-072, ABT-333, BMS-791325, VX-222, or tegobuvir; protease inhibitors such as boceprevir, danoprevir, faldaprevir, incivek, telaprevir, simeprevir, victrelis, ACH-1625, ACH-2684, ABT-450/r or VX-950; polymerase inhibitors such as deleobuvir, sofosbuvir or VX-135; NS3/4A protease inhibitors such as asunaprevir, danoprevir, MK-5172 or VX-950; ALN-VSP; PV-10; HDAC inhibitor such as abexinostat, resminostat, vorinostat, belinostat and panobinostat; thiazolides such as alinia (nitazoxanide); A3AR agonist such as CF102; GI-5005 (Tarmogen); MBL-HCV1; microRNA such as miravirsen; oral interferon; cyclophilin inhibitor such as SCY-635; TG4040; doxorubicin, livatag; immunomodulatory agents, such as Cc-, β-, and γ-interferons or thymosin, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase, polymerase, and metalloprotease inhibitors; inhibitors of internal ribosome entry; broad-spectrum viral inhibitors, such as IMPDH inhibitors (e.g., compounds described in U.S. Pat. Nos. 5,807,876, 6,498,178, 6,344,465, and 6,054, 472; and PCT publications WO 97/40028, WO 98/40381, and WO 00/56331; and mycophenolic acid and derivatives thereof, and including, but not limited to, VX-497, VX-148, and VX-944); cytochrome P-450 inhibitor such as ritonavir (WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497; kinase inhibitors such as methyl 2-cyano-3,12-dioxoolean-1,9-dien-28-oate (for the inhibition of CHUK); cetuximab (for the inhibition of EGFR), AEE 788, panitumumab, BMS-599626, ARRY-334543, XL647, canertinib, gefitinib, HKI-272, PD 153035, lapatinib, vandetanib, and erlotinib (for the inhibition of EGFR); BMS-387032 and fiavopiridol (for the inhibition of CDK2, CDK3, CDK4, and CDK8); XL647 (for the inhibition of EPHB4); dasatinib and AZM-475271 (for the inhibition of SRC); imatinib (for the inhibition of BCR); dasatinib (for the inhibition of EPHA2); and AZD-1152 (for the inhibition of AURKB). Other examples of known kinase inhibitors include, but are not limited to, sorafenib (for the inhibition of BRAF); BMS-599626 (for the inhibition of ERBB4); PD-0332991 and flavopiridol (for the inhibition of CDK4) for the treatment of a HCV infection. In some embodiments, the covalent TEC family kinase inhibitor is administered sequentially, simultaneously, or intermittently with the one or more therapies for the treatment of a HCV infection.

In some embodiments, ibrutinib is administered in combination with ribavirin for the treatment of an HCV infection. In some embodiments, ibrutinib is administered in combination with IFN-α for the treatment of an HCV infection. In some embodiments, ibrutinib is administered in combination with ribavirin and IFN-α for the treatment of an HCV infection.

In some embodiments, a covalent TEC family kinase inhibitor is administered for adjuvant therapy of an HBV infection. In some embodiments, a covalent TEC family kinase inhibitor is administered in combination with one or more therapies for the treatment of the HBV infection. Exemplary therapies for the treatment of HBV infection include, but are not limited to, interferons or interferon derivatives such as interferon alfa-2b and peginterferon alfa-2a; nucleoside analogues such as lamivudine (Epivir-HBV), adfovir dipivoxil (Hepsera), entecavir (Baraclude), telbivudine (Tyzeka/Sebivo), tenofovir (Viread), L-FMAU (Clevudine), LB80380 (Besifovir) and AGX-1009; non-nucleoside antivirals such as BAM 205 (NOV-205), Myrcludex B, HAP compound Bay 41-4109, REP 9AC, nitazoxanide (Alinia), dd-RNAi compound, ARC-520, NVR-1221 and IHVR-25; non-interferon immune enhancers such as thymosin alpha-1 (zadaxin), interleukin-7 (CYT107), DV-601, HBV core antigen vaccine, GS-9620 and GI13000; post-exposure and/or post-liver transplant treatment such as hyperHEP S/D, Nabi-HB and Hepa Gam B; and alternative natural agents such as milk thistle.

In some embodiments, the covalent TEC family kinase inhibitor is administered in combination with interferons or interferon derivatives such as interferon alfa-2b and peginterferon alfa-2a; nucleoside analogues such as lamivudine (Epivir-HBV), adfovir dipivoxil (Hepsera), entecavir (Baraclude), telbivudine (Tyzeka/Sebivo), tenofovir (Viread), L-FMAU (Clevudine), LB80380 (Besifovir) and AGX-1009; non-nucleoside antivirals such as BAM 205 (NOV-205), Myrcludex B, HAP compound Bay 41-4109, REP 9AC, nitazoxanide (Alinia), dd-RNAi compound, ARC-520, NVR-1221 and IHVR-25; non-interferon immune enhancers such as thymosin alpha-1 (zadaxin), interleukin-7 (CYT107), DV-601, HBV core antigen vaccine, GS-9620 and GI13000; post-exposure and/or post-liver transplant treatment such as hyperHEP S/D, Nabi-HB and Hepa Gam B; or alternative natural agents such as milk thistle. In some embodiments, the covalent TEC family kinase inhibitor is ibrutinib. In some embodiments, ibrutinib is administered in combination with interferons or interferon derivatives such as interferon alfa-2b and peginterferon alfa-2a; nucleoside analogues such as lamivudine (Epivir- HBV), adfovir dipivoxil (Hepsera), entecavir (Baraclude), telbivudine (Tyzeka/Sebivo), tenofovir (Viread), L-FMAU (Clevudine), LB80380 (Besifovir) and AGX-1009; non-nucleoside antivirals such as BAM 205 (NOV-205), Myrcludex B, HAP compound Bay 41-4109, REP 9AC, nitazoxanide (Alinia), dd-RNAi compound, ARC-520, NVR-1221 and IHVR-25; non-interferon immune enhancers such as thymosin alpha-1 (zadaxin), interleukin-7 (CYT107), DV-601, HBV core antigen vaccine, GS-9620 and GI13000; post-exposure and/or post-liver transplant treatment such as hyperHEP S/D, Nabi-HB and Hepa Gam B; or alternative natural agents such as milk thistle for the treatment of HBV infection. In some embodiments, the covalent TEC family kinase inhibitor is administered sequentially, simultaneously, or intermittently with the one or more therapies for the treatment of a HBV infection.

In some embodiments, a covalent TEC family kinase inhibitor is administered for adjuvant therapy of an HIV infection. In some embodiments, a covalent TEC family kinase inhibitor is administered in combination with one or more therapies for the treatment of the HIV infection. Exemplary therapies for the treatment of HIV infection include, but are not limited to, multi-class combination drugs such as atripla (efavirenz+tenofovir+emtricitabine); complera (eviplera, rilpivirine+tenofovir+emtricitabine); stribild (elvitegravir+cobicistat+tenofovir+emtricitabine); "572-Trii" (dolutegravir+abacavir+lamivudine or DTG+ABC+3TC); nucleoside/nucleotide reverse transcriptase inhibitors (NRTIs) include combivir (zidovudine+lamivudine, AZT+3TC); emtriva (emtricitabine, FTC); epivir (lamivudine, 3TC); epzicom (Livexa, abacavir+lamivudine, ABC+3TC); retrovir (zidovudine, AZT, ZDV); trizivir (abacavir+zidovudine+lamivudine, ABC+AZT+3TC); truvada (tenofovir DF+emtricitabine, TDF+FTC); videx and videx EC (didanosine, ddI); viread (tenofovir disoproxil fumarate, TDF); zerit (stavudine, d4T); ziagen (abacavir, ABC); amadoxovir (AMDX, DAPD); tenofovir alafenamide fumarate (TAF); non-nucleoside reverse transcriptase inhibitors (NNRTIs) include edurant (rilpivirine, RPV, TMC-278); intelence (etravirine, ETR, TMC-125); rescriptor (delavirdine, DLV); sustiva (Stocrin, efavirenz, EFV); viramune and viramune XR (nevirapine, NVP), lersivirine (UK-453061); immune-based therapies include aralen (chloroquine phosphate), dermaVir, interleukin-7, lexgenleucel-T (VRX-496), plaquenil (hydroxychloroquine), proleukin (aldesleukin, IL-2), SB-782-T and Vacc-4x; protease inhibitors such as aptivus (tipranavir, TPV), crixivan (indinavir, IDV), invirase (saquinavir, SQV), kaletra (Aluvia, lopinavir/ritonavir, LPV/r), lexiva (Telzir, fosamprenavir, FPV), norvir (ritonavir, RTV), prezista (darunavir, DRV), reyataz (atazanavir, ATV) and viracept (nelfinavir, NFV); entry inhibitors (including fusion inhibitors) such as fuzeon (enfuvirtide, ENF, T-20), selzentry (Celsentri, maraviroc, UK-427, 857), cenicriviroc (TBR-652, TAK-652), ibalizumab (TNX-355) and PRO140; integrase inhibitors such as isentress (raltegravir, MK-0518), tivicay (dolutegravir, S/GSK-572) and elvitegravir (GS-9137); pharmacokinetic enhancers such as norvir (ritonavir, RTV), cobicistat (GS-9350) and SPI-452; HIV vaccines such as peptide vaccine, recombinant subunit protein vaccine, live vector vaccine, DNA vaccine, virus-like particle vaccine (pseudovirion vaccine), vaccine combinations, rgp120 (AIDS VAX) (VAX003 and VAX004), ALVAC HIV (vCP1521)/AIDS VAX B/E (gp120) (RV144), Adenovirus type 5 (Ad5)/gag/pol/nef (HVTN 502/Merck 023), Ad5 gag/pol/nef (HVTB 503) and DNA-Ad5 gag/pol/nef/nev (HVTN505); combination therapy to elicit an immune response such as pegylated interferon alfa, hydroxyurea, mycophenolate mofetil (MPA) and its ester derivative mycophenolate mofetil (MMF); ribavirin, IL-2, IL-12, polymer polyethyleneimine (PEI), or a combination thereof; HIV-related opportunistic infection treatments such as Co-trimoxazole; and alternative life-style combination therapy such as acupuncture and exercise.

In some embodiments, the covalent TEC family kinase inhibitor is administered in combination with multi-class combination drugs such as atripla (efavirenz+tenofovir+emtricitabine); complera (eviplera, rilpivirine+tenofovir+emtricitabine); stribild (elvitegravir+cobicistat+tenofovir+emtricitabine); "572-Trii" (dolutegravir+abacavir+lamivudine or DTG+ABC+3TC); nucleoside/nucleotide reverse transcriptase inhibitors (NRTIs) include combivir (zidovudine+lamivudine, AZT+3TC); emtriva (emtricitabine, FTC); epivir (lamivudine, 3TC); epzicom (Livexa, abacavir+lamivudine, ABC+3TC); retrovir (zidovudine, AZT, ZDV); trizivir (abacavir+zidovudine+lamivudine, ABC+AZT+3TC); truvada (tenofovir DF+emtricitabine, TDF+FTC); videx and videx EC (didanosine, ddI); viread (tenofovir disoproxil fumarate, TDF); zerit (stavudine, d4T); ziagen (abacavir, ABC); amadoxovir (AMDX, DAPD); tenofovir alafenamide fumarate (TAF); non-nucleoside reverse transcriptase inhibitors (NNRTIs) include edurant (rilpivirine, RPV, TMC-278); intelence (etravirine, ETR, TMC-125); rescriptor (delavirdine, DLV); sustiva (Stocrin, efavirenz, EFV); viramune and viramune XR (nevirapine, NVP), lersivirine (UK-453061); immune-based therapies include aralen (chloroquine phosphate), dermaVir, interleukin-7, lexgenleucel-T (VRX-496), plaquenil (hydroxychloroquine), proleukin (aldesleukin, IL-2), SB-782-T and Vacc-4x; protease inhibitors such as aptivus (tipranavir, TPV), crixivan (indinavir, IDV), invirase (saquinavir, SQV), kaletra (Aluvia, lopinavir/ritonavir, LPV/r), lexiva (Telzir, fosamprenavir, FPV), norvir (ritonavir, RTV), prezista (darunavir, DRV), reyataz (atazanavir, ATV) and viracept (nelfinavir, NFV); entry inhibitors (including fusion inhibitors) such as fuzeon (enfuvirtide, ENF, T-20), selzentry (Celsentri, maraviroc, UK-427, 857), cenicriviroc (TBR-652, TAK-652), ibalizumab (TNX-355) and PRO140; integrase inhibitors such as isentress (raltegravir, MK-0518), tivicay (dolutegravir, S/GSK-572) and elvitegravir (GS-9137); pharmacokinetic enhancers such as norvir (ritonavir, RTV), cobicistat (GS-9350) and SPI-452; HIV vaccines such as peptide vaccine, recombinant subunit protein vaccine, live vector vaccine, DNA vaccine, virus-like particle vaccine (pseudovirion vaccine), vaccine combinations, rgp120 (AIDSVAX) (VAX003 and VAX004), ALVAC HIV (vCP1521)/AIDSVAX B/E (gp120) (RV144), Adenovirus type 5 (Ad5)/gag/pol/nef (HVTN 502/Merck 023), Ad5 gag/pol/nef (HVTB 503) and DNA-Ad5 gag/pol/nef/nev (HVTN505); combination therapy to elicit an immune response such as pegylated interferon alfa, hydroxyurea, mycophenolate mofetil (MPA) and its ester derivative mycophenolate mofetil (MMF); ribavirin, IL-2, IL-12, polymer polyethyleneimine (PEI), or a combination thereof; HIV-related opportunistic infection treatments such as Co-trimoxazole; or alternative life-style combination therapy such as acupuncture and exercise.

In some embodiments, a covalent TEC family kinase inhibitor is ibrutinib. In some embodiments, ibrutinib is administered in combination with multi-class combination drugs such as atripla (efavirenz+tenofovir+emtricitabine); complera (eviplera, rilpivirine+tenofovir+emtricitabine); stribild (elvitegravir+cobicistat+tenofovir+emtricitabine); "572-Trii" (dolutegravir+abacavir+lamivudine or DTG+ABC+3TC); nucleoside/nucleotide reverse transcriptase inhibitors (NRTIs) include combivir (zidovudine+lamivudine, AZT+3TC); emtriva (emtricitabine, FTC); epivir (lamivudine, 3TC); epzicom (Livexa, abacavir+lamivudine, ABC+3TC); retrovir (zidovudine, AZT, ZDV); trizivir (abacavir+zidovudine+lamivudine, ABC+AZT+3TC); truvada (tenofovir DF+emtricitabine, TDF+FTC); videx and videx EC (didanosine, ddI); viread (tenofovir disoproxil fumarate, TDF); zerit (stavudine, d4T); ziagen (abacavir, ABC); amadoxivir (AMDX, DAPD); tenofovir alafenamide fumarate (TAF); non-nucleoside reverse transcriptase inhibitors (NNRTIs) include edurant (rilpivirine, RPV, TMC-278); intelence (etravirine, ETR, TMC-125); rescriptor (delavirdine, DLV); sustiva (Stocrin, efavirenz, EFV); viramune and viramune XR (nevirapine, NVP), lersivirine (UK-453061); immune-based therapies include aralen (chloroquine phosphate), dermaVir, interleukin-7, lexgenleucel-T (VRX-496), plaquenil (hydroxychloroquine), proleukin (aldesleukin, IL-2), SB-782-T and Vacc-4x; protease inhibitors such as aptivus (tipranavir, TPV), crixivan (indinavir, IDV), invirase (saquinavir, SQV), kaletra (Aluvia, lopinavir/ritonavir, LPV/r), lexiva (Telzir, fosamprenavir, FPV), norvir (ritonavir, RTV), prezista (darunavir, DRV), reyataz (atazanavir, ATV) and viracept (nelfinavir, NFV); entry inhibitors (including fusion inhibitors) such as fuzeon (enfuvirtide, ENF, T-20), selzentry (Celsentri, maraviroc, UK-427, 857), cenicriviroc (TBR-652, TAK-652), ibalizumab (TNX-355) and PRO140; integrase inhibitors such as isentress (raltegravir, MK-0518), tivicay (dolutegravir, S/GSK-572) and elvitegravir (GS-9137); pharmacokinetic enhancers such as norvir (ritonavir, RTV), cobicistat (GS-9350) and SPI-452; HIV vaccines such as peptide vaccine, recombinant subunit protein vaccine, live vector vaccine, DNA vaccine, viruls-like particle vaccine (pseudovirion vaccine), vaccine combinations, rgp120 (AIDS VAX) (VAX003 and VAX004), ALVAC HIV (vCP1521)/AIDSVAX B/E (gp120) (RV144), Adenovirus type 5 (Ad5)/gag/pol/nef (HVTN 502/Merck 023), Ad5 gag/pol/nef (HVTB 503) and DNA-Ad5 gag/pol/nef/nev (HVTN505); combination therapy to elicit an immune response such as pegylated interferon alfa, hydroxyurea, mycophenolate mofetil (MPA) and its ester derivative mycophenolate mofetil (MMF); ribavirin, IL-2, IL-12, polymer polyethyleneimine (PEI), or a combination thereof; HIV-related opportunistic infection treatments such as Co-trimoxazole; or alternative life-style combination therapy such as acupuncture and exercise for the treatment of an HIV infection. In some embodiments, the covalent TEC family kinase inhibitor is administered sequentially, simultaneously, or intermittently with the one or more therapies for the treatment of an HIV infection.

In some embodiments, a covalent TEC family kinase inhibitor is administered for adjuvant therapy of an influenza virus infection. In some embodiments, a covalent TEC family kinase inhibitor is administered in combination with one or more therapies for the treatment of the influenza virus infection. Exemplary therapies for the treatment of an influenza virus infection include, but are not limited to, antiviral drugs such as neuraminidase inhibitors (e.g. oseltamivir, peramivir and zanamivir) and admantanes (e.g. amantadine and rimantadine); seasonal flu vaccines (antigens representing three (trivalent) or four (quadrivalent) influenza virus strains) such as Flumist Quadrivalent (MedImmune, Gaithersburg, Md.), Fluarix Quadrivalent (Glaxo Smith Kline, Research Triangle Park, North Carolina), Fluzone Quadrivalent (Sanofi Pasteur, Swiftwater, Pa.), Flulaval Quadrivalent, (ID Biomedical Corportation of Quebec/GlaxoSmith Kline, Research Triangle Park, North Carolina), Flucelvax (Novartis Vaccines and Diagnostics, Cambridge, Mass.), and FluBlok (Protein Sciences, Meriden, Conn.); and combination drugs for the treatment of influenza including one or more immunomodulators such as immune suppressors or enhancers and anti-inflammatory agents.

In certain embodiments, the anti-inflammatory agent can be non-steroidal, steroidal, or a combination thereof. Representative examples of non-steroidal anti-inflammatory agents include, but are not limited to, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, nifiumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

In some embodiments, the covalent TEC family kinase inhibitor is administered in combination with antiviral drugs such as neuraminidase inhibitors (e.g. oseltamivir, peramivir and zanamivir) and admantanes (e.g. amantadine and rimantadine); seasonal flu vaccines (antigens representing three (trivalent) or four (quadrivalent) influenza virus strains) such as Flumist Quadrivalent (MedImmune, Gaithersburg, Md.), Fluarix Quadrivalent (Glaxo Smith Kline, Research Triangle Park, North Carolina), Fluzone Quadrivalent (Sanofi Pasteur, Swiftwater, Pa.), Flulaval Quadrivalent, (ID Biomedical Corportation of Quebec/GlaxoSmith Kline, Research Triangle Park, North Carolina), Flucelvax (Novartis Vaccines and Diagnostics, Cambridge, Mass.), and FluBlok (Protein Sciences, Meriden, Conn.); or combination drugs for the treatment of influenza including one or more immunomodulators such as immune suppressors or enhancers and anti-inflammatory agents.

In some embodiments, the covalent TEC family kinase inhibitor is ibrutinib. In some embodiments, ibrutinib is administered in combination with antiviral drugs such as neuraminidase inhibitors (e.g. oseltamivir, peramivir and zanamivir) and admantanes (e.g. amantadine and rimantadine); seasonal flu vaccines (antigens representing three (trivalent) or four (quadrivalent) influenza virus strains) such as Flumist Quadrivalent (MedImmune, Gaithersburg, Md.), Fluarix Quadrivalent (Glaxo Smith Kline, Research Triangle Park, North Carolina), Fluzone Quadrivalent (Sanofi Pasteur, Swiftwater, Pa.), Flulaval Quadrivalent, (ID Biomedical Corportation of Quebec/GlaxoSmith Kline, Research Triangle Park, North Carolina), Flucelvax (Novartis Vaccines and Diagnostics, Cambridge, Mass.), and FluBlok (Protein Sciences, Meriden, Conn.); or combination drugs for the treatment of influenza including one or more immunomodulators such as immune suppressors or enhancers and anti-inflammatory agents for the treatment of an influenza infection. In some embodiments, the covalent TEC family kinase inhibitor is administered sequentially, simultaneously, or intermittently with the one or more therapies for the treatment of an influenza infection.

In some embodiments, a covalent TEC family kinase inhibitor is administered for adjuvant therapy of a measles virus infection. In some embodiments, a covalent TEC family kinase inhibitor is administered in combination with one or more therapies for the treatment of the measles virus infection. Exemplary therapies for the treatment of a measles virus infection include, but are not limited to the measles vaccination and immune serum globulin. In some embodiments, the covalent TEC family kinase inhibitor is administered in combination with the measles vaccination and immune serum globulin for the treatment of a measles virus infection. In some embodiments, the covalent TEC family kinase inhibitor is ibrutinib. In some embodiments, ibrutinib is administered in combination with the measles vaccination and immune serum globulin for the treatment of a measles virus infection. In some embodiments, the covalent TEC family kinase inhibitor is administered sequentially, simultaneously, or intermittently with the one or more therapies for the treatment of a measles virus infection.

In some embodiments, a covalent TEC family kinase inhibitor is administered for adjuvant therapy of a Human papilloma virus (HPV) infection. In some embodiments, a covalent TEC family kinase inhibitor is administered in combination with one or more therapies for the treatment of the HPV infection. Exemplary therapies for the treatment of a HPV infection include, but are not limited to, podofilox or imiquimod. In some embodiments, the covalent TEC family kinase inhibitor is administered in combination with podofilox or imiquimod for the treatment of a HPV infection. In some embodiments, the covalent TEC family kinase inhibitor is ibrutinib. In some embodiments, ibrutinib is administered in combination with podofilox or imiquimod for the treatment of a HPV infection. In some embodiments, the covalent TEC family kinase inhibitor is administered sequentially, simultaneously, or intermittently with the one or more therapies for the treatment of a HPV infection.

In some embodiments, a covalent TEC family kinase inhibitor is administered for adjuvant therapy of a Human herpesvirus 6A (HHV-6A), Human herpesvirus 6B (HHV-6B), or Human herpesvirus 7 (HHV-7) infection. In some embodiments, a covalent TEC family kinase inhibitor is administered in combination with one or more therapies for the treatment of the HHV-6A, HHV-6B, or HHV-7 infection. Exemplary therapies for the treatment of a HHV-6A, HHV-6B, or HHV-7 infection include, but are not limited to, valganciclovir, ganciclovir, cidofovir, and foscarnet. In some embodiments, the covalent TEC family kinase inhibitor is administered in combination with valganciclovir, ganciclovir, cidofovir, or foscarnet for the treatment of a HHV-6A, HHV-6B, or HHV-7 infection. In some embodiments, the covalent TEC family kinase inhibitor is ibrutinib. In some embodiments, ibrutinib is administered in combination with valganciclovir, ganciclovir, cidofovir, or foscarnet for the treatment of a HHV-6A, HHV-6B, or HHV-7 infection. In some embodiments, the covalent TEC family kinase inhibitor is administered sequentially, simultaneously, or intermittently with the one or more therapies for the treatment of a HHV-6A, HHV-6B, or HHV-7 infection.

In some embodiments, a covalent TEC family kinase inhibitor is administered for adjuvant therapy of a Herpes Simplex virus (HSV) infection. In some embodiments, a covalent TEC family kinase inhibitor is administered in combination with one or more therapies for the treatment of the HSV infection. Exemplary therapies for the treatment of a HSV infection include, but are not limited to, acyclovir, famciclovir, and valacyclovir. In some embodiments, the covalent TEC family kinase inhibitor is administered in combination with acyclovir, famciclovir, and valacyclovir for the treatment of a HSV infection. In some embodiments, the covalent TEC family kinase inhibitor is ibrutinib. In some embodiments, ibrutinib is administered in combination with acyclovir, famciclovir, or valacyclovir for the treatment of a HSV infection. In some embodiments, the covalent TEC family kinase inhibitor is administered sequentially, simultaneously, or intermittently with the one or more therapies for the treatment of a HSV infection.

In some embodiments, a covalent TEC family kinase inhibitor is administered for adjuvant therapy of an Epstein-Bar virus (EBV) infection. In some embodiments, a covalent TEC family kinase inhibitor is administered in combination with one or more therapies for the treatment of the EBV infection. Exemplary therapies for the treatment of an EBV infection include, but are not limited to acyclovir, ganciclovir, and foscarnet. In some embodiments, the covalent TEC family kinase inhibitor is administered in combination with acyclovir, ganciclovir, or foscarnet for the treatment of an EBV infection. In some embodiments, the covalent TEC family kinase inhibitor is ibrutinib. In some embodiments, ibrutinib is administered in combination with acyclovir, ganciclovir, and foscarnet for the treatment of an EBV infection. In some embodiments, the covalent TEC family kinase inhibitor is administered sequentially, simultaneously, or intermittently with the one or more therapies for the treatment of an EBV infection.

In some embodiments, a covalent TEC family kinase inhibitor is administered for adjuvant therapy of a Human cytomegalovirus (HCMV) infection. In some embodiments, a covalent TEC family kinase inhibitor is administered in combination with one or more therapies for the treatment of the HCMV infection. Exemplary therapies for the treatment of a HCMV infection include, but are not limited to ganciclovir, valganciclovir, foscarnet, cidofovir, maribavir, and leflunomide. In some embodiments, the covalent TEC family kinase inhibitor is administered in combination with ganciclovir for the treatment of a HCMV infection. In some embodiments, the covalent TEC family kinase inhibitor is ibrutinib. In some embodiments, ibrutinib is administered in combination with ganciclovir, foscarnet, cidofovir, maribavir, or leflunomide for the treatment of a HCMV infection. In some embodiments, the covalent TEC family kinase inhibitor is administered sequentially, simultaneously, or intermittently with the one or more therapies for the treatment of HCMV.

In some embodiments, a covalent TEC family kinase inhibitor is administered for adjuvant therapy of a Rous sarcoma virus (RSV) infection. In some embodiments, a covalent TEC family kinase inhibitor is administered in combination with one or more therapies for the treatment of the RSV infection. Exemplary therapies for the treatment of an RSV infection include, but are not limited to, a nucleoside analog, such as ribavirin, administration of intravenous infusion of immunoglobulin, administration of supplemental oxygen and fluids or assisted breathing, anti-RSV antibodies (e.g. palivizumab), antisense nucleic acids, one or more agents that regulate lung maturation and surfactant protein expression, such as, but not limited to, glucocorticoids, PPARy ligands, and vascular endothelial cell growth factor (VEGF). In some embodiments, the covalent TEC family kinase inhibitor is administered in combination with ribavirin or an anti-RSV antibody for the treatment of an RSV infection. In some embodiments, the covalent TEC family kinase inhibitor is ibrutinib. In some embodiments, ibrutinib is administered in combination with ribavirin or an anti-RSV antibody for the treatment of RSV. In some embodiments, the covalent TEC family kinase inhibitor is administered sequentially, simultaneously, or intermittently with the one or more therapies for the treatment of RSV.

In some embodiments, a covalent TEC family kinase inhibitor is administered for adjuvant therapy of a chronic granulomatous disease (CGD). In some embodiments, a covalent TEC family kinase inhibitor is administered in combination with one or more therapies for the treatment of CGD, such as for example, one or more therapies for the prophylaxis or treatment of pathogenic infections associated with CGD. Exemplary therapies for the treatment of CGD include, but are not limited to, administration of an antiviral, antibacterial, antifungal, or antiparasitic agent for the prophylaxis or treatment of pathogenic infections associated with CGD. Exemplary antiviral, antibacterial, antifungal, or antiparasitic agents are provided elsewhere herein and can be used in combination with a TEC family kinase inhibitor for the prophylaxis or treatment of pathogenic infections associated with CGD. In some embodiments, the covalent TEC family kinase inhibitor is administered in combination with gamma-interferon for the prophylaxis or treatment of pathogenic infections associated with CGD. In some embodiments, the covalent TEC family kinase inhibitor is ibrutinib. In some embodiments, ibrutinib is administered in combination with gamma-interferon for the prophylaxis or treatment of pathogenic infections associated with CGD. In some embodiments, the covalent TEC family kinase inhibitor is administered sequentially, simultaneously, or intermittently with the one or more therapies for the treatment of CGD.

In some embodiments, the patient has disease or condition characterized by a defective Th1 response. In some embodiments, the patient having disease or condition characterized by a defective Th1 response is administered a TEC family kinase inhibitor for adjuvant therapy of the disease or disorder. In some embodiments, the patient having disease or condition characterized by a defective Th1 response is administered a TEC family kinase inhibitor in combination with one or more therapies for the treatment of the disease or disorder, such as for example, one or more therapies for the prophylaxis or treatment of pathogenic infections associated with a disease or condition characterized by a defective Th1 response. Exemplary therapies for the treatment of disease or condition characterized by a defective Th1 response include, but are not limited to, administration of an antiviral, antibacterial, antifungal, or antiparasitic agent for the prophylaxis or treatment of pathogenic infections associated with the disease or condition characterized by a defective Th1 response. Exemplary antiviral, antibacterial, antifungal, or antiparasitic agents are provided elsewhere herein and can be used in combination with a TEC family kinase inhibitor for the prophylaxis or treatment of pathogenic infections associated with a disease or condition characterized by a defective Th1 response. In some embodiments, the covalent TEC family kinase inhibitor is administered in combination with gamma-interferon for the prophylaxis or treatment of pathogenic infections associated with a disease or condition characterized by a defective Th1 response. In some embodiments, the covalent TEC family kinase inhibitor is ibrutinib. In some embodiments, ibrutinib is administered in combination with gamma-interferon for the prophylaxis or treatment of pathogenic infections associated with a disease or condition characterized by a defective Th1 response. In some embodiments, the covalent TEC family kinase inhibitor is administered sequentially, simultaneously, or intermittently with the one or more therapies for the treatment of a disease or condition characterized by a defective Th1 response. In some embodiments, the patient having a disease or condition characterized by a defective Th1 response has a defect in Th1 cytokine production or a Th1 cytokine receptor, such as, for example, a defect in IFN-γ, IL-12 or IL-12 receptor. In some embodiments, disease or condition characterized by a defective Th1 response is secondary to a cancer in the patient (e.g. leukemia, lymphoma or a myeloma).

In some embodiments, the patient has disease or condition characterized by an overactive Th2 response. In some embodiments, the patient having disease or condition characterized by a an overactive Th2 response is administered a TEC family kinase inhibitor for adjuvant therapy of the disease or disorder. In some embodiments, the patient having disease or condition characterized by an overactive Th2 response is administered a TEC family kinase inhibitor in combination with one or more therapies for the treatment of the disease or disorder, such as for example, one or more therapies for the prophylaxis or treatment of pathogenic infections associated with a disease or condition characterized by an overactive Th2 response. Exemplary therapies for the treatment of disease or condition characterized by an overactive Th2 response include, but are not limited to, administration of an antiviral, antibacterial, antifungal, or antiparasitic agent for the prophylaxis or treatment of pathogenic infections associated with the disease or condition characterized by an overactive Th2 response. Exemplary antiviral, antibacterial, antifungal, or antiparasitic agents are provided elsewhere herein and can be used in combination with a TEC family kinase inhibitor for the prophylaxis or treatment of pathogenic infections associated with a disease or condition characterized by an overactive Th2 response. In some embodiments, the covalent TEC family kinase inhibitor is administered in combination with gamma-interferon for the prophylaxis or treatment of pathogenic infections associated with a disease or condition characterized by an overactive Th2 response. In some embodiments, the covalent TEC family kinase inhibitor is ibrutinib. In some embodiments, ibrutinib is administered in combination with gamma-interferon for the prophylaxis or treatment of pathogenic infections associated with a disease or condition characterized by an overactive Th2 response. In some embodiments, the covalent TEC family kinase inhibitor is administered sequentially, simultaneously, or intermittently with the one or more therapies for the treatment of a disease or condition characterized by an overactive Th2 response. In some embodiments, disease or condition characterized by an overactive Th2 response is secondary to a cancer in the patient (e.g. leukemia, lymphoma or a myeloma). In some embodiments, disease or condition characterized by an overactive Th2 response is an inflammatory or autoimmune disease.

In some embodiments, the covalent TEC family kinase inhibitor inhibits the kinase activity of one or more members of the TEC family of kinases (e.g. ITK, BTK, TEC, RLK and BMX). In some embodiments, the covalent TEC family kinase inhibitor inhibits the kinase activity of IL2-inducible T-cell kinase (ITK). In some embodiments, the covalent TEC family kinase inhibitor covalently binds to Cysteine 442 of ITK. In some embodiments, the covalent TEC family kinase inhibitor is selected from among ibrutinib (PCI-32765), PCI-45292, PCI-45466, AVL-101, AVL-263, AVL-291, AVL-292, ONO-WG-37, BMS-488516, BMS-509744, CGI-1746, CTA-056, GDC-0834, HY-11066 (also, CTK4I7891, HMS3265G21, HMS3265G22, HMS3265H21, HMS3265H22, 439574-61-5, AG-F-54930), ONO-4059, ONO-WG37, PLS-123, RN486, HM71224, or a combination thereof. In some embodiments, the covalent TEC family kinase inhibitor is ibrutinib. Additional covalent TEC family kinase inhibitors for use in any of the methods provided herein are found, for example, in U.S. Pat. Nos. 7,547,689, 7,960,396 and U.S. Patent Publication Nos. US 2009-0197853 A1 and US 2012-0065201 A1, all of which are incorporated by reference in their entirety.

In some embodiments, administration of a covalent TEC family kinase inhibitor decreases the number of Th2 polarized T cells in the subject. In some embodiments, administration of a covalent TEC family kinase inhibitor increases the number of Th1 polarized T cells in the subject. In some embodiments, administration of a covalent TEC family kinase inhibitor increases the ratio of Th1 polarized T cells to Th2 polarized T cells in the subject. In some embodiments, administration of a covalent TEC family kinase inhibitor increase the number of cytotoxic CD8+ T cells in the subject. In some embodiments, administration of a covalent TEC family kinase inhibitor decreases the expression of one or more Th2 cytokines in the subject. In some embodiments, administration of a covalent TEC family kinase inhibitor decreases IL-4, IL-5, IL-6, IL-9, IL-10 or IL-13 expression in the subject. In some embodiments, administration of a covalent TEC family kinase inhibitor increases the expression of one or more Th1 cytokines in the subject. In some embodiments, administration of a covalent TEC family kinase inhibitor increases IL-2, GM-CSF, IFN-$\gamma$, IL-12(p70), IL-18 and TNF-$\alpha$ expression in the subject.

Adjuvant for Vaccination

Described herein, in certain embodiments, are methods of adjuvant therapy to improve vaccine efficacy by administering to a subject an effective amount of a covalent TEC family kinase inhibitor in combination with a vaccine.

In some embodiments, the enhancing the efficacy of said adjuvant therapy comprises increasing the rate at which the viral load of a patient reduced measured during the administration of the course of adjuvant therapy as compared to the viral reduction rate achieved by administering either of said vaccine or said course of adjuvant therapy alone. In some embodiments, the increase in a rate at which the viral load of a patient is reduced during the administration of the course of adjuvant therapy as compared to the viral reduction rate achieved by administering of either vaccine or the course of adjuvant therapy alone is at least about 1%, 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%. In some embodiments, the rate at which the viral load of a patient is reduced during the administration of the course of adjuvant therapy is higher than the viral reduction rate achieved by administering of lectin affinity hemodialysis treatment alone combined with the viral load reduction rate achieved by administering the course of adjuvant therapy alone by a percentage of at least about 1%, 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 160%, 170%, 180%, 190%, 200%. In some embodiments, the rate at which the viral load of a patient is reduced during the administration of the course of adjuvant therapy is at least about 99%, 98%, 97%, 96%, 95%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2%, or 1% per hour, per 8 hours, per 12 hours, or per day.

In some embodiments, enhancing the efficacy of said adjuvant therapy is achieved by reducing the amount of time required to achieve a clinically relevant viral load in the patient during the administration of the course of adjuvant therapy as compared to administering of either said vaccine treatment or said course of adjuvant therapy alone. In some embodiments, the clinically relevant viral load is less than about 100000, 90000, 80000, 70000, 60000, 50000, 40000, 30000, 20000, 10000, 9000, 8000, 7000, 6000, 5000, 4000, 3000, 2000, 1000, 900, 800, 700, 600, 500, 400, 300, 200, 100, 90, 80, 70, 60, 50, 40, 30, 20, 10, 9, 8, 7, 6, 5, 4, 3, 2, or 1 copies/ml. In some embodiments, the amount of time required to achieve the clinically relevant viral load compared to administration of either vaccine or the course of adjuvant therapy alone is reduced by at least about 99%, 98%, 97%, 96%, 95%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2%, or 1%. In some embodiments, the amount of time required to achieve the clinically relevant viral load is less than about 36, 35, 34, 32, 31, 30, 29, 28, 27, 26, 25, 24, 23, 22, 21, 20, 19, 18, 17, 16, 15, 14, 13, or 12 months, or 56, 55, 50, 45, 40, 35, 30, 29, 28, 27, 26, 25, 24, 23, 22, 21, 20, 19, 18, 17, 16, 15, 14, 13, 12, 11, 10, 9, 8, 7, 6, 5, or 4 weeks, or 28, 27, 26, 25, 24, 23, 22, 21, 20, 19, 18, 17, 16, 15, 14, 13, 12, 11, 10, 9, 8, 7, 6, 5, 4, 3, 2 or 1 days.

In some embodiments, the covalent TEC family kinase inhibitor is administered sequentially, simultaneously or intermittently with the vaccine. In some embodiments, the covalent TEC family kinase inhibitor is administered prior to or following administration of the vaccine. In some embodiments, the covalent TEC family kinase inhibitor and the vaccine are administered as a single composition. In some embodiments, the covalent TEC family kinase inhibitor and the vaccine are administered as separate compositions. In some embodiments, the covalent TEC family kinase inhibitor and the vaccine are administered by the same route of administration. In some embodiments, the covalent TEC family kinase inhibitor and the vaccine are administered by the different routes of administration. In some embodiments, the vaccine is administered by any suitable method, such as, but not limited to, intramuscular, subcutaneous, intranasal, oral, intradermal, transcutaneous, or transdermal administration.

In some embodiments, the covalent TEC family kinase inhibitor and the vaccine are administered simultaneously, sequentially, or intermittently.

In some embodiments, the vaccine is an anticancer vaccine. In some embodiments, the cancer vaccine comprises one or more cancer or tumor antigens for immunization. In some embodiments, the cancer antigen is, but is not limited to, acute lymphoblastic leukemia (etv6, amll, cyclophilin b), B cell lymphoma (Ig-idiotype), glioma (E-cadherin, a-catenin, P-catenin, y-catenin, pl20ctn), bladder cancer (p21ras), biliary cancer (p21ras), breast cancer (MUC family, HER2/neu, c-erbB-2), cervical carcinoma (p53, p21ras), colon carcinoma (p21ras, HER2/neu, c-erbB-2, MUC family), colorectal cancer (Colorectal associated antigen (CRC)-C017-1A/GA733, APC), choriocarcinoma (CEA), epithelial cell cancer (cyclophilin b), gastric cancer (HER2/neu, c-erbB-2, ga733 glycoprotein), hepatocellular cancer (a-fetoprotein), Hodgkins lymphoma (lmp-1, EBNA-1), lung cancer (CEA, MAGE-3, NY-ESO-1), lymphoid cell-derived leukemia (cyclophilin b), melanoma (p15 protein, gp75, oncofetal antigen, GM2 and GD2 gangliosides, Melan-A/MART-1, cdc27, MAGE-3, p21ras, gplOO"), myeloma (MUC family, p21ras), non-small cell lung carcinoma (HER2/neu, c-erbB-2), nasopharyngeal cancer (lmp-1, EBNA-1), ovarian cancer (MUC family, HER2/neu, c-erbB-2), prostate cancer (Prostate Specific Antigen (PSA) and its antigenic epitopes PSA-1, PSA-2, and PSA-3, PSMA, HER2/neu, c-erbB-2, ga733 glycoprotein), renal cancer (HER2/neu, c-erbB-2), squamous cell cancers of the cervix and esophagus (viral products such as human papilloma virus proteins), testicular cancer (NY-ESO-1), and T cell leukemia (HTLV-1 epitopes).

In some embodiments, the vaccine is an antivirus vaccine. In some embodiments, the cancer vaccine comprises one or more viral antigens for immunization. In some embodiments, the vaccine comprises an attenuated virus or inactivated virus. In some embodiments, the vaccine is an adenovirus, measles, mump, rabies, rotavirus, yellow fever virus, varicella virus, rubella, polio, hepatitis A virus, hepatitis B virus, hepatitis C virus, human papilloma virus, human immunodeficiency virus, human herpesvirus, herpes simplex virus, Epstein-Bar virus, human cytomegalovirus, Rous sarcoma virus, smallpox virus or influenza virus vaccine.

In some embodiments, the vaccine is an antibacterial vaccine. In some embodiments, the cancer vaccine comprises one or more bacterial antigens for immunization. In some embodiments, the vaccine comprises attenuated bacteria or killed bacteria. In some embodiments, the vaccine comprises a toxin produced by the bacterium. In some embodiments, the vaccine comprises diphtheria, anthrax, pertussis, meningococcal, typhoid, pneonocaccal or tetanus vaccine.

In some embodiments, administration of a covalent TEC family kinase inhibitor decreases the number of Th2 polarized T cells in the subject. In some embodiments, administration of a covalent TEC family kinase inhibitor increases the number of Th1 polarized T cells in the subject. In some embodiments, administration of a covalent TEC family kinase inhibitor increases the ratio of Th1 polarized T cells to Th2 polarized T cells in the subject. In some embodiments, administration of a covalent TEC family kinase inhibitor decreases the expression of one or more Th2 cytokines in the subject. In some embodiments, administration of a covalent TEC family kinase inhibitor decreases IL-10, IL-2 or IL-13 expression in the subject. In some embodiments, administration of a covalent TEC family kinase inhibitor increases the expression of one or more Th1 cytokines in the subject. In some embodiments, administration of a covalent TEC family kinase inhibitor increases IL-2, GM-CSF, IFN-γ, IL-12(p70) and TNF-α expression in the subject. In some embodiments, administration of a covalent TEC family kinase inhibitor increase the number of cytotoxic CD8+ T cells in the subject.

In some embodiments, after administration of a covalent TEC family kinase inhibitor the profiles of Th1 and Th2 polarized T cells are examined. In some embodiments, the profiles of Th1 and Th2 polarized T cells are examined along with a third subset of T helper cells, Th17 polarized T cells. In some embodiments, after administration of a covalent TEC family kinase inhibitor Th1 and Th2 related markers are examined. In some embodiments, after administration of a covalent TEC family kinase inhibitor Th1, Th2 and Th17 related markers are examined. In some embodiments, Th1 related markers include IL-2, GM-CSF, IFN-γ, IL-12(p70) and TNF-α. In some embodiments, Th2 related markers include IL-10, IL-4 or IL-13. In some embodiments, Th17 related markers include IL17.

In some embodiments, the covalent TEC family kinase inhibitor inhibits the kinase activity of one or more members of the TEC family of kinases (e.g. ITK, BTK, TEC, RLK and BMX). In some embodiments, the covalent TEC family kinase inhibitor inhibits the kinase activity of IL2-inducible T-cell kinase (ITK). In some embodiments, the covalent TEC family kinase inhibitor covalently binds to Cysteine 442 of ITK. In some embodiments, the covalent TEC family kinase inhibitor is selected from among ibrutinib (PCI-32765), PCI-45292, PCI-45466, AVL-101, AVL-291, AVL-292, or ONO-WG-37. In some embodiments, the covalent TEC family kinase inhibitor is ibrutinib. Additional covalent TEC family kinase inhibitors for use in any of the methods provided herein are found, for example, in U.S. Pat. Nos. 7,547,689, 7,960,396 and U.S. Patent Publication Nos. US 2009-0197853 A1 and US 2012-0065201 A1, all of which are incorporated by reference in their entirety.

In some embodiments, the vaccine is administered in combination with a covalent TEC family kinase inhibitor and one or more additional adjuvants. In some embodiments, the one or more additional adjuvants improve the efficacy of the vaccine compared to the absence of the additional adjuvant. In some embodiments, the one or more additional adjuvants induces a Th1 polarized response, decreases a Th2 polarized response, improves antigen presentation on effector cells, induces CD8+ cytotoxic T cells, improves delivery of antigen to immune effector cells, and/or provide short term or long term depot delivery. In some embodiments, the one or more additional adjuvants include, but are not limited to, aluminum salts (e.g. aluminum hydroxide, aluminum phosphate or alum), water in oil emulsions (e.g. microdroplets of water stabilized by a surfactant (e.g. mannide monooleate, Freund's Incomplete Adjuvant (IFA), and MF59) in a continuous oil phase (e.g. mineral oil, squalene or squalane), oil in water emulsions, immune stimulating conlexes (e.g. ISCOM adjuvant-Iscotec AB), liposomes, nano- or microparticles, calcium salts, proteases, virosomes, stearyl tyrosine, γ-inulin, algammulin, muramyl dipeptides (MDP) (e.g. N-acetyle muramyl-L-alanyl-D-isoglutamine) and derivatives thereof (e.g. threonyl MDP, murabutide, N-acetylglucosaminyl-MDP, GMDP, merametide, and nor-MDP), non-ionic block copolymers (e.g. hydrophobic polyoxypropylene (POP)), saponins (e.g. QuilA, Spikoside, QS21 (Stimulon) and ISCOPREP703), lipid A (MPL), cytokines (e.g. IL-1, IFN-γ, IL-2, and IL-12), carbohydrate polymers (e.g. mannose polymers (e.g. mannan), glucan, acemannan and lentinan), derivatized polysaccharides (e.g. dectrins, diethylaminoethyl dextran), pattern recognition receptor (PRR) ligands, Toll-like receptor ligands (TLRs) (e.g. double stranded RNAs, poly (I:C), lipopolysacharides, monophosphoryl lipid A, bacterial flagellin, imadazoquinolines, imiquimod, gardiquimod, R848, CpG oligodepynucleotides, such as ODN1826 and ODB2006), Nod-like receptor (NLR) ligands (e.g. MDP), RIG-I-like receptor (RLR) ligands), and C-type lectin recptor (CLR) ligands.

In some embodiments, the subject for immunization is a mammal, such as, but not limited to a human, a non-human primate, mouse, rat, rabbit, goat, dog, cat, or cow. In some embodiments, the mammal is a human.

Kits and Articles of Manufacture

For use in the diagnostic and therapeutic applications described herein, kits and articles of manufacture are also described herein. Such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from any acceptable material including, e.g., glass or plastic.

In some embodiments, the container(s) comprise one or more covalent TEC family kinase inhibitors in a composition or in combination with another therapeutic agent as disclosed herein. The container(s) optionally have materials, such as syringes, needles, dosing cups or vials, for administration. Such kits optionally comprise a compound with an identifying description or label or instructions relating to its use in the methods described herein.

EXAMPLES

These examples are provided for illustrative purposes only and not to limit the scope of the claims provided herein.

Example 1

T-lymphocytes comprise an indispensable component of the adaptive immune response, yet certain autoimmune, infectious, parasitic, and neoplastic diseases subvert adaptive immunity by specifically misdirecting T-helper cell polarity. A common mechanism of immune subversion is the aberrant recruitment of a Th2 dominant response that directly promotes B-cell antibody production and interferes with direct effector cell cytotoxicity. In contrast, a Th1 dominant response evokes cytotoxic effects with the production of IFNγ and IL2, which contribute to effector cell-based immune surveillance. Clearance of certain intracellular bacterial pathogens such as *Listeria* and parasites such as *Leishmania*, as well as tumor immune surveillance, hinge upon the capacity to elicit robust Th1 and CD8 T-cell responses.

Interleukin-2 Inducible Kinase (ITK) is a T-cell dominant member of the covalent Tec-kinase family that drives proximal T-cell receptor (TCR) signaling. Upon TCR ligation in Th1 and CD8 T-cells, ITK and redundant resting lymphocyte kinase (RLK or TXK) activate PLCγ, launching a signaling cascade that includes the NFAT, NFκB, and MAPK pathways resulting in cellular activation, cytokine release, and rapid proliferation. Importantly ITK plays a supportive yet dispensable role to RLK in Th1 polarized and CD8 effector cells. However, the epigenetic evolution of Th2 cells conserves a singular dominant role for ITK, pinning it as the Achilles heel of Th2 T-cells. Clinically applicable ITK-specific inhibitors are sought by the medical community, given the potential to specifically inhibit a number of Th2 dominant autoimmune, inflammatory, and infectious diseases ranging from atopic dermatitis to inflammatory bowel disease to cancer immunosuppression and even HIV/AIDS. Although multiple chemical analogs have been reported, none have successfully transitioned into clinical trials. Ibrutinib is an irreversible inhibitor of Bruton's tyrosine kinase (BTK) that blocks downstream B-cell receptor (BCR) activation. Numerous in vitro and in vivo studies confirm the specific activity of ibrutinib against BTK restricted targets. Ibrutinib has demonstrated clinical activity in phase I/II clinical trials, with durable remissions against a variety of B-cell malignancies including mantle cell lymphoma, follicular lymphoma, and chronic lymphocytic leukemia (CLL). Intriguingly, ITK shares significant sequence and functional homology with BTK and both contain an ibrutinib inhibition motif consisting of an SH3 autophosphorylatable Tyrosine (Tyr) and a covalent binding Cysteine (Cys) residue within the hinge region connecting the C and N lobes of the active site. ITK had previously been discounted as a relevant target of ibrutinib given a subdued in vitro kinase inhibition profile and a lack of sufficient in vitro evidence. The striking homology between BTK and ITK combined with intriguing in silico docking studies and promising in vitro kinase inhibition profiles led to the hypothesis that ibrutinib is the first clinically viable irreversible ITK inhibitor. This was explored using healthy human T-cells and human and murine CLL as a model system of dysregulated Th2-biased immunosuppression. In CLL, an increasingly defective immune synapse enables malignant B-cells to evade immune detection by inducing T-cell energy as well as improper Th2 polarization. In addition to being incapable of responding to environmental pathogens, these improperly polarized T-cells contribute both cytokine and direct signaling support to malignant B-cells. The end result of this immunosuppression is a high incidence of severe infections which often leads to patient mortality.

Here, detailed molecular analysis confirms that ibrutinib irreversibly binds ITK at Cys442 and inhibits downstream activation of Th2 cells after TCR stimulation. This inhibition is specific to Th2 polarized CD4 T-cells, as RLK remains uninhibited by ibrutinib thus providing a compensatory platform for activation and proliferation of Th1 and CD8 T-cells. These data demonstrate that CD4 T-cell populations isolated from CLL patients are skewed at a molecular and phenotypic level towards a Th1 profile after brief exposure to ibrutinib. Findings were validated using mouse models of leukemia, cutaneous leishmaniasis, and *Listeria monocytogenes* infection. ITK inhibition in humans was confirmed using irreversible ITK binding, cytokine, and T-cell signaling analysis from CLL patients treated with ibrutinib in a phase I clinical trial. Together, these results demonstrate that ibrutinib is the first potent and selective irreversible inhibitor of ITK to achieve clinical viability, potentially repurposing the drug for a multitude of novel therapeutic applications.

Methods:

Subject Populations

Sera and peripheral blood mononuclear cells (PBMCs) were obtained from normal donors or patients with CLL in accordance with the Declaration of Helsinki. All subjects gave written, informed consent for their blood products to be used for research under an institutional review board (IRB)-approved protocol. Blood was collected at The Ohio State University Wexner Medical Center (Columbus, Ohio). PBMCs were used fresh or stored in 1 ml aliquots at −140° C. and sera were stored in aliquots at −80° C. until used.

Cell Culture, Drug Treatments, and T Cell Polarization

Primary T-cells were isolated using RosetteSep untouched CD3 or CD4 selection, EasySep Naïve CD4+ T cell enrichment kits (STEMCELL Technologies, Vancouver, BC, Canada) or magnetic separation (MACS Human CD8+ microbeads, Miltenyi, Auburn, Calif.) according to the manufacturer's protocol. Cells were cultured in vitro at 37° C. and 5% CO2 using RPMI1640/10% fetal calf serum. Cells were pretreated for 30 minutes with Ibrutinib, washed 2×, then stimulated with plate-bound anti-CD3 and soluble anti-CD28 (eBiosciences, San Diego, Calif.). Nuclear and cytoplasmic lysates (NEN-PER kit, Thermo, Rockford, Ill.) were collected after 45 minutes and whole cell lysates were collected at 2 hours. Th1 and Th2 polarized primary CD4 T-cells were generated according to our previously published methodology. In brief, T-cells were obtained from magnetically purified naïve human CD4 T cells. Cells were stimulated weekly with plate-bound anti-CD3, soluble anti-CD28, and IL-2 (20 U/ml) in the presence of IL-12 (10 ng/ml) and anti-IL-4 (1:100) for Th1 or IL-4 (5 ng/ml) and anti-IL-12 (1:100).

Reverse Transcriptase-PCR (RT-PCR)

Total RNA was prepared from pelleted cells (RNeasy mini columns and RNAse free DNAse, Qiagen, Valencia, CA). RT-PCR and qRT-PCR reactions were conducted using the Qiagen one-step RT-PCR kit (Qiagen) or the iScript SYBR green RT-PCR kit (BioRad, Hercules, CA) with transcript-specific primers (mITK: 5' GGTCATCAAGGT-GTCCGACT (SEQ ID NO: 1), 3' TCGTATGGGATTTT-GCCTTC (SEQ ID NO: 2)) (mBTK:5'AAAGGTTCCCG-TACCCATTC (SEQ ID NO: 3), 3'CCCATAGCATTCTTGGCTGT (SEQ ID NO: 4)) (mGAPDH: 5'CTCATGACCACAGTCCATGC (SEQ ID NO: 5), 3'CACATTGGGGGTAGGAACAC (SEQ ID NO: 6)) (hGAPDH: 5'AGAAGGCTGGGGCTCATTTG (SEQ ID NO: 7), 3'AGGGGCCATCCACAGTCTTC (SEQ ID NO: 8)) (hRLK: GTACGGAGGCTGCCATAAAA (SEQ ID NO: 9), 3'CAGCTGTGGCTGGTAAACAA (SEQ ID NO: 10)) and 200 ng of total RNA. RT-PCR amplification reactions were resolved on 2% agarose gels and the size of the amplified transcript confirmed by comparison with a standard DNA ladder (GelPilot 1 Kb Plus Ladder, Qiagen). qRT-PCR experiments were analyzed using the MyiQ software package. After confirming a single melt curve peak CT values for GAPDH were compared to CT values for the transcript of interest using the Pfaffl method42.

Calcium Flux Analysis

Jurkat cells were stained with Fluo4-AM (Invitrogen), washed twice, and resuspended in phenol-red free RPMI. Fluo4 fluorescence was measured using a plate reader at 535 nm.

Ibrutinib Probe Assay

Protein lysates were labeled with a biotinylated derivative of ibrutinib and added to a Streptavidin coated plate, washed 3×, and incubated with mouse anti-ITK. After washing with SULFO-TAG conjugated anti-mouse antibody (MSD, cat#R32AC-5), washed, and read on a S12400.

Flow Cytometry and Cytokine Bead Array (CBA)

Flow cytometric analysis was performed using fluorochrome-labeled monoclonal antibodies (mAbs; anti-CD3, -CD4, -CD5, -CD8, -CD19, -CD62L, -CD45RA, -IL-4, -IFNγ, Annexin V, PI, Becton Dickinson, San Jose, Calif.). Intracellular staining was conducted according the appropriate manufacturer protocol (Becton Dickinson). For intracellular staining of IL-4 and IFNγ, PMA and ionomycin stimulation was utilized. For phoflow analysis of PLCγ1 cells were fixed with 4% paraformaldehyde/PBS after surface staining and permeablized in cold 90% methanol. Intracellular staining used anti-pPLCγ1-Tyr783 (Cell Signaling Technologies, cat#28215) followed by anti-rabbit Alexa488 (Invitrogen, cat#A11008). CBA (Becton Dickinson) was conducted according to the manufacturers published protocol using cellular supernatant from three replicate experiments or mouse plasma. CFSE and PKH26-based cell proliferation assays were performed as previously described (Dubovsky, J. A., et al. Leukemia research 35, 1193-1199 (2011) and Dubovsky, J. A., et al. Leukemia research 35, 394-404 (2011)). Flow cytometric data was analyzed with FlowJo or Kaluza software (Tree Star, Ashland, Oreg.) or what software (Beckman Coulter, Indianapolis, Ind.) on a minimum of 30,000 collected events. Flow cytometry-based tetramer staining was conducted on 50 μl of whole blood for 1 hour on ice in PBS (+5% FBS, +0.02% NaN3) with anti-CD4, CD8, CD19 (Becton Dickinson) and 2 μg/ml Alexa647-H-2K(b) SIINFEKL tetramer (NIH Tetramer Facility). Afterwards, RBCs were lysed according to the manufacturer's protocol (eBiosciences) and samples were washed once prior to analysis. Gates for tetramer positive CD8 T-cells were verified using the baseline samples obtained 7 days prior to Listeria infection and confirmed using FMO controls.

Immunoblot Analysis

Experiments were conducted using conventional methodology previously described in Lapalombella, R., et al. Cancer Cell 21, 694-708 (2012). Blotting was conducted using pSTAT1 #9177S, STAT1 #9176, NFAT1 #4389S, pITK #3531S, ITK #2380S, JUNB #3746S, pIKBα #9246L, pSTAT6 #9361S, and STAT6 #9362S (Cell Signaling Technologies, Danvers, Mass.), T-bet #14-5825-82 (eBiosciences), IkBα #sc-371, BRG1 #sc-17796, TCL1 #sc-32331, and β-Actin #sc-1616 (Santa Cruz Biotechnology, Santa Cruz, Calif.) specific antibodies.

Confocal Immunofluorescence Microscopy of Fixed Cells

Cells were centrifugally concentrated on microscope slides using a Cytospin3 (Thermo) centrifuge and stained as previously described (Dubovsky, J. A., et al. Leukemia research 35, 394-404 (2011)). Cells were then fixed in PBS/2% paraformaldehyde. Slides were incubated in blocking solution (4% bovine serum albumin in PBS) and stained for NFAT1 (Cell Signaling, Boston, Mass.) by incubating with the primary antibodies overnight at 4° C., followed by incubation with fluorescent secondary antibody Alexa fluor 488 (Invitrogen, Carlsbad, Calif.). Nuclei were stained blue with DAPI (Vector Laboratories, Burlingame, Calif.). Images were taken using a 60× objective and 4× digital zoom with Olympus Fluoview 1000 Laser Scanning Confocal microscope at the Ohio State University Campus Microscopy and Imaging Facility.

Mouse Models

C57BL/6 mice and EμTCL1 transgenic (Tg) mice on a C57BL/6 background were housed in microisolator cages under controlled temperature and humidity. All animal procedures were performed in accordance with Federal and Institutional Animal Care and Use Committee requirements. For longitudinal analysis of Th1/Th2 skewing 4 week old EμTCL1 transgenic animals were given drinking water containing sterile control vehicle (1% HP-β-CD) or ibrutinib in 1% HP-β-CD, at 0.16 mg/mL. The volume of water consumed and the body weight of mice were recorded. On average, mice took 0, 2.5, or 25 mg/kg/d ibrutinib for a total of 16 days. For leukemia/listeriosis studies adoptive transfer of 1×107 freshly isolated splenocytes from EμTCL1 animals was performed. In this model, mice usually succumb from tumor in 8-10 weeks.

One week after injection mice were given drinking water containing sterile control vehicle (1% HP-β-CD) or ibrutinib in 1% HP-β-CD, at 0.16 mg/mL. On average, mice took 25 mg/kg/d ibrutinib for a total of 16 days. 14 days after engraftment mice were challenged with a sub-lethal I.V.

dose (5000 CFU) of recombinant *Listeria monocytogenes* (rLM-OVA, a kind gift from Dr. Michael J. Bevan, University of Washington, Seattle, Wash.). During treatment, blood was drawn regularly to track disease progression. Individual mice were euthanized and assessed for *Listeria* growing in the liver compartment at days 2, 8 and 13. Two days prior to infection 6-8 week old BALB/c mice (Jackson labs, Bar Harbor, Me.) were randomly assigned to vehicle or ibrutinib treatment groups. Ibrutinib was administered via drinking water as previously described for *L. monocytogenes* experiments. At day zero 2E6 stationary phase *Leishmania major* promastigotes were injected into the rear left footpad and lesions were monitored weekly for development of cutaneous leishmaniasis. Popletial lymph nodes were collected for Interim analysis of T-cell cytokines at weeks 6 and 9. Footpad lesions were mashed and parasite load calculations were determined using standard methodology (Fowell, D. J., et al. Immunity 11, 399-409 (1999)).

Enzyme Linked Immunoabsorbent Assay (ELISA)

Submandibular blood was collected and plasma was centrifugally separated. An ELISA assay was performed for each IgG subisotype using a clonotyping system (B6/C57J-AP-5300-04B, Southern Biotech, Birmingham, Ala.) according to manufacturer's instructions on EIA/RIA high binding 96 well plates (Costar 3590, Corning, N.Y.). Plasma dilutions were made in 1×BBS as follows: IgG1-1:10,000, IgG2c-1:10,000. A standard curve was utilized for each isotype on each individual plate (B6/C57J Mouse Immunoglobulin Panel-5300-01B, Southern Biotech) and the sample triplicate averages were read from the curve at 405 nm using a spectrophotometer (Labsystem Multiskan MCC/340, Fisher Scientific). IL4, IL10, IL13, and IFNγ analysis of popletial lymph node cells derived from *L. major* infected mice was conducted as previously described (Cummings, H. E., et al. *PNAS USA* 109, 1251-1256 (2012)). In brief, cells were stimulated with soluble *L. major* antigen for 72 hr. Culture supernatants were collected for ELISA based analysis.

Kinase Screening

In vitro kinase inhibition assays were conducted as previously described by Honigberg et al. in PNAS USA 107, 13075-13080 (2010).

Statistics

Unless otherwise noted, a two-tailed student's T-test was used for normal data at equal variance. Significance was considered for $p<0.05$. Comparisons of IL4 and IFNγ expression in CD4 T-cells were performed using mixed effects models to allow for dependencies among observations from the same patient. From the model, estimated differences in expression at each of the five dose levels were estimated, with 95% CI, with an adjusted significance level of $\alpha=0.01$. Similarly, for *Listeria*/leukemia mouse models a mixed effects model was applied to log-transformed data, and the interaction between condition and time was assessed. From the model, the change in percentage tetramer positive from baseline (day −7) to the peak (day+8) between the ibrutinib and vehicle groups, as well as healthy *Listeria* and control groups, were estimated with 95% CI. All analyses were performed using SAS/STAT software, v9.2 (SAS Institute Inc., Cary, N.C.).

Ibrutinib is an Irreversible Inhibitor of ITK and Displays Cytotoxic Potential Against an ITK Expressing, BTK-Null T-Cell Leukemia.

Figure 1B:
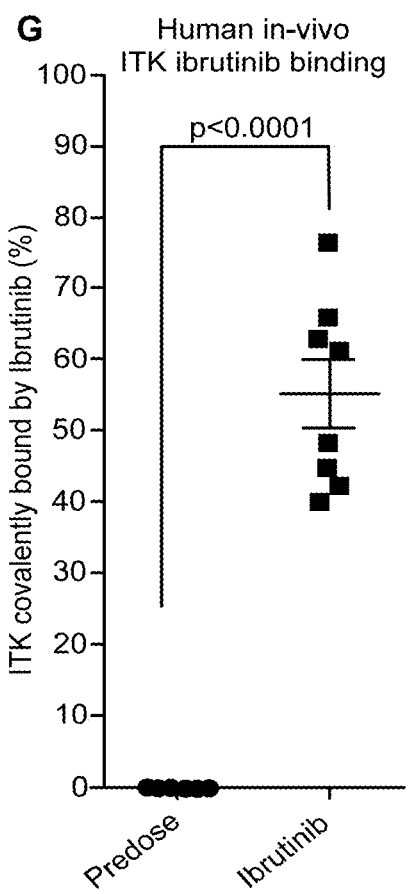
FIG. 1B illustrates a graphical depiction of the sequence and domain homology between ITK and BTK. The relevant phosphorylation sites as well as ibrutinib irreversible covalent binding sites are labeled.
Figure 1B:
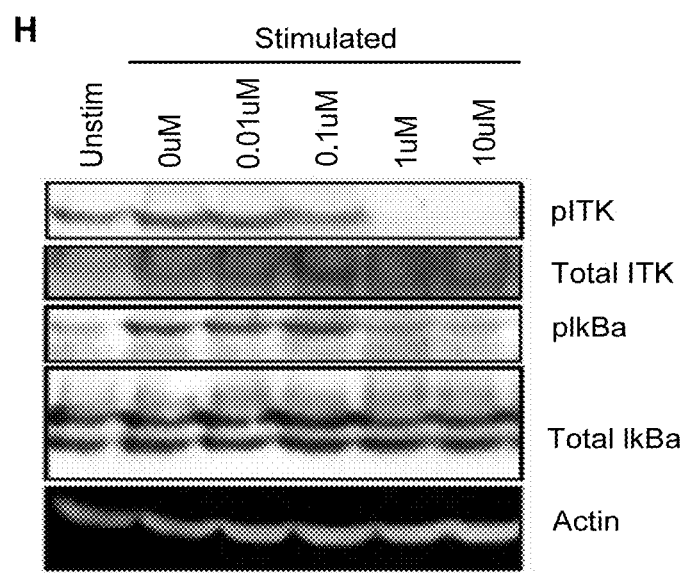
Figure 1B:
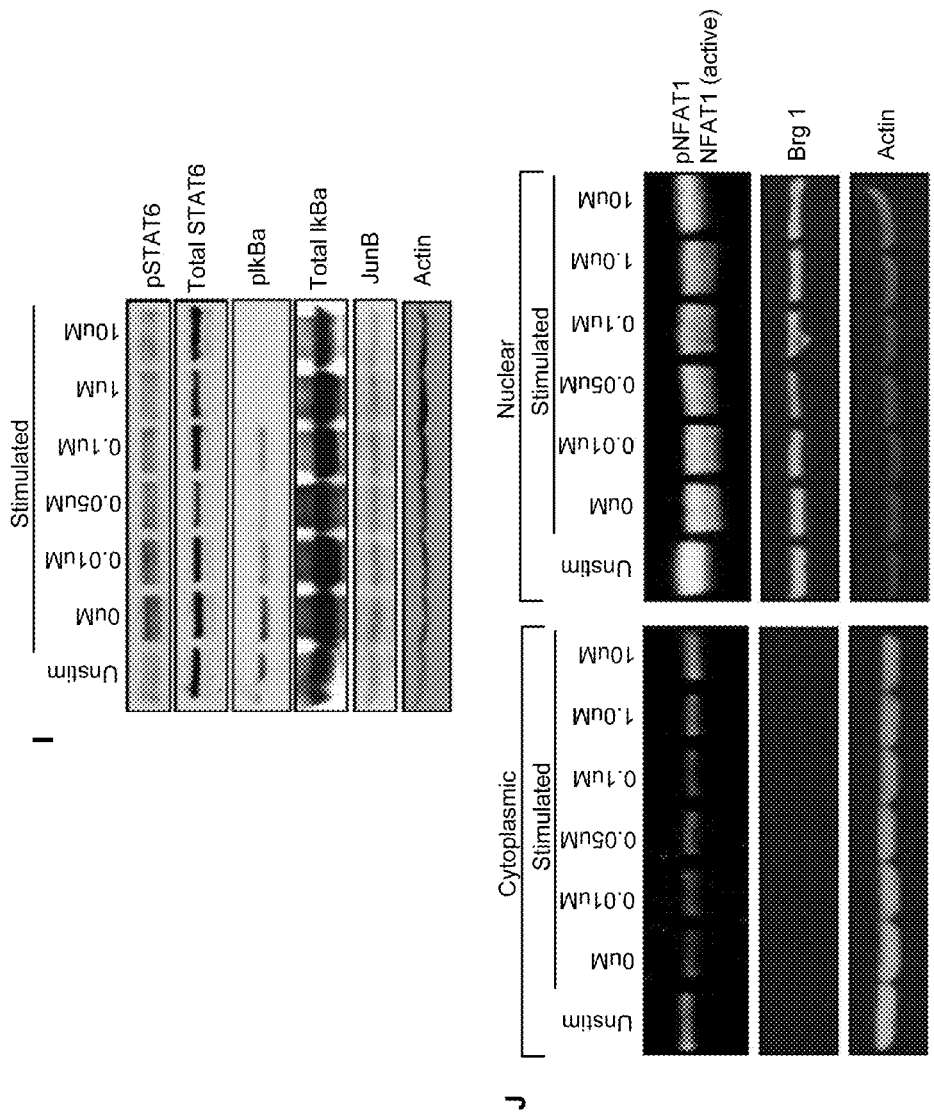

In vitro kinase screening of Ibrutinib revealed a small number of unvalidated targets that include the T-cell dominant ITK (FIG. 1a). Potential irreversible targets were identified by the presence of a cysteine residue homologous to Cys481 in BTK. ITK retains significant structural and functional homology to BTK, including a Cys442 covalent binding site located within the hinge region of the active site and an autophosphorylatable Tyr180 in the SH3 domain (FIG. 1b). In silico docking studies showed potential covalent binding of ITK at Cys442 and occupancy of the active site (FIG. 1c). In vitro probe binding assays confirmed that ibrutinib was capable of irreversibly binding a significant percentage of endogenous ITK in the Jurkat T cell leukemia cell line at physiologically relevant concentrations (FIG. 1d). qRT-PCR analysis of a novel CD8+ T-cell leukemia which rarely develops in the EµTCL1 mouse model due to leaky expression of the Eµ promoter in T-cells revealed elevated transcript levels of ITK compared to healthy C57BL/6 mouse spleen lymphocytes (FIGS. 1e, 7-9). Our prior studies identified an in vitro, LD50 (dose lethal to 50% of cells) for Ibrutinib in BTK relevant leukemia targets between 1 and 10 µM with 72 hr continuous exposure. Using these same conditions, similar cytotoxicity levels were identified in BTK-null EµTCL1 T-cell leukemia cells (FIG. 1f).

To confirm that ibrutinib irreversibly binds ITK in vivo we conducted an ITK probe assay on PBMC samples obtained from CLL patients on a phase I clinical trial of ibrutinib. Samples were tested immediately prior to receiving ibrutinib and after eight days of daily oral administration. The data revealed that a significant percentage (40 to 80%) of ITK is irreversibly bound by ibrutinib (FIG. 1g).

Figure 10:
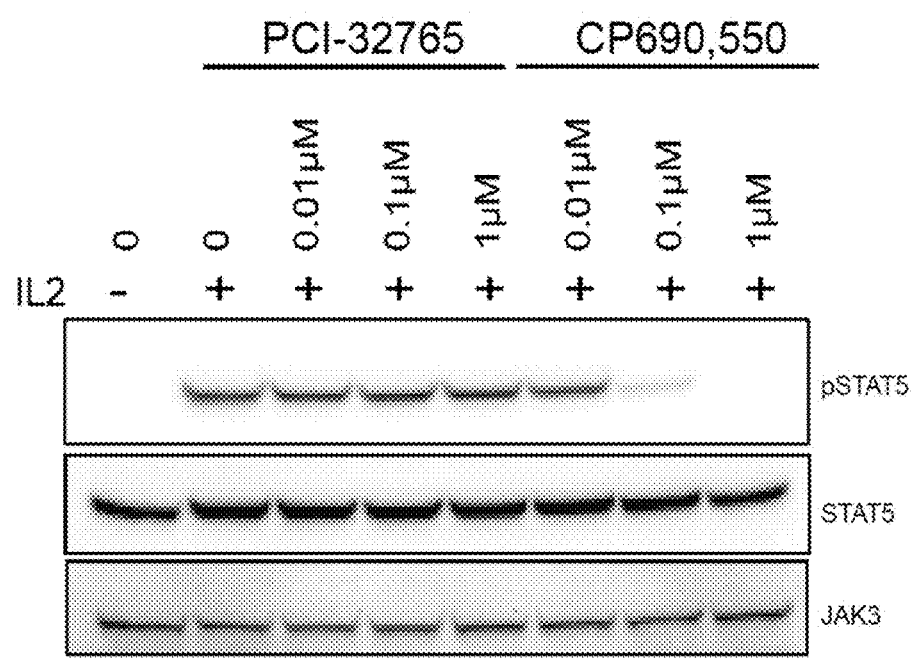
FIG. 10 illustrates immunoblot analysis of JAK3 inhibitory effects of ibrutinib in primary T-cells. Primary T cells were isolated using RosetteSep Human T cell enrichment kit, and treated with either PCI-32765 or CP-690, 550 (JAK1/3 inhibitor) at 0, 0.01, 0.1 or 1 µM for 1 hr and stimulated with 100 nM rhIL-2 for 10 minutes. Blots were probed for STAT5 (Cell Signaling 9358), pSTAT5 (Cell signaling 9359) and JAK3 (Cell signaling 3775).

The Jurkat T-cell line is a well accepted transformed tumor model of Th2-like CD4 T-cells. Immunoblots conducted on ibrutinib-pretreated, CD3/CD28 stimulated Jurkat cells confirmed functional inhibition of the Tyr180 autophosphorylation site of ITK (FIG. 1h). Downstream T-cell activation is predicated upon robust NFκB, MAPK, and NFAT signaling; therefore, components of each pathway were examined to determine the T-cell specific effects of ibrutinib. As expected, ibrutinib treatment resulted a dose-dependent inhibition of IkBα, JunB, and NFAT signaling, supporting ibrutinib's role in inhibiting ITK and thus the proximal TCR signalosome (FIGS. 1i and j). Notably, an inhibition of both JunB and pSTAT6 signaling was observed, indicating that the Th2 dominant IL4/STAT6 autocrine axis had been disrupted by brief exposure to ibrutinib. While JAK3 inhibition could explain some of our in vitro data, our initial target validation studies demonstrated that ibrutinib does not directly influence this kinase in cell-based assays (FIG. 10).

Ibrutinib Disproportionately Inhibits Th2 Signaling Pathways Yet does not Inhibit Proliferative Capacity of a Mixed Population T-Cell Culture.

Figure 2:
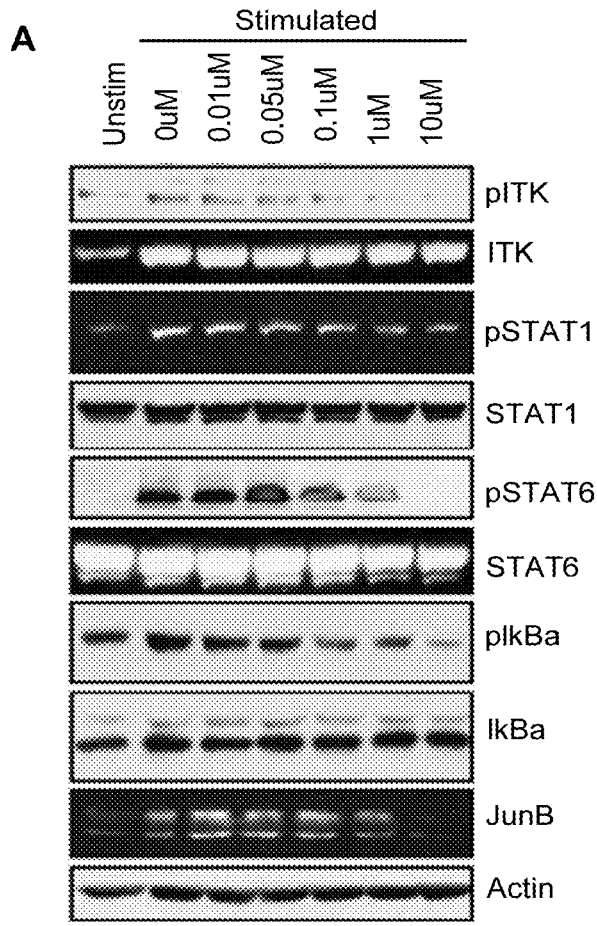
FIG. 2 illustrates ibrutinib inhibiting ITK derived TCR signaling, specific Th2 signaling pathways, but not overall proliferative capacity in primary CD4 T-cells.
Figure 2:
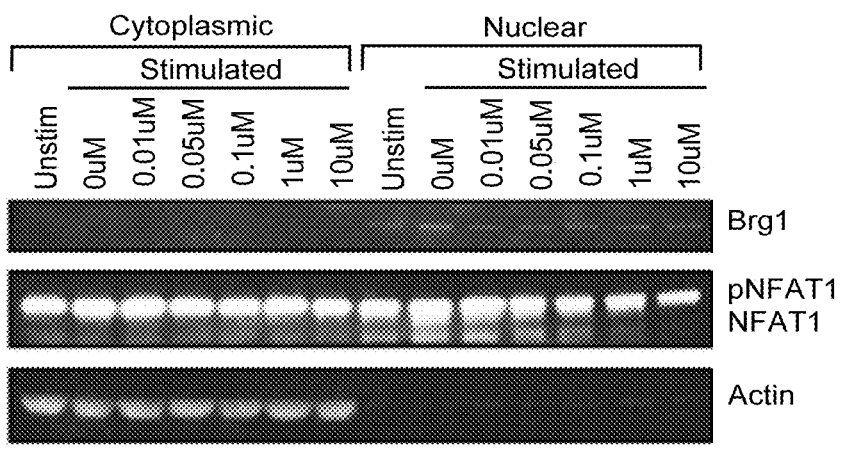
Figure 2:
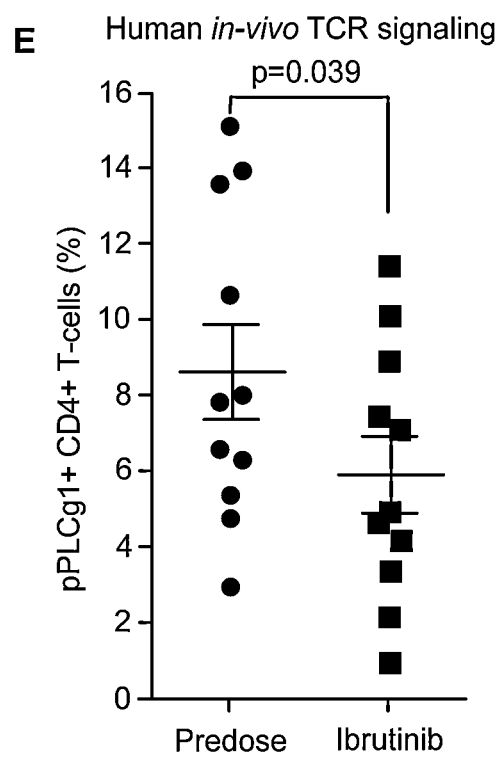
Figure 2:
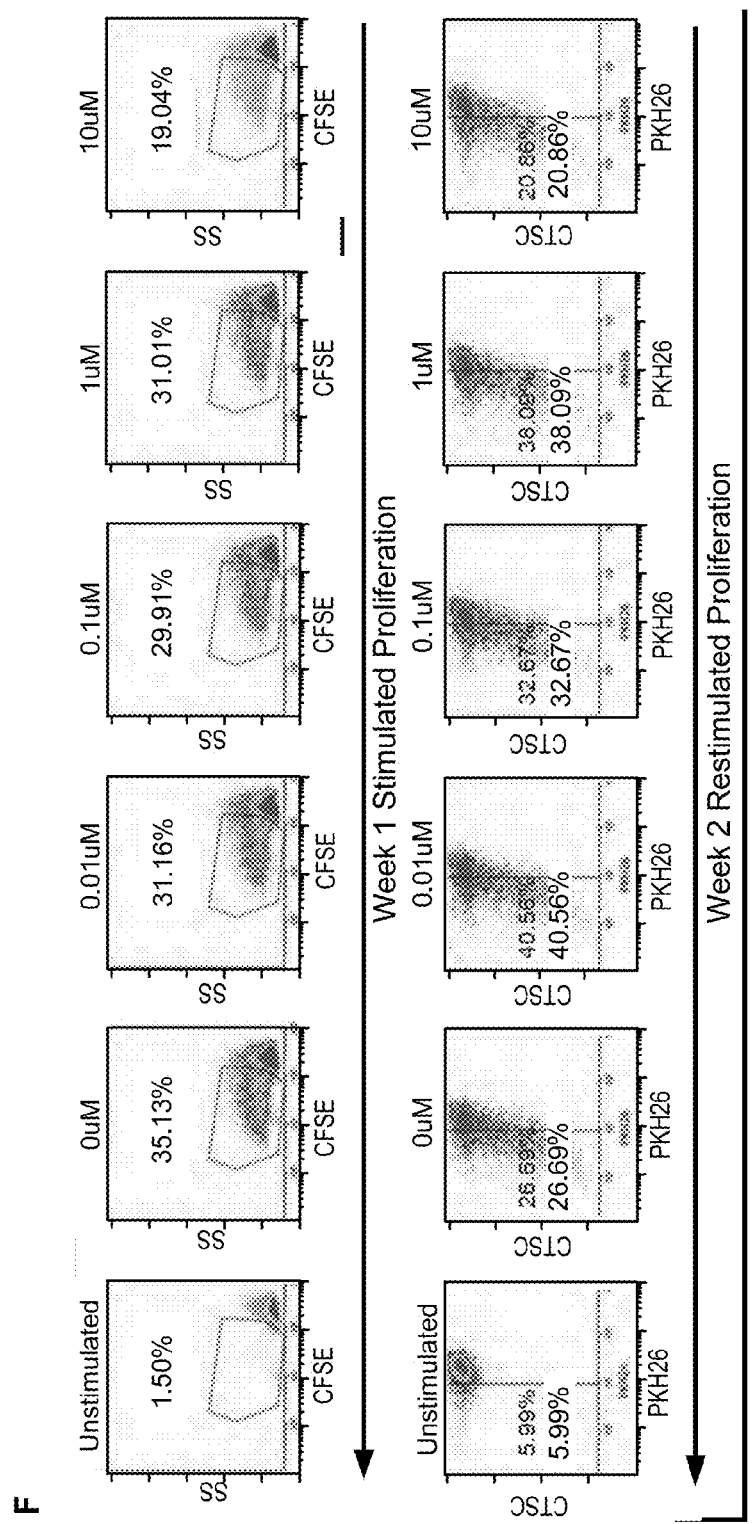
Figure 11:
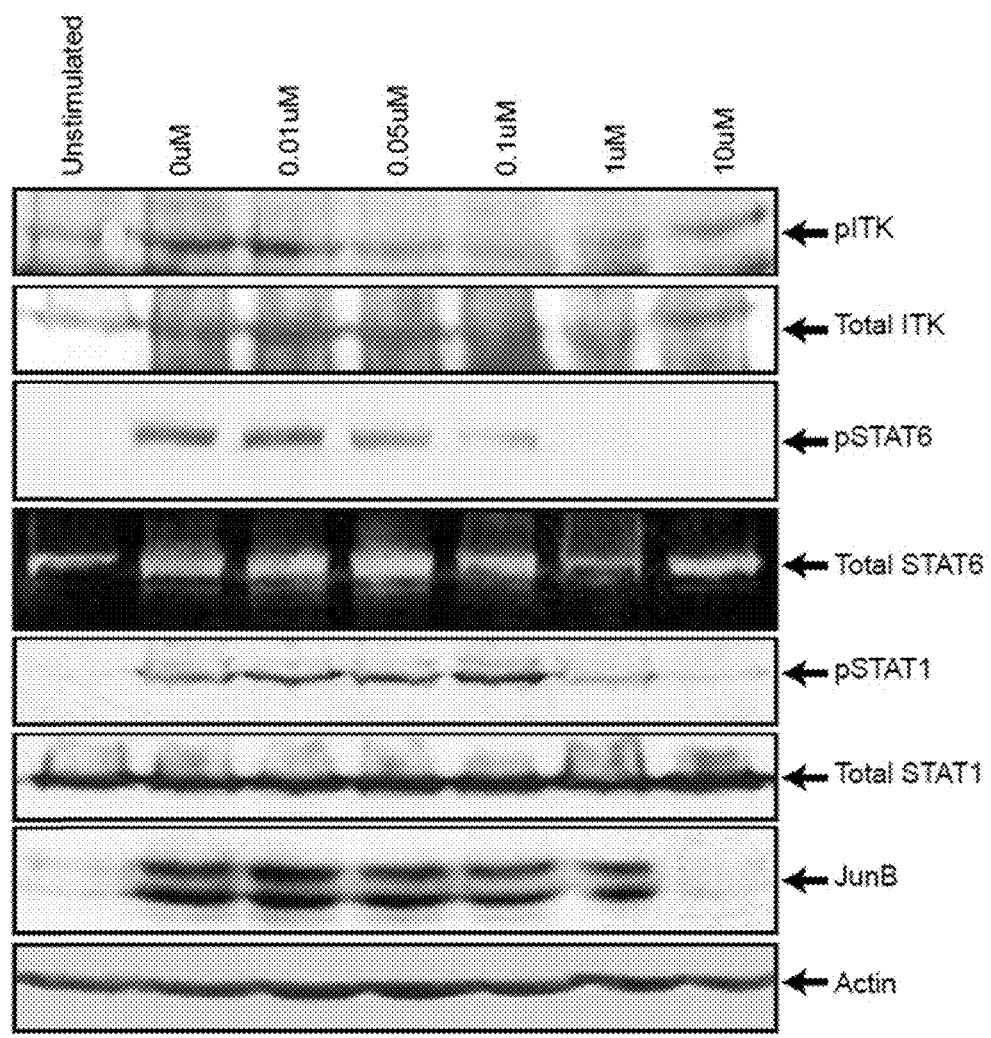
FIG. 11 illustrates immunoblot analysis of primary CD4 T-cells pretreated with ibrutinib and stimulated via anti-CD28 and anti-CD3. Immunoblot analysis of freshly isolated ibrutinib pretreated primary CD4+ cells from a healthy donor, 2 hr anti-CD3/anti-CD28 stimulated (or unstimulated), whole cell lysates. Blot probed for pITK-$Y_{180}$, Total ITK, pSTAT1-$Y_{701}$, Total STAT1, pSTAT6-$Y_{641}$, Total STAT6, pIkBα-$S_{32/36}$, Total IkBα, JunB, and Actin.

To translate these findings into primary human CD4 T-cells, ITK and downstream TCR inhibition was assessed following ibrutinib treatment. Consistent with prior work in Jurkat cells, potent irreversible inhibition of TCR-induced ITK phosphorylation was identified (FIG. 2a). Moreover, inhibition of NFAT, JunB, and IkBα downstream signaling was confirmed in primary CD4 T-cells (FIG. 2a and b). Again the JunB-IL4/pSTAT6 Th2 signaling axis was disrupted, although the IFNγ/pSTAT1 Th1 molecular axis remained intact at approximately 10-fold higher concentrations of ibrutinib, as evidenced by immunoblot (FIGS. 2a and 11). NFAT nuclear localization was inhibited in a proportion of CD4 T-cells (FIG. 2c and d), further confirming the inhibition of CD4 T-cell activation. However, remnant populations of activated CD4 T-cells were present even at ibrutinib pretreatment doses exceeding 1 µM.

To confirm that TCR-induced activation events preceding ITK autophosphorylation were not altered, the proximal pathway components were examined using both primary CD4 and Jurkat T-cells. Immunoblot data revealed that upstream phosphorylation of LCK, ZAP70 and LAT remain unchanged. Furthermore, the PKC activator, phorbol 12-myristate 13-acetate (PMA), and the calcium ionophore, ionomycin, were utilized to confirm that distal elements of TCR activation including NFAT activity and ikBa phosphorylation were engaged regardless of ibrutinib treatment in Jurkat cells.

Figure 12:
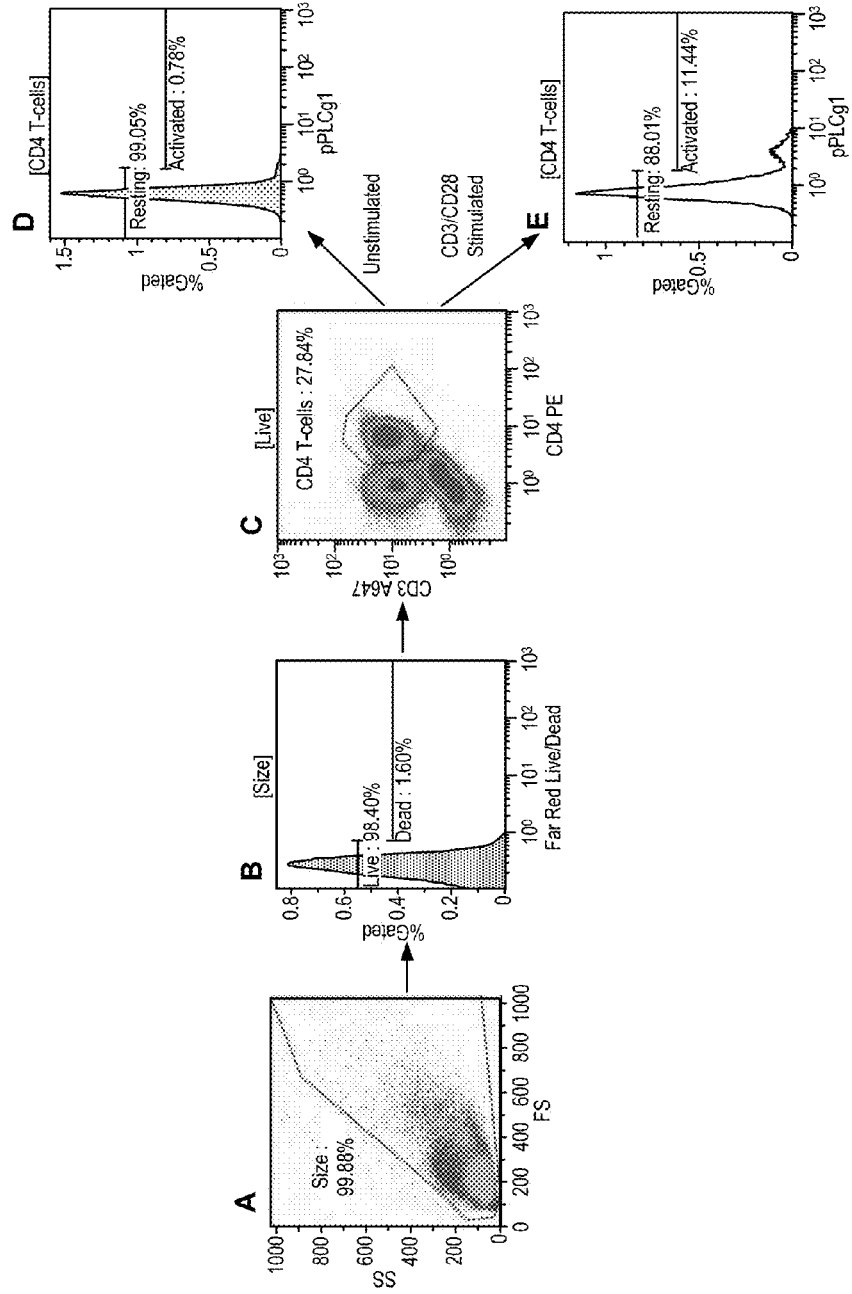
FIG. 12 illustrates gating strategy for pPLCγ-Tyr783 analysis in CD3+CD4+ cells. A minimum of 400,000 cellular events were collected and gated on forward and side scatter to isolate lymphocytes (FIGS. 12A-12B). Size selected cells were subgated using a fixable live dead marker and live cells were gated on CD3 and CD4 to isolate double positive cells (FIG. 12C). Living CD3+CD4+ were gated on pPLCγ1-Tyr783 and relative positive and negative gates were generated based upon unstimulated and stimulated control samples (FIGS. 12D-12E).

Given that PLCγ1 is directly phosphorylated at Tyr783 by active ITK, pPLCγ1-Tyr783 phosflow analysis were conducted on CD3/CD28 stimulated CD4 T-cells from predose and day eight cryopreserved PBMCs. This was to confirm functional ITK inhibition in CLL patients receiving oral ibrutinib. Results reveal a significant decrease in TCR-induced pPLCγ1 activation confirming inhibition of CD4 T-cell ITK signaling in these patients (FIGS. 2e and 12).

Prior work in mice has demonstrated that loss of ITK attenuates but does not ablate intracellular calcium flux in response to TCR signaling. Ibrutinib treatment of Jurkat cells yielded similar results. This demonstrates that ibrutinib-based ITK inhibition significantly reduces intracellular calcium flux in response to TCR stimulation.

Figure 13:
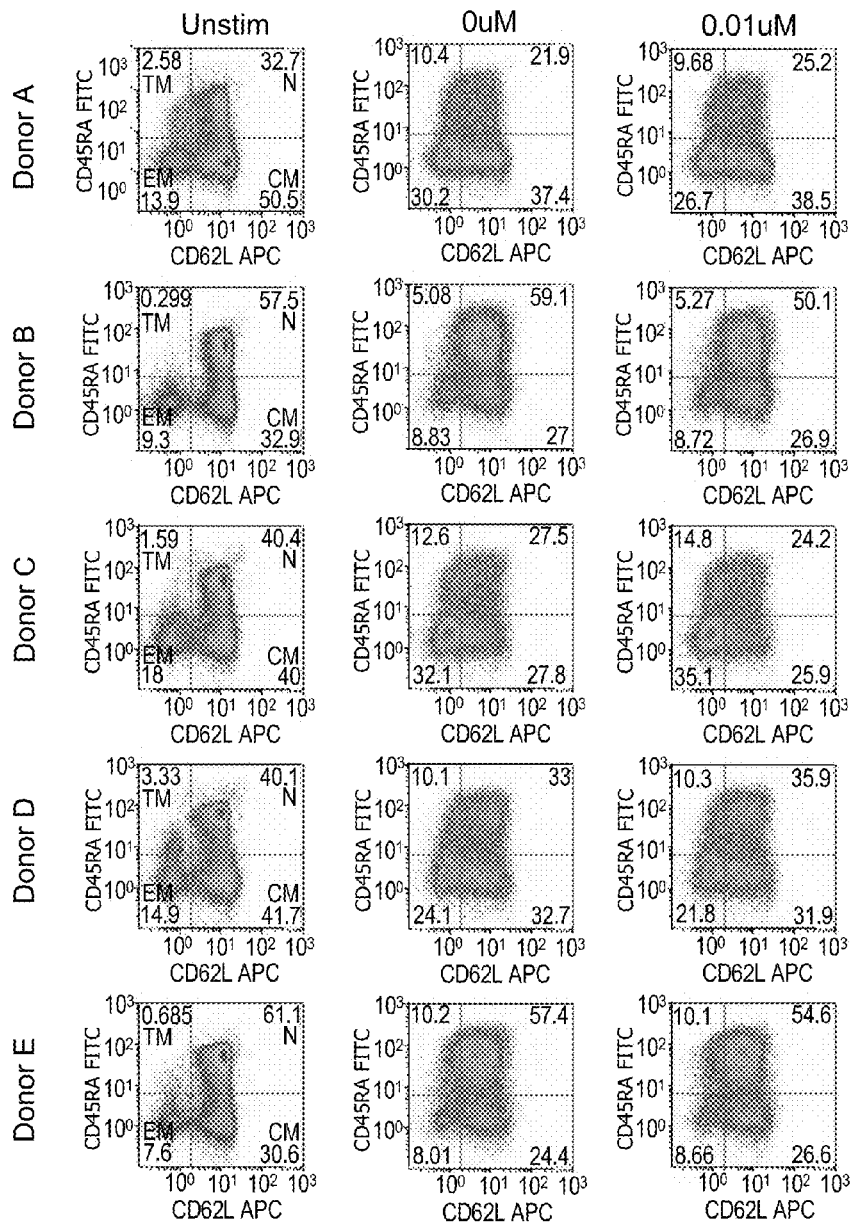
FIG. 13 illustrates flow cytometry analysis of naïve, terminal, central, and effector memory CD4+ T-cells before and after ibrutinib treatment. Flow cytometric analysis of naïve (N)(CD62L+CD45RA+), central memory (CM) (CD62L+CD45RA−), effector memory (EM)(CD62L−CD45RA−), and terminal memory TM(CD62L-CD45RA+) CD4+ selected T-cells isolated from a healthy donor. Cells were pretreated with the indicated concentration of ibrutinib and stimulated (or unstimulated) with anti-CD3/anti-CD28 for 24 hours prior to analysis. Percentages are represented in each quadrant and each row represents a different healthy donor of varying age (between 30 and 56 years of age).
Figure 13:
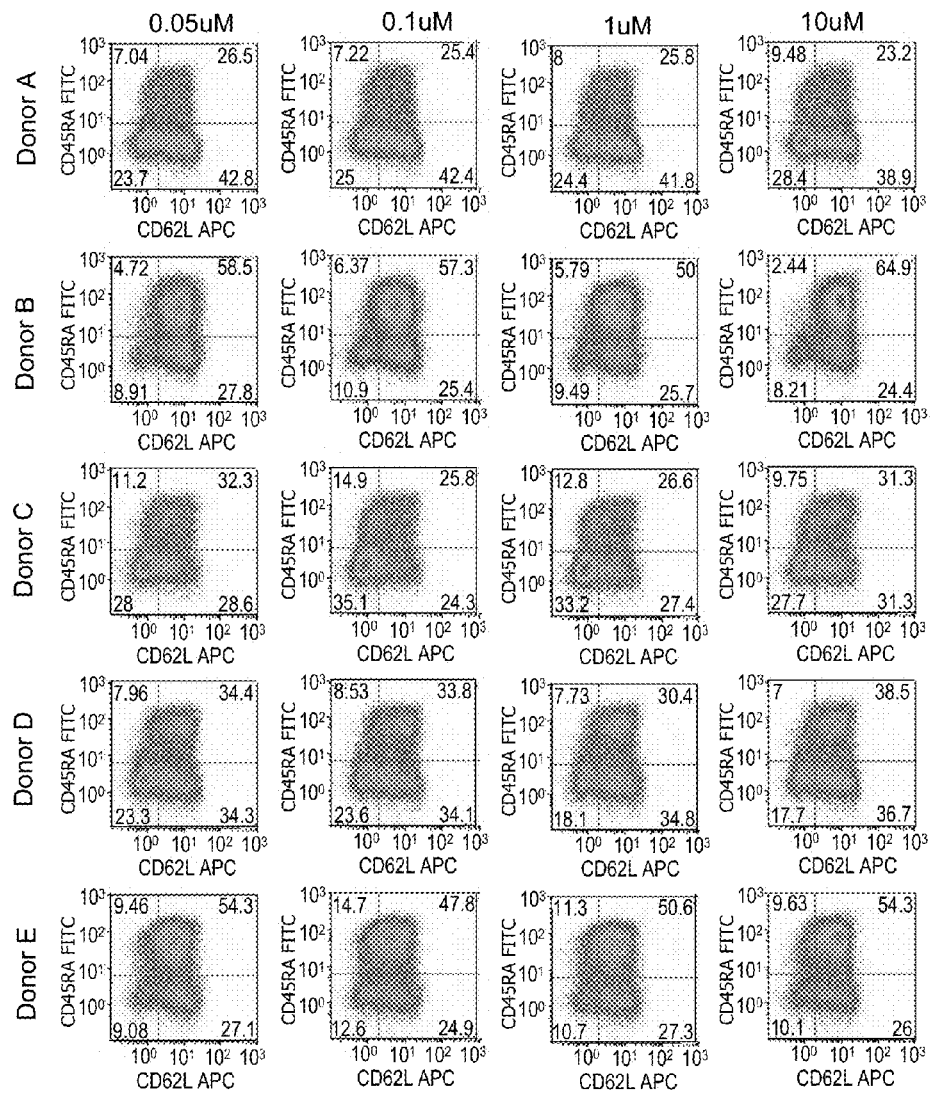
Figure 15:
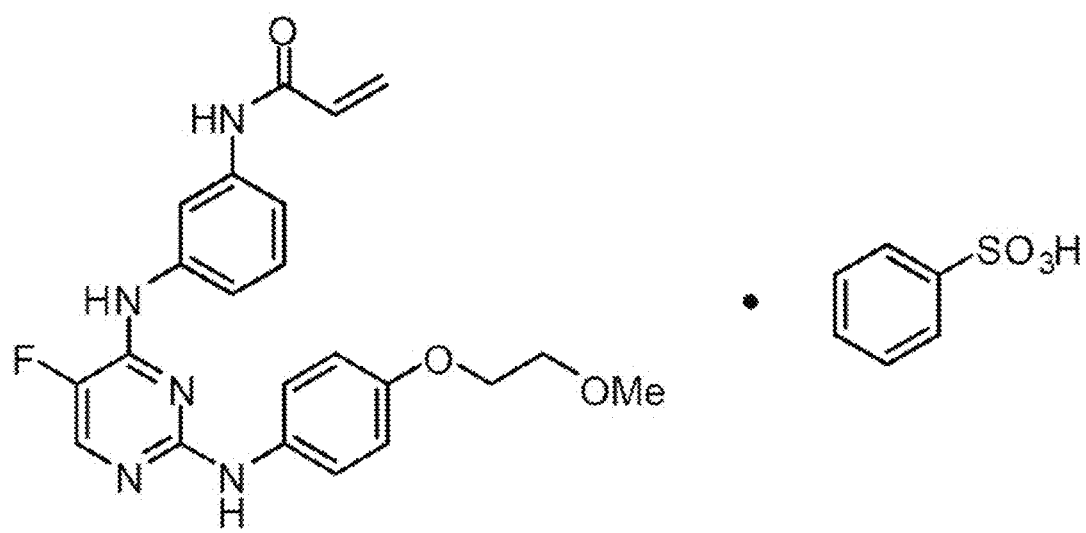
FIG. 15 illustrates a chemical structure of an alternate BTK inhibitor.
Figure 16:
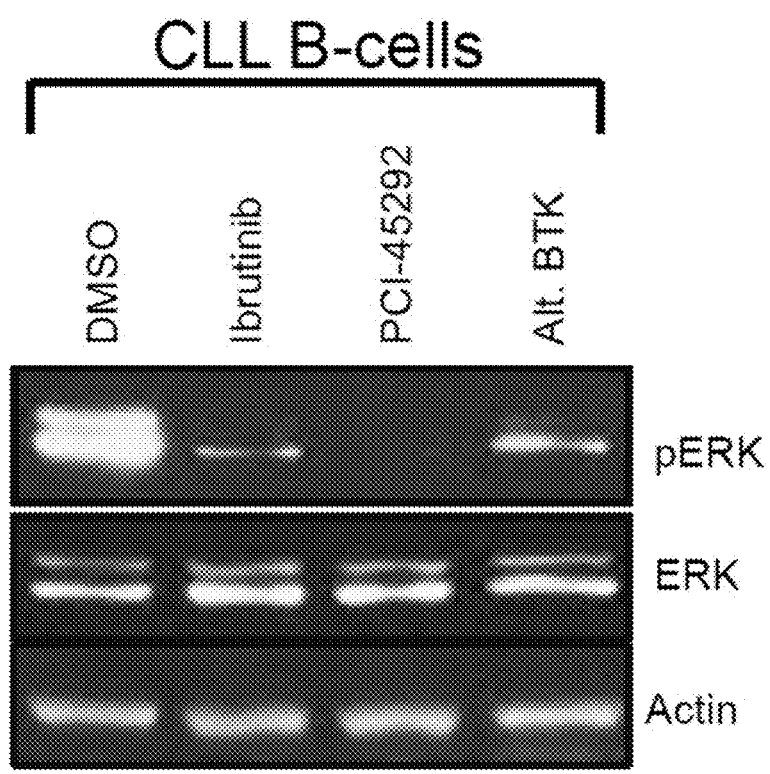
FIG. 16 illustrates immunoblot analysis of constitutive downstream BTK signaling in leukemic B-cells treated in vitro with three irreversible BTK inhibitors. Immunoblot analysis of whole cell lysates from freshly isolated 1 µM ibrutinib, PCI45292, Alt. BTK inhibitor, or vehicle (DMSO) treated primary CD19+ B-cells from a CLL donor. Blot was probed for pERK, Total ERK, and Actin.
Figure 17:
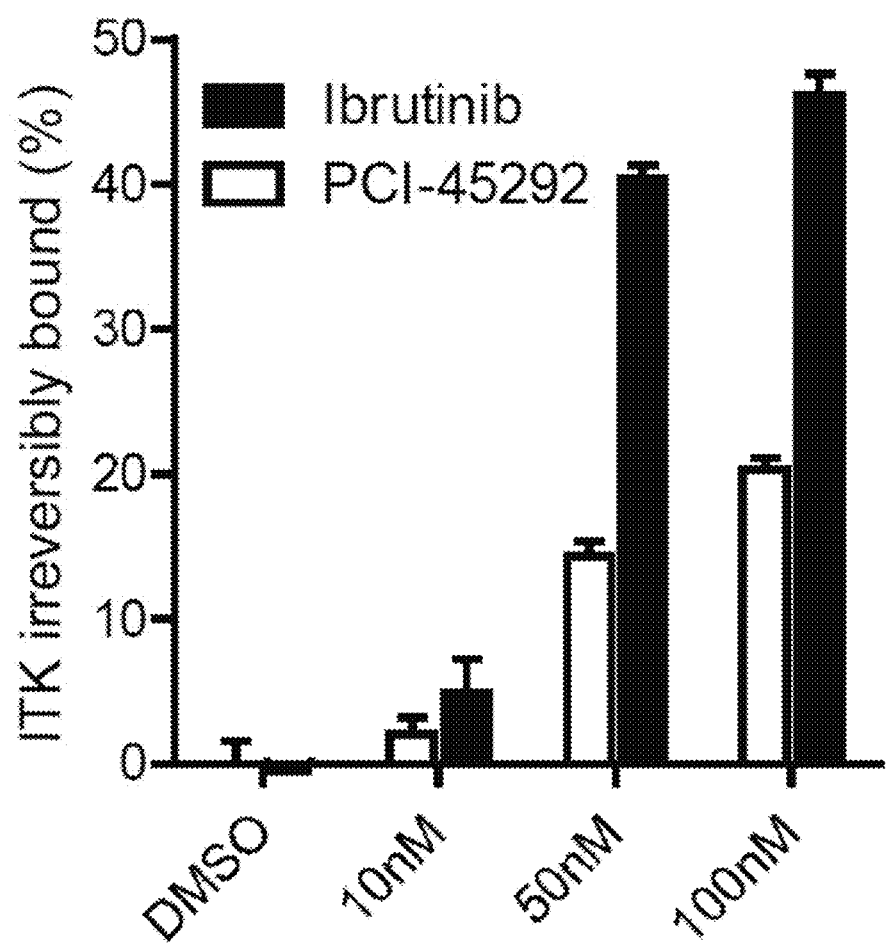
FIG. 17 illustrates ITK binding probe assay conducted on Jurkat lysates pretreated with ibrutinib or PCI-45292. Fluorescent probe assay was used to calculate the percent occupancy of total ITK in Jurkat whole cell lysates irreversibly bound by ibrutinib (dark bars) or PCI-45292 (open bars). Error bars, s.e.m.
Figure 18:
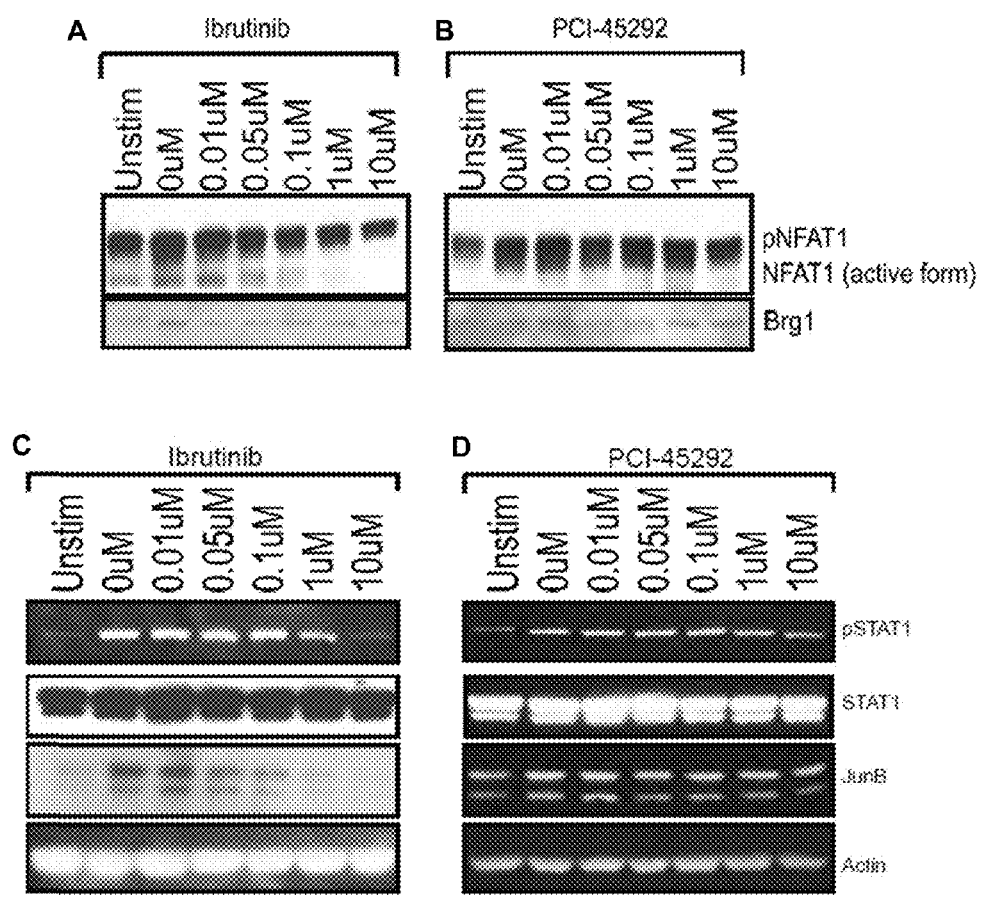
FIG. 18 illustrates ITK specific downstream signaling is attenuated by ibrutinib but not a structurally similar ITK non-targeting BTK inhibitor. Immunoblot analysis of 45 minute nuclear and 2 hr whole cell extracts from ibrutinib or PCI-45292 pretreated, freshly purified healthy donor primary CD4+ cells stimulated with anti-CD3/anti-CD28. Nuclear extracts were probed for NFAT1 and Brg1 (FIG. 18A-B); whole cell extracts were probed for pSTAT1-Y701, Total STAT1, JunB, and Actin (FIG. 18C-D).

Rapid proliferation is a hallmark of TCR-induced stimulation. To study the effects of ibrutinib pretreatment on repeated CD3/CD28 induced proliferation, 7 day cultures of CFSE-stained CD4 T cells were analyzed. Very minor inhibition of overall CD4 T-cell proliferative capacity was observed in the initial 7 days following ibrutinib treatment (FIG. 2f). To ensure that recall response proliferation was also unaffected, the culture was re-stimulated via CD3/CD28 and cells were re-stained with the PKH26 proliferative tracker dye. Ibrutinib treated CD4 T-cell cultures proliferated more upon recall stimulation than untreated cultures, with the exception of the supra-pharmacologic dose of 10 µM. Furthermore, the naïve, central memory, effector memory, and terminal memory subsets were unaffected by ibrutinib (FIG. 13). Collectively, these data indicate that a remnant population of Th1-biased T-cells is resistant to ibrutinib inhibition and retain the functional capacity to activate via TCR stimulation, achieving a proliferative advantage in an otherwise inhibited polyclonal population of CD4 T-cells.

Ibrutinib-Induced ITK-C442 Irreversible Inhibition Provides a Selective Advantage to RLK-Expressing Th1 and CD8 T Cells.

Figure 3:
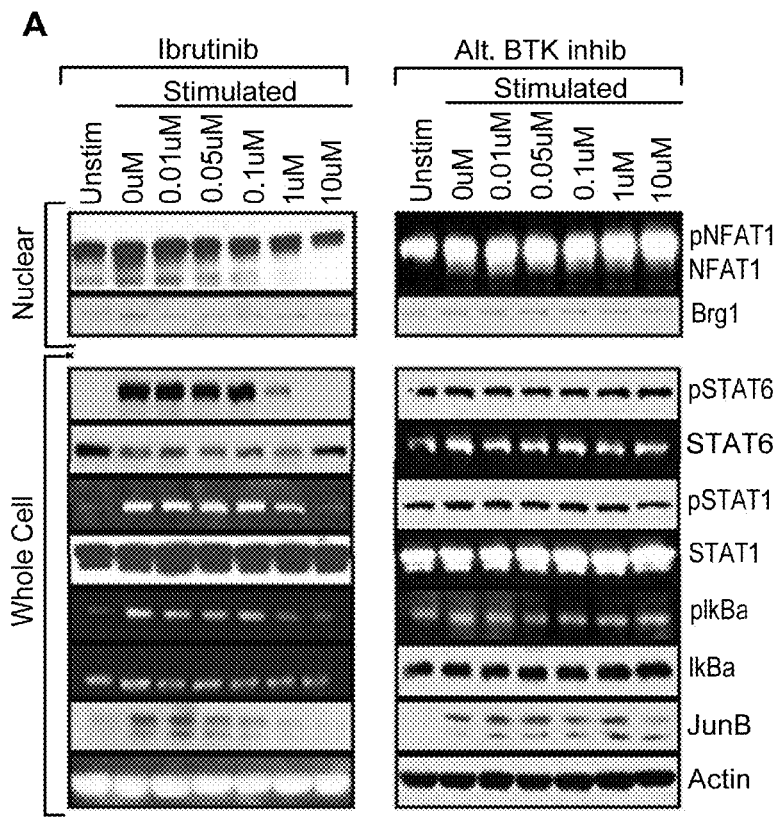
FIG. 3 illustrates ibrutinib irreversibly binding to ITK-C442 and RLK expression provides compensatory kinase activity in Th1 and CD8 T-cells.
Figure 3:
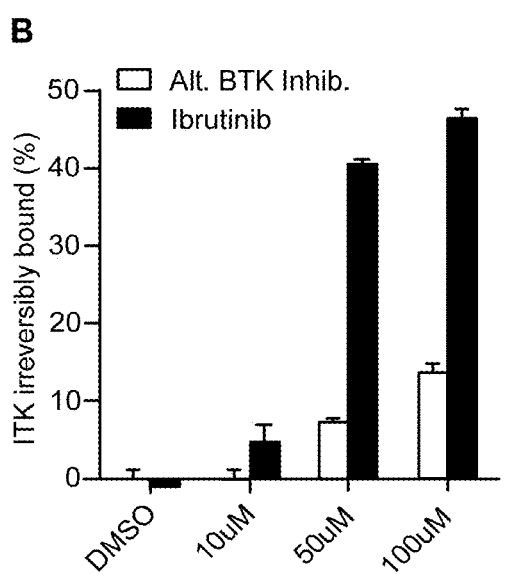
Figure 3:
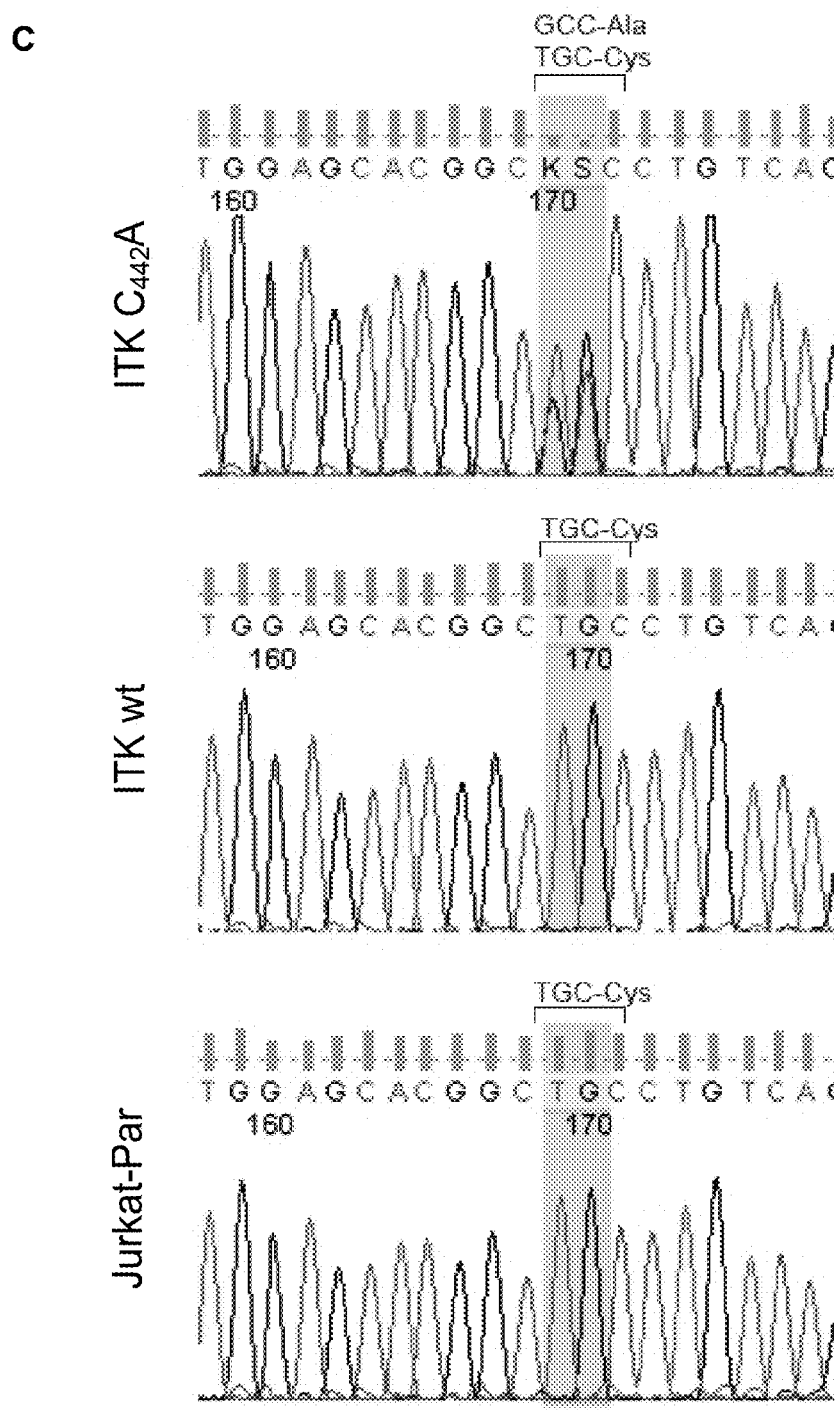
Figure 3:
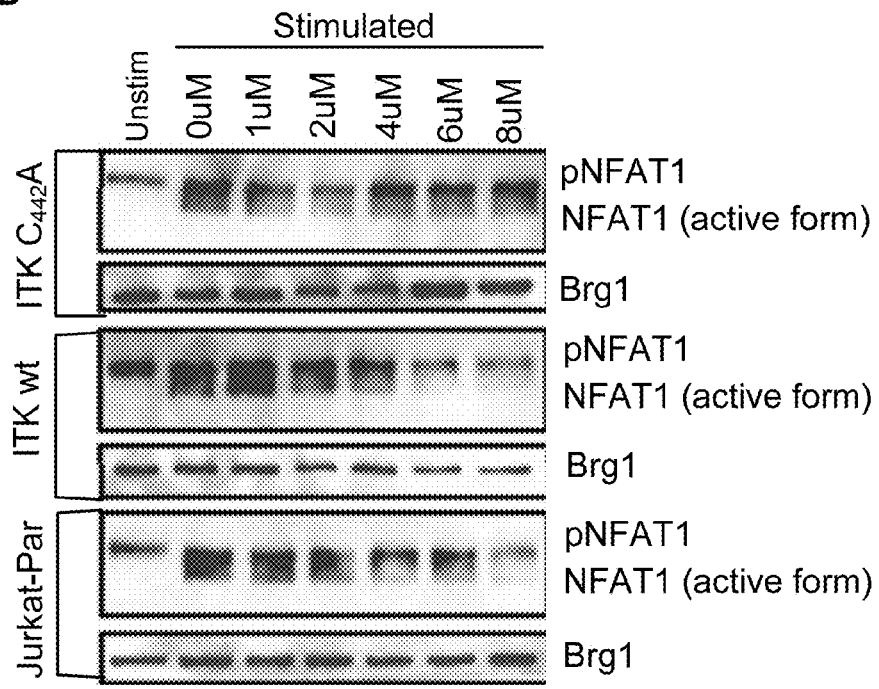
Figure 3:
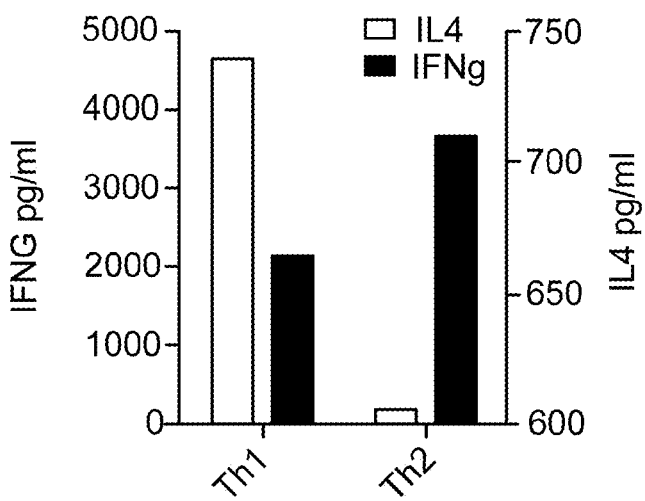
Figure 3:
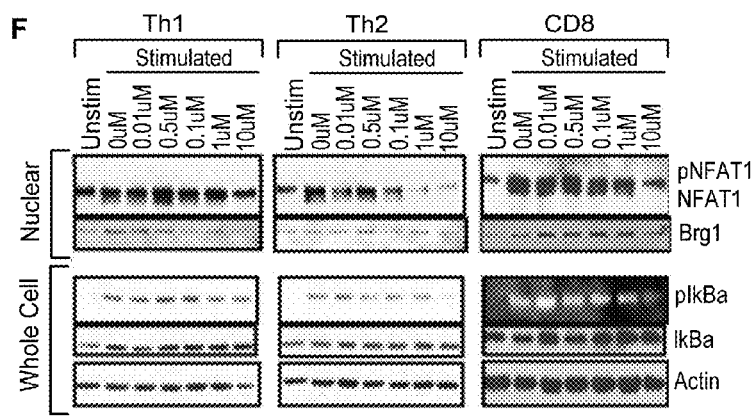
Figure 3:
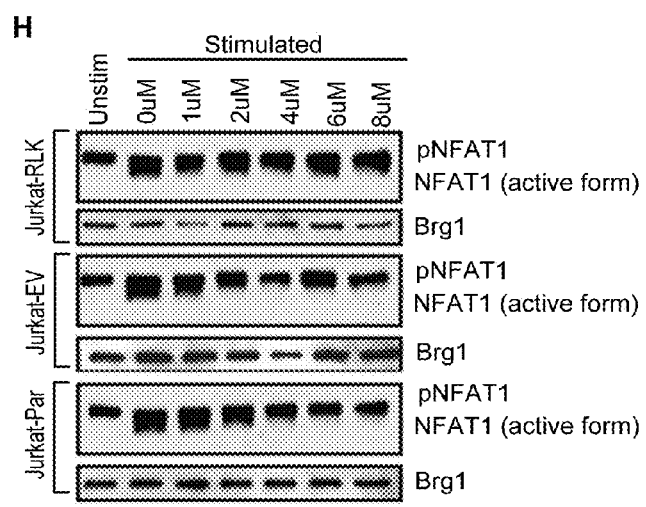

To confirm that the primary irreversible molecular target of ibrutinib in CD4 T-cells was ITK, TCR-induced activation of NFAT, pSTAT1, pSTAT6, pIkBα, and JunB was evaluated in primary CD4 T cells pretreated with Ibrutinib or one of two alternative BTK inhibitors that do not target ITK (IC50>22.5 nM) (FIGS. 3a,b and 14-18). Only ibrutinib (ITK IC50=2.2 nM) was capable of inhibiting TCR downstream molecular activation ex vivo when compared to these two ITK non-targeting alternative BTK inhibitors.

As molecular confirmation that ITK was the primary irreversible target in CD4 T-cells, a stably transduced Jurkat line was generated with ITK-C442A, a version of ITK that lacks the covalent irreversible binding site for ibrutinib (FIG. 3c). The ITK-C442A Jurkat line maintained NFAT activation to drug concentrations exceeding 8 µM, whereas the wild-type and parental lines were inhibited at 2-4 µM (FIG. 3d).

Ibrutinib skews ex vivo Th1/Th2 responses and attenuates certain Th2-critical signaling pathways such as JunB and STATE while preserving Th1 related signaling pathways like STAT1 at physiologically relevant doses between 0.1 and 1 µM. This molecular inhibition pattern occurs alongside an outgrowth uninhibited CD4 T-cells. To elucidate the differential inhibition of Th2 polarized T-cells in relation to Th1, naïve CD4 T-cells were polarized in vitro using a previously described strategy to obtain enriched cultures of IFNγ-producing Th1 cells and IL4-producing Th2 cells (FIG. 3e). Only Th2 cultures were sensitive to physiologically relevant levels of ibrutinib as demonstrated by reduced IL4 production. Additionally, ibrutinib inhibited NFAT and IkBα activation in Th2 T-cells, whereas both Th1 polarized CD4 T-cells as well as purified CD8 T-cells were resistant to ibrutinib pretreatment levels sub-10 µM (FIG. 3f).

In Th1 CD4 and conventional CD8 T-cells, RLK plays a redundant role to ITK; however, both Th2 polarized CD4 T-cells and the Th2-like Jurkat cell line do not express RLK31. To test the hypothesis that RLK expression protects Th1 T-cells from ibrutinib inhibition, Jurkat cells stably transduced to express RLK were tested (FIG. 3g). TCR downstream activation of NFAT was protected in the Jurkat-RLK cell line at ibrutinib doses exceeding 8 µM, whereas both the parental and empty vector stable transfectants were susceptible to ibrutinib inhibition at in-vitro concentrations of 2-4 µM (FIG. 3h). Confirmatory intracellular calcium release experiments demonstrate a significant restoration of calcium flux in Jurkat cells stably expressing RLK. This result demonstrates that RLK compensate for ibrutinib-inhibited ITK, thereby providing an alternate activation platform for specific RLK-expressing subsets of T-cells.

Ibrutinib Limits Th2 Activation Thereby Selectively Promoting Th1 Expansion in a Mixed Population of CD4 T-Cells from Healthy Donors and Chronic Lymphocytic Leukemia Patients.

Figure 4:
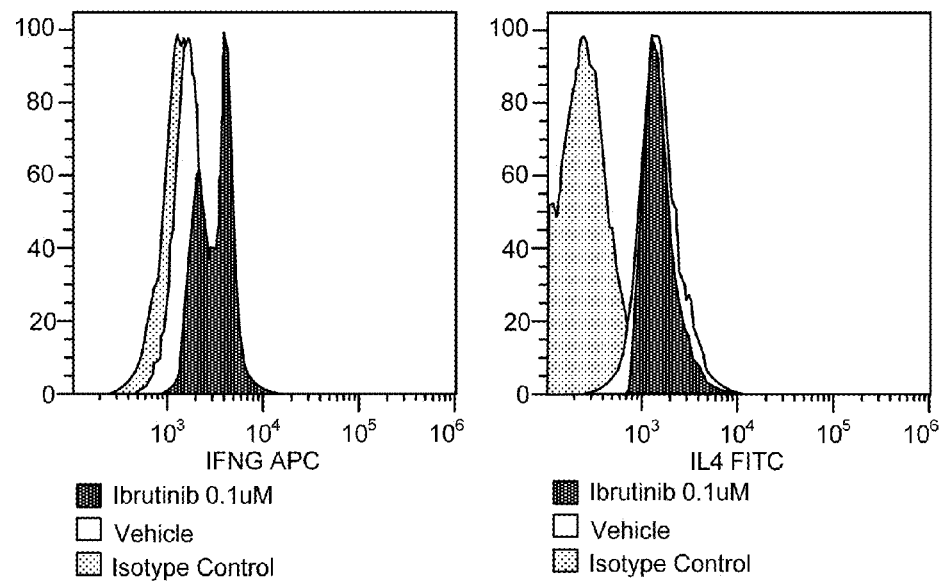
FIG. 4 illustrates ibrutinib which limits Th2 activation, thus selectively promoting Th1 expansion in a mixed population of CD4 T-cells.
Figure 4:
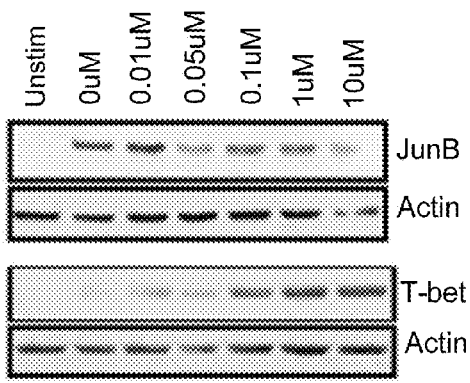
Figure 4:
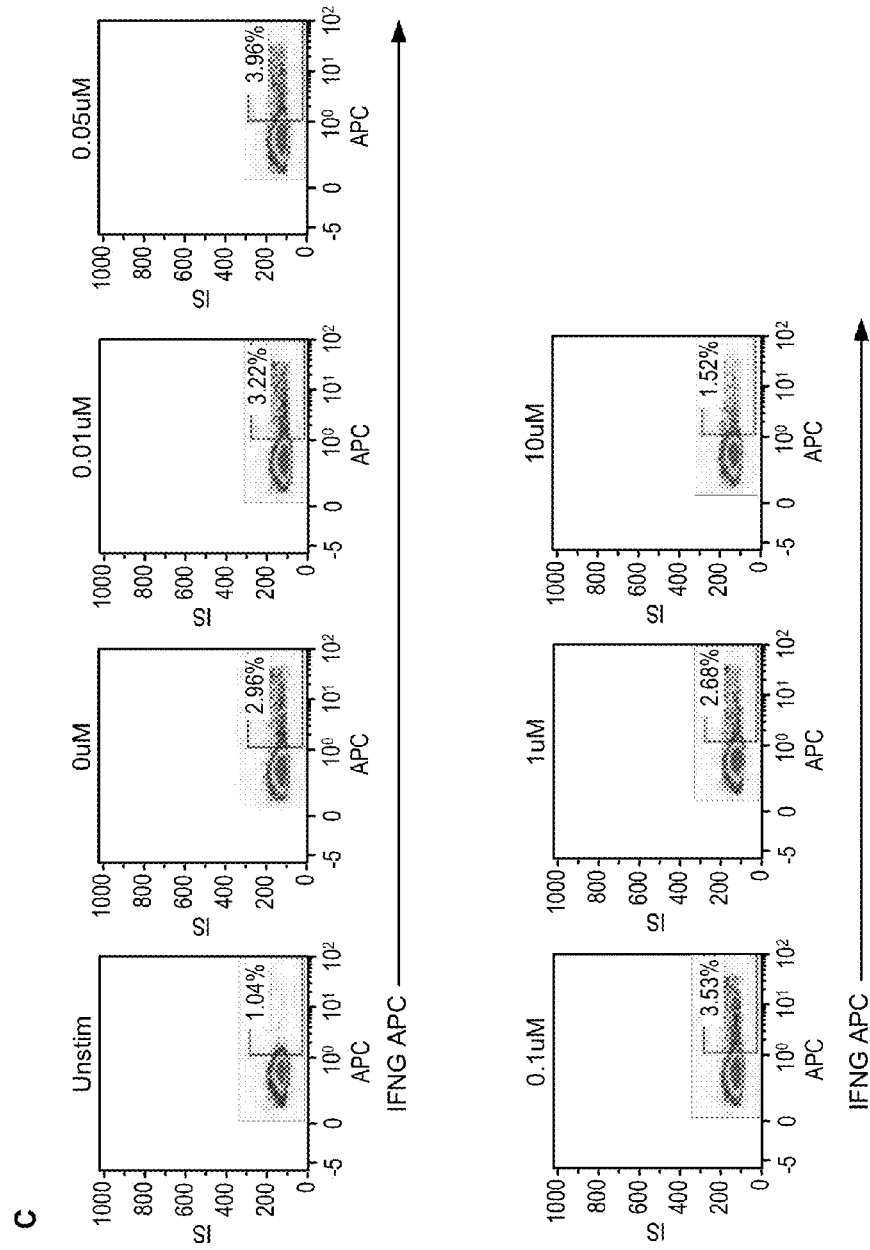
Figure 4:
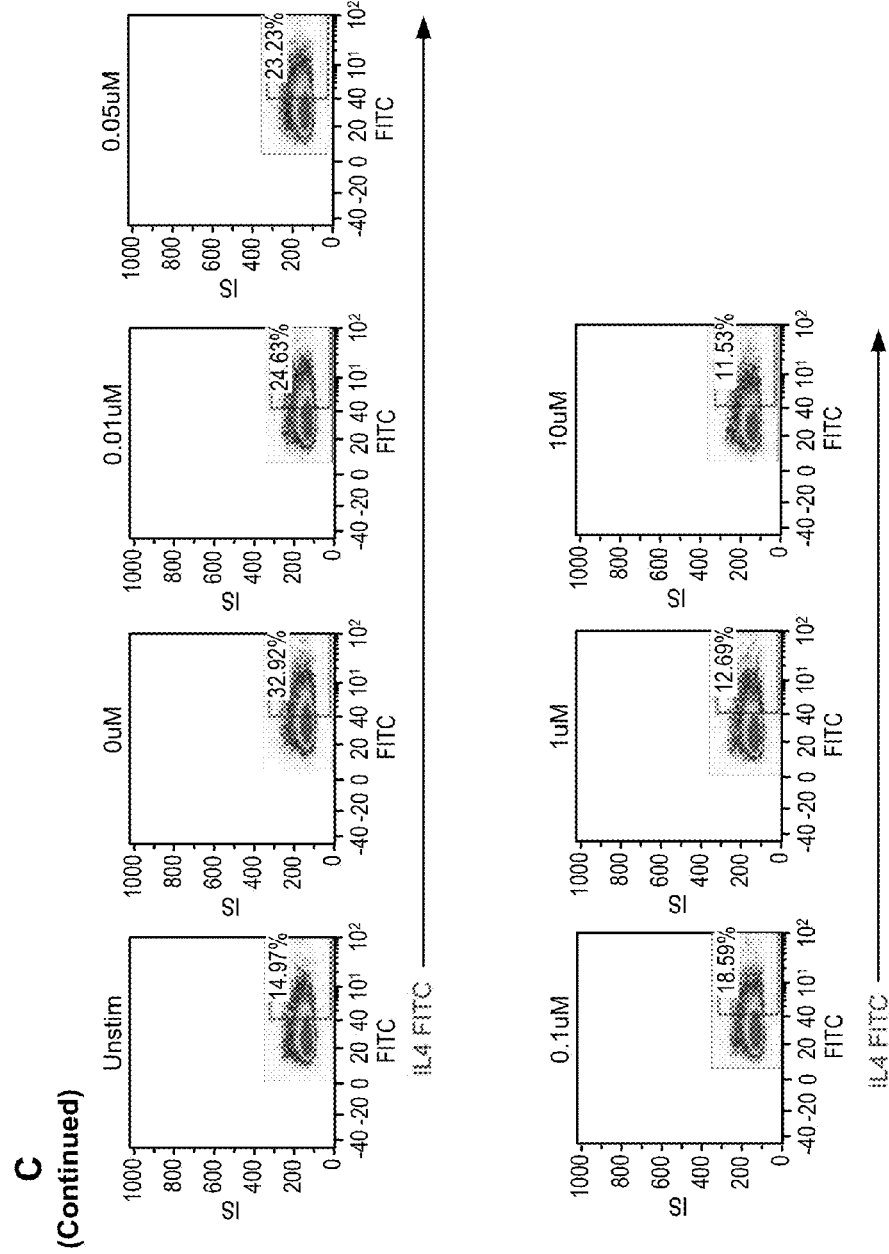
Figure 4:
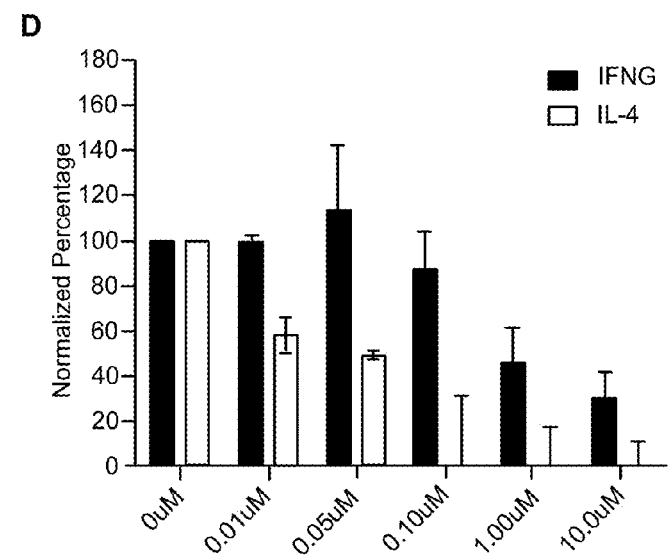
Figure 4:
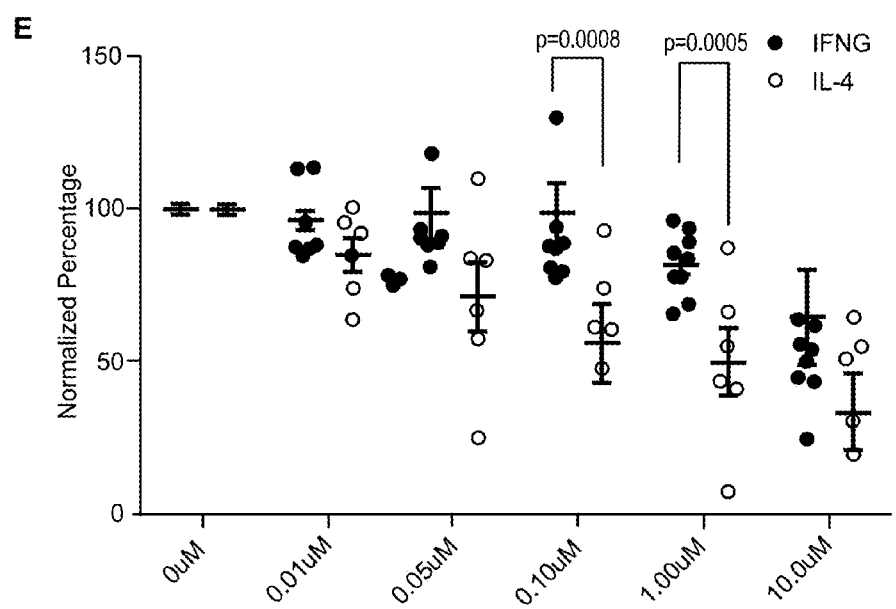

To evaluate the effects of ibrutinib on the Th1/Th2 polarization of a CD4 T-cell population over time, CD4 T-cells isolated from healthy donors were cultured for three days following ibrutinib pretreatment. Outgrowth of IFNγ positive T-cells was confirmed by intracellular staining analysis (FIG. 4a). This outgrowth correlated with a decrease in JunB protein levels and a sharp increase in T-bet expression (FIG. 4b). These data indicate that Th1 cells form a rapidly expanding dominant subpopulation in ibrutinib-treated CD4 T-cell cultures.

To confirm the functional relevance of these results in the setting of CLL, intracellular staining was performed for IFNγ and IL4 in ibrutinib-pretreated, CD3/CD28 stimulated bulk CD4 T-cell cultures purified from CLL patients not treated with ibrutinib. The data revealed a decrease in IL4+ Th2 CD4 T-cells while IFNγ+ Th1 CD4 T-cells were unaffected (FIG. 4c). To confirm that ibrutinib induced Th2 suppression was relevant in a larger cohort of patients, CD4 T-cells isolated from healthy donors and CLL patients were pre-treated with ibrutinib. Following stimulation, a significant decrease was identified in the IL4-producing Th2 population of CD4 T-cells; whereas IFNγ-producing Th1 cells were largely unaffected in ibrutinib pre-treatment doses less than 1 µM (FIG. 4d and e). A significant divergence of the two populations was observed at ibrutinib doses of 0.1-1 µM, which is consistent with the attainable concentrations in patients from in vivo pharmacokinetics of administration of this agent in both mouse and human trials.

Ibrutinib Drives Th1 Mediated *L. major* Immunity in an In Vivo Model of Th2 Dominant Cutaneous Leishmaniasis.

Figure 5:
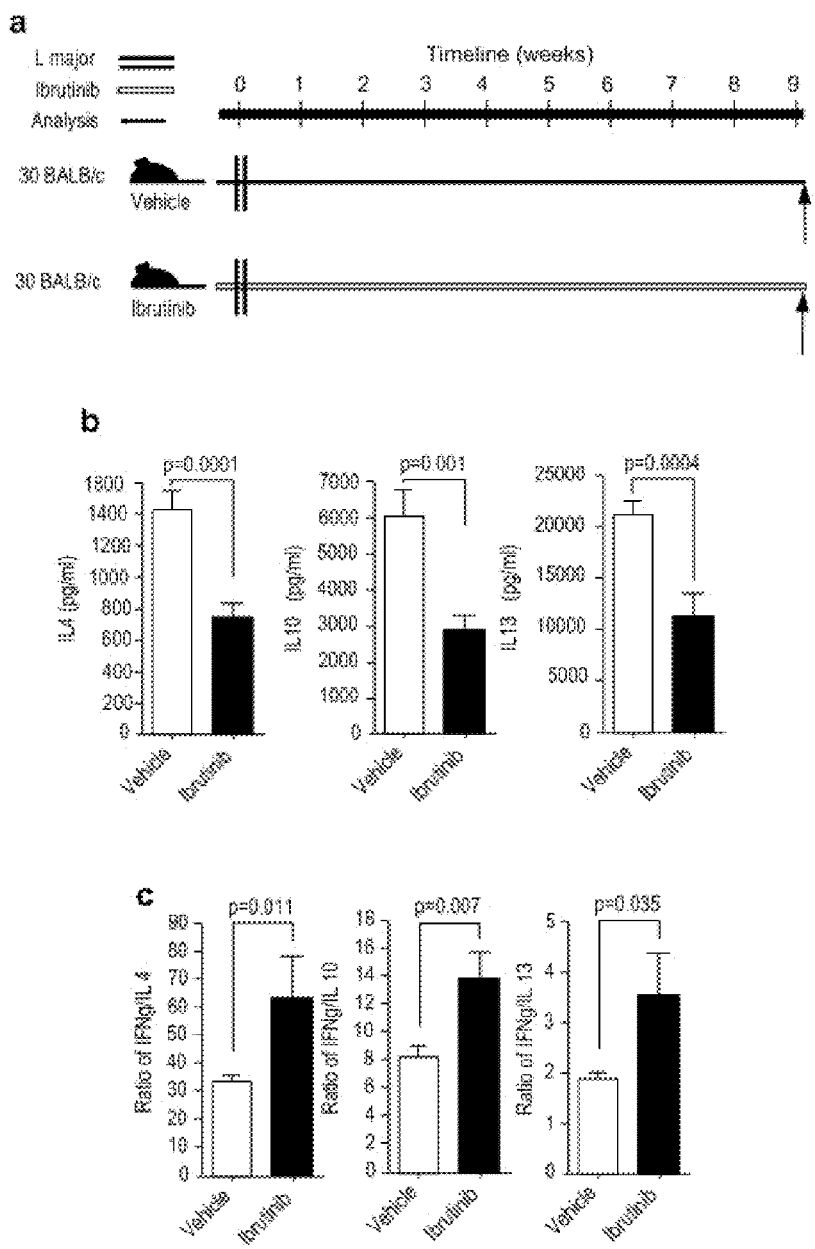
FIG. 5 illustrates ibrutinib driving Th1 mediated *L. major* immunity in an in vivo model of Th2 dominant cutaneous leishmaniasis.
Figure 5:
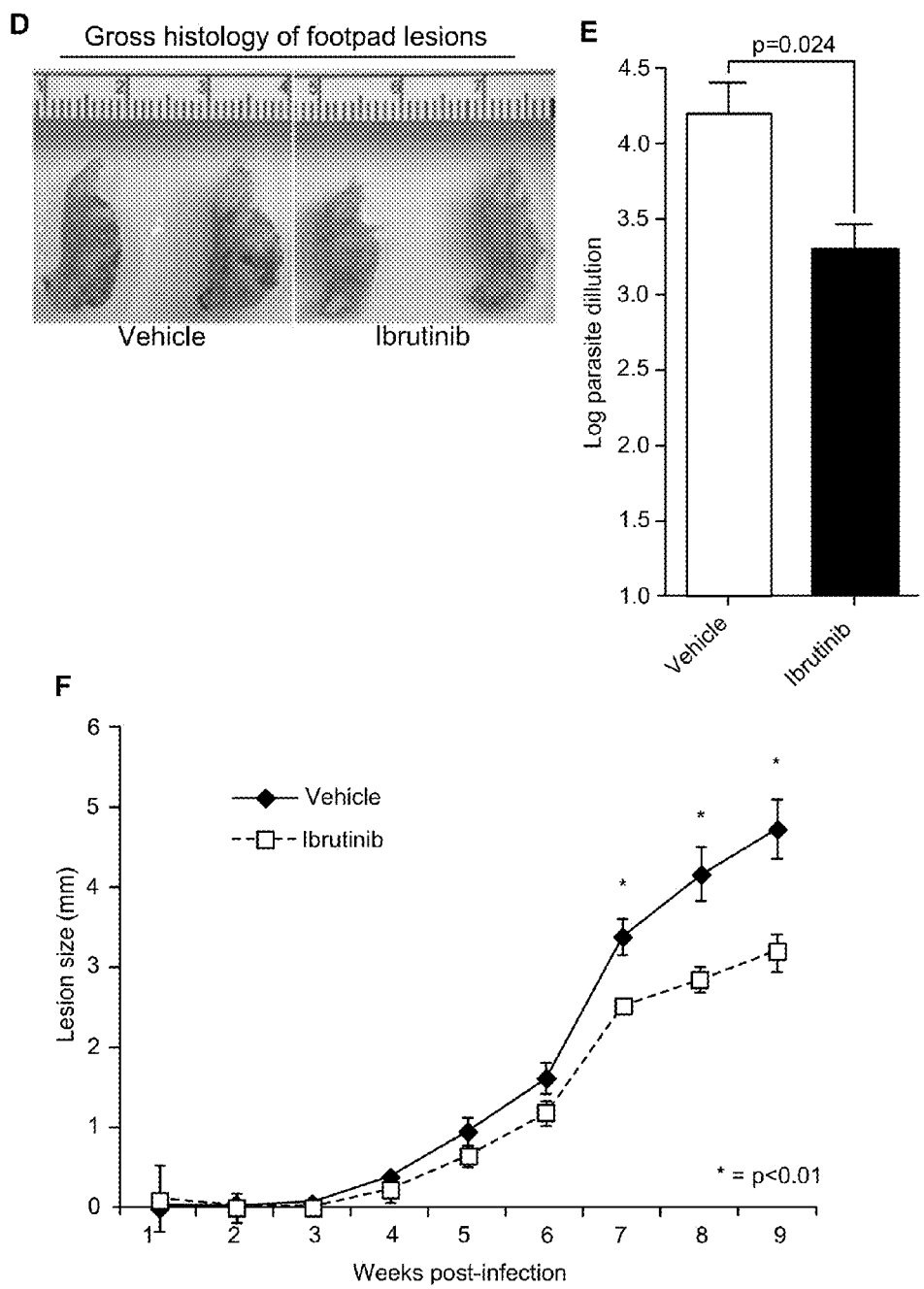

Studies conducted in ITK knockout mice revealed Th1 biased immunity which was specifically capable of mounting effective responses against cutaneous *L. major* parasitic infection8. Using this archetypal model of Th1/Th2 immunity we sought to demonstrate comparable results using ibrutinib as an ITK inhibitor (FIG. 5a). T-cell cytokine analysis demonstrated a significant decrease in Th2 cytokines IL10, IL4, and IL13 relative the Th1 cytokine IFNγ (FIG. 5b and c). Enhanced Th1 immunity was correlated with improved parasite clearance in ibrutinib treated mice as evidenced by smaller cutaneous lesions and lower parasitic burden (FIG. 5d, e, and f).

Ibrutinib Phase I Clinical Trials Along with the EμTCL1 Leukemia Model Confirm Th1/Th2 Skewing and a Direct Functional Relevance in the Setting of Infection.

Figure 6A:
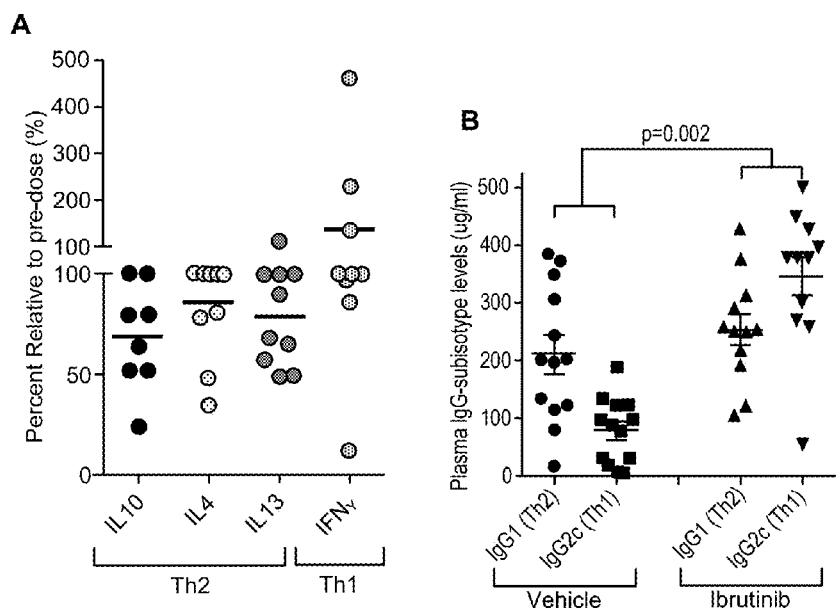
FIG. 6A illustrates percent relative alteration in plasma cytokine levels from pre-treatment to day 28 of therapy in relapsed refractory CLL patients enrolled in a phase I trial of oral ibrutinib.
Figure 6A:
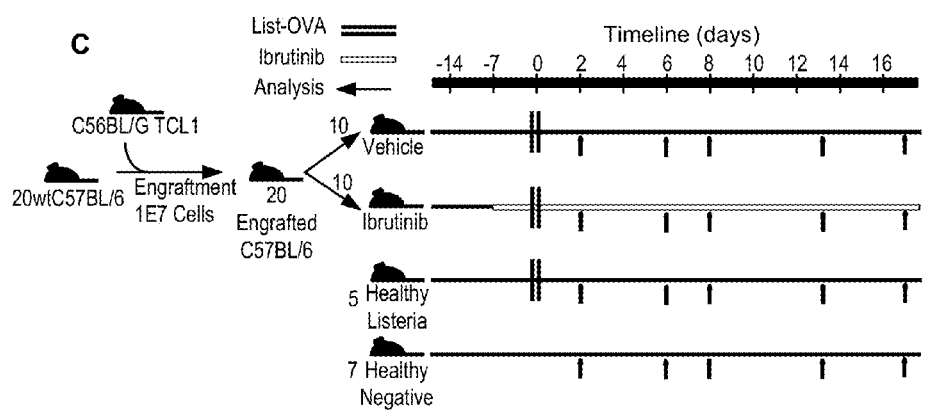
Figure 6A:
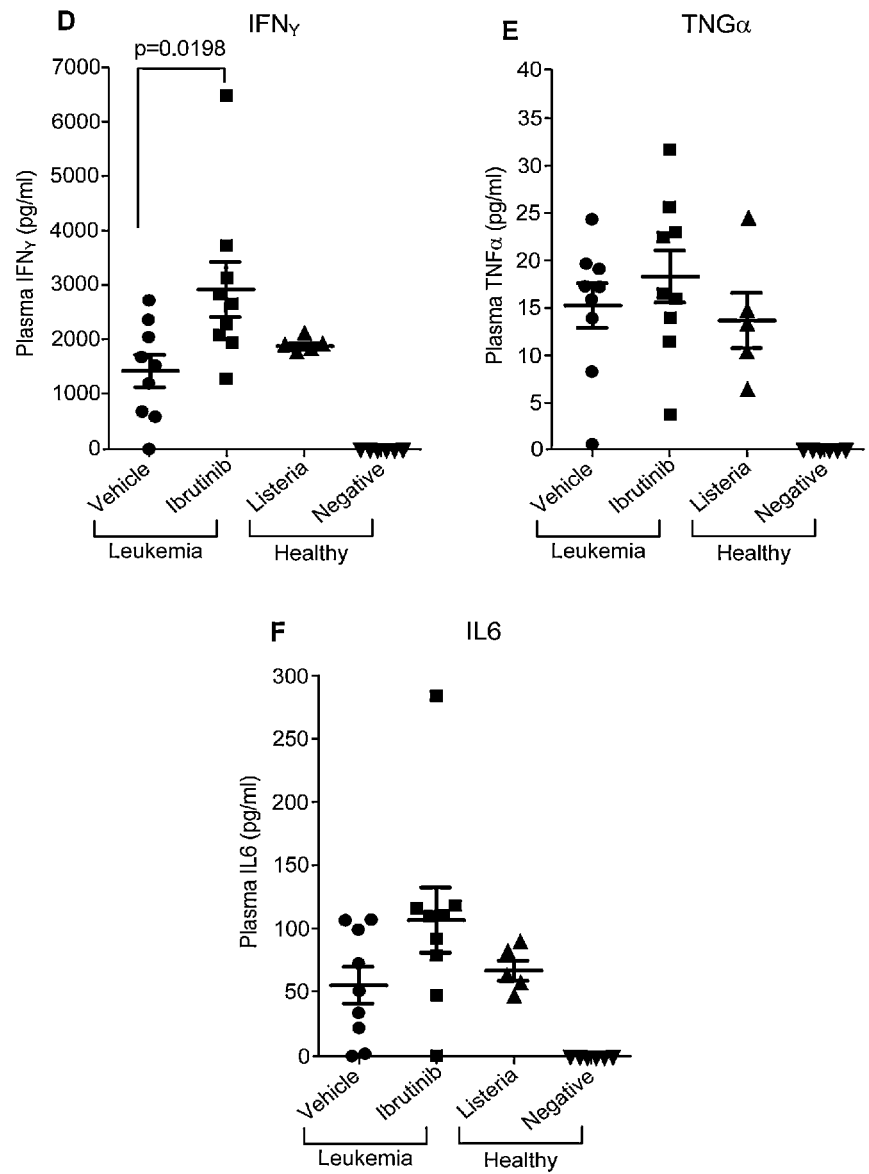
Figure 19:
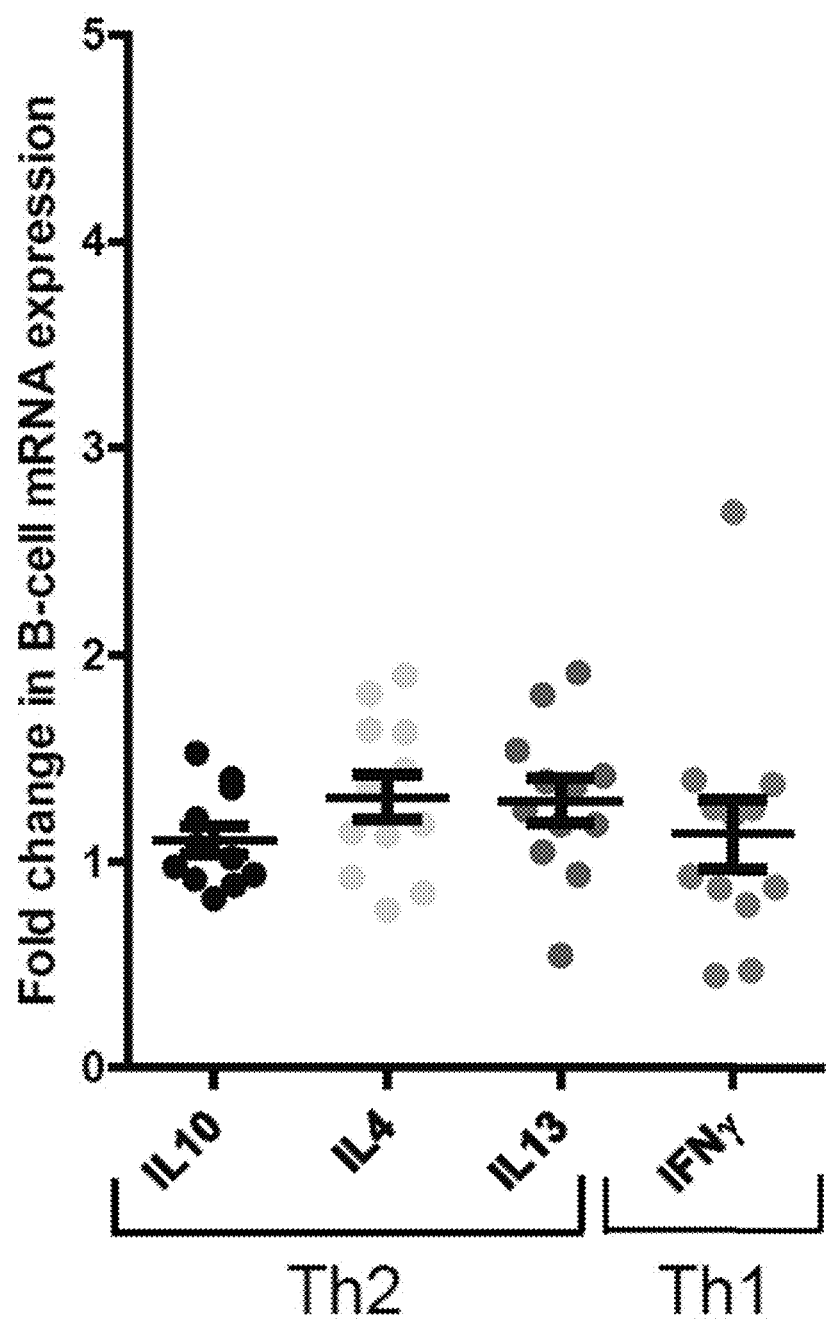
FIG. 19 illustrates B and CLL cell cytokine mRNA analysis reveals no ibrutinib-induced modulation of IL10, IL13, IL4, or IFNγ. CD19+ B-cells and CLL cells were isolated from peripheral blood at pre-dose and after 28 days on ibrutinib. Transcript-specific qRT-PCR analysis of IL10, IL13, IL4, and IFNγ mRNA levels were compared to GAPDH and subsequently to day 28 levels using the Pfaffl fold-change calculation.

To validate these biochemical findings in human patients, serial serum cytokine levels were investigated in relapsed or refractory CLL patients receiving ibrutinib as part of a phase I study. The data demonstrated a decrease in serum Th2-type cytokines including IL10, IL4, and IL13 from pre-treatment to day 28 of ibrutinib therapy (FIG. 6a). This was in sharp contrast to a simultaneous increase in the Th1-type cytokine IFNγ. These augmented cytokine levels could not readily be attributed to the inhibition of B-cells or BTK driven targets since the majority of plasma IFNγ, IL4, and IL13 is derived from activated effector T-cells. To further rule out any potential contribution of B-cells to the observed Th1 cytokine skewing we analyzed peripheral CD19+ B-cell and CLL mRNA levels at identical timepoints and found no such alteration in B-cell cytokine expression (FIG. 19).

Figure 6B:
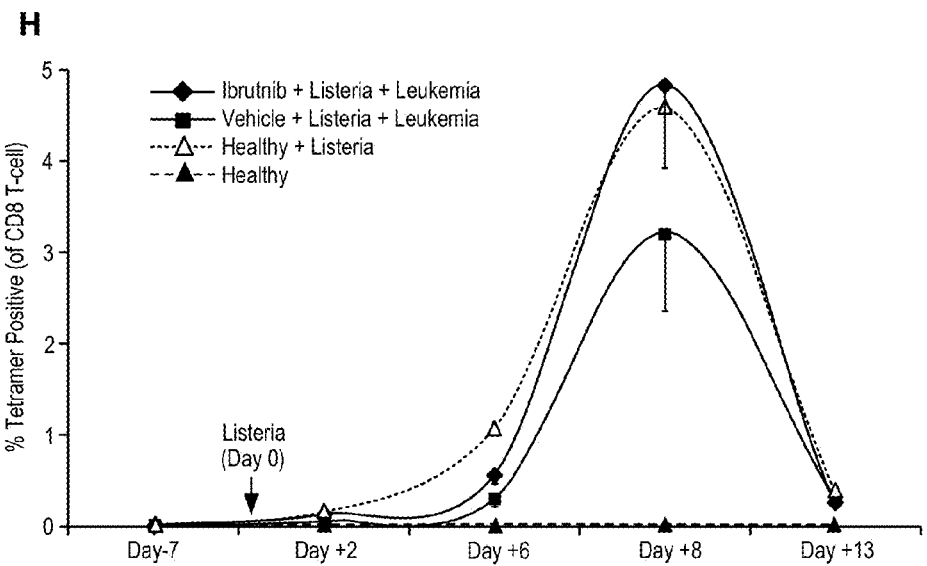
FIG. 6B illustrates plasma IgG1 (Th2) and IgG2c (Th1) subisotype analysis of C57BL/6 EμTCL1 mice at 8 months of age after 7 consecutive months of ibrutinib (n=12) or vehicle (n=13) administration via drinking water.
Figure 6B:
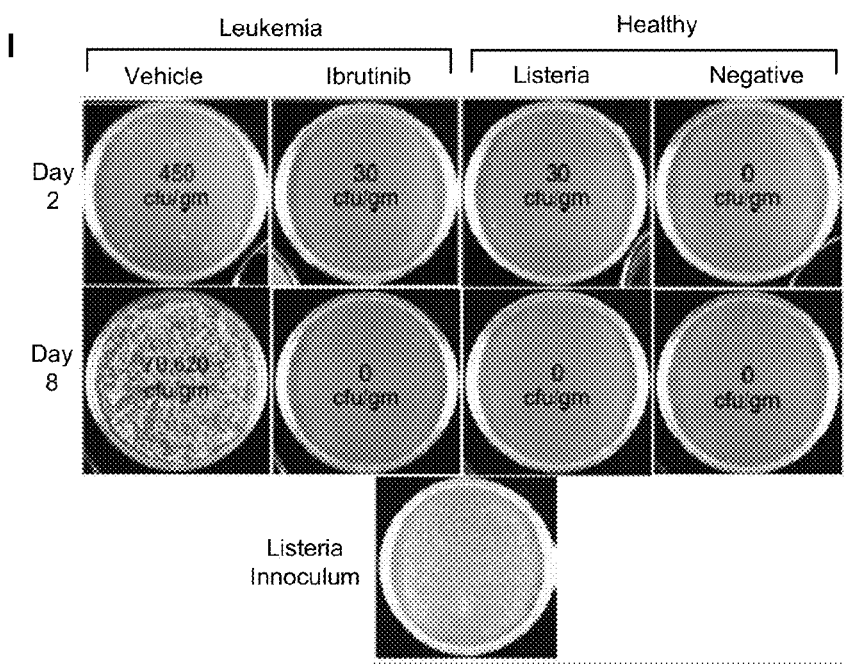
Figure 7:
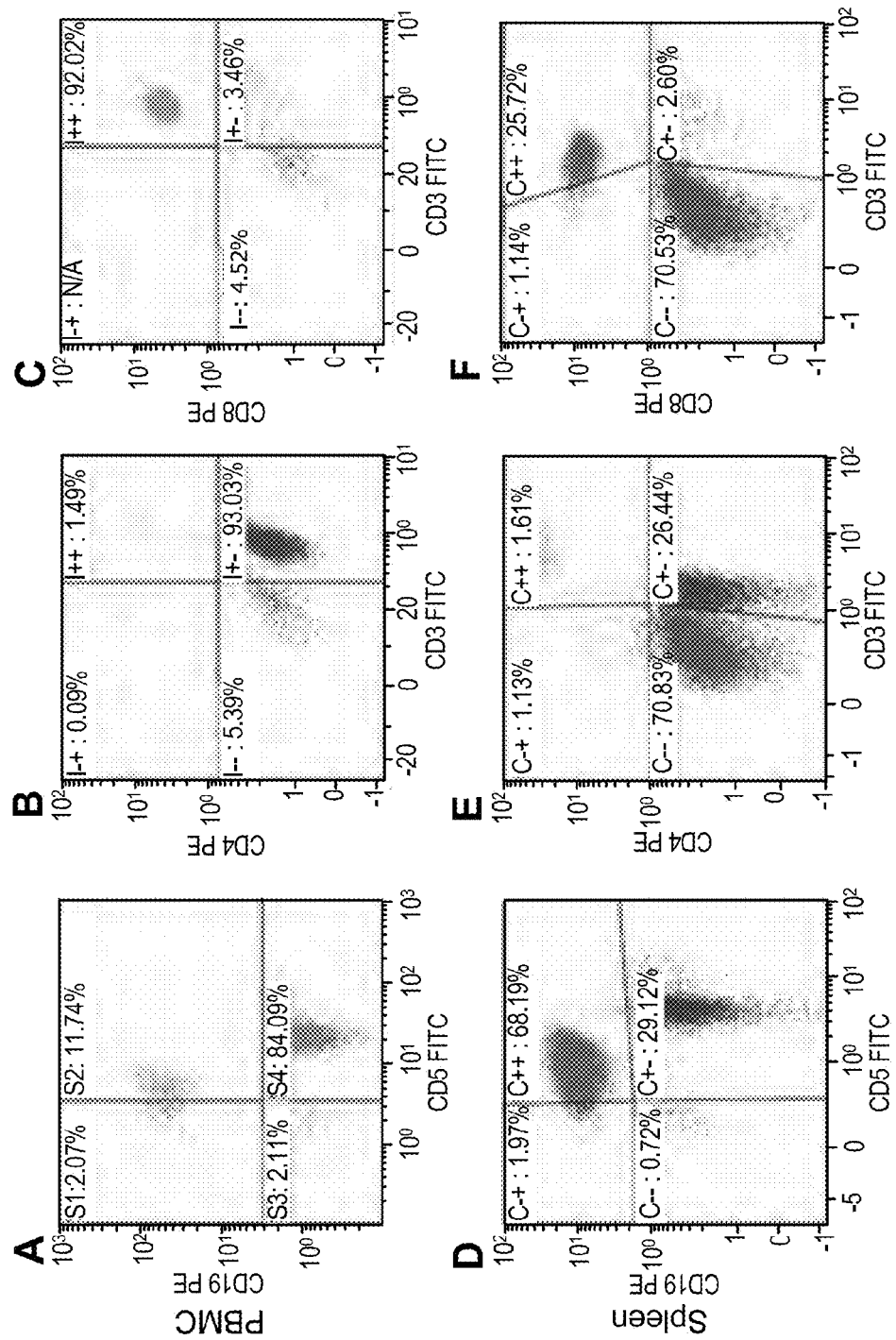
FIG. 7 illustrates flow cytometric analysis of T-cell leukemia arising in C57BL/6 EµTCL1 mice. Flow cytometric analysis of peripheral blood (PBMC) (FIG. 7A-7C), splenocytes (Spleen) (FIG. 7D-7F), bone marrow (FIG. 7G-7I), and mesenteric lymph nodes (FIG. 7J-7L) from animals presenting with enlarged spleen, elevated lymphocyte count, and apparent CD8+ T-cell leukemia. Cells were gated on CD45+ and subsequently analyzed by CD5 and CD19 (left panels), CD3 and CD4 (middle panels), and CD3 and CD8 (right panels). CD5+CD19+ B-cell leukemias were often concomitant with CD3+CD5+CD8+ T-cell leukemias in these animals.
Figure 7:
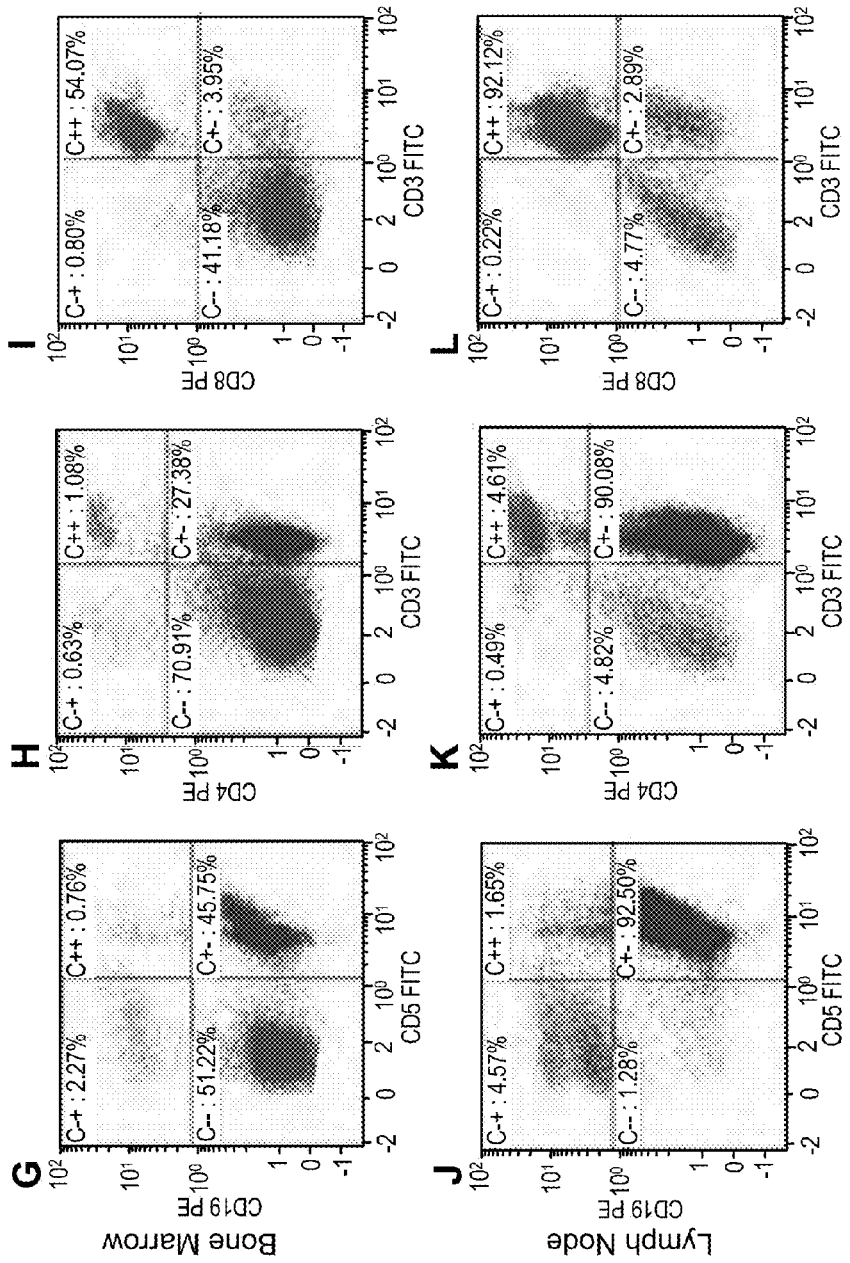
Figure 8:
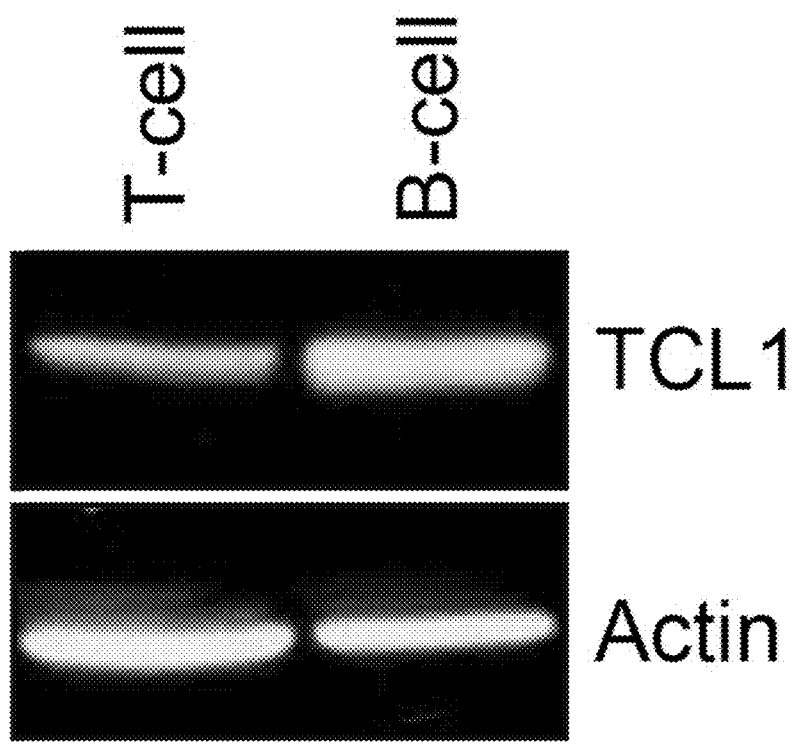
FIG. 8 illustrates immunoblot analysis of TCL1 oncoprotein expression in CD8 selected T-cell leukemias. Immunoblot analysis of TCL1 protein levels (and Actin control) in purified CD8+ T-cells and CD19+ B-cells isolated from a C57BL/6 EµTCL1 mouse spleen presenting with a CD3+CD5+CD8+ T-cell leukemia.
Figure 9:
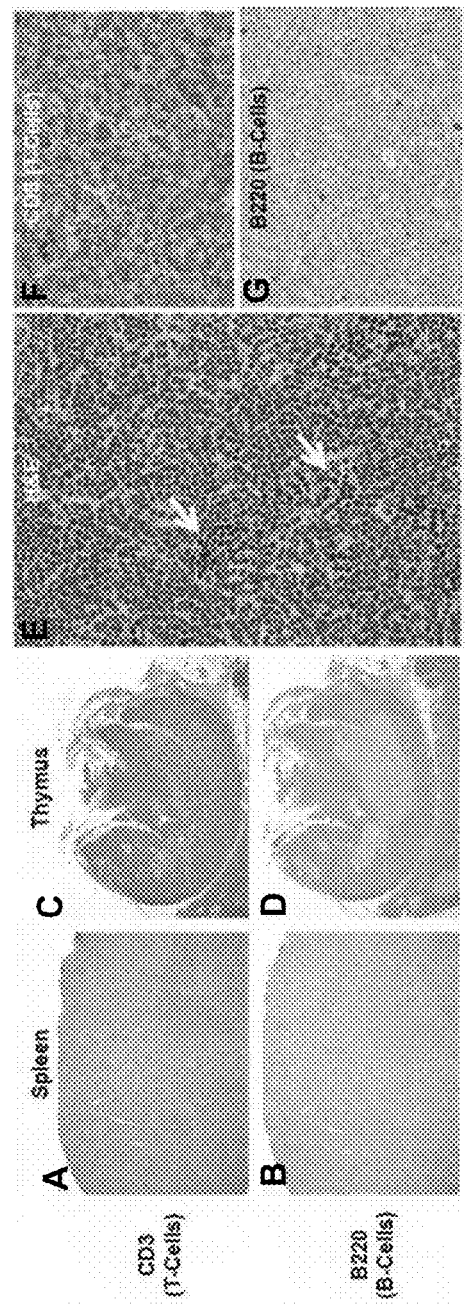
FIG. 9 illustrates immunohistochemical analysis of spleen and thymus from C57BL/6 EµTCL1 mice presenting with T-cell leukemia. IHC revealed that the secondary lymphoid organs, spleen (FIG. 9A-9B) and thymus (FIG. 9C-9D) were expanded by neoplastic round cells expressing the CD3 cell surface marker of the T-lymphocyte lineage (100×). The splenic pulp contained numerous pale basophilic, CD3+ neoplastic T-lymphocytes with scattered clusters of dark basophilic erythrocytic precursors (arrows)(400×)(FIG. 9E).

To assess the long-term functional implications of this ibrutinib-induced Th1 cytokine skewing IgG subisotype analyses were conducted in a cohort of 8 month old C57BL/6 EμTCL1 mice. These mice were treated continuously for 7 months with ibrutinib or vehicle. This analysis revealed a significant (p=0.002) inversion of the Th1/Th2 ratio as measured by the relative levels of IgG1 (Th2) and IgG2c (Th1), confirming an in vivo ibrutinib related Th1 skewing (FIG. 6b).

Figure 20:
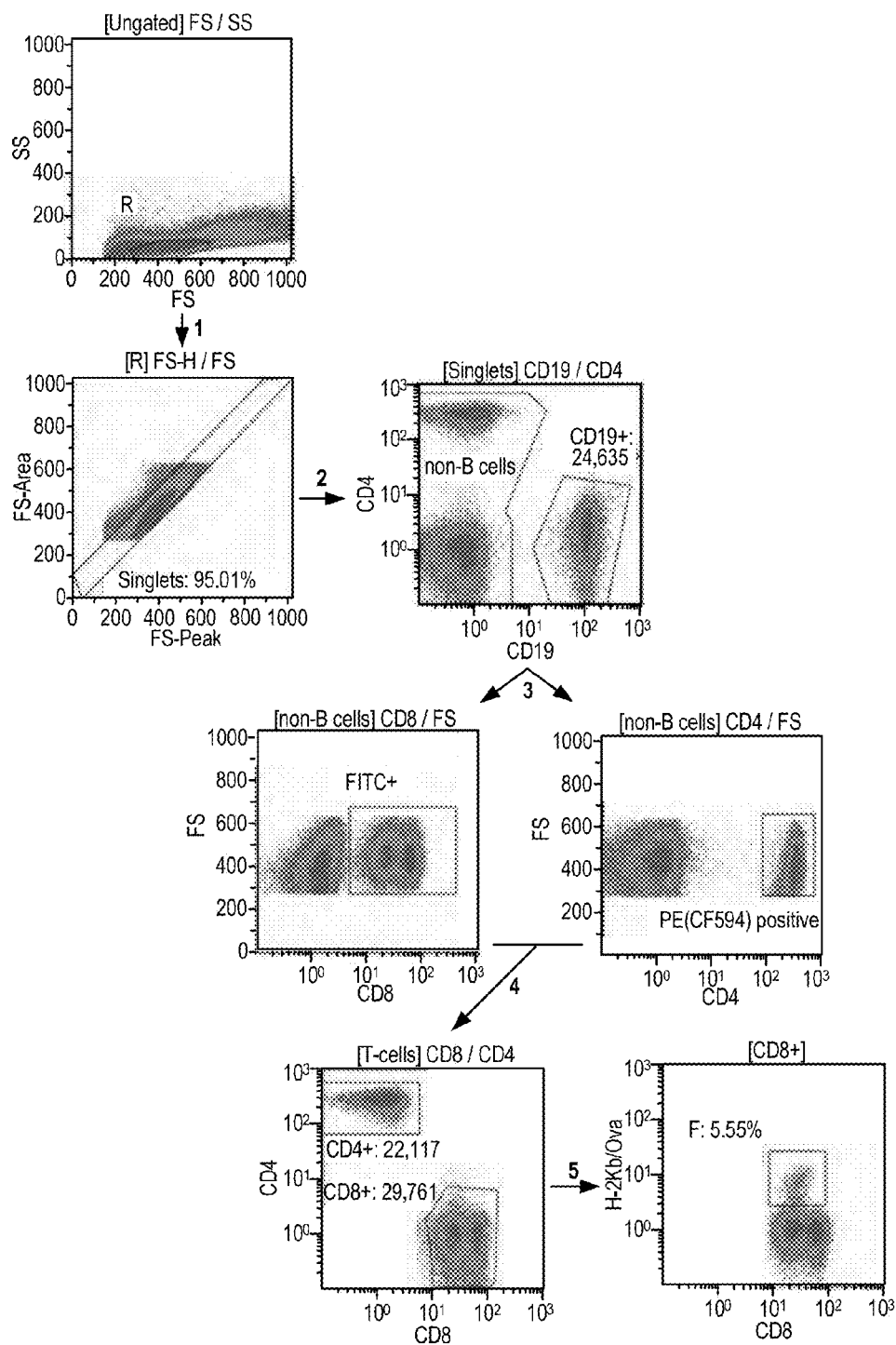
FIG. 20 illustrates gating strategy for OVA-Tetramer positive CD8 T-cells. (1) FS/SS gate for T and B lymphocytes. Backgating verified this gate included all CD19/CD4/CD8 positive events. (2) Gated on singlet events using FS-Peak vs. FS-Area plot. (3) Excluded CD19+ B-cells (4) Gated on CD4+ and CD8+ T-cells (5) Refined gate on CD8+ T-cells for tetramer analysis. The gate for tetramer positive CD8 T-cells was generating on an individual basis using the baseline tetramer staining 7 days prior to *Listeria* injection. The tetramer positive gate was set such that less than 0.04% CD8+ events would appear tetramer positive at day −7.

Infection linked to immunosuppression is the primary cause of death in CLL patients. Therefore, the therapeutic relevance of ibrutinib immunomodulation in a concurrent leukemia/listeriosis mouse model was investigated. In this model, EμTCL1 leukemia-engrafted mice were treated with ibrutinib or vehicle. After 7 days of therapy, mice (along with non-leukemic control cohorts) were challenged with a sub-lethal intravenous dose (5000 CFU) of L. monocytogenes (Listeria) expressing the immunodominant chicken ovalbumin (OVA) protein (FIG. 6c). As Listeria is an intracellular pathogen, a robust Th1 and CD8 T-cell response is required to achieve sterilizing immunity. Listeria-responsive Th1-biased immunity is indicated by elevated plasma IFNγ and TNFα, along with robust monocyte IL6 production. Plasma cytokine analysis at day 2 post infection revealed that ibrutinib-treated mice had significantly elevated (p=0.0198) IFNγ, TNFα, and IL6 in comparison to vehicle-treated leukemic animals (FIG. 6d-f). Tetramer analysis revealed a depression in the OVA-specific CD8 T-cell response in the vehicle treated leukemic group; however, this immunosuppression was reversed by ibrutinib therapy (FIGS. 6g and 20). Longitudinal analysis confirmed that the overall magnitude of Listeria response was significantly attenuated in leukemic mice (p=0.025 for day 6). However, ibrutinib significantly restored the veracity of response (p=0.028) to that approximating a healthy non-leukemic mouse (FIG. 6h). Interim analyses revealed that all healthy and ibrutinib-treated leukemic mice cleared the infection by day 8, yet half of vehicle treated mice analyzed at day 8 displayed uncontrolled Listeria infections within the liver which would likely have resulted in mortality (FIG. 6i).

Example 2

Ibrutinib PCYC-04753 Phase I Clinical Trial Demonstrates Th1/Th2 Skewing Due to an Elevated Level of IFNγ

Figure 21A:
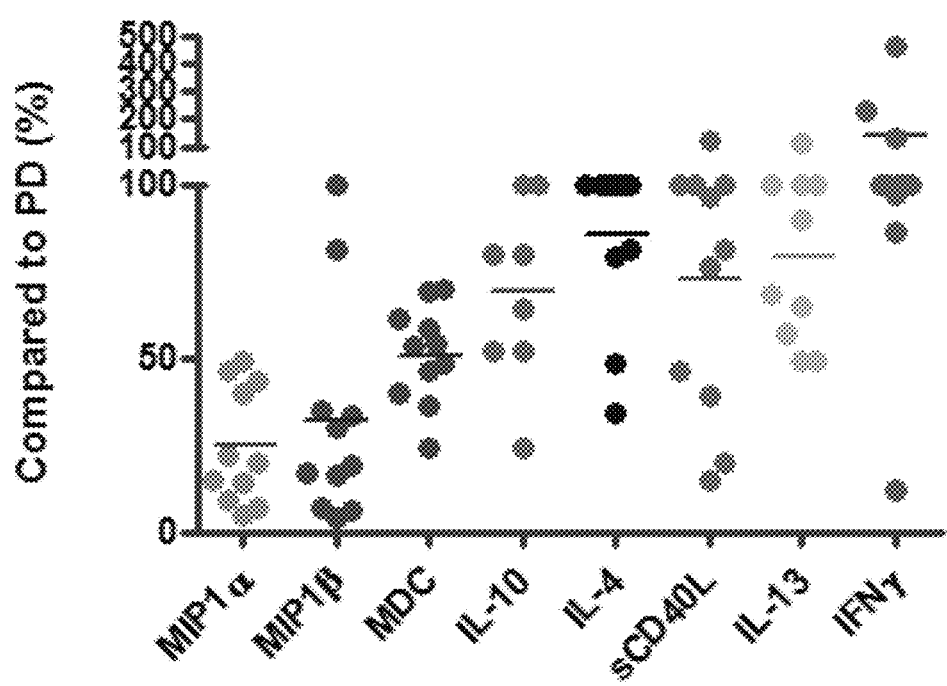
FIG. 21A illustrates cytokine and chemokine responses at the end of phase I PCYC-04753 study in CLL patients. Th2-type markers IL10, IL4, IL13, MIP1α, MIP1β and MDC exhibited a decrease from pre-treatment to day 28 of ibrutinib therapy. In contrast, Th1-type marker IFNγ exhibited an increase during the phase I study. Soluble CD40L (sCD40L), a Th1-type cytokine, showed a decrease in patients receiving ibrutinib as part of the phase I study.
Figure 21B:
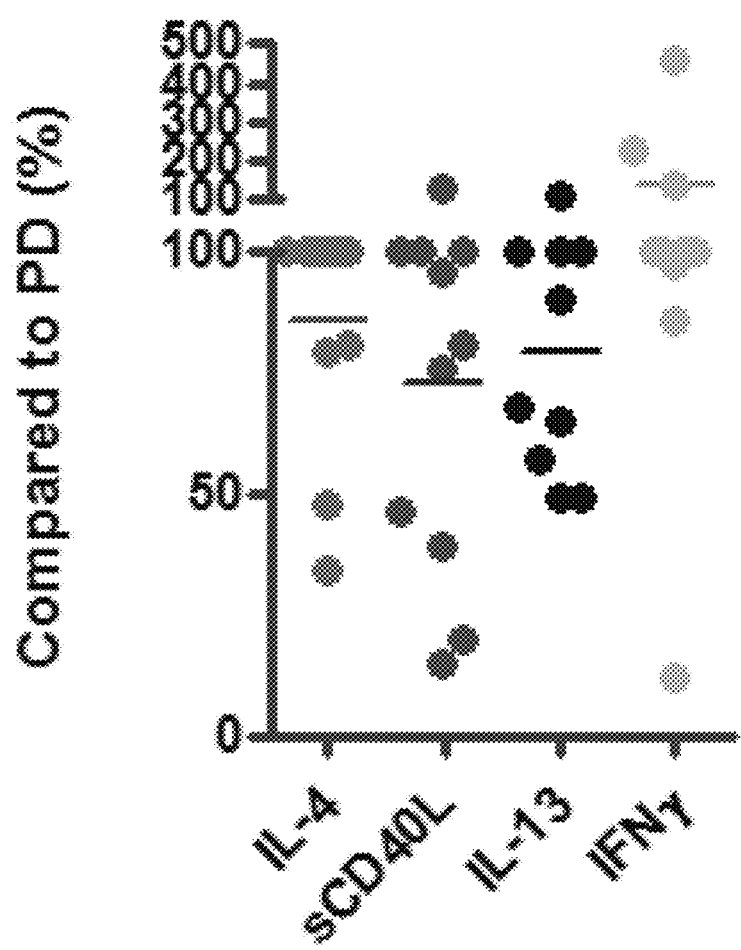
FIG. 21B illustrates Th1 and Th2 responses at the end of phase I PCYC-04753 study in CLL patients. The data demonstrated a decrease in serum markers IL4, IL13 and sCD40L and an increase in IFNγ.

A serial serum cytokine and chemokine levels were investigated in CLL patients receiving ibrutinib as part of a phase I study. The data demonstrated a decrease in serum Th2-type cytokines including IL10, IL4, and IL13 from pre-treatment to day 28 of ibrutinib therapy (FIG. 21a). Th2-type chemokines including MIP1α, MIP1β and MDC also exhibited a decrease from pre-treatment to day 28. These Th2-type cytokine/chemokine levels were in sharp contrast to a simultaneous increase in the Th1-type cytokine IFNγ. Soluble CD40L (sCD40L), a Th1-type cytokine, showed a decrease in patients receiving ibrutinib as part of the phase I study. Th1/Th2 ratio was also investigated in CLL patients receiving ibrutinib as part of the phase I study (FIG. 21b). The data demonstrated a decrease in serum cytokines IL4, IL13 and sCD40L and an increase in IFNγ.

Example 3

Ibrutinib Effect on Cytokine/Chemokine Response in High Risk RR CLL Patients

Figure 22:
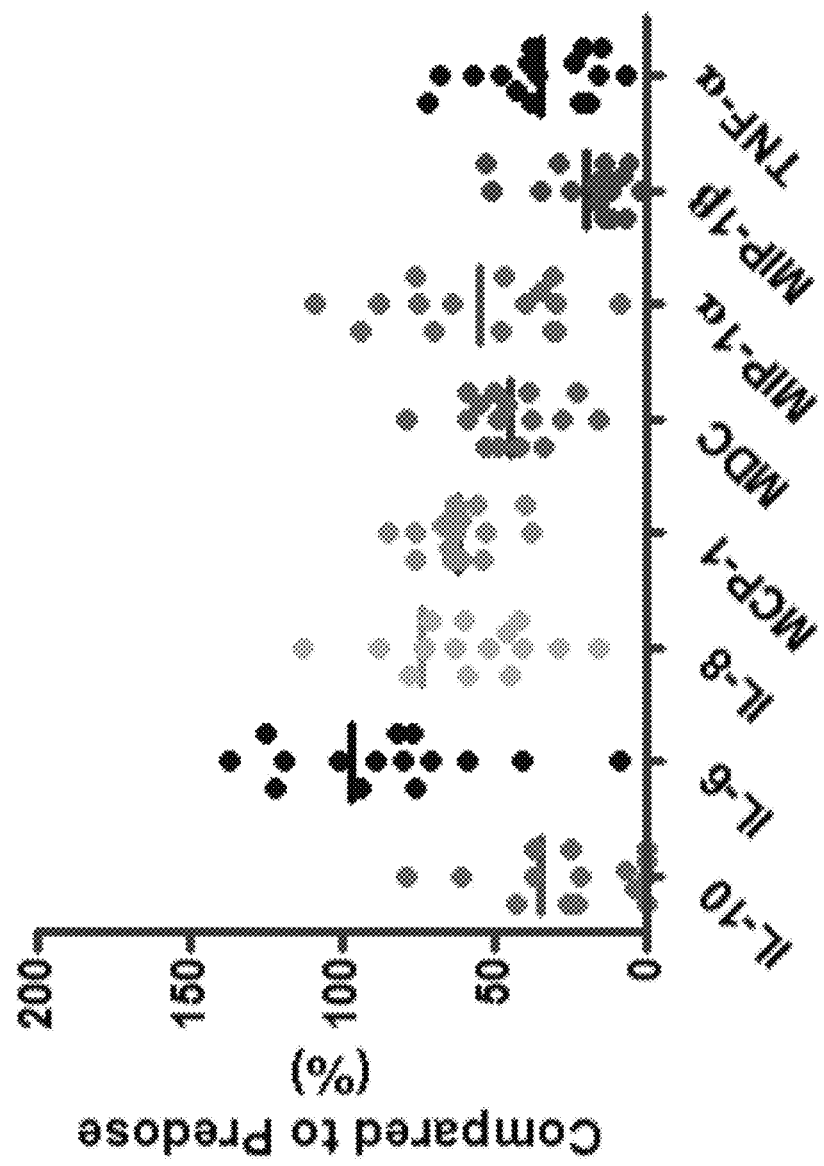
FIG. 22 illustrates ibrutinib effect on cytokine/chemokine response in high risk RR CLL patients as part of a cohort 4 study. The data demonstrated a decrease in the level of serum Th2-type cytokines including IL10, IL8, MCP-1, MDC, MIP1α, and MIP1β from pre-treatment to day 28 of ibrutinib therapy. The level of the Th2-type cytokine IL6 remained constant during the course of the ibrutinib therapy. The level of the Th1-type cytokine TNF-α also decreased during the course of the ibrutinib therapy.

A serial serum cytokine and chemokine levels were investigated in high risk RR CLL patients receiving ibrutinib as part of a cohort 4 study. The data demonstrated a decrease in the level of serum Th2-type cytokines including IL10, IL8, MCP-1, MDC, MIP1α, and MIP1β from pre-treatment to day 28 of ibrutinib therapy (FIG. 22). The level of the Th2-type cytokine IL6 remained constant during the course of the ibrutinib therapy. The level of the Th1-type cytokine TNF-α also decreased during the course of the ibrutinib therapy.

Example 4

Figure 23:
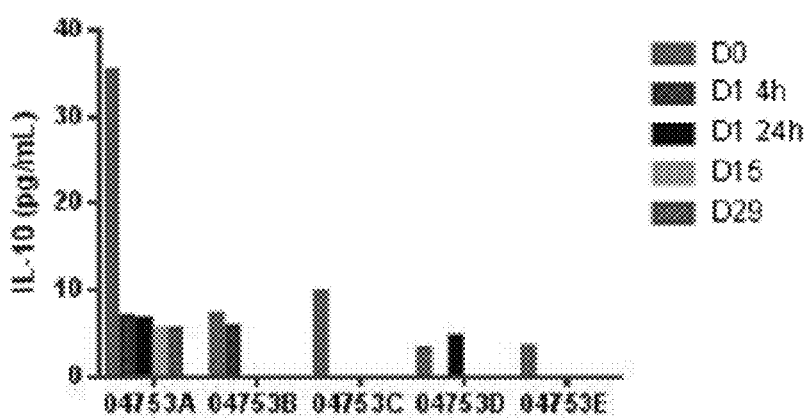
FIG. 23 illustrates ibrutinib effect on Th1/Th2 skewing in mentel cell lymphoma patients. Levels of cytokines and chemokine including IL10 (FIG. 23A), MIP1β (FIG. 23B), sCD40L (FIG. 23C), IL13 (FIG. 23D), IL4 (FIG. 23E) and IFNγ (FIG. 23F) were measured on day 0, day 1 at 4 hours, day 1 at 24 hours, day 15 and day 29. Reduction in the levels of IL10, IL13 and IL4 were observed following ibrutinib treatment. This was in sharp contrast to an increase in the IFNγ level.
Figure 23:
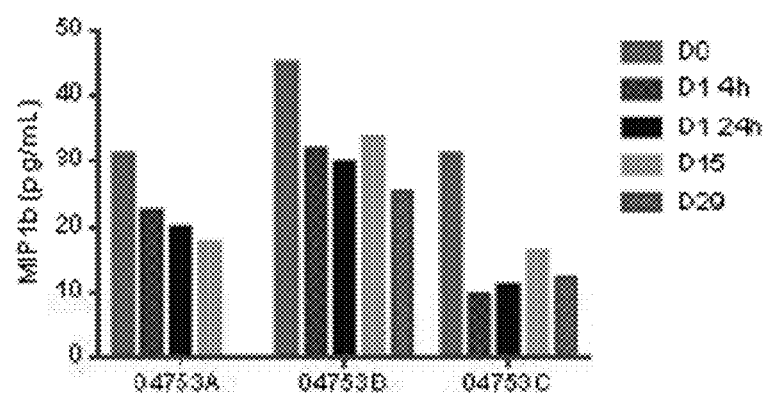
Figure 23:
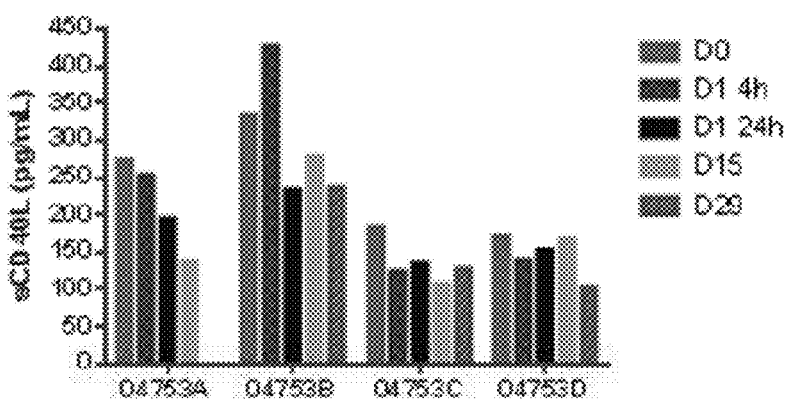
Figure 23:
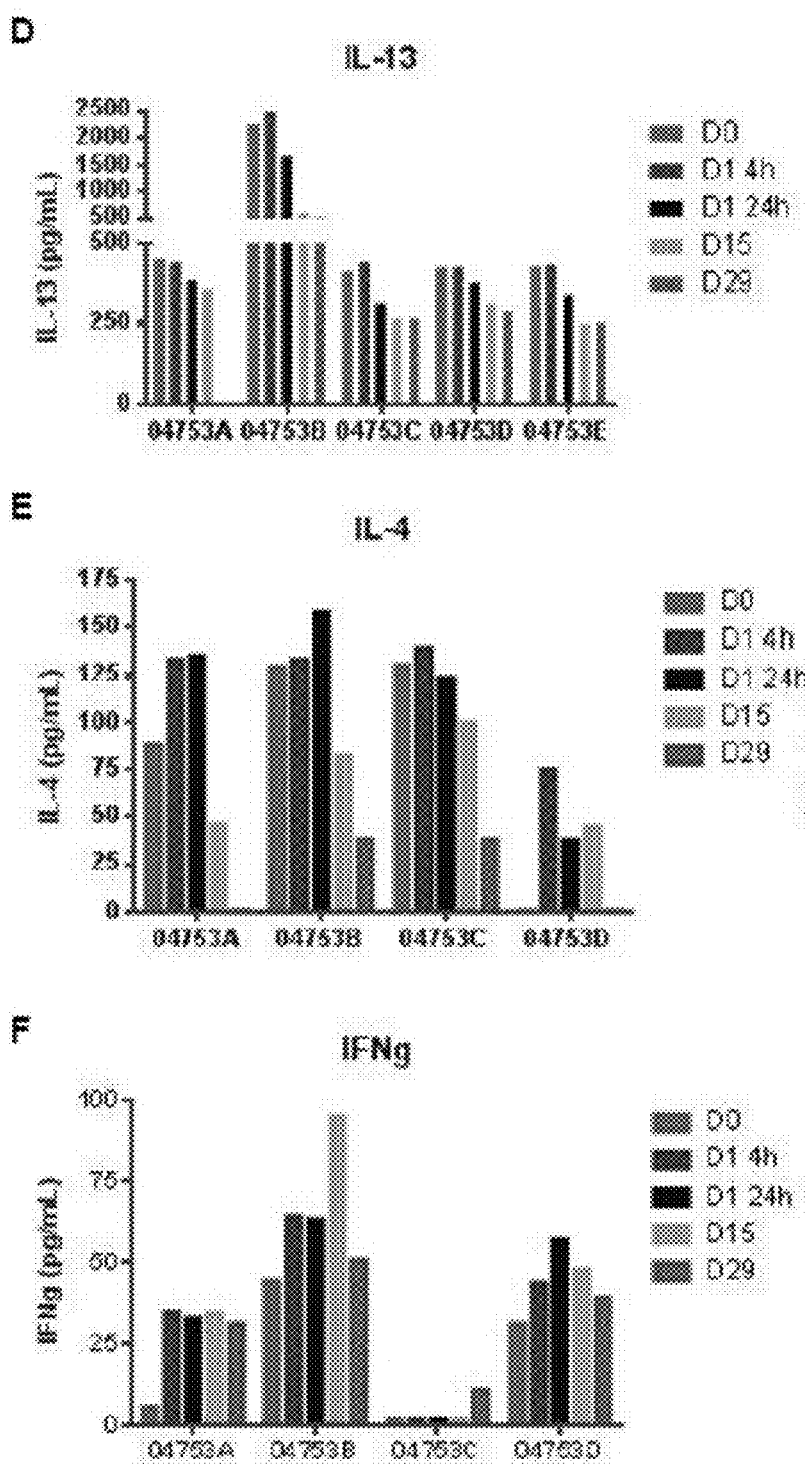

Ibrutinib Clinical Trial Demonstrates Th1/Th2 Skewing in Mantel Cell Lymphoma Patients A serial serum cytokine and chemokine levels were investigated in MCL patients receiving ibrutinib as part of a clinical study. Levels of cytokines and chemokine including IL10, IL13, IL4, sCD40L, IFNγ and MIP1β were measured on day 0, day 1 at 4 hours, day 1 at 24 hours, day 15 and day 29 (FIG. 23). Reduction in the levels of IL10, IL13 and IL4 were observed following ibrutinib treatment. This was in sharp contrast to an increase in the IFNγ level.

The examples and embodiments described herein are for illustrative purposes only and various modifications or changes suggested to persons skilled in the art are to be included within the spirit and purview of this application and scope of the appended claims.

What is claimed is:

1. A method of treating a subject having adult T-cell leukemia/lymphoma (ATLL) following treatment with a first anticancer therapy, comprising
administering to the subject an effective amount of ibrutinib to treat the adult T-cell leukemia/lymphoma (ATLL), after the discontinuation of the first anticancer therapy, and wherein the first anticancer therapy does not comprise administration of ibrutinib.

2. The method of claim 1, wherein the first anticancer therapy comprises administration of a chemotherapeutic agent, a biologic agent, radiation therapy, bone marrow transplant, surgery, or a combination thereof.

3. The method of claim 1, wherein the first anticancer therapy is a chemotherapeutic agent or biologic agent selected from among CHOP (cyclophosphamide, hydroxydoxorubicin, vincristine, and prednisone), EPOCH (etoposide, prednisone, vincristine, cyclophosphamide, hydroxydoxorubicin), Hyper-CVAD (cyclophosphamide, vincristine, hydroxydoxorubicin, dexamethasone), ICE (ifosfamide, carboplatin, etoposide), DHAP (high-dose cytarabine [ara-C], dexamethasone, cisplatin), ESHAP (etoposide, methylprednisolone, cytarabine [ara-C], cisplatin), anthracycline-based chemotherapy, a histone deacetylase (HDAC) inhibitor, a proteasome inhibitor, an immunomodulatory agent, an antibody, a nucleoside analogs, a PI3K inhibitor, an IAP inhibitor, an mTOR inhibitor, a radioimmunotherapeutic, a DNA damaging agent, a protein kinase inhibitor, a hedgehog inhibitor, an Hsp90 inhibitor, a telomerase inhibitor, a Jak1/2inhibitor, a protease inhibitor, an IRAK inhibitor, a PKC inhibitor, a PARP inhibitor, a CYP3A4inhibitor, an alkylating agent, an anti metabolite, a plant alkaloid, a terpenoid, a cytotoxin, a topoisomerase inhibitor, or a combination thereof.

4. The method of claim 1, wherein ibrutinib is administered at a dosage of about 40 mg/day to about 1000 mg/day.

5. The method of claim 1, wherein the subject has a high risk of cancer recurrence prior to administration of ibrutinib.

6. The method of claim 1, wherein the administering of ibrutinib is initiated less than 3 weeks after discontinuation of the first anticancer therapy.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: 5' Synthetic primer

<400> SEQUENCE: 1
ggtcatcaag gtgtccgact                                                   20

<210> SEQ ID NO 2
<211> LENGTH: 20
<212> TYPE: DNA
<213> ORGANISM: Artificial Sequence
<220> FEATURE:
<223> OTHER INFORMATION: 3' Synthetic primer

<400> SEQUENCE: 2
tcgtatggga ttttgccttc                                                   20

<210> SEQ ID NO 3
<211> LENGTH: 20
<212> TYPE: DNA
<213> ORGANISM: Artificial Sequence
<220> FEATURE:
<223> OTHER INFORMATION: 5' Synthetic primer

<400> SEQUENCE: 3
aaaggttccc gtacccattc                                                   20

<210> SEQ ID NO 4
<211> LENGTH: 20
<212> TYPE: DNA
<213> ORGANISM: Artificial Sequence
<220> FEATURE:
<223> OTHER INFORMATION: 3' Synthetic primer

<400> SEQUENCE: 4
cccatagcat tcttggctgt                                                   20

<210> SEQ ID NO 5
<211> LENGTH: 20
<212> TYPE: DNA
<213> ORGANISM: Artificial Sequence
<220> FEATURE:
<223> OTHER INFORMATION: 5' Synthetic primer

<400> SEQUENCE: 5
ctcatgacca cagtccatgc                                                   20

<210> SEQ ID NO 6
<211> LENGTH: 20
<212> TYPE: DNA
<213> ORGANISM: Artificial Sequence
<220> FEATURE:
<223> OTHER INFORMATION: 3' Synthetic primer

<400> SEQUENCE: 6
cacattgggg gtaggaacac                                                   20

<210> SEQ ID NO 7
<211> LENGTH: 20
<212> TYPE: DNA
<213> ORGANISM: Artificial Sequence

```
<220> FEATURE:
<223> OTHER INFORMATION: 5' Synthetic primer

<400> SEQUENCE: 7
agaaggctgg ggctcatttg                                           20

<210> SEQ ID NO 8
<211> LENGTH: 20
<212> TYPE: DNA
<213> ORGANISM: Artificial Sequence
<220> FEATURE:
<223> OTHER INFORMATION: 3' Synthetic primer

<400> SEQUENCE: 8
aggggccatc cacagtcttc                                           20

<210> SEQ ID NO 9
<211> LENGTH: 20
<212> TYPE: DNA
<213> ORGANISM: Artificial Sequence
<220> FEATURE:
<223> OTHER INFORMATION: 5' Synthetic primer

<400> SEQUENCE: 9
gtacggaggc tgccataaaa                                           20

<210> SEQ ID NO 10
<211> LENGTH: 20
<212> TYPE: DNA
<213> ORGANISM: Artificial Sequence
<220> FEATURE:
<223> OTHER INFORMATION: 3' Synthetic primer

<400> SEQUENCE: 10
cagctgtggc tggtaaacaa                                           20
```